US011530419B2

(12) United States Patent
Schultink et al.

(10) Patent No.: US 11,530,419 B2
(45) Date of Patent: Dec. 20, 2022

(54) PATHOGEN RESISTANCE IN PLANTS

(71) Applicant: Fortiphyte, Inc., Berkeley, CA (US)

(72) Inventors: Alexander Christiaan Schultink, Berkeley, CA (US); Laura A. Wetzel, Berkeley, CA (US)

(73) Assignee: Fortiphyte, Inc., Berkeley, CA (US)

( * ) Notice: Subject to any disclaimer, the term of this patent is extended or adjusted under 35 U.S.C. 154(b) by 0 days.

(21) Appl. No.: 17/512,329

(22) Filed: Oct. 27, 2021

(65) Prior Publication Data

US 2022/0135997 A1 May 5, 2022

Related U.S. Application Data

(60) Provisional application No. 63/108,023, filed on Oct. 30, 2020.

(51) Int. Cl.

| | |
|---|---|
| ***C12N 15/82*** | (2006.01) |
| *C12N 15/11* | (2006.01) |
| *C12N 15/90* | (2006.01) |

(52) U.S. Cl.

CPC ........ *C12N 15/8282* (2013.01); *C12N 15/111* (2013.01); *C12N 15/902* (2013.01); *C12N 2310/20* (2017.05)

(58) Field of Classification Search

CPC .................................................. C12N 15/8282

See application file for complete search history.

(56) References Cited

U.S. PATENT DOCUMENTS

| | | | |
|---|---|---|---|
| 4,399,216 | A | 8/1983 | Axel et al. |
| 4,536,475 | A | 8/1985 | Anderson |
| 4,795,855 | A | 1/1989 | Fillatti et al. |
| 5,015,580 | A | 5/1991 | Christou et al. |
| 5,034,322 | A | 7/1991 | Rogers et al. |
| 5,164,316 | A | 11/1992 | McPherson et al. |
| 5,196,525 | A | 3/1993 | McPherson et al. |
| 5,204,253 | A | 4/1993 | Sanford et al. |
| 5,302,523 | A | 4/1994 | Coffee et al. |
| 5,322,938 | A | 6/1994 | McPherson et al. |
| 5,352,605 | A | 10/1994 | Fraley et al. |
| 5,359,142 | A | 10/1994 | McPherson et al. |
| 5,376,543 | A | 12/1994 | Chee et al. |
| 5,378,824 | A | 1/1995 | Bedbrook et al. |
| 5,405,765 | A | 4/1995 | Vasil et al. |
| 5,416,011 | A | 5/1995 | Hinchee et al. |
| 5,451,513 | A | 9/1995 | Maliga et al. |
| 5,472,869 | A | 12/1995 | Krzyzek et al. |
| 5,501,967 | A | 3/1996 | Offringa et al. |
| 5,527,695 | A | 6/1996 | Hodges et al. |
| 5,530,196 | A | 6/1996 | Fraley et al. |
| 5,538,877 | A | 7/1996 | Lundquist et al. |
| 5,538,880 | A | 7/1996 | Lundquist et al. |
| 5,550,318 | A | 8/1996 | Adams et al. |
| 5,569,834 | A | 10/1996 | Hinchee et al. |
| 5,591,616 | A | 1/1997 | Hiei et al. |
| 5,641,664 | A | 6/1997 | D'Halluin et al. |
| 5,693,512 | A | 12/1997 | Finer et al. |
| 5,731,179 | A | 3/1998 | Komari et al. |
| 5,736,369 | A | 4/1998 | Bowen et al. |
| 5,767,378 | A | 6/1998 | Bojsen et al. |
| 5,858,742 | A | 1/1999 | Fraley et al. |
| 5,959,185 | A | 9/1999 | Streit et al. |
| 5,968,830 | A | 10/1999 | Dan et al. |
| 5,973,234 | A | 10/1999 | Mueller et al. |
| 5,977,445 | A | 11/1999 | Soper et al. |
| 5,994,629 | A | 11/1999 | Bojsen et al. |
| 6,051,757 | A | 4/2000 | Barton et al. |
| 6,107,549 | A | 8/2000 | Feng et al. |
| 6,156,953 | A | 12/2000 | Preuss et al. |
| 6,174,724 | B1 | 1/2001 | Rogers et al. |
| 6,255,560 | B1 | 7/2001 | Fraley et al. |
| 7,250,554 | B2 | 7/2007 | Rommens et al. |
| 2004/0197909 | A1 | 10/2004 | McKnight et al. |

(Continued)

FOREIGN PATENT DOCUMENTS

| | | | |
|---|---|---|---|
| EP | 0068730 | A1 | 1/1983 |
| EP | 0265556 | A1 | 5/1988 |

(Continued)

OTHER PUBLICATIONS

Friedberg (Automated protein function prediction—the genomic challenge. Brief. Bioinformatics. 7:225-242, 2006) (Year: 2006).*

Wang et al (From Protein Sequence to Protein Function via Multi-Label Linear Discriminant Analysis. IEEE/ACM Transactions on Computational Biology and Bioinformatics, vol. 14, No. 3, 503-513, 2017) (Year: 2017).*

Dinesh-Kumar et al (Structure-function analysis of the tobacco mosaic virus resistance gene N. PANS, 14789-14794, 2000) (Year: 2000).*

Kang et al (Genome sequence of mungbean and insights into evolution within *Vigna* species. Nature Communication. 1-9, 2014). (Year: 2014).*

(Continued)

*Primary Examiner* — Charles Logsdon
*Assistant Examiner* — Wayne Zhong
(74) *Attorney, Agent, or Firm* — Cooley LLP

(57) ABSTRACT

The present disclosure provides an isolated, recombinant, or synthetic polynucleotide comprising a FIT1 protein, and homologs, fragments, and variations thereof. The disclosure further relates to transgenic plants, plant parts, and plant cells comprising one or more of these polynucleotides, and exhibit resistance or tolerance to a pathogen, such as *Phakopsora pachyrhizi*. The disclosure further relates to methods of genetically engineering a pathogen resistance or tolerance trait in a plant, plant part, or plant cell, comprising targeted gene editing of a FIT1 homolog, and plants produced therefrom. The disclosure further relates to methods for identifying new functional FIT1 genes and/or alleles thereof.

22 Claims, 16 Drawing Sheets
(14 of 16 Drawing Sheet(s) Filed in Color)
Specification includes a Sequence Listing.

(56) References Cited

U.S. PATENT DOCUMENTS

| | | | | |
|---|---|---|---|---|
| 2008/0057093 | A1* | 3/2008 | Wan | C12N 9/12 424/405 |
| 2008/0120750 | A1* | 5/2008 | Budworth | C12N 15/8225 800/300.1 |
| 2010/0076057 | A1 | 3/2010 | Sontheimer et al. | |
| 2010/0313307 | A1 | 12/2010 | Herman et al. | |
| 2014/0179006 | A1 | 6/2014 | Zhang | |
| 2014/0294773 | A1 | 10/2014 | Brouns et al. | |
| 2018/0103600 | A1 | 4/2018 | Rairdan et al. | |
| 2018/0195082 | A1 | 7/2018 | Guo et al. | |
| 2019/0169629 | A1 | 6/2019 | Coffin | |

FOREIGN PATENT DOCUMENTS

| | | | |
|---|---|---|---|
| EP | 0270822 | A1 | 6/1988 |
| EP | 0604662 | A1 | 7/1994 |
| EP | 0672752 | A1 | 9/1995 |
| EP | 0904362 | A1 | 3/1999 |
| WO | WO-1983003259 | A1 | 9/1983 |
| WO | WO-1985004899 | A1 | 11/1985 |
| WO | WO-1986003516 | A1 | 6/1986 |
| WO | WO-1986003776 | A1 | 7/1986 |
| WO | WO-1992009696 | A1 | 6/1992 |
| WO | WO-1994019930 | A1 | 9/1994 |
| WO | WO-1995016031 | A1 | 6/1995 |
| WO | WO-1999067357 | A2 | 12/1999 |
| WO | WO-2002038779 | A1 | 5/2002 |
| WO | WO-2009117555 | A8 | 10/2009 |

OTHER PUBLICATIONS

NCBI (XP_027941564, published Feb. 2019; XM_028085763, published Feb. 2019; XM_014646001, published Oct. 2017) (Year: 2019).*

Aime et al., "An Overview of the Higher Level Classification of Pucciniomycotina Based on Combined Analyses of Nuclear Large and Small Subunit rDNA Sequences," Mycologia, 98(6), 896-905 (2006).

Altschul, SF et al., 'Issues in searching molecular sequence databases,' Nat. Genet., vol. 6, pp. 119-129, (Feb. 1994).

Bevan et al., "A chimaeric antibiotic resistance gene as a selectable marker for plant cell transformation," Nature 304:184-187 (1983).

Bourouis et al., "Vectors containing a prokaryotic dihydrofolate reductase gene transform *Drosophila* cells to methotrexate-resistance," EMBO J. 2(7):1099-1104 (1983).

Corpet, F et al., 'Multiple sequence alignment with hierarchical clustering,' vol. 16 No. 22, pp. 10881-10890, (Oct. 1988).

Daboussi et al., "Engineering Meganuclease for Precise Plant Genome Modification" in Advances in New Technology for Targeted Modification of Plant Genomes. Springer Science+Business, pp. 21-38 (2015).

De Carvalho et al., "Prediction of the in planta *Phakopsora pachyrhizi* secretome and potential effector families," Mol Plant Pathol. 18(3):363-377 (2017).

Depicker et al., "Nopaline synthase: transcript mapping and DNA sequence," Mol. and Appl. Genet. 1(6):561-573 (1982).

Dodds et al., "Plant immunity: towards an integrated view of plant-pathogen interactions," Nat Rev Genet 11, 539-548 (2010).

Elmore et al., "De novo transcriptome of Phakopsora pachyrhizi uncovers putative effector repertoire during infection," Physiological and Molecular Plant Patholoty 110, pp. 1-9 (2020).

Fauquet et al., "Geminivirus strain demarcation and nomenclature," Archives of Virology 153(4):783-821 (2008).

Fromm et al., "Inheritance and expression of chimeric genes in the progeny of transgenic maize plants," Bio/Tech. 8:833-839 (1990).

Fromm et al., "Stable transformation of maize after gene transfer by electroporation," Nature 319:791-793 (1986).

Gielen et al., "The complete nucleotide sequence of the TL-DNA of the Agrobacterium tumefaciens plasmid pTiAch5," EMBO J 3(4):835-846 (1984).

Han et al., Creation of early flowering germplasm of soybean by CRISPR/Cas9 Technology, Front. Plant Sci., pp. 1-10 (2019).

Henikoff et al., "Amino acid substitution matrices from protein blocks." Proc Natl Acad Sci U S A (Nov. 1992); 89(Nov.); 10915-10919.

Hiei et al., "Transformation of rice mediated by Agrobacterium tumefaciens," Plant Molecular Biology 35(1-2):205-218 (1997).

Higgins, DG and Sharp, PM, "CLUSTAL: a package for performing multiple sequence alignment on a microcomputer." Gene (1988); 73.1: 237-244.

Higgins, DG and Sharp, PM, 'Fast and sensitive multiple sequence alignments on a microcomputer,' Comput Appl Biosci., 5(2):151-3, (Apr. 1989).

Hinchee et al., "Production of Transgenic Soybean Plants Using Agrobacterium-Mediated DNA Transfer," Bio/Tech. 6(8):915-922 (1988).

Huang et al., "Parallelization of a local similarity algorithm," Comp. Appls Biosci. 8:155-165 (1992).

Ishida et al., "High efficiency transformation of maize (*Zea mays* L.) mediated by Agrobacterium tumefaciens," Nature Biotechnology A79 14(6):745-750 (1996).

Ishino et al., "Nucleotide sequence of the iap gene, responsible for alkaline phosphatase isozyme conversion in *Escherichia coli*, and identification of the gene product," J. Bacteriol., 169:5429-5433 (1987).

Ivics et al. "Molecular Reconstruction of Sleeping Beauty, a Tc1-like Transposon from Fish, and Its Transposition in Human Cells", Cell, 1997, vol. 91, p. 501-510.

Jones and Dangi, "The Plant immune system," Nature 444(7117):323-329 (2006).

Jones et al., "Intracellular innate immune surveillance devices in plants and animals," Science 354(6316):aaf6395-1-aaf6395-8 (2016).

Jones et al., "Transient Gene Expression in Electroporated Solanum Protoplasts," Plant Mol. Biol. 13:503-511 (1989).

Kaeppler et al., "Silicon Carbide Fiber-Mediated Stable Transformation of Plant Cells," Theoretical and Applied Genetics, 84, 560-566 (1992).

Kay et al.,"Gene Therapy," Proc. Natl. Acad Sci. U.S.A. 94:12744-12746 (1997).

Ku, M. S. et al., "High-level expression of maize phosphoenolpyruvate carboxylase in transgenic rice plants", Nat Biotechnol.; 17(1):76-80. (Jan. 1999).

Laboratory Manual for Studies on Soybean Rust Resistance, 2013-2021, Japanese International Research Center for Agricultural Sciences (JIRCAS), 52 pages.

Link et al., The haustorial transcriptomes of Uromyces appendiculatus and Phakopsora pachyrhizi and their candidate effector families. Mol Plant Pathol. 15(4):379-393 (2014).

Lu et al., "Generation of transgenic plants of a potential oilseed crop *Camelina sativa* by Agrobacterium-mediated transformation," Plant Cell Reports, 27:273-278 (2008).

Malzhan et al. "Plant genome editing with TALEN and CRISPR," Cell & Bioscience, vol. 7:21 (Apr. 2017), 18 pages.

Mccabe et al., "Stable Transformation of Soybean (*Glycine max*) by Particle Acceleration," Bio/Tech. 6:923-926 (1988).

Michelmore et al., "Identification of markers linked to disease-resistance genes by bulked segregant analysis: a rapid method to detect markers in specific genomic regions by using segregating populations," Proceedings of the National Academy of Sciences, USA, 88:9828-9832 (1991).

Mizuno et al.,"Improvement of the Aluminum Borate Whisker-Mediated Method of DNA Delivery into Rice Callus," Plant Production Science 7:45-49 (2004).

Paz et al., "Assessment of conditions affecting Agrobacterium-mediated soybean transformation using the cotyledonary node explant," Euphytica 136:167-179 (2004).

Pearson, "Using the FASTA program to search protein and DNA sequence databases," Methods Mol. Biol. (1994) 24: 307-331.

Petolino et al., "Whisker-mediated transformation of embryogenic callus of maize," Plant Cell Reports 19, 781-786 (2000).

Petolino, "Genome editing in plants via designed zinc finger nucleases," In Vitro Cell Dev Biol Plant, 51(1):1-8 (2015).

(56) References Cited

OTHER PUBLICATIONS

Quarrie et al., Bulk segregant analysis with molecular markers and its use for improving drought resistance in maize, Journal of Experimental Botany, 50(337):1299-1306 (1999).
Raineri et al., “Agrobacterium-Mediated Transformation of Rice (*Oryza sativa* L.),” Bio/Tech. 8:33-38 (1990).
Sander and Joung, “CRISPR-Cas systems for editing, regulating and targeting genomes,” Nature Biotechnology, 32:347-355 (2014).
Sedeek et al., Plant genome engineering for targeted improvement of crop traits, Front. Plant Sci. (2019).
Slaminko et al.,“New Legume Hosts of Phakopsora pachyrhizi Based on Greenhouse Evaluations,” Plant Disease 92(5):767-771 2008.
Sorek et al., “CRISPR-Mediated Adaptive Immune Systems in Bacteria and Archaea,” Annu. Rev. Biochem. 82:237-266 (2013).
Spencer et al., “Bialaphos selection of stable transformants from maize cell culture,” Theor Appl Genet 79: 625-631 (1990).
Suh et al., “Restoration of visual function in adult mice with an inherited retinal disease via adenine base editing,” Nat Biomed Eng, pp. 1-25 (2020).
Toriyama et al., “Transgenic rice plants after direct gene transfer into protoplasts,” Bio/Tech. 6:1072-1074 (1988).
Turpen et al., “Transfection of whole plants from wounds inoculated with Agrobacterium tumefaciens containing cDNA of tobacco mosaic virus,” J Virol Methods 42:227-239 (1993).
Vieira and Messing, “The pUC plasmids, an M13mp7-derived system for insertion mutagenesis and sequencing with synthetic universal primers,” Gene 19:(3) 259-268 (1982).
Wang et al., “Efficient targeted mutagenesis in potato by the CRISPR/Cas9 system,” Plant Cell Reports, 34:1473-1476 (2015).
Wang et al.,“Whisker-Mediated Plant Transformation: An Alternative Technology,” In Vitro Cellular & Developmental Biology—Plant, 31, 101-104 (1995).
Wang J, et al., “The rapidly advancing Class 2 CRISPR-Cas technologies: A customizable toolbox for molecular manipulations,” J Cell Mal Med. 24(6):3256-3270 (2020).
White et al., “A cassette containing the bar gene of Streptomyces hygroscopicus: a selectable marker for plant transformation,” Nucl Acids Res 18:1062 (1990).
Wright, “Commercial Hybrid Seed Production,” In Hybridization of Crop Plants 8:161-176 (1980).
Yang et al., “Production of kanamycin resistant rice tissues following DNA uptake into protoplasts,” Plant Cell Reports 7:421-425 (1988).
Yi et al., Transformation of multiple soybean cultivars by infecting cotyledonary-node with Agrobacterium tumefaciens, African Journal of Biotechnology 5(20):1989-1993 (2006).
Zhang et al., “Agrobacterium-mediated transformation of elite indica and japonica rice cultivars,” Molecular Biotechnology 8:223-231 (1997).
De Carvalho, D., et al., “UniProt Accession No. A0A0S1MIK1,” Aug. 12, 2020, 5 pages, Retrieved from the Internet: https://www.uniprot.org/uniprot/A0A0S1MIK1.
International Search Report and Written Opinion for International Application No. PCT/US2021/056877 dated Mar. 11, 2022, 17 pages.
Invitation to Pay Fees for International Application No. PCT/US2021/056877 dated Jan. 6, 2022, 3 pages.
NCBI Reference Sequence: XP_014501487.1 “TMV Resistance Protein N [*Vigna radiata* Var. *radiata*],” Oct. 12, 2017, 2 pages.
Sakai, H., et al., “The Power of Single Molecule Real-time Sequencing Technology in the De Novo Assembly of a Eukaryotic Genome,” Scientific Reports, Nov. 30, 2015, vol. 5, pp. 1-13.
Santos J.R.P., et al., “QTL Mapping and Transcriptome Analysis of Cowpea Reveals Candidate Genes for Root-Knot Nematode Resistance,” PloS One, Jan. 2018, vol. 13(1), e0189185, 22 pages.

* cited by examiner

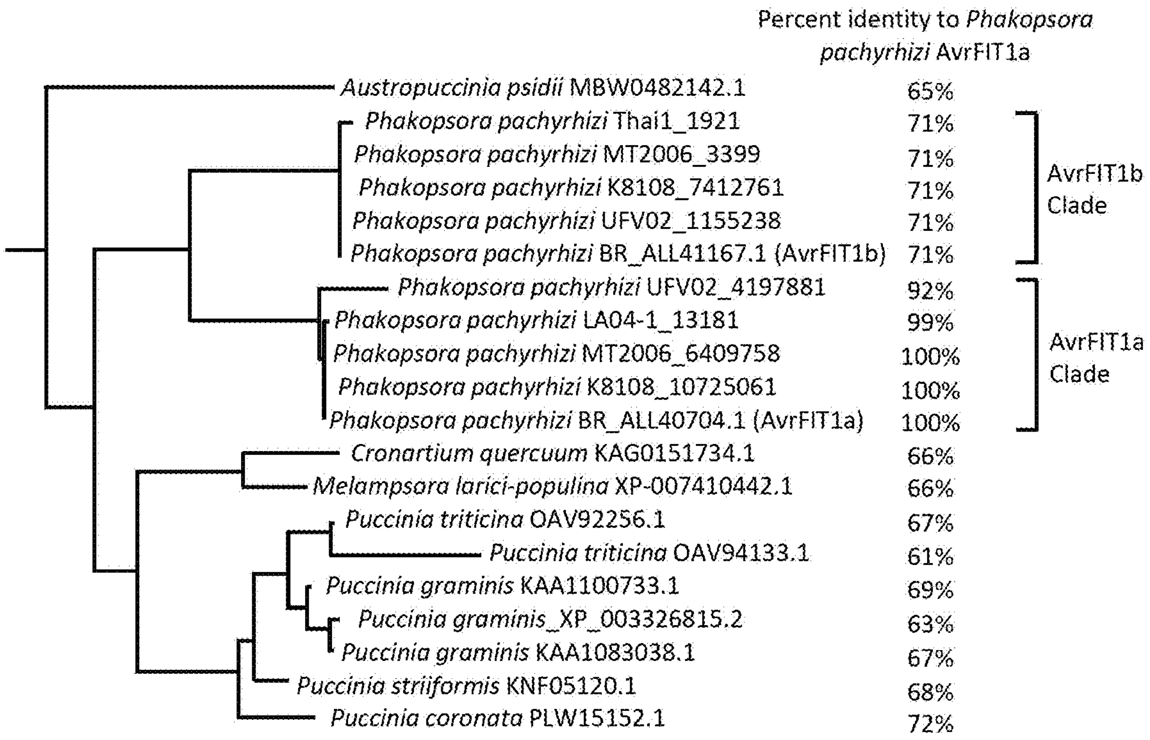

Figure 1

| | Percent identity to *Phakopsora pachyrhizi* AvrFIT1a | |
|---|---|---|
| *Austropuccinia psidii* MBW0482142.1 | 65% | |
| *Phakopsora pachyrhizi* Thai1_1921 | 71% | |
| *Phakopsora pachyrhizi* MT2006_3399 | 71% | |
| *Phakopsora pachyrhizi* K8108_7412761 | 71% | AvrFIT1b Clade |
| *Phakopsora pachyrhizi* UFV02_1155238 | 71% | |
| *Phakopsora pachyrhizi* BR_ALL41167.1 (AvrFIT1b) | 71% | |
| *Phakopsora pachyrhizi* UFV02_4197881 | 92% | |
| *Phakopsora pachyrhizi* LA04-1_13181 | 99% | |
| *Phakopsora pachyrhizi* MT2006_6409758 | 100% | AvrFIT1a Clade |
| *Phakopsora pachyrhizi* K8108_10725061 | 100% | |
| *Phakopsora pachyrhizi* BR_ALL40704.1 (AvrFIT1a) | 100% | |
| *Cronartium quercuum* KAG0151734.1 | 66% | |
| *Melampsora larici-populina* XP-007410442.1 | 66% | |
| *Puccinia triticina* OAV92256.1 | 67% | |
| *Puccinia triticina* OAV94133.1 | 61% | |
| *Puccinia graminis* KAA1100733.1 | 69% | |
| *Puccinia graminis*_XP_003326815.2 | 63% | |
| *Puccinia graminis* KAA1083038.1 | 67% | |
| *Puccinia striiformis* KNF05120.1 | 68% | |
| *Puccinia coronata* PLW15152.1 | 72% | |

Figure 2

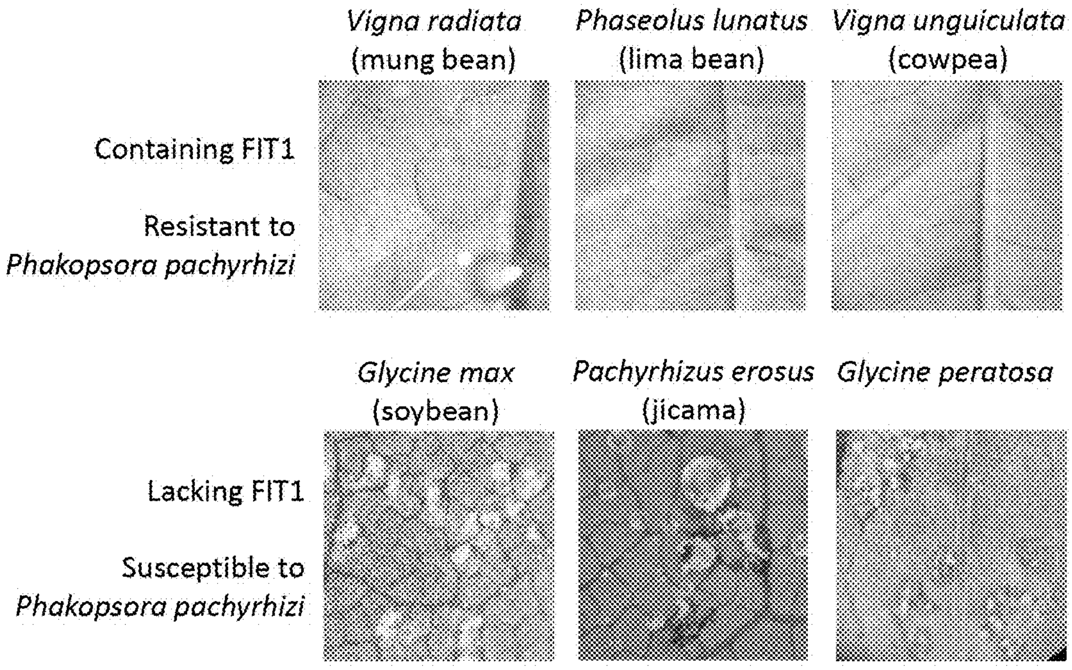

Figure 3A

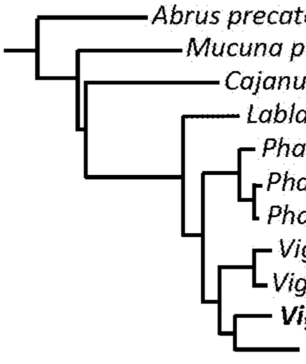

| | % identity to *Vu*FIT1 | Recognition activity AvrFIT1a | Recognition activity AvrFIT1b |
|---|---|---|---|
| *Abrus precatorius* XP_027357710.1 | 72% | Yes | No |
| *Mucuna pruriens* RDX66260.1 | 75% | nt | nt |
| *Cajanus cajan* XP_020211972.1 | 74% | nt | nt |
| *Lablab purpureus* c22535_g1_i3 | 85% | Yes | Yes |
| *Phaseolus lunatus* Pl05g0000042900.1 | 86% | Yes | Yes |
| *Phaseolus vulgaris* PvUI111.05g037200.1 | 86% | Yes | Yes |
| *Phaseolus acutifolius* 005G036500.1 | 86% | nt | nt |
| *Vigna radiata* XP_014501487.1 | 89% | Yes | Yes |
| *Vigna angularis* XP_017423114.1 | 90% | Yes | Yes |
| ***Vigna unguiculata* Vu01g041300.1 VuFIT1** | 100% | Yes | No |
| *Vigna unguiculata* Vu01g041400.1 | 89% | No | No |

Expressing FIT1

Wild type (lacking FIT1)

LRR domain

SEQUENCE LISTING

<160> NUMBER OF SEQ ID NOS: 34

<210> SEQ ID NO 1
<211> LENGTH: 3192
<212> TYPE: DNA
<213> ORGANISM: Vigna unguiculata

<400> SEQUENCE: 1

```
atggctgtgc catcattctc cttttccttc acctatgacg ttttcctgag cttcagagga     60

gaagacactc gttacggttt caccggaaat ctttacagag cccttcgtga cagaggaatt    120

cacaccttca tcgacgacga ggagcttcgc aaaggagacg aaatcacctc tgcacttgag    180

aaggcaatcg aaggttctag aattttcatc atcgttttct ctctcaacta cgcctcttcc    240

tctttttgct tgaacgagct cgcctacatc cttccccacg ctaagagaaa tgctttgctg    300

gttttgccac tcttctacga cgtcgttcct tcccacgtgc gacaccacac gggtagcttt    360

ggagaagcat tggatgctca tgaaaagagg ttcagaggta tgagtcaggg ttttgagctt    420

aacattgaga agctcaacaa atggaagatg gctctgcgtc gagcagctaa cttgtctggc    480

tatcatttca aacatgggga ggaatatgaa taccagttta tcgagaggat agttgaattg    540

gtctctaaga agattaaccg tgctccttta cacgttgggg attatccagt tggactagag    600

gcgcgggtgc tagaagtaaa gttgcttcta gaagtaggat ctgatgatgt tgtccacttg    660

gtagggatcc atggactcgg tggaatcggt aaaaccacac ttgctcttgc actctacaat    720

tccatcgctg accattttga aggtttgtgt ttcctcgaaa atgtgagaga gaattcaaac    780

aaacacggcc tacatcatct tcaaagaatc cttctttctc aagtgcttgg agaaaataat    840

atcaacataa ctagtgtgag acaaggaatt tcaatgatgc agcataggct acggcagaag    900

aagattctct tgattctaga tgatgttgac aagcacgaac agttacaggc aattgttgga    960

agacctgatt ggtttggtcc cggcagtaga gtcatcatca caaccaggga caaacagttg   1020

ttgtcgtgtc acttggttga aaaattatat aaagtgaaga agttggaaaa gaacaatgct   1080

cttcgactgc ttagttggaa aggttttaga acagaagaag ttgatacaag ttatttgaac   1140
```

-continued gtcatggatc gtgtactagc ttatgcttct ggacatccat tggctttgga agtaataggt 1200
tcgaagttgt ttagtaaaag tgtaaaagaa tgggaatctg ccatcaaaca gtacgagaaa 1260
attcctagca atcaaatcct tgaggtactt aaagtaagtt ttgatgcttt agaggaagta 1320
gagaagagtg tttttcttga cattgcttgt tgtttcaaag gatatgcatt gtcagagata 1380
gaagatattc ttcgtgctca ttatggtgat tgcatgaaat atcatattgg agtgttagtt 1440
gaaaaatctc tcatgaaata tggctataat tctgtagtta cgttgcatga cttgatagaa 1500
gacatgggga aagaaattgt ccgagagaaa tcaccaaaaa atccagggaa gcgcagtaga 1560
ttatggtcac cagaagatat aattcaagtt ttggaagaca attcgggaag tggagaaatt 1620
gaaatcatat gtttgaattc ctccttacct gacaaagaag aaatagtagg atggaacaga 1680
aaggccttca aaaagatgaa aaacctcaaa acacttatca ttaaaaaagg taaattttcg 1740
gaaggtccta aatatcttcc aaatagttta agagtacttg aatggttgaa atatccttca 1800
caagggctac caccagattt tcgttcaaag aaacttgcca tatgcaaatt accttcaagt 1860
agttttgggt cactcgaatt ggctgagttt tcaaagaagt tcatgaatat gactcttctg 1920
aattttgatg aatgtgaagg tttaacacat atacctgatg tgtctgggct gccaaattta 1980
gaaaaagttt cattcaagaa ttgtaagagt ttagttacaa tccatgactc cttcgggttc 2040
ctaggtaagc ttaactcctt gagtgctgtt ggttgcagca agcttaggag ttttcctccc 2100
ctcaaattga cttctctgga aaatcttgaa ctttcatatt gtcacagtct cgagagcttc 2160
ccagaaatat tagaaaaaat gggaaagata acagaacttg tcttggagga ttgtcacata 2220
aaagaattac cattttcatt tcataatctc accgagcttc aaacattaca gttgcgttgg 2280
tgtccaatat taaggttacc aagtagtatt gtcatgatgc caaaactggc ccagattatt 2340
gcttgggaat ctaaaggatg gctatttcca aaacaggttg atggggaaga aaaaggaagc 2400
tcaatggtgt cttcaaatgt agattgtctt gttctctcag ggtgcaaact ctcagatgac 2460
tttttcccag taattcctga atggttttct aatgtaaaag atttagacct gtcaaggaat 2520
aatttcacgg ttcttcctga atgcatcagc aattgtcatt ctttatgcaa gcttacttta 2580
gatagctgtc atagtcttca agagattcga gggattccac ctaacatacg acatttatca 2640
gcaagaaatt gtaaatcctt cacttcctct tgcagaagca ctttactgaa tcagaaactg 2700
catgaggctg ggaacaccat gttttggttg tcaggagcaa agtttccaga atggttcgat 2760
caccacggtc ggggaccatc ttgttctttc tgggttggca acaaattccc ttcaattgct 2820
ctttgtattg ctattggaca aactcatatc gaacaagttg aaatcgttgg acctatcatg 2880
atcatcaacg gcattgaatg ttcatttgat gaggaggagg atccttattt atatatgctc 2940
cctcatcaca cacatatttt cgatttgcaa catatagttt tttcagatta tctagacaga 3000
tatgtttcag aaaatgaatg gaaccatgtg gagatcacat actcagtgga gcagagattc 3060
aataaaaaag acaaacatgc ggtgacccca atctctatag aaaatggaat ctatgtgttg 3120
aaacagagga gcagcatgga ggatattcaa ttcactgatc cccacaaaaa gagaagatta 3180
gatgttgtct aa 3192

<210> SEQ ID NO 2
<211> LENGTH: 1063
<212> TYPE: PRT
<213> ORGANISM: Vigna unguiculata

<400> SEQUENCE: 2

-continued

```
Met Ala Val Pro Ser Phe Ser Phe Ser Phe Thr Tyr Asp Val Phe Leu
1               5                   10                  15

Ser Phe Arg Gly Glu Asp Thr Arg Tyr Gly Phe Thr Gly Asn Leu Tyr
            20                  25                  30

Arg Ala Leu Arg Asp Arg Gly Ile His Thr Phe Ile Asp Asp Glu Glu
        35                  40                  45

Leu Arg Lys Gly Asp Glu Ile Thr Ser Ala Leu Glu Lys Ala Ile Glu
    50                  55                  60

Gly Ser Arg Ile Phe Ile Ile Val Phe Ser Leu Asn Tyr Ala Ser Ser
65                  70                  75                  80

Ser Phe Cys Leu Asn Glu Leu Ala Tyr Ile Leu Pro His Ala Lys Arg
                85                  90                  95

Asn Ala Leu Leu Val Leu Pro Leu Phe Tyr Asp Val Val Pro Ser His
            100                 105                 110

Val Arg His His Thr Gly Ser Phe Gly Glu Ala Leu Asp Ala His Glu
        115                 120                 125

Lys Arg Phe Arg Gly Met Ser Gln Gly Phe Glu Leu Asn Ile Glu Lys
    130                 135                 140

Leu Asn Lys Trp Lys Met Ala Leu Arg Arg Ala Ala Asn Leu Ser Gly
145                 150                 155                 160

Tyr His Phe Lys His Gly Glu Glu Tyr Glu Tyr Gln Phe Ile Glu Arg
                165                 170                 175

Ile Val Glu Leu Val Ser Lys Lys Ile Asn Arg Ala Pro Leu His Val
            180                 185                 190

Gly Asp Tyr Pro Val Gly Leu Glu Ala Arg Val Leu Glu Val Lys Leu
        195                 200                 205

Leu Leu Glu Val Gly Ser Asp Asp Val Val His Leu Val Gly Ile His
    210                 215                 220

Gly Leu Gly Gly Ile Gly Lys Thr Thr Leu Ala Leu Ala Leu Tyr Asn
225                 230                 235                 240

Ser Ile Ala Asp His Phe Glu Gly Leu Cys Phe Leu Glu Asn Val Arg
                245                 250                 255

Glu Asn Ser Asn Lys His Gly Leu His His Leu Gln Arg Ile Leu Leu
            260                 265                 270

Ser Gln Val Leu Gly Glu Asn Asn Ile Asn Ile Thr Ser Val Arg Gln
        275                 280                 285

Gly Ile Ser Met Met Gln His Arg Leu Arg Gln Lys Lys Ile Leu Leu
    290                 295                 300

Ile Leu Asp Asp Val Asp Lys His Glu Gln Leu Gln Ala Ile Val Gly
305                 310                 315                 320

Arg Pro Asp Trp Phe Gly Pro Gly Ser Arg Val Ile Ile Thr Thr Arg
                325                 330                 335

Asp Lys Gln Leu Leu Ser Cys His Leu Val Glu Lys Leu Tyr Lys Val
            340                 345                 350

Lys Lys Leu Glu Lys Asn Asn Ala Leu Arg Leu Leu Ser Trp Lys Gly
        355                 360                 365

Phe Arg Thr Glu Glu Val Asp Thr Ser Tyr Leu Asn Val Met Asp Arg
    370                 375                 380

Val Leu Ala Tyr Ala Ser Gly His Pro Leu Ala Leu Glu Val Ile Gly
385                 390                 395                 400

Ser Lys Leu Phe Ser Lys Ser Val Lys Glu Trp Glu Ser Ala Ile Lys
                405                 410                 415

Gln Tyr Glu Lys Ile Pro Ser Asn Gln Ile Leu Glu Val Leu Lys Val
```

-continued

```
            420                 425                 430

Ser Phe Asp Ala Leu Glu Glu Val Glu Lys Ser Val Phe Leu Asp Ile
        435                 440                 445

Ala Cys Cys Phe Lys Gly Tyr Ala Leu Ser Glu Ile Glu Asp Ile Leu
    450                 455                 460

Arg Ala His Tyr Gly Asp Cys Met Lys Tyr His Ile Gly Val Leu Val
465                 470                 475                 480

Glu Lys Ser Leu Met Lys Tyr Gly Tyr Asn Ser Val Val Thr Leu His
                485                 490                 495

Asp Leu Ile Glu Asp Met Gly Lys Glu Ile Val Arg Glu Lys Ser Pro
            500                 505                 510

Lys Asn Pro Gly Lys Arg Ser Arg Leu Trp Ser Pro Glu Asp Ile Ile
        515                 520                 525

Gln Val Leu Glu Asp Asn Ser Gly Ser Gly Glu Ile Glu Ile Ile Cys
    530                 535                 540

Leu Asn Ser Ser Leu Pro Asp Lys Glu Glu Ile Val Gly Trp Asn Arg
545                 550                 555                 560

Lys Ala Phe Lys Lys Met Lys Asn Leu Lys Thr Leu Ile Ile Lys Lys
                565                 570                 575

Gly Lys Phe Ser Glu Gly Pro Lys Tyr Leu Pro Asn Ser Leu Arg Val
            580                 585                 590

Leu Glu Trp Leu Lys Tyr Pro Ser Gln Gly Leu Pro Pro Asp Phe Arg
        595                 600                 605

Ser Lys Lys Leu Ala Ile Cys Lys Leu Pro Ser Ser Ser Phe Gly Ser
    610                 615                 620

Leu Glu Leu Ala Glu Phe Ser Lys Lys Phe Met Asn Met Thr Leu Leu
625                 630                 635                 640

Asn Phe Asp Glu Cys Glu Gly Leu Thr His Ile Pro Asp Val Ser Gly
                645                 650                 655

Leu Pro Asn Leu Glu Lys Val Ser Phe Lys Asn Cys Lys Ser Leu Val
            660                 665                 670

Thr Ile His Asp Ser Phe Gly Phe Leu Gly Lys Leu Asn Ser Leu Ser
        675                 680                 685

Ala Val Gly Cys Ser Lys Leu Arg Ser Phe Pro Pro Leu Lys Leu Thr
    690                 695                 700

Ser Leu Glu Asn Leu Glu Leu Ser Tyr Cys His Ser Leu Glu Ser Phe
705                 710                 715                 720

Pro Glu Ile Leu Glu Lys Met Gly Lys Ile Thr Glu Leu Val Leu Glu
                725                 730                 735

Asp Cys His Ile Lys Glu Leu Pro Phe Ser Phe His Asn Leu Thr Glu
            740                 745                 750

Leu Gln Thr Leu Gln Leu Arg Trp Cys Pro Ile Leu Arg Leu Pro Ser
        755                 760                 765

Ser Ile Val Met Met Pro Lys Leu Ala Gln Ile Ile Ala Trp Glu Ser
    770                 775                 780

Lys Gly Trp Leu Phe Pro Lys Gln Val Asp Gly Glu Glu Lys Gly Ser
785                 790                 795                 800

Ser Met Val Ser Ser Asn Val Asp Cys Leu Val Leu Ser Gly Cys Lys
                805                 810                 815

Leu Ser Asp Asp Phe Phe Pro Val Ile Pro Glu Trp Phe Ser Asn Val
            820                 825                 830

Lys Asp Leu Asp Leu Ser Arg Asn Asn Phe Thr Val Leu Pro Glu Cys
        835                 840                 845
```

```
Ile Ser Asn Cys His Ser Leu Cys Lys Leu Thr Leu Asp Ser Cys His
    850                 855                 860

Ser Leu Gln Glu Ile Arg Gly Ile Pro Pro Asn Ile Arg His Leu Ser
865                 870                 875                 880

Ala Arg Asn Cys Lys Ser Phe Thr Ser Ser Cys Arg Ser Thr Leu Leu
                885                 890                 895

Asn Gln Lys Leu His Glu Ala Gly Asn Thr Met Phe Trp Leu Ser Gly
            900                 905                 910

Ala Lys Phe Pro Glu Trp Phe Asp His His Gly Arg Gly Pro Ser Cys
        915                 920                 925

Ser Phe Trp Val Gly Asn Lys Phe Pro Ser Ile Ala Leu Cys Ile Ala
    930                 935                 940

Ile Gly Gln Thr His Ile Glu Gln Val Glu Ile Val Gly Pro Ile Met
945                 950                 955                 960

Ile Ile Asn Gly Ile Glu Cys Ser Phe Asp Glu Glu Glu Asp Pro Tyr
                965                 970                 975

Leu Tyr Met Leu Pro His His Thr His Ile Phe Asp Leu Gln His Ile
            980                 985                 990

Val Phe Ser Asp Tyr Leu Asp Arg  Tyr Val Ser Glu Asn  Glu Trp Asn
        995                 1000                1005

His Val  Glu Ile Thr Tyr Ser  Val Glu Gln Arg Phe  Asn Lys Lys
    1010                1015                1020

Asp Lys  His Ala Val Thr Pro  Ile Ser Ile Glu Asn  Gly Ile Tyr
    1025                1030                1035

Val Leu  Lys Gln Arg Ser Ser  Met Glu Asp Ile Gln  Phe Thr Asp
    1040                1045                1050

Pro His  Lys Lys Arg Arg Leu  Asp Val Val
    1055                1060
```

<210> SEQ ID NO 3
<211> LENGTH: 3201
<212> TYPE: DNA
<213> ORGANISM: Vigna radiata

<400> SEQUENCE: 3

```
atggctgtgg catcattctc ttcttccttc acctatgacg tgttcctcag cttcagagga      60

gaagatactc gttacagttt caccggcaat ctctacagag cccttcgtga cagaggaatt     120

cacaccttca tcgacgacga gaagcttccc aaaggagacg aaatcacctc tgcacttgag     180

aaggcaatag aaggttccag aattttcatc atcgttttct ctcgcaacta cgcctcttcc     240

tccttttgct tgaacgagct cgcctacatt cttccctacg ctaatagaaa tggtttgctg     300

gttttgccac tcttctacga cgtcgttcct tcccacgtgc gccaccacat gggtagctat     360

ggagaagctt tggatactca tgaaaacagg ttcaaagcta cgagtcaggg ttttgagctt     420

aacatggaga agctcaacaa atggaagatg gctctgcgtg gaacagctaa cttatctggc     480

tatcatttca aacatgggga ggaatatgaa tacgagttta tcaagaggat agttgacttg     540

gtctccaaca agattaaccg tgctccttta cacgttgcgg attatccagt tggactagag     600

actcgagtgc tagaagtaaa gttgcttctg gatataggat ctgatgatgg tgtccacatg     660

gtagggatcc atggactcgg tggagttggt aaaaccacac ttgctcttgc agtttacaat     720

tccatcgctg accattttga aggcttgtgt ttcctcgaaa atgtgagaga gaattcaaac     780

aaacacggcc tacagcatct tcaaagaatc cttctttctc aaatggttgg agaaaataat     840
```

-continued

```
gtcaacataa ctagtgtgag acaaggaatt tcaatgatgc agcataggct acgacagaag    900
aagattctct tgattttaga tgacgttgac aaacatgaac agttacaagc tattgttgga    960
agacctgatt ggtttggtcc cggcagtaga gtcatcatca caactaggga caaacatttg   1020
ttgtcatgtc acttgatcga aaaattatat aaagtgaaga agttgaaaaa gaacaatgct   1080
catcgactgc ttagttggaa agcttttaga acagaagaag ttgatacaag ttatttgaat   1140
gtaatggatc gtgtactagc ttatgcttct ggccatccat tggctttgga agtaatcggt   1200
tcgaagttgt ttagaaaaag tgtaaaggaa tgggaatctg ccatcaaaca gtatgagaaa   1260
attcctaaca atcaaatcct ggaggtgctt aaaataagtt ttgatgcttt agaggaagta   1320
gagaagagtg tttttcttga catttcttgt tgctttaaag gatatgcatt gtcagaggtg   1380
gaagatatac ttcgtgctca ttatggtgat tgcatgaaat atcatattgg ggtgttggtt   1440
gaaaagtctc tcataaaata tggttggagt tgtgtggtta caatgcatga cttgatagaa   1500
gacatgggta aagaaattgt ccggcagaaa tctccaaata ggccagggaa gcgcagtaga   1560
ttatggtcac cagaagagat aattaaagtt ttggaagaca acttggggag tggagaaatt   1620
gaaatcatat gtttaaattc ctccttacct gacaaagaag aaatagtaga atggaacaga   1680
aaggccttca agaagatgaa aaacctcaaa acacttatca ttaaaaatgg taatttttcg   1740
gaaggtcctg aatatcttcc aaatagttta agagtactgg aatggttgaa atatccttca   1800
catgggctac cgccagattt tcgttcaaag aaactttcct tatgcaaatt accttcaagt   1860
tgttttgggt cactcgaatt ggctgagttt tcaaagaagt tcatgaatat gactcttctg   1920
aattttgacg aatgtgaagg tttaacacag atacctgatc tatctgggat gccaaattta   1980
gaaagatttt cattcaagaa ttgtaagagt ttaattacaa ttcatgactc cattggcttc   2040
ctaggtaagc ttaactcctt gaatgctgtt ggttgcagca agcttaggag ttttcccccc   2100
ctcaaattga cttctctgga aaatcttgaa ctttcatatt gttacagtct tgagagcttc   2160
ccagaaatat taggaaaaat gggacagata acagaacttg tcttggagga ctgtcacata   2220
aaagaattgc caatttcatt tcaaaatctc accgagcttc gaacattaca gttgcgttcg   2280
tgtccaacgt taaggttacc tagtagtatt gtcatgatgc caaaactggc caacattatt   2340
gcttgggaat ctaaagggtg gctatttcca aaacaggtcg agagggaaga gaaaataggc   2400
tcaatggtgt cttcaaacgt agattgtctt gttctctcag ggtgcaaact ctcggatgac   2460
tttttcccaa taattcttga atggtttgct aatgtaaaag atttaaacct atcaaggaat   2520
aacttcacgg ttcttcctga gtgcatcgcc aattgtcact tgttatgcaa gcttacttta   2580
gatgcctgtc atagtcttcg agagattaga gggattccac caaacatacg acagttacta   2640
gcaagaaatt gtaaatcctt cacttcttct tgcagaagaa ctttactgaa tcagaaactg   2700
catgaggctg gaaacaccat gttttcgttt tcaggagcaa ggtttccaga atggttcgat   2760
caccacagtc ggggagcatc ttgttctttc tgggttggca aaaaattccc ttccattgct   2820
ctttgtattg ctattggacc aactcatttg gaacaccttg aaattgttgg acctatcatg   2880
atcatcaact gcattgaatg ttcatttgat tgggaggaga atccttattt atatatgctc   2940
cctcatcaca catatatttt cgatttgcaa aatatagttt ttccagatta tctagacaga   3000
tttgtttcag aaaatgaatg gaaccacgtg gagattacat actcagtcaa gcagagattc   3060
aagggaaaag acaaacatga ggtgacccca atctctatag aaaatggaat ctatgtgttc   3120
aaacagaaga gcagcatgga ggatattcaa ttcactgatc cccacaaaaa gagaagatta   3180
gatgttgatc cagagttgta a                                             3201
```

<210> SEQ ID NO 4
<211> LENGTH: 1066
<212> TYPE: PRT
<213> ORGANISM: Vigna radiata

<400> SEQUENCE: 4

```
Met Ala Val Ala Ser Phe Ser Ser Ser Phe Thr Tyr Asp Val Phe Leu
1               5                   10                  15

Ser Phe Arg Gly Glu Asp Thr Arg Tyr Ser Phe Thr Gly Asn Leu Tyr
            20                  25                  30

Arg Ala Leu Arg Asp Arg Gly Ile His Thr Phe Ile Asp Asp Glu Lys
        35                  40                  45

Leu Pro Lys Gly Asp Glu Ile Thr Ser Ala Leu Glu Lys Ala Ile Glu
    50                  55                  60

Gly Ser Arg Ile Phe Ile Ile Val Phe Ser Arg Asn Tyr Ala Ser Ser
65                  70                  75                  80

Ser Phe Cys Leu Asn Glu Leu Ala Tyr Ile Leu Pro Tyr Ala Asn Arg
                85                  90                  95

Asn Gly Leu Leu Val Leu Pro Leu Phe Tyr Asp Val Val Pro Ser His
            100                 105                 110

Val Arg His His Met Gly Ser Tyr Gly Glu Ala Leu Asp Thr His Glu
        115                 120                 125

Asn Arg Phe Lys Ala Thr Ser Gln Gly Phe Glu Leu Asn Met Glu Lys
    130                 135                 140

Leu Asn Lys Trp Lys Met Ala Leu Arg Gly Thr Ala Asn Leu Ser Gly
145                 150                 155                 160

Tyr His Phe Lys His Gly Glu Glu Tyr Glu Tyr Glu Phe Ile Lys Arg
                165                 170                 175

Ile Val Asp Leu Val Ser Asn Lys Ile Asn Arg Ala Pro Leu His Val
            180                 185                 190

Ala Asp Tyr Pro Val Gly Leu Glu Thr Arg Val Leu Glu Val Lys Leu
        195                 200                 205

Leu Leu Asp Ile Gly Ser Asp Asp Gly Val His Met Val Gly Ile His
    210                 215                 220

Gly Leu Gly Gly Val Gly Lys Thr Thr Leu Ala Leu Ala Val Tyr Asn
225                 230                 235                 240

Ser Ile Ala Asp His Phe Glu Gly Leu Cys Phe Leu Glu Asn Val Arg
                245                 250                 255

Glu Asn Ser Asn Lys His Gly Leu Gln His Leu Gln Arg Ile Leu Leu
            260                 265                 270

Ser Gln Met Val Gly Glu Asn Asn Val Asn Ile Thr Ser Val Arg Gln
        275                 280                 285

Gly Ile Ser Met Met Gln His Arg Leu Arg Gln Lys Lys Ile Leu Leu
    290                 295                 300

Ile Leu Asp Asp Val Asp Lys His Glu Gln Leu Gln Ala Ile Val Gly
305                 310                 315                 320

Arg Pro Asp Trp Phe Gly Pro Gly Ser Arg Val Ile Ile Thr Thr Arg
                325                 330                 335

Asp Lys His Leu Leu Ser Cys His Leu Ile Glu Lys Leu Tyr Lys Val
            340                 345                 350

Lys Lys Leu Lys Lys Asn Asn Ala His Arg Leu Leu Ser Trp Lys Ala
        355                 360                 365

Phe Arg Thr Glu Glu Val Asp Thr Ser Tyr Leu Asn Val Met Asp Arg
```

```
    370                 375                 380

Val Leu Ala Tyr Ala Ser Gly His Pro Leu Ala Leu Glu Val Ile Gly
385                 390                 395                 400

Ser Lys Leu Phe Arg Lys Ser Val Lys Glu Trp Glu Ser Ala Ile Lys
                405                 410                 415

Gln Tyr Glu Lys Ile Pro Asn Asn Gln Ile Leu Glu Val Leu Lys Ile
            420                 425                 430

Ser Phe Asp Ala Leu Glu Glu Val Glu Lys Ser Val Phe Leu Asp Ile
        435                 440                 445

Ser Cys Cys Phe Lys Gly Tyr Ala Leu Ser Glu Val Glu Asp Ile Leu
    450                 455                 460

Arg Ala His Tyr Gly Asp Cys Met Lys Tyr His Ile Gly Val Leu Val
465                 470                 475                 480

Glu Lys Ser Leu Ile Lys Tyr Gly Trp Ser Cys Val Val Thr Met His
                485                 490                 495

Asp Leu Ile Glu Asp Met Gly Lys Glu Ile Val Arg Gln Lys Ser Pro
            500                 505                 510

Asn Arg Pro Gly Lys Arg Ser Arg Leu Trp Ser Pro Glu Glu Ile Ile
        515                 520                 525

Lys Val Leu Glu Asp Asn Leu Gly Ser Gly Glu Ile Glu Ile Ile Cys
    530                 535                 540

Leu Asn Ser Ser Leu Pro Asp Lys Glu Glu Ile Val Glu Trp Asn Arg
545                 550                 555                 560

Lys Ala Phe Lys Lys Met Lys Asn Leu Lys Thr Leu Ile Ile Lys Asn
                565                 570                 575

Gly Asn Phe Ser Glu Gly Pro Glu Tyr Leu Pro Asn Ser Leu Arg Val
            580                 585                 590

Leu Glu Trp Leu Lys Tyr Pro Ser His Gly Leu Pro Pro Asp Phe Arg
        595                 600                 605

Ser Lys Lys Leu Ser Leu Cys Lys Leu Pro Ser Ser Cys Phe Gly Ser
    610                 615                 620

Leu Glu Leu Ala Glu Phe Ser Lys Lys Phe Met Asn Met Thr Leu Leu
625                 630                 635                 640

Asn Phe Asp Glu Cys Glu Gly Leu Thr Gln Ile Pro Asp Leu Ser Gly
                645                 650                 655

Met Pro Asn Leu Glu Arg Phe Ser Phe Lys Asn Cys Lys Ser Leu Ile
            660                 665                 670

Thr Ile His Asp Ser Ile Gly Phe Leu Gly Lys Leu Asn Ser Leu Asn
        675                 680                 685

Ala Val Gly Cys Ser Lys Leu Arg Ser Phe Pro Pro Leu Lys Leu Thr
    690                 695                 700

Ser Leu Glu Asn Leu Glu Leu Ser Tyr Cys Tyr Ser Leu Glu Ser Phe
705                 710                 715                 720

Pro Glu Ile Leu Gly Lys Met Gly Gln Ile Thr Glu Leu Val Leu Glu
                725                 730                 735

Asp Cys His Ile Lys Glu Leu Pro Ile Ser Phe Gln Asn Leu Thr Glu
            740                 745                 750

Leu Arg Thr Leu Gln Leu Arg Ser Cys Pro Thr Leu Arg Leu Pro Ser
        755                 760                 765

Ser Ile Val Met Met Pro Lys Leu Ala Asn Ile Ile Ala Trp Glu Ser
    770                 775                 780

Lys Gly Trp Leu Phe Pro Lys Gln Val Glu Arg Glu Glu Lys Ile Gly
785                 790                 795                 800
```

```
Ser Met Val Ser Ser Asn Val Asp Cys Leu Val Leu Ser Gly Cys Lys
                805                 810                 815

Leu Ser Asp Asp Phe Phe Pro Ile Ile Leu Glu Trp Phe Ala Asn Val
            820                 825                 830

Lys Asp Leu Asn Leu Ser Arg Asn Asn Phe Thr Val Leu Pro Glu Cys
        835                 840                 845

Ile Ala Asn Cys His Leu Leu Cys Lys Leu Thr Leu Asp Ala Cys His
    850                 855                 860

Ser Leu Arg Glu Ile Arg Gly Ile Pro Pro Asn Ile Arg Gln Leu Leu
865                 870                 875                 880

Ala Arg Asn Cys Lys Ser Phe Thr Ser Ser Cys Arg Arg Thr Leu Leu
                885                 890                 895

Asn Gln Lys Leu His Glu Ala Gly Asn Thr Met Phe Ser Phe Ser Gly
            900                 905                 910

Ala Arg Phe Pro Glu Trp Phe Asp His His Ser Arg Gly Ala Ser Cys
        915                 920                 925

Ser Phe Trp Val Gly Lys Lys Phe Pro Ser Ile Ala Leu Cys Ile Ala
    930                 935                 940

Ile Gly Pro Thr His Leu Glu His Leu Glu Ile Val Gly Pro Ile Met
945                 950                 955                 960

Ile Ile Asn Cys Ile Glu Cys Ser Phe Asp Trp Glu Glu Asn Pro Tyr
                965                 970                 975

Leu Tyr Met Leu Pro His His Thr Tyr Ile Phe Asp Leu Gln Asn Ile
            980                 985                 990

Val Phe Pro Asp Tyr Leu Asp Arg  Phe Val Ser Glu Asn  Glu Trp Asn
        995                 1000                1005

His Val  Glu Ile Thr Tyr Ser  Val Lys Gln Arg Phe  Lys Gly Lys
    1010                1015                1020

Asp Lys  His Glu Val Thr Pro  Ile Ser Ile Glu Asn  Gly Ile Tyr
    1025                1030                1035

Val Phe  Lys Gln Lys Ser Ser  Met Glu Asp Ile Gln  Phe Thr Asp
    1040                1045                1050

Pro His  Lys Lys Arg Arg Leu  Asp Val Asp Pro Glu  Leu
    1055                1060                1065
```

<210> SEQ ID NO 5
<211> LENGTH: 3195
<212> TYPE: DNA
<213> ORGANISM: Phaseolus lunatus

<400> SEQUENCE: 5

```
atgtctgtgt catcattctc ctcttccttc acctatgacg tcttcctcag cttcagagga     60

gaagacactc gttacggttt caccggaaat ctctattcag cccttcgtga cggcggaatt    120

tgcaccttca tcgatgacga ggagctcccc aaaggagacg aaatcaccac tgcacttgag    180

aaggctatcg aaggttccag aattttcatc atcgttttct ctcacaacta cgcatcttct    240

tccttttgct tgaatgagct cgcctacatt cttccctacg ctaagagaaa tggtttgctg    300

gttttgccac tcttctacga cgtcgttcct tcccacgtgc gaaaccacac gggtaccttt    360

ggagaagcgt tagatactca tgaaaacagg ttcaaagcta cgagtgaggg ttttgagctt    420

aacatggaga agctcaacag atggaagatg gctctgcgtg gagctgctaa cttatctggc    480

tatcatttca aacatgggga ggaatatgaa taccagttta tcaagaggat agtggaattg    540

gtctctaaca agattaaccg tgctccttta catgttgcgg attatccagt tggactagag    600
```

-continued

```
acacgagtgc tagaagtaaa attgcttcta gatgtaggat ctgatgatgg tgtccacatg    660
gtagggatcc atggattcgg tggagttggt aaaaccacac ttgctcttgc agtttacaat    720
tccatagctg acaattttga aggcttgtgt ttccttgaaa atgtcagaga gaattcaaac    780
aaacacggcc tacaacatct tcagagtctc cttctttctc aaatggttgg agaaaataat    840
atcaacataa ctagtgtgaa acaaggaatt tcaatgatgc agcatagact acggcagaag    900
aagattcttt tgattcttga tgatgttgac aagcatgaac agttacaagc aattgttgga    960
agagctgatt ggtttggtcc cggcagtaga gtgatcatca caactaggga caaacatttg   1020
ttgtcatgtc agttggttga aaaaatatat gaagtgaaga agttgaaaaa gaaagatgct   1080
cttcgactgc ttagttggaa aggttttaaa acagaagaag ttcatccaag ttatgtgaat   1140
gtcatggatc gtgtactggc ttatgcttct ggccatccat tggctttgga agtaataggt   1200
tcgaagttgt ttagaaaaag tgtaaaagaa tgggaatctg ccatccacca gtatgagaaa   1260
attcctaaca atcaaattct ggagatgctt aaaataagtt ttgattcttt agaggaagta   1320
gagaagagtg tttttcttga cattgcttgt tgtttcaaag gatatgcgtt gtcagaggtg   1380
gaaaatatac ttcgtgctca ttatggtgat tgcatgaaat atcatattgg ggtgttggtt   1440
gaaaaatctc tcataaaata tggatggaat tctgtagtta cattgcatga cttgatagaa   1500
gacatgggta aagaaattgt ccgacagaaa tcaccaaata agccagggaa gcgcagtaga   1560
ttatggtcac cagaagatat aattcaagtt ttggaagaca actcgggaag tggagaaatt   1620
gaaatcatat gtttgaatta ctctttacct gacaaagcag aaatagtaga atggaacaga   1680
aaggccttca agaagatgaa aaacctcaaa acacttatca ttaaaagtgg taaattttcg   1740
gaaggtccta agtatcttcc aaacagttta agagtaatgg aatggttaaa atatccttca   1800
caagggctac cgccagattt tcgttcaaag gaacttgcca tatgcaaatt acctgcaagt   1860
tgttttgggt ctctcgaatt ggccgagtta tcaaagaagt tcaagaatat gacccttttg   1920
aattttgacg aatgtgaagg tttaacacag atacctgatg tatctgggct gccaaattta   1980
gtagaaattt cattcaagaa ttgtaagagt ttaattacaa tccatgactc cattgggttc   2040
ctaggtaagc ttatctcctt gaatgctgtt ggttgcagca agcttaggag tttccccccc   2100
ctcaaattga cttctctgga aaatcttgaa ctttcatatt gttacagtct tgagagcttc   2160
ccagaaatat tgggaaaaat gggaaagata acagaacttt tgttggagtg ctgtgacata   2220
aaagaattgc cattttcatt tcaaaatctc actgagcttc aaacattaca gttgcgttac   2280
tgtccaatgt tgaggttgcc aagtagtatt gtcatgatgc caaaactgac cgagattatt   2340
gcttgggaat ctaaaggatg gctatttcca aaacaggttg agggtgaaga gaaagtaagc   2400
tcaatggtgt cttcaaatgt agattgtctt cttctcccag ggtgcaaact ctcggatgat   2460
tttttcccaa taacatggtt tgctaatgta aaagagttag acctgtcaag gaatactttc   2520
acggttcttc ctgaatgcat cagcaattgt catttttat gtaagcttat tttagataac   2580
tgtcagagtc ttcgagagat tagagggatt ccgccaaacg tacgacattt atcagcaaga   2640
tattgtaaat ccttcacttc ttcttgcaga agcactttac tgaatcagaa actgcatgag   2700
gcgggaaaca ccatgttttg gttttcagga gcaagttttc cagaatggtt cgagcaccac   2760
agtcggggac catcttgttc tttctgggtt gacaagaaat tccctgccat tgctctttgt   2820
attgttattg gaccaactca tttggaacat actgagattg ttggacctat cataatcatc   2880
aatggcgttg attgttcact tgttgatgag ttggataatc cttatttacg gatactccct   2940
```

-continued

```
catcacacat atcttttcga tttgcaacat atagtttctt cagattatct agacagattt   3000

gtttcagaaa aggaatggaa tcacgtggag attagatact cagtagagca gagattcagt   3060

gaagaagaca aacatgtggt gataccagtc tccgtagaaa atggaatcta tgtgttcaaa   3120

cagaggagca gcatggagga tattcaattc actgatcccc acaaaaagag aagattagat   3180

gttgatccag agtag                                                    3195


<210> SEQ ID NO 6
<211> LENGTH: 1064
<212> TYPE: PRT
<213> ORGANISM: Phaseolus lunatus

<400> SEQUENCE: 6

Met Ser Val Ser Ser Phe Ser Ser Ser Phe Thr Tyr Asp Val Phe Leu
1               5                   10                  15

Ser Phe Arg Gly Glu Asp Thr Arg Tyr Gly Phe Thr Gly Asn Leu Tyr
            20                  25                  30

Ser Ala Leu Arg Asp Gly Gly Ile Cys Thr Phe Ile Asp Asp Glu Glu
        35                  40                  45

Leu Pro Lys Gly Asp Glu Ile Thr Thr Ala Leu Glu Lys Ala Ile Glu
    50                  55                  60

Gly Ser Arg Ile Phe Ile Ile Val Phe Ser His Asn Tyr Ala Ser Ser
65                  70                  75                  80

Ser Phe Cys Leu Asn Glu Leu Ala Tyr Ile Leu Pro Tyr Ala Lys Arg
                85                  90                  95

Asn Gly Leu Leu Val Leu Pro Leu Phe Tyr Asp Val Val Pro Ser His
            100                 105                 110

Val Arg Asn His Thr Gly Thr Phe Gly Glu Ala Leu Asp Thr His Glu
        115                 120                 125

Asn Arg Phe Lys Ala Thr Ser Glu Gly Phe Glu Leu Asn Met Glu Lys
    130                 135                 140

Leu Asn Arg Trp Lys Met Ala Leu Arg Gly Ala Ala Asn Leu Ser Gly
145                 150                 155                 160

Tyr His Phe Lys His Gly Glu Glu Tyr Glu Tyr Gln Phe Ile Lys Arg
                165                 170                 175

Ile Val Glu Leu Val Ser Asn Lys Ile Asn Arg Ala Pro Leu His Val
            180                 185                 190

Ala Asp Tyr Pro Val Gly Leu Glu Thr Arg Val Leu Glu Val Lys Leu
        195                 200                 205

Leu Leu Asp Val Gly Ser Asp Asp Gly Val His Met Val Gly Ile His
    210                 215                 220

Gly Phe Gly Gly Val Gly Lys Thr Thr Leu Ala Leu Ala Val Tyr Asn
225                 230                 235                 240

Ser Ile Ala Asp Asn Phe Glu Gly Leu Cys Phe Leu Glu Asn Val Arg
                245                 250                 255

Glu Asn Ser Asn Lys His Gly Leu Gln His Leu Gln Ser Leu Leu Leu
            260                 265                 270

Ser Gln Met Val Gly Glu Asn Asn Ile Asn Ile Thr Ser Val Lys Gln
        275                 280                 285

Gly Ile Ser Met Met Gln His Arg Leu Arg Gln Lys Lys Ile Leu Leu
    290                 295                 300

Ile Leu Asp Asp Val Asp Lys His Glu Gln Leu Gln Ala Ile Val Gly
305                 310                 315                 320

Arg Ala Asp Trp Phe Gly Pro Gly Ser Arg Val Ile Ile Thr Thr Arg
```

-continued

```
                325                 330                 335

Asp Lys His Leu Leu Ser Cys Gln Leu Val Glu Lys Ile Tyr Glu Val
            340                 345                 350

Lys Lys Leu Lys Lys Lys Asp Ala Leu Arg Leu Leu Ser Trp Lys Gly
        355                 360                 365

Phe Lys Thr Glu Glu Val His Pro Ser Tyr Val Asn Val Met Asp Arg
    370                 375                 380

Val Leu Ala Tyr Ala Ser Gly His Pro Leu Ala Leu Glu Val Ile Gly
385                 390                 395                 400

Ser Lys Leu Phe Arg Lys Ser Val Lys Glu Trp Glu Ser Ala Ile His
                405                 410                 415

Gln Tyr Glu Lys Ile Pro Asn Asn Gln Ile Leu Glu Met Leu Lys Ile
            420                 425                 430

Ser Phe Asp Ser Leu Glu Glu Val Glu Lys Ser Val Phe Leu Asp Ile
        435                 440                 445

Ala Cys Cys Phe Lys Gly Tyr Ala Leu Ser Glu Val Glu Asn Ile Leu
    450                 455                 460

Arg Ala His Tyr Gly Asp Cys Met Lys Tyr His Ile Gly Val Leu Val
465                 470                 475                 480

Glu Lys Ser Leu Ile Lys Tyr Gly Trp Asn Ser Val Val Thr Leu His
                485                 490                 495

Asp Leu Ile Glu Asp Met Gly Lys Glu Ile Val Arg Gln Lys Ser Pro
            500                 505                 510

Asn Lys Pro Gly Lys Arg Ser Arg Leu Trp Ser Pro Glu Asp Ile Ile
        515                 520                 525

Gln Val Leu Glu Asp Asn Ser Gly Ser Gly Glu Ile Glu Ile Ile Cys
    530                 535                 540

Leu Asn Tyr Ser Leu Pro Asp Lys Ala Glu Ile Val Glu Trp Asn Arg
545                 550                 555                 560

Lys Ala Phe Lys Lys Met Lys Asn Leu Lys Thr Leu Ile Ile Lys Ser
                565                 570                 575

Gly Lys Phe Ser Glu Gly Pro Lys Tyr Leu Pro Asn Ser Leu Arg Val
            580                 585                 590

Met Glu Trp Leu Lys Tyr Pro Ser Gln Gly Leu Pro Pro Asp Phe Arg
        595                 600                 605

Ser Lys Glu Leu Ala Ile Cys Lys Leu Pro Ala Ser Cys Phe Gly Ser
    610                 615                 620

Leu Glu Leu Ala Glu Leu Ser Lys Lys Phe Lys Asn Met Thr Leu Leu
625                 630                 635                 640

Asn Phe Asp Glu Cys Glu Gly Leu Thr Gln Ile Pro Asp Val Ser Gly
                645                 650                 655

Leu Pro Asn Leu Val Glu Ile Ser Phe Lys Asn Cys Lys Ser Leu Ile
            660                 665                 670

Thr Ile His Asp Ser Ile Gly Phe Leu Gly Lys Leu Ile Ser Leu Asn
        675                 680                 685

Ala Val Gly Cys Ser Lys Leu Arg Ser Phe Pro Pro Leu Lys Leu Thr
    690                 695                 700

Ser Leu Glu Asn Leu Glu Leu Ser Tyr Cys Tyr Ser Leu Glu Ser Phe
705                 710                 715                 720

Pro Glu Ile Leu Gly Lys Met Gly Lys Ile Thr Glu Leu Leu Leu Glu
                725                 730                 735

Cys Cys Asp Ile Lys Glu Leu Pro Phe Ser Phe Gln Asn Leu Thr Glu
            740                 745                 750
```

-continued

```
Leu Gln Thr Leu Gln Leu Arg Tyr Cys Pro Met Leu Arg Leu Pro Ser
        755                 760                 765

Ser Ile Val Met Met Pro Lys Leu Thr Glu Ile Ile Ala Trp Glu Ser
    770                 775                 780

Lys Gly Trp Leu Phe Pro Lys Gln Val Glu Gly Glu Glu Lys Val Ser
785                 790                 795                 800

Ser Met Val Ser Ser Asn Val Asp Cys Leu Leu Leu Pro Gly Cys Lys
                805                 810                 815

Leu Ser Asp Asp Phe Phe Pro Ile Thr Trp Phe Ala Asn Val Lys Glu
            820                 825                 830

Leu Asp Leu Ser Arg Asn Thr Phe Thr Val Leu Pro Glu Cys Ile Ser
        835                 840                 845

Asn Cys His Phe Leu Cys Lys Leu Ile Leu Asp Asn Cys Gln Ser Leu
    850                 855                 860

Arg Glu Ile Arg Gly Ile Pro Pro Asn Val Arg His Leu Ser Ala Arg
865                 870                 875                 880

Tyr Cys Lys Ser Phe Thr Ser Ser Cys Arg Ser Thr Leu Leu Asn Gln
                885                 890                 895

Lys Leu His Glu Ala Gly Asn Thr Met Phe Trp Phe Ser Gly Ala Ser
            900                 905                 910

Phe Pro Glu Trp Phe Glu His His Ser Arg Gly Pro Ser Cys Ser Phe
        915                 920                 925

Trp Val Asp Lys Lys Phe Pro Ala Ile Ala Leu Cys Ile Val Ile Gly
    930                 935                 940

Pro Thr His Leu Glu His Thr Glu Ile Val Gly Pro Ile Ile Ile Ile
945                 950                 955                 960

Asn Gly Val Asp Cys Ser Leu Val Asp Glu Leu Asp Asn Pro Tyr Leu
                965                 970                 975

Arg Ile Leu Pro His His Thr Tyr Leu Phe Asp Leu Gln His Ile Val
            980                 985                 990

Ser Ser Asp Tyr Leu Asp Arg Phe  Val Ser Glu Lys Glu  Trp Asn His
        995                 1000                1005

Val Glu  Ile Arg Tyr Ser Val  Glu Gln Arg Phe Ser  Glu Glu Asp
    1010                1015                1020

Lys His  Val Val Ile Pro Val  Ser Val Glu Asn Gly  Ile Tyr Val
    1025                1030                1035

Phe Lys  Gln Arg Ser Ser Met  Glu Asp Ile Gln Phe  Thr Asp Pro
    1040                1045                1050

His Lys  Lys Arg Arg Leu Asp  Val Asp Pro Glu
    1055                1060
```

<210> SEQ ID NO 7
<211> LENGTH: 3195
<212> TYPE: DNA
<213> ORGANISM: Phaseolus vulgaris

<400> SEQUENCE: 7

```
atggctgtgc catcattctc ctcttccttc acctacgacg tcttcctcag cttcagagga      60

gaagatactc gttacggttt caccggcaat ctctatacag cccttcatga cagcggaatt     120

tgcaccttca tcgacgacga ggagctcccc aaaggagacg aaatcaccac ctcactacag     180

aaggcaatcg aagcttccag aattttcatc atcgttttct ctcacaacta cgcatcttct     240

tccttttgct tgaacgagct cgcctacatt cttccctacg ctaagagaaa tggtttgctg     300
```

-continued

```
gttttgccac tcttctacga cgtcgttcct tcccacgtgc gacaccacac gggtaccttt    360
ggagaagcgt tagatactca tgaaaacaag ttcaaaggta cgagtgaggg ttttgagctt    420
aacatggaga agctcaacag atggaaaatg gctctgcgtg gagctgctaa cttatctggc    480
tatcatttca aacatgggga ggaatatgaa taccagttta tcaagaggat agtgaaattg    540
gtctctaaca agattaaccg tgctacttta catgttgcgg attatccagt tggactagag    600
acacgaatgc tagaagtaaa gttgcttcta gatgtaggat ctgatgatgg tgtccacatg    660
gtagggatcc atggattcgg tggagttggt aaaaccacac ttgctcttgc agtttacaac    720
tccatagctg acaatttgga aggcttgtgt ttccttgaaa atgtgagaga gaattcaaac    780
aaacacggcc tacaacatct tcagagcctc cttctttctc aaatggttgg agaaaataat    840
atcaacataa ctagtgtgaa acaagggatt tcaatgatgc agcataggct acggcagaag    900
aagattcttt tgattcttga tgatgttgac aagcatgaac agttacaagc aattgttgga    960
agagctgatt ggtttggtcc cggcagtaga gtcatcatca caactaggga caaacatttg   1020
ttgtcatgtc agttggttga aaaaatatat gaagtgaaga agttgaaaaa gaaagatgct   1080
cttcgactgc ttagttggaa aggttttaaa acagaagaag ttcatccaag ttatgtgaat   1140
gtcatgggtc gtgtactggc ttatgcttct ggccatccat tggctttgga agtaataggt   1200
tcgaagttgt ttagaaaaag tgtaaaagaa tgggaatctg ccatccagca gtatgagaaa   1260
attcctaaca atcaaatcct ggagatactt aaaataagtt ttgattcatt agaggaagta   1320
gagaagagtg tttttcttga cattgcttgt tgtttcaaag gatatgcatt gtcagaggtg   1380
gaaaatatac ttcgtgctca ttatggtgat tgcatgaaat atcatattgg agtgttggtt   1440
gaaaaatctc tcataaaata tagatggaat tctgtagtta cactgcatga cttgatagaa   1500
gacatgggta aagaaattgt ccgacagaaa tcaccaaata aaccggggaa gcgcagtaga   1560
ttatggtcac cagaagatat aattcaagtt ttggaagaca actcgggaag tggagaaatt   1620
gaaatcatat gtttgaatta ctctttacct ggcaaagaag aaatagtaga atggaacaga   1680
aaggccttca agaagatgaa aaacctcaaa acacttatta ttaaaagtgg taatttttcg   1740
gaaggtccta aatatcttcc aaacagttta agagtaatgg aatggttaaa atatccttca   1800
caagggctac cgccagattt tcgttcaaag gaacttacca tatgcaaatt acctgcaagt   1860
tgttttgggt ccctcgaatt ggccgagtta tcaaagaagt tcatgaatat gacccttttg   1920
aattttgacg aatgtgaagg tttaacacag atacctgatg tatctgggct gccaaattta   1980
gtagaaattt cattcaagaa ttgtaagagt ttaattacaa tccatgactc cattgggttc   2040
ctaggtaagc ttaactcctt gaatgctgtt ggttgcagca agcttaggag ttttccaccc   2100
ctcaaattga cttctctgga aaatcttgaa ctttcatatt gttacagtct tgagagcttc   2160
ccagaaatat taggaaaaat gggaaagata acagaacttt tcttggagtg ctgtgacata   2220
aaagaattgc cattttcatt tcaaaatctc actgagcttc aaacattaca gttgcgttac   2280
tgtccaatgt taaggttgcc aagtagtatt gtcatgatgc caaaactgac cgagattatt   2340
gcttgggaat ctgaaggatg gctatttcca aaacaggttg agggtgaaga gaaagtaagc   2400
tcaatggtgt cttcaaatgt agattgtctt cttctcccag ggtgcaaact ctcagatgat   2460
tttttcccaa taacatggtt tgctaatgta aaagagttag acctgtcaag gaatactttc   2520
acggttcttc ctgaatgcat aagcaattgt tattttttat gtaagcttat tttagataac   2580
tgtcatagtc ttcgagagat tagagggatt ccgccaaaca tacgacattt atcagcaaga   2640
tattgtaaat ccttcacttc ttcttgcaga agcactttac tgaatcagaa actgcatgag   2700
```

-continued

```
acgggaaaca ccatgttttg gttttcagga gcaagttttc cagaatggtt cgagcaccgc   2760

agtcagggac catcttgttc tttctgggtt ggcaacaaat tccctgccat tgctctttgt   2820

attgttattg gaccaactca tttggaccat attgagattg ttggacctat catgatcatc   2880

aatggcattg attgttcact tgatgatggg ttggttaatc cttatttatg gatacccccct   2940

catcacacat atcttttcga tttgcaacat atagtttctt cagattatct tgacagattt   3000

gtttcagaaa aggaatggaa tcacgtggag attagatact cagtcaagca gagattcagt   3060

gaaaaagaca aacatgtggt gataccagtc tctatagaaa atggaatcta tgtgttcaaa   3120

cagaggagca gcatggagga tattcaattc actgatcccc acaaaaagag aagattagat   3180

gttgatccag agtag                                                    3195
```

```
<210> SEQ ID NO 8
<211> LENGTH: 1064
<212> TYPE: PRT
<213> ORGANISM: Phaseolus vulgaris

<400> SEQUENCE: 8

Met Ala Val Pro Ser Phe Ser Ser Ser Phe Thr Tyr Asp Val Phe Leu
1               5                   10                  15

Ser Phe Arg Gly Glu Asp Thr Arg Tyr Gly Phe Thr Gly Asn Leu Tyr
            20                  25                  30

Thr Ala Leu His Asp Ser Gly Ile Cys Thr Phe Ile Asp Asp Glu Glu
        35                  40                  45

Leu Pro Lys Gly Asp Glu Ile Thr Thr Ser Leu Gln Lys Ala Ile Glu
    50                  55                  60

Ala Ser Arg Ile Phe Ile Ile Val Phe Ser His Asn Tyr Ala Ser Ser
65                  70                  75                  80

Ser Phe Cys Leu Asn Glu Leu Ala Tyr Ile Leu Pro Tyr Ala Lys Arg
                85                  90                  95

Asn Gly Leu Leu Val Leu Pro Leu Phe Tyr Asp Val Val Pro Ser His
            100                 105                 110

Val Arg His His Thr Gly Thr Phe Gly Glu Ala Leu Asp Thr His Glu
        115                 120                 125

Asn Lys Phe Lys Gly Thr Ser Glu Gly Phe Glu Leu Asn Met Glu Lys
    130                 135                 140

Leu Asn Arg Trp Lys Met Ala Leu Arg Gly Ala Ala Asn Leu Ser Gly
145                 150                 155                 160

Tyr His Phe Lys His Gly Glu Glu Tyr Glu Tyr Gln Phe Ile Lys Arg
                165                 170                 175

Ile Val Lys Leu Val Ser Asn Lys Ile Asn Arg Ala Thr Leu His Val
            180                 185                 190

Ala Asp Tyr Pro Val Gly Leu Glu Thr Arg Met Leu Glu Val Lys Leu
        195                 200                 205

Leu Leu Asp Val Gly Ser Asp Asp Gly Val His Met Val Gly Ile His
    210                 215                 220

Gly Phe Gly Gly Val Gly Lys Thr Thr Leu Ala Leu Ala Val Tyr Asn
225                 230                 235                 240

Ser Ile Ala Asp Asn Phe Glu Gly Leu Cys Phe Leu Glu Asn Val Arg
                245                 250                 255

Glu Asn Ser Asn Lys His Gly Leu Gln His Leu Gln Ser Leu Leu Leu
            260                 265                 270

Ser Gln Met Val Gly Glu Asn Asn Ile Asn Ile Thr Ser Val Lys Gln
```

-continued

```
        275                 280                 285

Gly Ile Ser Met Met Gln His Arg Leu Arg Gln Lys Lys Ile Leu Leu
    290                 295                 300

Ile Leu Asp Asp Val Asp Lys His Glu Gln Leu Gln Ala Ile Val Gly
305                 310                 315                 320

Arg Ala Asp Trp Phe Gly Pro Gly Ser Arg Val Ile Ile Thr Thr Arg
                325                 330                 335

Asp Lys His Leu Leu Ser Cys Gln Leu Val Glu Lys Ile Tyr Glu Val
            340                 345                 350

Lys Lys Leu Lys Lys Lys Asp Ala Leu Arg Leu Leu Ser Trp Lys Gly
        355                 360                 365

Phe Lys Thr Glu Glu Val His Pro Ser Tyr Val Asn Val Met Gly Arg
    370                 375                 380

Val Leu Ala Tyr Ala Ser Gly His Pro Leu Ala Leu Glu Val Ile Gly
385                 390                 395                 400

Ser Lys Leu Phe Arg Lys Ser Val Lys Glu Trp Glu Ser Ala Ile Gln
                405                 410                 415

Gln Tyr Glu Lys Ile Pro Asn Asn Gln Ile Leu Glu Ile Leu Lys Ile
            420                 425                 430

Ser Phe Asp Ser Leu Glu Glu Val Glu Lys Ser Val Phe Leu Asp Ile
        435                 440                 445

Ala Cys Cys Phe Lys Gly Tyr Ala Leu Ser Glu Val Glu Asn Ile Leu
    450                 455                 460

Arg Ala His Tyr Gly Asp Cys Met Lys Tyr His Ile Gly Val Leu Val
465                 470                 475                 480

Glu Lys Ser Leu Ile Lys Tyr Arg Trp Asn Ser Val Val Thr Leu His
                485                 490                 495

Asp Leu Ile Glu Asp Met Gly Lys Glu Ile Val Arg Gln Lys Ser Pro
            500                 505                 510

Asn Lys Pro Gly Lys Arg Ser Arg Leu Trp Ser Pro Glu Asp Ile Ile
        515                 520                 525

Gln Val Leu Glu Asp Asn Ser Gly Ser Gly Glu Ile Glu Ile Ile Cys
    530                 535                 540

Leu Asn Tyr Ser Leu Pro Gly Lys Glu Glu Ile Val Glu Trp Asn Arg
545                 550                 555                 560

Lys Ala Phe Lys Lys Met Lys Asn Leu Lys Thr Leu Ile Ile Lys Ser
                565                 570                 575

Gly Asn Phe Ser Glu Gly Pro Lys Tyr Leu Pro Asn Ser Leu Arg Val
            580                 585                 590

Met Glu Trp Leu Lys Tyr Pro Ser Gln Gly Leu Pro Pro Asp Phe Arg
        595                 600                 605

Ser Lys Glu Leu Thr Ile Cys Lys Leu Pro Ala Ser Cys Phe Gly Ser
    610                 615                 620

Leu Glu Leu Ala Glu Leu Ser Lys Lys Phe Met Asn Met Thr Leu Leu
625                 630                 635                 640

Asn Phe Asp Glu Cys Glu Gly Leu Thr Gln Ile Pro Asp Val Ser Gly
                645                 650                 655

Leu Pro Asn Leu Val Glu Ile Ser Phe Lys Asn Cys Lys Ser Leu Ile
            660                 665                 670

Thr Ile His Asp Ser Ile Gly Phe Leu Gly Lys Leu Asn Ser Leu Asn
        675                 680                 685

Ala Val Gly Cys Ser Lys Leu Arg Ser Phe Pro Pro Leu Lys Leu Thr
    690                 695                 700
```

-continued

```
Ser Leu Glu Asn Leu Glu Leu Ser Tyr Cys Tyr Ser Leu Glu Ser Phe
705                 710                 715                 720

Pro Glu Ile Leu Gly Lys Met Gly Lys Ile Thr Glu Leu Phe Leu Glu
                725                 730                 735

Cys Cys Asp Ile Lys Glu Leu Pro Phe Ser Phe Gln Asn Leu Thr Glu
            740                 745                 750

Leu Gln Thr Leu Gln Leu Arg Tyr Cys Pro Met Leu Arg Leu Pro Ser
        755                 760                 765

Ser Ile Val Met Met Pro Lys Leu Thr Glu Ile Ile Ala Trp Glu Ser
    770                 775                 780

Glu Gly Trp Leu Phe Pro Lys Gln Val Glu Gly Glu Glu Lys Val Ser
785                 790                 795                 800

Ser Met Val Ser Ser Asn Val Asp Cys Leu Leu Leu Pro Gly Cys Lys
                805                 810                 815

Leu Ser Asp Asp Phe Phe Pro Ile Thr Trp Phe Ala Asn Val Lys Glu
            820                 825                 830

Leu Asp Leu Ser Arg Asn Thr Phe Thr Val Leu Pro Glu Cys Ile Ser
        835                 840                 845

Asn Cys Tyr Phe Leu Cys Lys Leu Ile Leu Asp Asn Cys His Ser Leu
    850                 855                 860

Arg Glu Ile Arg Gly Ile Pro Pro Asn Ile Arg His Leu Ser Ala Arg
865                 870                 875                 880

Tyr Cys Lys Ser Phe Thr Ser Ser Cys Arg Ser Thr Leu Leu Asn Gln
                885                 890                 895

Lys Leu His Glu Thr Gly Asn Thr Met Phe Trp Phe Ser Gly Ala Ser
            900                 905                 910

Phe Pro Glu Trp Phe Glu His Arg Ser Gln Gly Pro Ser Cys Ser Phe
        915                 920                 925

Trp Val Gly Asn Lys Phe Pro Ala Ile Ala Leu Cys Ile Val Ile Gly
    930                 935                 940

Pro Thr His Leu Asp His Ile Glu Ile Val Gly Pro Ile Met Ile Ile
945                 950                 955                 960

Asn Gly Ile Asp Cys Ser Leu Asp Asp Gly Leu Val Asn Pro Tyr Leu
                965                 970                 975

Trp Ile Pro Pro His His Thr Tyr Leu Phe Asp Leu Gln His Ile Val
            980                 985                 990

Ser Ser Asp Tyr Leu Asp Arg Phe  Val Ser Glu Lys Glu  Trp Asn His
        995                 1000                1005

Val Glu  Ile Arg Tyr Ser Val  Lys Gln Arg Phe Ser  Glu Lys Asp
    1010                1015                1020

Lys His  Val Val Ile Pro Val  Ser Ile Glu Asn Gly  Ile Tyr Val
    1025                1030                1035

Phe Lys  Gln Arg Ser Ser Met  Glu Asp Ile Gln Phe  Thr Asp Pro
    1040                1045                1050

His Lys  Lys Arg Arg Leu Asp  Val Asp Pro Glu
    1055                1060
```

<210> SEQ ID NO 9
<211> LENGTH: 3195
<212> TYPE: DNA
<213> ORGANISM: Phaseolus acutifolius

<400> SEQUENCE: 9

```
atggctgtgc catcattctc ctcttccttc acctacgacg tcttcctcag cttcagagga      60
```

```
gaagatactc gttacggttt caccggcaat ctctatacag cccttcatga cagcggaatt    120
tacaccttca tcgatgacga ggagctcccc aaaggagacg aaatcaccac ctcactacag    180
aaggcaatcg aaggttccag aattttcatc atcgttttct ctcacaacta cgcatcttct    240
tccttttgct tgaacgagct cgcctacatt cttccctacg ctaagagaaa tggtttgctg    300
gttttgccac tcttctacga cgtcgttcct tcccacgtgc gacaccacac gggtaccttt    360
ggagaagcgt tagatactca tgaaaacaag ttcaaaggta cgagtgaggg ttttgagctt    420
aacatggaga agctcaacag atggaagatg gctctgcgtg gagctgctaa cttatctggc    480
tatcatttca aacatgggga ggaatatgaa taccagttta tcaagaggat agtgaaattg    540
gtctctaaca agattaaccg tgctccttta catgttgcgg attatccagt tggactagag    600
acacgaatgc tagaagtaaa gttgcttcta gatgtaggat ctgatgatgg tgtccacatg    660
gtagggatcc atggattcgg tggagttggt aaaaccacac ttgctcttgc agtttacaac    720
tccatagctg acaattttga aggcttgtgt ttccttgaaa atgtgagaga gaattcaaac    780
aaacacggcc tacaacatct tcagagcctc cttctttctc aaatggttgg agaaaataat    840
atcaacataa ctagtgtgaa acaagggatt tcaatgatgc agcataggct acggcagaag    900
aagattcttt tgattcttga tgatgttgac aagcatgaac agttacaagc aattgttgga    960
agagctgatt ggtttggtcc cggcagtaga gtcatcatca caactaggga caaacatttg   1020
ttgtcatgtc agttggttga aaaaatatat gaagtgaaga agttgaaaaa gaaagatgct   1080
cttcgactgc ttagttggaa aggttttaaa acagaagaag ttcatccaag ttatgtgaat   1140
gtcatgggtc gtgtactggc ttatgcttct ggccatccat tggctttgga agtaataggt   1200
tcgaagttgt ttagaaaaag tgtaaaagaa tgggaatctg ccatccacca gtatcagaaa   1260
attcctaaca atcaaatcct ggagatgctt aaaataagtt ttgattcttt agaggaagta   1320
gagaagagtg tttttcttga cattgcttgt tgtttcaaag gatatgcatt gtcagaggtg   1380
gaaaatatac ttcgtgctca ttatggtgat tgcatgaaat atcatattgg ggtgttggtt   1440
gaaaaatctc tcataaaata tagatggaat tctgtagtta cattgcatga cttgatagaa   1500
gacatgggta aagaaattgt ccgacagaaa tcaccaaata agccagggaa gcgcagtaga   1560
ttatggtcac cagaagatat aattcaagtt ttggaagaca actcgggaag tggagaaatt   1620
gaaatcatat gtttgaatta ctctttacct gacaaagaag aaatagtaga atggaacaga   1680
aaggccttca agaagatgaa aaacctcaaa acacttatta ttaaaagtgg taatttttcg   1740
gaaggtccta aatatcttcc aaacagttta agagtaatgg aatggttaaa atatccttca   1800
caagggctac cgccagattt tcgttcaaag gaacttgcca tatgcaaatt acctgcaagt   1860
tgttttgggt cactcgaatt ggccgagtta tcaaagaagt tcatgaatat gacccttttg   1920
aattttgacg aatgtgaagg tttaacacag atacctgatg tatctgggct gccaaattta   1980
gtagaaattt cattcaagaa ttgtaagagt ttaattacaa tccatgactc cattgggctc   2040
ctaggtaagc ttaactcctt gaatgctgtt ggttgcagca agcttaggag ttttccaccc   2100
ctcaaattga cttctctgga aaatcttgaa ctttcatatt gttacagtct tgagagcttc   2160
ccagaaatat tagggaaaat gggaaagata acagaacttt tcttggagtg ctgtgacata   2220
aaagaattgc cattttcatt tcaaaatctc actgagcttc aaacattaca gttgcgttac   2280
tgtcccatgt taaggttgcc aagtagtatt gtcatgatgc caaaactgac caagattatt   2340
gcttgggaat ctgaaggatg gttatttcca aaacaggttg agggtgaaga gaaagtaagc   2400
```

-continued

```
tcaatggtgt cttcaagtgt agattgtctt cttctcccag ggtgcaaact ctcagatgat   2460

tttttcccaa taacatggtt tgctaatgta aaagagttag acctgtcaag gaatactttc   2520

acggttcttc ctgaatgcat aagcaattgt tattttttat gtaagcttat tttagataac   2580

tgtcatagtc ttcgagagat tagagggatt ccgccaaaca tacgacattt atcagcaaga   2640

tattgtaaat ccttcacttc ttctggcaga agcactttac tgaatcagaa actgcatgag   2700

acgggaaaca ccatgttttg gttttcagga gcaagttttc cagaatggtt cgagcaccgc   2760

agtcagggac catcttgttc tttctgggtt gggaacaaat tccctgccat tgctctttgt   2820

attgttattg gaccaactca tttggaccat attgagattg ttggacctat catgatcatc   2880

aatggcattg actgttcact tgttgatggg ttggttaatc cttatttatg gatacccccct   2940

catcacacat atcttttcga tttgcaacat atagtttctt cagattatct tgacagattt   3000

gtttcagaaa aggaatggaa tcacgtggag attagatact cagtcaagca gagattcagt   3060

gaaaaagaca aacatgtggt gataccagtc tctatagaaa atggaatcta tgtgttcaaa   3120

cagaggagca gcatggagga tattcaattc actgatcccc acaaaaagag aagattagat   3180

gttgatccag agtag                                                    3195

<210> SEQ ID NO 10
<211> LENGTH: 1064
<212> TYPE: PRT
<213> ORGANISM: Phaseolus acutifolius

<400> SEQUENCE: 10

Met Ala Val Pro Ser Phe Ser Ser Ser Phe Thr Tyr Asp Val Phe Leu
1               5                   10                  15

Ser Phe Arg Gly Glu Asp Thr Arg Tyr Gly Phe Thr Gly Asn Leu Tyr
            20                  25                  30

Thr Ala Leu His Asp Ser Gly Ile Tyr Thr Phe Ile Asp Asp Glu Glu
        35                  40                  45

Leu Pro Lys Gly Asp Glu Ile Thr Thr Ser Leu Gln Lys Ala Ile Glu
    50                  55                  60

Gly Ser Arg Ile Phe Ile Ile Val Phe Ser His Asn Tyr Ala Ser Ser
65                  70                  75                  80

Ser Phe Cys Leu Asn Glu Leu Ala Tyr Ile Leu Pro Tyr Ala Lys Arg
                85                  90                  95

Asn Gly Leu Leu Val Leu Pro Leu Phe Tyr Asp Val Val Pro Ser His
            100                 105                 110

Val Arg His His Thr Gly Thr Phe Gly Glu Ala Leu Asp Thr His Glu
        115                 120                 125

Asn Lys Phe Lys Gly Thr Ser Glu Gly Phe Glu Leu Asn Met Glu Lys
    130                 135                 140

Leu Asn Arg Trp Lys Met Ala Leu Arg Gly Ala Ala Asn Leu Ser Gly
145                 150                 155                 160

Tyr His Phe Lys His Gly Glu Glu Tyr Glu Tyr Gln Phe Ile Lys Arg
                165                 170                 175

Ile Val Lys Leu Val Ser Asn Lys Ile Asn Arg Ala Pro Leu His Val
            180                 185                 190

Ala Asp Tyr Pro Val Gly Leu Glu Thr Arg Met Leu Glu Val Lys Leu
        195                 200                 205

Leu Leu Asp Val Gly Ser Asp Asp Gly Val His Met Val Gly Ile His
    210                 215                 220

Gly Phe Gly Gly Val Gly Lys Thr Thr Leu Ala Leu Ala Val Tyr Asn
```

-continued

```
225                 230                 235                 240

Ser Ile Ala Asp Asn Phe Glu Gly Leu Cys Phe Leu Glu Asn Val Arg
                245                 250                 255

Glu Asn Ser Asn Lys His Gly Leu Gln His Leu Gln Ser Leu Leu Leu
            260                 265                 270

Ser Gln Met Val Gly Glu Asn Asn Ile Asn Ile Thr Ser Val Lys Gln
        275                 280                 285

Gly Ile Ser Met Met Gln His Arg Leu Arg Gln Lys Lys Ile Leu Leu
    290                 295                 300

Ile Leu Asp Asp Val Asp Lys His Glu Gln Leu Gln Ala Ile Val Gly
305                 310                 315                 320

Arg Ala Asp Trp Phe Gly Pro Gly Ser Arg Val Ile Ile Thr Thr Arg
                325                 330                 335

Asp Lys His Leu Leu Ser Cys Gln Leu Val Glu Lys Ile Tyr Glu Val
            340                 345                 350

Lys Lys Leu Lys Lys Lys Asp Ala Leu Arg Leu Leu Ser Trp Lys Gly
        355                 360                 365

Phe Lys Thr Glu Glu Val His Pro Ser Tyr Val Asn Val Met Gly Arg
    370                 375                 380

Val Leu Ala Tyr Ala Ser Gly His Pro Leu Ala Leu Glu Val Ile Gly
385                 390                 395                 400

Ser Lys Leu Phe Arg Lys Ser Val Lys Glu Trp Glu Ser Ala Ile His
                405                 410                 415

Gln Tyr Gln Lys Ile Pro Asn Asn Gln Ile Leu Glu Met Leu Lys Ile
            420                 425                 430

Ser Phe Asp Ser Leu Glu Glu Val Glu Lys Ser Val Phe Leu Asp Ile
        435                 440                 445

Ala Cys Cys Phe Lys Gly Tyr Ala Leu Ser Glu Val Glu Asn Ile Leu
    450                 455                 460

Arg Ala His Tyr Gly Asp Cys Met Lys Tyr His Ile Gly Val Leu Val
465                 470                 475                 480

Glu Lys Ser Leu Ile Lys Tyr Arg Trp Asn Ser Val Val Thr Leu His
                485                 490                 495

Asp Leu Ile Glu Asp Met Gly Lys Glu Ile Val Arg Gln Lys Ser Pro
            500                 505                 510

Asn Lys Pro Gly Lys Arg Ser Arg Leu Trp Ser Pro Glu Asp Ile Ile
        515                 520                 525

Gln Val Leu Glu Asp Asn Ser Gly Ser Gly Glu Ile Glu Ile Ile Cys
    530                 535                 540

Leu Asn Tyr Ser Leu Pro Asp Lys Glu Glu Ile Val Glu Trp Asn Arg
545                 550                 555                 560

Lys Ala Phe Lys Lys Met Lys Asn Leu Lys Thr Leu Ile Ile Lys Ser
                565                 570                 575

Gly Asn Phe Ser Glu Gly Pro Lys Tyr Leu Pro Asn Ser Leu Arg Val
            580                 585                 590

Met Glu Trp Leu Lys Tyr Pro Ser Gln Gly Leu Pro Pro Asp Phe Arg
        595                 600                 605

Ser Lys Glu Leu Ala Ile Cys Lys Leu Pro Ala Ser Cys Phe Gly Ser
    610                 615                 620

Leu Glu Leu Ala Glu Leu Ser Lys Lys Phe Met Asn Met Thr Leu Leu
625                 630                 635                 640

Asn Phe Asp Glu Cys Glu Gly Leu Thr Gln Ile Pro Asp Val Ser Gly
                645                 650                 655
```

```
Leu Pro Asn Leu Val Glu Ile Ser Phe Lys Asn Cys Lys Ser Leu Ile
            660                 665                 670

Thr Ile His Asp Ser Ile Gly Leu Leu Gly Lys Leu Asn Ser Leu Asn
        675                 680                 685

Ala Val Gly Cys Ser Lys Leu Arg Ser Phe Pro Pro Leu Lys Leu Thr
    690                 695                 700

Ser Leu Glu Asn Leu Glu Leu Ser Tyr Cys Tyr Ser Leu Glu Ser Phe
705                 710                 715                 720

Pro Glu Ile Leu Gly Lys Met Gly Lys Ile Thr Glu Leu Phe Leu Glu
                725                 730                 735

Cys Cys Asp Ile Lys Glu Leu Pro Phe Ser Phe Gln Asn Leu Thr Glu
            740                 745                 750

Leu Gln Thr Leu Gln Leu Arg Tyr Cys Pro Met Leu Arg Leu Pro Ser
        755                 760                 765

Ser Ile Val Met Met Pro Lys Leu Thr Lys Ile Ile Ala Trp Glu Ser
    770                 775                 780

Glu Gly Trp Leu Phe Pro Lys Gln Val Glu Gly Glu Glu Lys Val Ser
785                 790                 795                 800

Ser Met Val Ser Ser Ser Val Asp Cys Leu Leu Leu Pro Gly Cys Lys
                805                 810                 815

Leu Ser Asp Asp Phe Phe Pro Ile Thr Trp Phe Ala Asn Val Lys Glu
            820                 825                 830

Leu Asp Leu Ser Arg Asn Thr Phe Thr Val Leu Pro Glu Cys Ile Ser
        835                 840                 845

Asn Cys Tyr Phe Leu Cys Lys Leu Ile Leu Asp Asn Cys His Ser Leu
    850                 855                 860

Arg Glu Ile Arg Gly Ile Pro Pro Asn Ile Arg His Leu Ser Ala Arg
865                 870                 875                 880

Tyr Cys Lys Ser Phe Thr Ser Ser Gly Arg Ser Thr Leu Leu Asn Gln
                885                 890                 895

Lys Leu His Glu Thr Gly Asn Thr Met Phe Trp Phe Ser Gly Ala Ser
            900                 905                 910

Phe Pro Glu Trp Phe Glu His Arg Ser Gln Gly Pro Ser Cys Ser Phe
        915                 920                 925

Trp Val Gly Asn Lys Phe Pro Ala Ile Ala Leu Cys Ile Val Ile Gly
    930                 935                 940

Pro Thr His Leu Asp His Ile Glu Ile Val Gly Pro Ile Met Ile Ile
945                 950                 955                 960

Asn Gly Ile Asp Cys Ser Leu Val Asp Gly Leu Val Asn Pro Tyr Leu
                965                 970                 975

Trp Ile Pro Pro His His Thr Tyr Leu Phe Asp Leu Gln His Ile Val
            980                 985                 990

Ser Ser Asp Tyr Leu Asp Arg Phe  Val Ser Glu Lys Glu  Trp Asn His
        995                 1000                 1005

Val Glu  Ile Arg Tyr Ser Val  Lys Gln Arg Phe Ser  Glu Lys Asp
    1010                 1015                 1020

Lys His  Val Val Ile Pro Val  Ser Ile Glu Asn Gly  Ile Tyr Val
    1025                 1030                 1035

Phe Lys  Gln Arg Ser Ser Met  Glu Asp Ile Gln Phe  Thr Asp Pro
    1040                 1045                 1050

His Lys  Lys Arg Arg Leu Asp  Val Asp Pro Glu
    1055                 1060
```

<210> SEQ ID NO 11
<211> LENGTH: 3201
<212> TYPE: DNA
<213> ORGANISM: Vigna angularis

<400> SEQUENCE: 11
atggctgtgc catcattctc ctcttccttc acctatgacg tgttcctcag cttcagagga 60
gaagatactc gttacagttt caccggcaat ctctacagag cccttcgtga cagaggaatt 120
cacaccttca tcgacgacga gaagcttccc aaaggagacg aaatcacctc tgcacttgag 180
aaggcaatcg aaggttccag aattttcatc atcgttttct ctcgcaacta cgcctcttcc 240
tccttttgct tgaacgagct cgcctacatt cttccctacg ctaatagaaa tggtttgctg 300
gttttgccac tcttctacga cgtcgttcct tcccacgtgc gccaccacac gggtagcttc 360
ggagaagctt tggatacaca tgaaaacagg ttcaaagcta cgagtcaggg ttttgagctt 420
aacatggaga agctcaacaa atggaagatg gctctgcgtg gaacagctaa cttatctggc 480
tatcatttca aacatgggga ggaatatgaa tacgagttta tcaagaggat agttgacttg 540
gtctccaaca agattaaccg tgctccttta cacgttgcgg attatccagt tggactagag 600
actcgagtgc tagaagtaaa gttgcttcta gatataggat ctgatgatgg tgtccacatg 660
gtagggatcc atggactcgg tggagttggt aaaaccacac ttgctcttgc agtgtacaat 720
tccatcgctg accattttga aggcttgtgt ttcctcgaaa atgtgagaga gaattcaaac 780
aaacatggcc tacagcatct tcaaagaatc cttctttctc aaatgattgg agaaaataat 840
gtcaacataa ctagtgcgag acaagggatt tcaatgatgg agcataggct acgacagaag 900
aagattctct tgattctaga tgatgttgac aaacatgaac agttacaagc aattgttgga 960
agacctgatt ggtttggtcc cggcagtaga gtcatcatca caactaggga caaacatttg 1020
ttatcatgtc acttgatcga aaaattatat aaagtgaaga agttggaaaa gaacaatgct 1080
cttcgactgc ttagttggaa agctttcaga acagaagaag ttgatacaag ttatttgaat 1140
gtaatggatc gtgtactagc ttatgcttct ggccatccat tggctttgga agtaatcggt 1200
tcgaagttgt ttagaaaaag tgtaaaggaa tgggaatctg ccatcaaaca gtatgagaaa 1260
attcctaaca atcaaatcct tgaggtgctt aaaataagtt ttgatgcttt agaggaagta 1320
gagaagagtg tttttcttga catttcttgt tgcttcaaag catatgcatt gtcagaggtg 1380
gaagatatac ttcgtgctca ttatggtgat tgcatgaaat atcatattgg ggtgttggtt 1440
gaaaagtctc tgataaaata tggttataat tctgtagtta caatgcatga cttgatagaa 1500
gacatgggta aagaaattgt ccggcagaaa tctccaaata agccagggaa gcgcagtaga 1560
ttatggtcac cagaagagat aattaaagtt ttggaagaca acttgggaag tggagaaatt 1620
gaaatcatat gtttaaattc ctccttacct gacaaagaag aaatagtgga atggaacaga 1680
aaggtcttca aaaagatgaa aaacctcaaa acacttatca ttaaaaatgg taatttttcg 1740
gaaggtcctg aatatcttcc gaatagttta agagtactgg aatggttgaa atatccttca 1800
caagggctac cgccagattt tcgttcaaag caactttcct tatgcaaatt accttcaagt 1860
tgttttgggt cactcggatt gactgagttt tcaaagaagt tcatgaatat gactcttctg 1920
aattttgacg aatgtgaagg tttaacacag atacctgatc tatctgggct gccaaattta 1980
gaaagatttt cattcaagaa ttgtaagagt ttaattacaa tccatgactc cattggcttc 2040
ctaggtaagc ttaactcctt gaatgctgtt ggttgcagca agcttaggag ttttcccccc 2100
ctcaaattga cttctctgga aatcttgaa ctttcatatt gttacagtct tgagagcttc 2160
ccagaaatat taggaaaaat gggacagata acagaacttg tcttggagga ctgtcacata 2220
aaggaattgc caatttcatt tcaaaatctc accgagcttc aaacattaca gttgcgttcg 2280
tgtccaaggt taaggttacc tagtagtata gtcatgatgc caaaactggc caacattatt 2340
gcttgggaat ctaaagggtg gctatttcca aaacaggtcg agggggaaga gaaaataggc 2400
tcaatggtgt cttcaaacgt agattgtctt tatctctcag ggtgcaaact ctcagatcat 2460
tttttcccaa taattcttga atggtttgct aatgtaaaag atttaaacct atcaaggaat 2520
aatttcacgg ttcttcctga atgcatcgcc aattgtcact tgttatgcaa gcttacttta 2580
gatgcctgtc atagtcttcg agagattaga gggattccac caaacatacg acagttatca 2640
gcaagaaatt gtaaatcctt cacttcttct tgcggaagaa ctttactgaa tcagaaactg 2700
catgaggctg gaaacaccat gttttcgttt tcaggagcaa ggtttccaga atggttcgat 2760
caccacagtt ggggaccatc ttgttctttc tgggttggca aaaaattccc ttccattgct 2820
ctttgtattg ctattggacc aactcatttg gaacacgttg aaattgttgg acctatcatg 2880
atcatcaaca gcattgaatg ttcattggat gaggaggaga atccttattt atatatgctc 2940
cctcatcaca cacatatttt cgatttgcaa catatagttt tttcagatta tctagacaga 3000
tttgtttcag aaaatgaatg gaaccacgtg gagattacat actcagtcga gcagagattc 3060
gaggaaaaag acaaacatgc ggtgacccaa atctctatag aaaatggaat ctatgtgttc 3120
aaacagaata gcagcatgga ggatattcaa ttcactgatc cccacaaaaa gagaagatta 3180
gatgttgatc cagagttgta a 3201

<210> SEQ ID NO 12
<211> LENGTH: 1066
<212> TYPE: PRT
<213> ORGANISM: Vigna angularis

<400> SEQUENCE: 12

Met Ala Val Pro Ser Phe Ser Ser Ser Phe Thr Tyr Asp Val Phe Leu
1 5 10 15

Ser Phe Arg Gly Glu Asp Thr Arg Tyr Ser Phe Thr Gly Asn Leu Tyr
20 25 30

Arg Ala Leu Arg Asp Arg Gly Ile His Thr Phe Ile Asp Asp Glu Lys
35 40 45

Leu Pro Lys Gly Asp Glu Ile Thr Ser Ala Leu Glu Lys Ala Ile Glu
50 55 60

Gly Ser Arg Ile Phe Ile Ile Val Phe Ser Arg Asn Tyr Ala Ser Ser
65 70 75 80

Ser Phe Cys Leu Asn Glu Leu Ala Tyr Ile Leu Pro Tyr Ala Asn Arg
85 90 95

Asn Gly Leu Leu Val Leu Pro Leu Phe Tyr Asp Val Val Pro Ser His
100 105 110

Val Arg His His Thr Gly Ser Phe Gly Glu Ala Leu Asp Thr His Glu
115 120 125

Asn Arg Phe Lys Ala Thr Ser Gln Gly Phe Glu Leu Asn Met Glu Lys
130 135 140

Leu Asn Lys Trp Lys Met Ala Leu Arg Gly Thr Ala Asn Leu Ser Gly
145 150 155 160

Tyr His Phe Lys His Gly Glu Glu Tyr Glu Tyr Glu Phe Ile Lys Arg
165 170 175

Ile Val Asp Leu Val Ser Asn Lys Ile Asn Arg Ala Pro Leu His Val

```
            180                 185                 190

Ala Asp Tyr Pro Val Gly Leu Glu Thr Arg Val Leu Glu Val Lys Leu
        195                 200                 205

Leu Leu Asp Ile Gly Ser Asp Asp Gly Val His Met Val Gly Ile His
    210                 215                 220

Gly Leu Gly Gly Val Gly Lys Thr Thr Leu Ala Leu Ala Val Tyr Asn
225                 230                 235                 240

Ser Ile Ala Asp His Phe Glu Gly Leu Cys Phe Leu Glu Asn Val Arg
                245                 250                 255

Glu Asn Ser Asn Lys His Gly Leu Gln His Leu Gln Arg Ile Leu Leu
            260                 265                 270

Ser Gln Met Ile Gly Glu Asn Asn Val Asn Ile Thr Ser Ala Arg Gln
        275                 280                 285

Gly Ile Ser Met Met Glu His Arg Leu Arg Gln Lys Lys Ile Leu Leu
    290                 295                 300

Ile Leu Asp Asp Val Asp Lys His Glu Gln Leu Gln Ala Ile Val Gly
305                 310                 315                 320

Arg Pro Asp Trp Phe Gly Pro Gly Ser Arg Val Ile Ile Thr Thr Arg
                325                 330                 335

Asp Lys His Leu Leu Ser Cys His Leu Ile Glu Lys Leu Tyr Lys Val
            340                 345                 350

Lys Lys Leu Glu Lys Asn Asn Ala Leu Arg Leu Leu Ser Trp Lys Ala
        355                 360                 365

Phe Arg Thr Glu Glu Val Asp Thr Ser Tyr Leu Asn Val Met Asp Arg
    370                 375                 380

Val Leu Ala Tyr Ala Ser Gly His Pro Leu Ala Leu Glu Val Ile Gly
385                 390                 395                 400

Ser Lys Leu Phe Arg Lys Ser Val Lys Glu Trp Glu Ser Ala Ile Lys
                405                 410                 415

Gln Tyr Glu Lys Ile Pro Asn Asn Gln Ile Leu Glu Val Leu Lys Ile
            420                 425                 430

Ser Phe Asp Ala Leu Glu Glu Val Glu Lys Ser Val Phe Leu Asp Ile
        435                 440                 445

Ser Cys Cys Phe Lys Ala Tyr Ala Leu Ser Glu Val Glu Asp Ile Leu
    450                 455                 460

Arg Ala His Tyr Gly Asp Cys Met Lys Tyr His Ile Gly Val Leu Val
465                 470                 475                 480

Glu Lys Ser Leu Ile Lys Tyr Gly Tyr Asn Ser Val Val Thr Met His
                485                 490                 495

Asp Leu Ile Glu Asp Met Gly Lys Glu Ile Val Arg Gln Lys Ser Pro
            500                 505                 510

Asn Lys Pro Gly Lys Arg Ser Arg Leu Trp Ser Pro Glu Glu Ile Ile
        515                 520                 525

Lys Val Leu Glu Asp Asn Leu Gly Ser Gly Glu Ile Glu Ile Ile Cys
    530                 535                 540

Leu Asn Ser Ser Leu Pro Asp Lys Glu Glu Ile Val Glu Trp Asn Arg
545                 550                 555                 560

Lys Val Phe Lys Lys Met Lys Asn Leu Lys Thr Leu Ile Ile Lys Asn
                565                 570                 575

Gly Asn Phe Ser Glu Gly Pro Glu Tyr Leu Pro Asn Ser Leu Arg Val
            580                 585                 590

Leu Glu Trp Leu Lys Tyr Pro Ser Gln Gly Leu Pro Pro Asp Phe Arg
        595                 600                 605
```

```
Ser Lys Gln Leu Ser Leu Cys Lys Leu Pro Ser Ser Cys Phe Gly Ser
    610                 615                 620

Leu Gly Leu Thr Glu Phe Ser Lys Lys Phe Met Asn Met Thr Leu Leu
625                 630                 635                 640

Asn Phe Asp Glu Cys Glu Gly Leu Thr Gln Ile Pro Asp Leu Ser Gly
                645                 650                 655

Leu Pro Asn Leu Glu Arg Phe Ser Phe Lys Asn Cys Lys Ser Leu Ile
            660                 665                 670

Thr Ile His Asp Ser Ile Gly Phe Leu Gly Lys Leu Asn Ser Leu Asn
        675                 680                 685

Ala Val Gly Cys Ser Lys Leu Arg Ser Phe Pro Pro Leu Lys Leu Thr
    690                 695                 700

Ser Leu Glu Asn Leu Glu Leu Ser Tyr Cys Tyr Ser Leu Glu Ser Phe
705                 710                 715                 720

Pro Glu Ile Leu Gly Lys Met Gly Gln Ile Thr Glu Leu Val Leu Glu
                725                 730                 735

Asp Cys His Ile Lys Glu Leu Pro Ile Ser Phe Gln Asn Leu Thr Glu
            740                 745                 750

Leu Gln Thr Leu Gln Leu Arg Ser Cys Pro Arg Leu Arg Leu Pro Ser
        755                 760                 765

Ser Ile Val Met Met Pro Lys Leu Ala Asn Ile Ile Ala Trp Glu Ser
    770                 775                 780

Lys Gly Trp Leu Phe Pro Lys Gln Val Glu Gly Glu Glu Lys Ile Gly
785                 790                 795                 800

Ser Met Val Ser Ser Asn Val Asp Cys Leu Tyr Leu Ser Gly Cys Lys
                805                 810                 815

Leu Ser Asp His Phe Phe Pro Ile Ile Leu Glu Trp Phe Ala Asn Val
            820                 825                 830

Lys Asp Leu Asn Leu Ser Arg Asn Asn Phe Thr Val Leu Pro Glu Cys
        835                 840                 845

Ile Ala Asn Cys His Leu Leu Cys Lys Leu Thr Leu Asp Ala Cys His
    850                 855                 860

Ser Leu Arg Glu Ile Arg Gly Ile Pro Pro Asn Ile Arg Gln Leu Ser
865                 870                 875                 880

Ala Arg Asn Cys Lys Ser Phe Thr Ser Ser Cys Gly Arg Thr Leu Leu
                885                 890                 895

Asn Gln Lys Leu His Glu Ala Gly Asn Thr Met Phe Ser Phe Ser Gly
            900                 905                 910

Ala Arg Phe Pro Glu Trp Phe Asp His His Ser Trp Gly Pro Ser Cys
        915                 920                 925

Ser Phe Trp Val Gly Lys Lys Phe Pro Ser Ile Ala Leu Cys Ile Ala
    930                 935                 940

Ile Gly Pro Thr His Leu Glu His Val Glu Ile Val Gly Pro Ile Met
945                 950                 955                 960

Ile Ile Asn Ser Ile Glu Cys Ser Leu Asp Glu Glu Glu Asn Pro Tyr
                965                 970                 975

Leu Tyr Met Leu Pro His His Thr His Ile Phe Asp Leu Gln His Ile
            980                 985                 990

Val Phe Ser Asp Tyr Leu Asp Arg  Phe Val Ser Glu Asn  Glu Trp Asn
        995                 1000                1005

His Val  Glu Ile Thr Tyr Ser  Val Glu Gln Arg Phe  Glu Glu Lys
    1010                1015                1020
```

```
Asp Lys  His Ala Val Thr Gln  Ile Ser Ile Glu Asn  Gly Ile Tyr
    1025                 1030                 1035

Val Phe  Lys Gln Asn Ser Ser  Met Glu Asp Ile Gln  Phe Thr Asp
    1040                 1045                 1050

Pro His  Lys Lys Arg Arg Leu  Asp Val Asp Pro Glu  Leu
    1055                 1060                 1065


<210> SEQ ID NO 13
<211> LENGTH: 3198
<212> TYPE: DNA
<213> ORGANISM: Lablab purpureus

<400> SEQUENCE: 13

atggctgagc catcattctc ctcttccttc acctatgacg tcttcctcag cttcagagga     60

gaagatactc gttacagctt caccggcaat ctctacagag cccttcgtga cagcggaatc    120

tgcaccttca tcgacgacga ggagctccgc aaaggagacg agatcacctc tgcgctcgag    180

aaggcaatcg aaggctccag aatcttcatc atcgtcctct ctcacaacta cgcctcttcc    240

tctttctgct tgaacgagct cgcctacatc cttccctacg ctaagagaaa gggtttgctg    300

gttttgcctc tcttctacga tgtcgttcct tcccacgtgc gccaccacac aggtagcttt    360

ggagaagcat tggatactca tgagaagagg ttcaaaggta cgagtgaggg ttttgagctt    420

aacatggaga agctcaacga atggaagatg gctctacgtc atgtagctaa cttctctggc    480

tatcatttca aacatgggga ggagtatgaa tatgagttta tcaagaagat agttgaattg    540

gtctctaaca agattaaccg tgctccttta catgttgcgg attatccagt tggactagag    600

tcacgagtgc tagaaataaa gttgcttcta gatgtaggat ctgatgatgg tgtccacatg    660

gttgggatct atggactcgg tggagttggt aaaaccacac ttgctgttgc agtttataat    720

tccatcgctg accattttga aggcttgtgt ttccttgaaa atgtgagaga gaattcaaac    780

aaacacggcc tacatcatct tcagagcctt cttctttctc aaatggttgg agaaaagaat    840

atcaacatat ctagtgtgaa acaaggaatt tcaattatgc agcacaggct aaggcagaag    900

aagattcttc tgattctaga tgatgttgac aagcttgaac agttacagtc aattgttgga    960

agacctgatt ggtttggtcc tggaagtaga gtcatcatca caactaggga caaacaattg   1020

ttgtcatgtc acttggttga aaaaacatat gaagtgaaga agttgaaaaa gaaggatgct   1080

tttcgactgc taagttggaa aggttttaga acagaagaag ttgatacaag ttatgtgaat   1140

gtcatggatc gtgtactagc ttatgcttct ggccatccat tggctttgga agtaataggt   1200

tccaagttgt ttagaaaaag tataaaagaa tgggaatctg ccatcaacca gtatgagaaa   1260

attcctaaca atcagatcct ggagatactt aaaataagtt ttgattcttt agaggaagta   1320

gagaagagtg tttttcttga tatttcatgt tgcttcaaag gatatgcatt gtcagaggtg   1380

gaagatatac ttcgtgctca ttatggtgat tgcatgaaat atcatattgg agtgttggtt   1440

gaaaaatctc tcataaaata taggtggggt tgtatagtta cattgcatga cttgatagaa   1500

gacatgggta aagaaattgt ccgacagaaa tcaccacaaa agccagggaa gcgcagtaga   1560

ttatggtcac cagaagatat aattcaagtt ttggaagaca actcgggaag tggagaaatt   1620

gaaatcatat gcttgaactc ctccttactt gacaaagaag aaacaataga atggaacaga   1680

aaggccttca agaagatgaa aaacctcaaa acacttatca ttaaaaatgg taatttttcg   1740

gaaggtccta aatatcttcc aaatagttta agagtactgg aatggttgaa atatccttca   1800

caagggttac ccccagattt tcgttcaaag aaacttgtca tttgcaaatt accctcaagt   1860
```

-continued tgttttggga cactcgaact ggctgagtta tcaaagaagt tcatgaatat gactgttttg 1920
aattttgacg aatgtgaagg tttaacacag atacctgatg tatctgggct gccaaattta 1980
gaaaacattt cattcaagaa ttgtaagagt ttaattacaa ttcatgactc cattgggttc 2040
ctagataagc ttaactcctt gaatgctgtt ggttgcagca ggcttaggag ttttccacct 2100
ctcaaattga cttctctgga aatcttgaa ctttcatatt gttacagtct tgagtgcttc 2160
ccagaaatat taggaaaaat ggaaaagatg acagaacttg tgttggagga ctgtgacatc 2220
aaggaaattc cattttcatt taaaaatctc actgagcttc aaacattaga tttgcgtttc 2280
tgtcgaatgt taaggttacc aactagcatt gtcatgatgc caaaactgtc tgagattatc 2340
gcttgggaag ctgaaggatg cctatttcca aaacaggttg agggtgaaga gaaagtaagc 2400
tcaatggtgt cttcaaatgt agattctctt cgtctctcag ggtgcaaact ctcggatgat 2460
tttttcccaa caactcttgc atggttttct aatgtaaaag atttgaacct ctcaaggaat 2520
aatttcaccg ttcttcctga atgcatcagc aattgtcatt ttttatataa gcttacttta 2580
gattactgtc atagtcttcg agagattaga gggcttccgc caaacataca acatttatct 2640
gcaataaatt gtacatcctt cacttcttct tgcagaagta ctttactgaa tcagaaactg 2700
catgaggctg gaaacaccat gttttcgttt tcaggagcaa tgtttccaga atggttcgag 2760
aaccacagtc ggggaccatc ttattctttc tgggttggga acaaattccc tgccattgct 2820
ctttgtattg ctattggacc aactcatgtg gaatatgttc aaattgttgg acctatcatg 2880
atcatcaatg gcattgaatg ttcacttcct ggggtcgatc cctatttaaa gatgctccct 2940
gatcacacat atcttttcga tctgcagcag atagtttttc cggattatct agacagattt 3000
gtttcagaaa atgaatggaa ccacgtggag attacatacg cagtcgagaa gagattcagt 3060
aaaaaagaca aacatgtggt gatcccggtc tctatagaaa atggaatcta tgtgtcaaaa 3120
cagaggagca gcatggagaa tgttcgattc actgatcccc ggaaaaaaag aagattagat 3180
gttgattcgg agttgtaa 3198

<210> SEQ ID NO 14
<211> LENGTH: 1065
<212> TYPE: PRT
<213> ORGANISM: Lablab purpureus

<400> SEQUENCE: 14

Met Ala Glu Pro Ser Phe Ser Ser Ser Phe Thr Tyr Asp Val Phe Leu
1 5 10 15

Ser Phe Arg Gly Glu Asp Thr Arg Tyr Ser Phe Thr Gly Asn Leu Tyr
20 25 30

Arg Ala Leu Arg Asp Ser Gly Ile Cys Thr Phe Ile Asp Asp Glu Glu
35 40 45

Leu Arg Lys Gly Asp Glu Ile Thr Ser Ala Leu Glu Lys Ala Ile Glu
50 55 60

Gly Ser Arg Ile Phe Ile Ile Val Leu Ser His Asn Tyr Ala Ser Ser
65 70 75 80

Ser Phe Cys Leu Asn Glu Leu Ala Tyr Ile Leu Pro Tyr Ala Lys Arg
85 90 95

Lys Gly Leu Leu Val Leu Pro Leu Phe Tyr Asp Val Val Pro Ser His
100 105 110

Val Arg His His Thr Gly Ser Phe Gly Glu Ala Leu Asp Thr His Glu
115 120 125

Lys Arg Phe Lys Gly Thr Ser Glu Gly Phe Glu Leu Asn Met Glu Lys

```
    130                 135                 140

Leu Asn Glu Trp Lys Met Ala Leu Arg His Val Ala Asn Phe Ser Gly
145                 150                 155                 160

Tyr His Phe Lys His Gly Glu Glu Tyr Glu Tyr Glu Phe Ile Lys Lys
                165                 170                 175

Ile Val Glu Leu Val Ser Asn Lys Ile Asn Arg Ala Pro Leu His Val
            180                 185                 190

Ala Asp Tyr Pro Val Gly Leu Glu Ser Arg Val Leu Glu Ile Lys Leu
        195                 200                 205

Leu Leu Asp Val Gly Ser Asp Asp Gly Val His Met Val Gly Ile Tyr
    210                 215                 220

Gly Leu Gly Gly Val Gly Lys Thr Thr Leu Ala Val Ala Val Tyr Asn
225                 230                 235                 240

Ser Ile Ala Asp His Phe Glu Gly Leu Cys Phe Leu Glu Asn Val Arg
                245                 250                 255

Glu Asn Ser Asn Lys His Gly Leu His His Leu Gln Ser Leu Leu Leu
            260                 265                 270

Ser Gln Met Val Gly Glu Lys Asn Ile Asn Ile Ser Ser Val Lys Gln
        275                 280                 285

Gly Ile Ser Ile Met Gln His Arg Leu Arg Gln Lys Lys Ile Leu Leu
    290                 295                 300

Ile Leu Asp Asp Val Asp Lys Leu Glu Gln Leu Gln Ser Ile Val Gly
305                 310                 315                 320

Arg Pro Asp Trp Phe Gly Pro Gly Ser Arg Val Ile Ile Thr Thr Arg
                325                 330                 335

Asp Lys Gln Leu Leu Ser Cys His Leu Val Glu Lys Thr Tyr Glu Val
            340                 345                 350

Lys Lys Leu Lys Lys Lys Asp Ala Phe Arg Leu Leu Ser Trp Lys Gly
        355                 360                 365

Phe Arg Thr Glu Glu Val Asp Thr Ser Tyr Val Asn Val Met Asp Arg
    370                 375                 380

Val Leu Ala Tyr Ala Ser Gly His Pro Leu Ala Leu Glu Val Ile Gly
385                 390                 395                 400

Ser Lys Leu Phe Arg Lys Ser Ile Lys Glu Trp Glu Ser Ala Ile Asn
                405                 410                 415

Gln Tyr Glu Lys Ile Pro Asn Asn Gln Ile Leu Glu Ile Leu Lys Ile
            420                 425                 430

Ser Phe Asp Ser Leu Glu Glu Val Glu Lys Ser Val Phe Leu Asp Ile
        435                 440                 445

Ser Cys Cys Phe Lys Gly Tyr Ala Leu Ser Glu Val Glu Asp Ile Leu
    450                 455                 460

Arg Ala His Tyr Gly Asp Cys Met Lys Tyr His Ile Gly Val Leu Val
465                 470                 475                 480

Glu Lys Ser Leu Ile Lys Tyr Arg Trp Gly Cys Ile Val Thr Leu His
                485                 490                 495

Asp Leu Ile Glu Asp Met Gly Lys Glu Ile Val Arg Gln Lys Ser Pro
            500                 505                 510

Gln Lys Pro Gly Lys Arg Ser Arg Leu Trp Ser Pro Glu Asp Ile Ile
        515                 520                 525

Gln Val Leu Glu Asp Asn Ser Gly Ser Gly Glu Ile Glu Ile Ile Cys
    530                 535                 540

Leu Asn Ser Ser Leu Leu Asp Lys Glu Glu Thr Ile Glu Trp Asn Arg
545                 550                 555                 560
```

-continued

```
Lys Ala Phe Lys Lys Met Lys Asn Leu Lys Thr Leu Ile Ile Lys Asn
                565                 570                 575

Gly Asn Phe Ser Glu Gly Pro Lys Tyr Leu Pro Asn Ser Leu Arg Val
            580                 585                 590

Leu Glu Trp Leu Lys Tyr Pro Ser Gln Gly Leu Pro Pro Asp Phe Arg
        595                 600                 605

Ser Lys Lys Leu Val Ile Cys Lys Leu Pro Ser Ser Cys Phe Gly Thr
    610                 615                 620

Leu Glu Leu Ala Glu Leu Ser Lys Lys Phe Met Asn Met Thr Val Leu
625                 630                 635                 640

Asn Phe Asp Glu Cys Glu Gly Leu Thr Gln Ile Pro Asp Val Ser Gly
                645                 650                 655

Leu Pro Asn Leu Glu Asn Ile Ser Phe Lys Asn Cys Lys Ser Leu Ile
            660                 665                 670

Thr Ile His Asp Ser Ile Gly Phe Leu Asp Lys Leu Asn Ser Leu Asn
        675                 680                 685

Ala Val Gly Cys Ser Arg Leu Arg Ser Phe Pro Pro Leu Lys Leu Thr
    690                 695                 700

Ser Leu Glu Asn Leu Glu Leu Ser Tyr Cys Tyr Ser Leu Glu Cys Phe
705                 710                 715                 720

Pro Glu Ile Leu Gly Lys Met Glu Lys Met Thr Glu Leu Val Leu Glu
                725                 730                 735

Asp Cys Asp Ile Lys Glu Ile Pro Phe Ser Phe Lys Asn Leu Thr Glu
            740                 745                 750

Leu Gln Thr Leu Asp Leu Arg Phe Cys Arg Met Leu Arg Leu Pro Thr
        755                 760                 765

Ser Ile Val Met Met Pro Lys Leu Ser Glu Ile Ile Ala Trp Glu Ala
    770                 775                 780

Glu Gly Cys Leu Phe Pro Lys Gln Val Glu Gly Glu Glu Lys Val Ser
785                 790                 795                 800

Ser Met Val Ser Ser Asn Val Asp Ser Leu Arg Leu Ser Gly Cys Lys
                805                 810                 815

Leu Ser Asp Asp Phe Phe Pro Thr Thr Leu Ala Trp Phe Ser Asn Val
            820                 825                 830

Lys Asp Leu Asn Leu Ser Arg Asn Asn Phe Thr Val Leu Pro Glu Cys
        835                 840                 845

Ile Ser Asn Cys His Phe Leu Tyr Lys Leu Thr Leu Asp Tyr Cys His
    850                 855                 860

Ser Leu Arg Glu Ile Arg Gly Leu Pro Pro Asn Ile Gln His Leu Ser
865                 870                 875                 880

Ala Ile Asn Cys Thr Ser Phe Thr Ser Ser Cys Arg Ser Thr Leu Leu
                885                 890                 895

Asn Gln Lys Leu His Glu Ala Gly Asn Thr Met Phe Ser Phe Ser Gly
            900                 905                 910

Ala Met Phe Pro Glu Trp Phe Glu Asn His Ser Arg Gly Pro Ser Tyr
        915                 920                 925

Ser Phe Trp Val Gly Asn Lys Phe Pro Ala Ile Ala Leu Cys Ile Ala
    930                 935                 940

Ile Gly Pro Thr His Val Glu Tyr Val Gln Ile Val Gly Pro Ile Met
945                 950                 955                 960

Ile Ile Asn Gly Ile Glu Cys Ser Leu Pro Gly Val Asp Pro Tyr Leu
                965                 970                 975
```

```
Lys Met Leu Pro Asp His Thr Tyr Leu Phe Asp Leu Gln Gln Ile Val
            980                 985                 990

Phe Pro Asp Tyr Leu Asp Arg Phe  Val Ser Glu Asn Glu  Trp Asn His
        995                 1000                1005

Val Glu  Ile Thr Tyr Ala Val  Glu Lys Arg Phe Ser  Lys Lys Asp
    1010                 1015                1020

Lys His  Val Val Ile Pro Val  Ser Ile Glu Asn Gly  Ile Tyr Val
    1025                 1030                1035

Ser Lys  Gln Arg Ser Ser Met  Glu Asn Val Arg Phe  Thr Asp Pro
    1040                 1045                1050

Arg Lys  Lys Arg Arg Leu Asp  Val Asp Ser Glu Leu
    1055                 1060                1065
```

<210> SEQ ID NO 15
<211> LENGTH: 3195
<212> TYPE: DNA
<213> ORGANISM: Mucuna pruriens

<400> SEQUENCE: 15

```
atgggtttgg catcatattc cttgtccttc agctacgatg tgttcctcag tttcagaggc     60
tcagacacgc gccatggttt cactggtaat ctctacaaag ccctgcgtga caggggaatt    120
cacaccttca tcgacgacga ggacctccag agaggggacc aaatcacgtt ggcacttgag    180
aaggcaattg aatgctctag aattttcatc attgtgctct ctcacaacta tgcttcttct    240
tcgttttgct tgaacgaact cgcttacatc ctcgactgca ttaagactaa aggtttgttg    300
gttttgccaa ttttttatga cgtgagacac cacattggta gtttcggaga agcgttggct    360
aatcatgaaa agaagttcaa tgctaagagg gatggcttcg accttaatgt tgagaagctg    420
aataaatgga aaatgtctct acatcaagca gctaacttat ctggctatca tttcaaacac    480
ggggatggat acgaacacga gtttattaag aggatagttg atttagtctc tagcaaggtt    540
aaccgtgctc ctttacatgt tgcggattac ccgattggac ttgagtcacg agtgctacaa    600
gtaaagtcac ttctggatgt tggatctgat gatggtgtcc acatggtagg gatccatgga    660
ctcggtggaa ttggtaaaac cacactggct gttgcagttt ataattccat tgctgaccac    720
tttgaaggtt tatgttttct tgaaaacgtg agagaaaact cacacaaaca tgggttacaa    780
cacgtccaga gcatccttct ttctgaattg gttggtgaaa agaatatcaa cttagcaagt    840
gtgaaacaag gaatttcaat gatacagcat aggctacgcc aaaagaagat tcttttgatt    900
cttgatgacg ttgacaaaca cgagcagtta caagcaattg ttggaaaacc tgattggttg    960
ggtcctggca gcagagtcat catcacgact cgggacaaac aattgttggc atgtcatgaa   1020
gttaaaagaa catacgaagt gaagaagttg aacaaaaacg attctcttca actgcttagt   1080
tggaaagctt ttagaacaga aaaagttgat acaagttatg tggatgtcat gaatcgtgta   1140
gtaacttatg cttctggcct tccattggct ttggaagtaa taggttccaa cttgtttgga   1200
aaaagtatac aagaatggga atctgctata aatcagtata aaaaaattcc taataatcaa   1260
atcctaaagg tgcttaaaat aagttttgat gctttagagg aagaagagaa gagtgttttt   1320
cttgacattg cttgttgctt caaaggatat gaattgacag aggttgaaga tatacttggt   1380
gctcattatg gtgattgcat gaaatatcat attggggtgt tggttaaaaa atctctcata   1440
aaacttagtt ggcatggttc agttacattg cataacttga tagaggacat gggtaaggaa   1500
attgtccgac agaaatcacc aaaagagcca gggaagcgta gtagattatg gtcatcggaa   1560
gatataattc aagttttgga agagaactcg ggaactagtc aaattgaaat catatgtttg   1620
```

gttttttcct ttcatgacaa agaacaaata gtagaatgga atcgaaaggc cttcaagaag 1680
atgaaaaacc tcaaaacact tattattaaa aatggtaatt tttccaaagg tcccaaacat 1740
cttccaaata gtttaagagt actggaatgg tgtaaatatc ctgcacaagg gttaccacct 1800
gattttcgtt caaagaaact agccgtatgc aagttacctg aaagttgttt tgggtcactc 1860
gagttggccg acttatcaaa ggcaagtaag ttcgtgaata tcaatgtctt gaattttgac 1920
gaatgtgaag gtttaaccca aatacctgac atatctgggc tgtcaaattt agaaaaaatt 1980
tcattccgaa atagtgagaa tttaattaca atccatgagt ccttagggtt cctaggtaag 2040
cttaaattct tggatgcctt tggttgcagc aagcttagga gttttccacc cctcatgttg 2100
acttctctgg aaaaacttga actttcatat tgttccagtc ttgagagttt cccagaaata 2160
ttaggaaaaa tggaaaatat aagtgaactt gtgttagagg cctctggaat taaagaattg 2220
ccattttcat ttcaaaatct cagtgggctt gaaacattac aattgcgtca ttgtggaatg 2280
ttaaggttac caagtagcat tgtcatgatg ccaagattgg ctgagattat tgcttgggaa 2340
tggaaaggat ggctattgcc agaacaggtt gaggatgaag aaaaagtaaa ctcaatggtg 2400
gtgccttcaa atgtagattg tcttcgtctc tccggctgca acctgtccga taatctttta 2460
tcaataggtc tcacatggtt tgctaatgta aaagatttag acctatcgag gaataatttc 2520
acagttcttc ctgaatgcat cagttattgt catttttttat ggaagcttca tttagattat 2580
tgtcattttc ttcgagagat tagagggatt ccgccaaaca tacaacattt ctcagcaaga 2640
gtttgtaaat ccttgagttc gtcttctaga agcacattac tgaatcagaa agtgcatgag 2700
gctggaaaca ccatgttttg gttgtcagga gcaatatttc cagagtggtt ggagcagcac 2760
aggcagggac catctaattg tttctggttt cgtaacaagt tccctgccat tgctctctgt 2820
attgctattg gaccaactca ttacaaatat gttgaaattg ttggacctat tgtgatcatc 2880
aatggcattg aatgtttact tgacacggac catgatccct atttatggat gatgactgat 2940
cacacttatc tttttgatct gcaaaagaca aaagttgcag atattctgaa caaactagct 3000
atagaaaatg aatggaagca tgtggagatt acatacgaag ttacgcagag attcattgca 3060
aaagaaaagc aggtggagat cccagtcttt attgaaagcg gtatatatgt gttcaaagag 3120
aggaatagca tggaggatat tcaatttgtt gatccttata aaaagagaag attagatgat 3180
gaccaaagag catag 3195

<210> SEQ ID NO 16
<211> LENGTH: 1064
<212> TYPE: PRT
<213> ORGANISM: Mucuna pruriens

<400> SEQUENCE: 16

Met Gly Leu Ala Ser Tyr Ser Leu Ser Phe Ser Tyr Asp Val Phe Leu
1 5 10 15

Ser Phe Arg Gly Ser Asp Thr Arg His Gly Phe Thr Gly Asn Leu Tyr
20 25 30

Lys Ala Leu Arg Asp Arg Gly Ile His Thr Phe Ile Asp Asp Glu Asp
35 40 45

Leu Gln Arg Gly Asp Gln Ile Thr Leu Ala Leu Glu Lys Ala Ile Glu
50 55 60

Cys Ser Arg Ile Phe Ile Ile Val Leu Ser His Asn Tyr Ala Ser Ser
65 70 75 80

Ser Phe Cys Leu Asn Glu Leu Ala Tyr Ile Leu Asp Cys Ile Lys Thr

-continued

```
                85                  90                  95

Lys Gly Leu Leu Val Leu Pro Ile Phe Tyr Asp Val Arg His His Ile
            100                 105                 110

Gly Ser Phe Gly Glu Ala Leu Ala Asn His Glu Lys Lys Phe Asn Ala
        115                 120                 125

Lys Arg Asp Gly Phe Asp Leu Asn Val Glu Lys Leu Asn Lys Trp Lys
    130                 135                 140

Met Ser Leu His Gln Ala Ala Asn Leu Ser Gly Tyr His Phe Lys His
145                 150                 155                 160

Gly Asp Gly Tyr Glu His Glu Phe Ile Lys Arg Ile Val Asp Leu Val
                165                 170                 175

Ser Ser Lys Val Asn Arg Ala Pro Leu His Val Ala Asp Tyr Pro Ile
            180                 185                 190

Gly Leu Glu Ser Arg Val Leu Gln Val Lys Ser Leu Leu Asp Val Gly
        195                 200                 205

Ser Asp Asp Gly Val His Met Val Gly Ile His Gly Leu Gly Gly Ile
    210                 215                 220

Gly Lys Thr Thr Leu Ala Val Ala Val Tyr Asn Ser Ile Ala Asp His
225                 230                 235                 240

Phe Glu Gly Leu Cys Phe Leu Glu Asn Val Arg Glu Asn Ser His Lys
                245                 250                 255

His Gly Leu Gln His Val Gln Ser Ile Leu Leu Ser Glu Leu Val Gly
            260                 265                 270

Glu Lys Asn Ile Asn Leu Ala Ser Val Lys Gln Gly Ile Ser Met Ile
        275                 280                 285

Gln His Arg Leu Arg Gln Lys Lys Ile Leu Leu Ile Leu Asp Asp Val
    290                 295                 300

Asp Lys His Glu Gln Leu Gln Ala Ile Val Gly Lys Pro Asp Trp Leu
305                 310                 315                 320

Gly Pro Gly Ser Arg Val Ile Ile Thr Thr Arg Asp Lys Gln Leu Leu
                325                 330                 335

Ala Cys His Glu Val Lys Arg Thr Tyr Glu Val Lys Lys Leu Asn Lys
            340                 345                 350

Asn Asp Ser Leu Gln Leu Leu Ser Trp Lys Ala Phe Arg Thr Glu Lys
        355                 360                 365

Val Asp Thr Ser Tyr Val Asp Val Met Asn Arg Val Val Thr Tyr Ala
    370                 375                 380

Ser Gly Leu Pro Leu Ala Leu Glu Val Ile Gly Ser Asn Leu Phe Gly
385                 390                 395                 400

Lys Ser Ile Gln Glu Trp Glu Ser Ala Ile Asn Gln Tyr Lys Lys Ile
                405                 410                 415

Pro Asn Asn Gln Ile Leu Lys Val Leu Lys Ile Ser Phe Asp Ala Leu
            420                 425                 430

Glu Glu Glu Glu Lys Ser Val Phe Leu Asp Ile Ala Cys Cys Phe Lys
        435                 440                 445

Gly Tyr Glu Leu Thr Glu Val Glu Asp Ile Leu Gly Ala His Tyr Gly
    450                 455                 460

Asp Cys Met Lys Tyr His Ile Gly Val Leu Val Lys Lys Ser Leu Ile
465                 470                 475                 480

Lys Leu Ser Trp His Gly Ser Val Thr Leu His Asn Leu Ile Glu Asp
                485                 490                 495

Met Gly Lys Glu Ile Val Arg Gln Lys Ser Pro Lys Glu Pro Gly Lys
            500                 505                 510
```

```
Arg Ser Arg Leu Trp Ser Ser Glu Asp Ile Ile Gln Val Leu Glu Glu
        515                 520                 525

Asn Ser Gly Thr Ser Gln Ile Glu Ile Ile Cys Leu Val Phe Ser Phe
    530                 535                 540

His Asp Lys Glu Gln Ile Val Glu Trp Asn Arg Lys Ala Phe Lys Lys
545                 550                 555                 560

Met Lys Asn Leu Lys Thr Leu Ile Ile Lys Asn Gly Asn Phe Ser Lys
                565                 570                 575

Gly Pro Lys His Leu Pro Asn Ser Leu Arg Val Leu Glu Trp Cys Lys
            580                 585                 590

Tyr Pro Ala Gln Gly Leu Pro Pro Asp Phe Arg Ser Lys Lys Leu Ala
        595                 600                 605

Val Cys Lys Leu Pro Glu Ser Cys Phe Gly Ser Leu Glu Leu Ala Asp
    610                 615                 620

Leu Ser Lys Ala Ser Lys Phe Val Asn Ile Asn Val Leu Asn Phe Asp
625                 630                 635                 640

Glu Cys Glu Gly Leu Thr Gln Ile Pro Asp Ile Ser Gly Leu Ser Asn
                645                 650                 655

Leu Glu Lys Ile Ser Phe Arg Asn Ser Glu Asn Leu Ile Thr Ile His
            660                 665                 670

Glu Ser Leu Gly Phe Leu Gly Lys Leu Lys Phe Leu Asp Ala Phe Gly
        675                 680                 685

Cys Ser Lys Leu Arg Ser Phe Pro Pro Leu Met Leu Thr Ser Leu Glu
    690                 695                 700

Lys Leu Glu Leu Ser Tyr Cys Ser Ser Leu Glu Ser Phe Pro Glu Ile
705                 710                 715                 720

Leu Gly Lys Met Glu Asn Ile Ser Glu Leu Val Leu Glu Ala Ser Gly
                725                 730                 735

Ile Lys Glu Leu Pro Phe Ser Phe Gln Asn Leu Ser Gly Leu Glu Thr
            740                 745                 750

Leu Gln Leu Arg His Cys Gly Met Leu Arg Leu Pro Ser Ser Ile Val
        755                 760                 765

Met Met Pro Arg Leu Ala Glu Ile Ile Ala Trp Glu Trp Lys Gly Trp
    770                 775                 780

Leu Leu Pro Glu Gln Val Glu Asp Glu Glu Lys Val Asn Ser Met Val
785                 790                 795                 800

Val Pro Ser Asn Val Asp Cys Leu Arg Leu Ser Gly Cys Asn Leu Ser
                805                 810                 815

Asp Asn Leu Leu Ser Ile Gly Leu Thr Trp Phe Ala Asn Val Lys Asp
            820                 825                 830

Leu Asp Leu Ser Arg Asn Asn Phe Thr Val Leu Pro Glu Cys Ile Ser
        835                 840                 845

Tyr Cys His Phe Leu Trp Lys Leu His Leu Asp Tyr Cys His Phe Leu
    850                 855                 860

Arg Glu Ile Arg Gly Ile Pro Pro Asn Ile Gln His Phe Ser Ala Arg
865                 870                 875                 880

Val Cys Lys Ser Leu Ser Ser Ser Ser Arg Ser Thr Leu Leu Asn Gln
                885                 890                 895

Lys Val His Glu Ala Gly Asn Thr Met Phe Trp Leu Ser Gly Ala Ile
            900                 905                 910

Phe Pro Glu Trp Leu Glu Gln His Arg Gln Gly Pro Ser Asn Cys Phe
        915                 920                 925
```

```
Trp Phe Arg Asn Lys Phe Pro Ala Ile Ala Leu Cys Ile Ala Ile Gly
    930                 935                 940

Pro Thr His Tyr Lys Tyr Val Glu Ile Val Gly Pro Ile Val Ile Ile
945                 950                 955                 960

Asn Gly Ile Glu Cys Leu Leu Asp Thr Asp His Asp Pro Tyr Leu Trp
                965                 970                 975

Met Met Thr Asp His Thr Tyr Leu Phe Asp Leu Gln Lys Thr Lys Val
            980                 985                 990

Ala Asp Ile Leu Asn Lys Leu Ala  Ile Glu Asn Glu Trp  Lys His Val
        995                 1000                1005

Glu Ile  Thr Tyr Glu Val Thr  Gln Arg Phe Ile Ala  Lys Glu Lys
    1010                1015                1020

Gln Val  Glu Ile Pro Val Phe  Ile Glu Ser Gly Ile  Tyr Val Phe
    1025                1030                1035

Lys Glu  Arg Asn Ser Met Glu  Asp Ile Gln Phe Val  Asp Pro Tyr
    1040                1045                1050

Lys Lys  Arg Arg Leu Asp Asp  Asp Gln Arg Ala
    1055                1060
```

<210> SEQ ID NO 17
<211> LENGTH: 3201
<212> TYPE: DNA
<213> ORGANISM: Cajanus cajun

<400> SEQUENCE: 17

```
atggctgtgg catcatcttc cttgatctat gattatgaat atgatgtgtt cctgagcttc     60

agaggagaag atacccgtta cggtttcacc ggaaatctct acaacgccct ccgtgacaac    120

ggaattcaca cattcatcga cgacgaccaa ctccaaaaag gggacgagat cacatcagca    180

cttgagaagg ccatcgaaca ctcgagaatt ttcatcatcg tcctctctct caactacgct    240

tcttcctctt tttgcttaaa cgagctcact tacatccttc actgcactaa gagaaaatct    300

ttgttggttt tgcctctctt ttataacatc gatccttctg accttcgtca ccacagaggt    360

agcttcggag aagcgttgac caatcatgaa aacaatttca aagctaagaa ggaggggttg    420

gagcataaca tggacaagct ccacaaatgg aagatggctc ttcatcaagc agccagcttg    480

tctggctatc atttcaaaca aggggatgga tatgaatacg agtttattaa aaagatagtt    540

aaattggtat ctagcaagat taaccgtgct cctttgcatg ttgcggatta cacggttgga    600

cttgagtctc gagtgctgga agtaaagttg cttctaaatg ttgggtctga tgactgtgtc    660

cacatggttg gaatccatgg tattggtgga attggtaaaa ccacacttgc tgttgaagtt    720

tataattcca ttgctgacca ttttgaaggt ttatgctttc ttgaaaacgt cagagaaaat    780

tcaaataaac atggtttaca acatctccag agcatccttc tatctgaaat ggttggagaa    840

aagaatatca acttagcaag tgttagacaa ggaatttcaa tgatacaaca taggttacgg    900

caaaagaagg ttcttttgat tgtagatgat gttgataagc acgagcagtt acaggctatt    960

gttggagaac ctaattggtt tggtcccggc agcagagtca tcatcactac tcgagacaaa   1020

caactgctgg catgtcacca ggttaaaaca aactatgaag ttgaaaagtt gaataagagc   1080

gatgctctac aactgctcag ttggaaagct tttaaaactg acaaagttga tacaagttat   1140

gtaaatgtca tgaatcgtgt agtaacttat gcttctggcc ttccattggc tttggaagta   1200

ataggttcca acttattcgg aaaaactgta ggagaatggg aatctgctat aaatcaatat   1260

gaaaaaattc ctaataatca aatctttaag atacttaaaa aaagttttga tgctttagaa   1320
```

-continued

```
gaacaagaga agagcgtttt tcttgacatt gcttgttgct tcaaaggatt tcgattgaaa   1380
gaggtcgaag atatactttg tgctcactat ggggattgca tgaaatatca tattagggtg   1440
ttggttgaaa aatctctcat aaaacagaac tggtatggtg cagttacatt gcatgacttg   1500
atagaagaca tgggtaaaga aattgtccga cagaaatcac caaaagagcc agggaagcgc   1560
agtagattat ggtctccgga tgatataatt caagttttgg aagatgactc gggtactggt   1620
aaaattgaaa tcatatgttt ggatttctcc ctacttgaca aagaagaaat agtagaatgg   1680
aatcgaaagg ctttcaagaa gatgaaaaat ctcaaaacac ttattattaa aaatggtcat   1740
ttttccaaag gtcccaaaca tcttccgaat agtttaagag tactggaatg gttgaaatat   1800
ccttcaaaag ggttaccaac tgatttttgt tcaaagaaac tctccatatg caagttacct   1860
aaaagctgtt ttgggtcact ggagttggct gacttatcaa agaagttcac gaatatgact   1920
gttttgaatt ttgaggaatg ccaaggatta acacaaatac cagatgtatc tgggctgcca   1980
aatttagaaa atatttcatt ccgaaatagt gacaatttag ctacaatcca tgactccatt   2040
gggttccttg gtaagcttaa aattttgaat gcttttggtt gcaagaaact taggagtttt   2100
ccaccgctca agttggaatc tcttgaaaaa cttgaacttt catattgttc cagtctagag   2160
agtttcccag aaatattagg aaaaatggaa aacataacag aacttgtgtt ggaggcttct   2220
gccataaaga attttccagt ttcatttcaa aatctcactg ggcttcaaga attactgttg   2280
cgtcactgtg gagtgttaac gttaccaagt agcattgtca tgatgccaaa attggttcag   2340
atcattgctt gggaatggaa agggtggcta ttcccaaaac aggttgaggg tgaagaaaaa   2400
gttcgttcaa tgatgtcttc aaacgtaaat tgtcttcgtc tctcaggctg taacctgtcc   2460
gatgattttt tttcaatagg tctttcatgg tttgctaatg taaaagaatt agacctatca   2520
agaaataatt tcaaagttct tcctgaatgc atcagtgatt gtcaattcct actggagctt   2580
aacttagatt attgttattg tcttcaagaa attagaggga ttccgccaag catagaactt   2640
ttctctgcaa gagaatgtaa atccttgacc tcttctggta gaagcacatt agtgaatcag   2700
aagctgcatg aggttggaaa caccttgttt aggttttcag gagcaaggtt tccagagtgg   2760
ttcgaccacc aaagccgggg atcatctaat tctttttggt ttcgccacaa gttccctgcc   2820
atttgtcttt gtattgctat tggaccaact cattacgaat attttaaaat tgttggacct   2880
accttgacca tcaatggcat tgaatgttta cctgacgatg aggattttga ctatttttgg   2940
atggagcctg atcacacaca tcttttcgat ctgcaaaaga tgcatctcag agataatcta   3000
gacaaatatg ttgtagaaaa tgaatggaac catgtggaga ttacttacca tccgacaatc   3060
ggggaaagac agaaggttgt ggagatccca gtctttactg aaactggtat ctatgtgtac   3120
aaacagagga gtagcatggt ggatattcaa tttactgatc cttataaaag gagaagattg   3180
gatgatgact caggatcata a                                              3201
```

<210> SEQ ID NO 18
<211> LENGTH: 1066
<212> TYPE: PRT
<213> ORGANISM: Cajanus cajun

<400> SEQUENCE: 18

```
Met Ala Val Ala Ser Ser Ser Leu Ile Tyr Asp Tyr Glu Tyr Asp Val
1               5                   10                  15

Phe Leu Ser Phe Arg Gly Glu Asp Thr Arg Tyr Gly Phe Thr Gly Asn
            20                  25                  30

Leu Tyr Asn Ala Leu Arg Asp Asn Gly Ile His Thr Phe Ile Asp Asp
```

```
        35                  40                  45

Asp Gln Leu Gln Lys Gly Asp Glu Ile Thr Ser Ala Leu Glu Lys Ala
    50                  55                  60

Ile Glu His Ser Arg Ile Phe Ile Ile Val Leu Ser Leu Asn Tyr Ala
65                  70                  75                  80

Ser Ser Ser Phe Cys Leu Asn Glu Leu Thr Tyr Ile Leu His Cys Thr
                85                  90                  95

Lys Arg Lys Ser Leu Leu Val Leu Pro Leu Phe Tyr Asn Ile Asp Pro
            100                 105                 110

Ser Asp Leu Arg His His Arg Gly Ser Phe Gly Glu Ala Leu Thr Asn
        115                 120                 125

His Glu Asn Asn Phe Lys Ala Lys Lys Glu Gly Leu Glu His Asn Met
    130                 135                 140

Asp Lys Leu His Lys Trp Lys Met Ala Leu His Gln Ala Ala Ser Leu
145                 150                 155                 160

Ser Gly Tyr His Phe Lys Gln Gly Asp Gly Tyr Glu Tyr Glu Phe Ile
                165                 170                 175

Lys Lys Ile Val Lys Leu Val Ser Ser Lys Ile Asn Arg Ala Pro Leu
            180                 185                 190

His Val Ala Asp Tyr Thr Val Gly Leu Glu Ser Arg Val Leu Glu Val
        195                 200                 205

Lys Leu Leu Leu Asn Val Gly Ser Asp Asp Cys Val His Met Val Gly
    210                 215                 220

Ile His Gly Ile Gly Gly Ile Gly Lys Thr Thr Leu Ala Val Glu Val
225                 230                 235                 240

Tyr Asn Ser Ile Ala Asp His Phe Glu Gly Leu Cys Phe Leu Glu Asn
                245                 250                 255

Val Arg Glu Asn Ser Asn Lys His Gly Leu Gln His Leu Gln Ser Ile
            260                 265                 270

Leu Leu Ser Glu Met Val Gly Glu Lys Asn Ile Asn Leu Ala Ser Val
        275                 280                 285

Arg Gln Gly Ile Ser Met Ile Gln His Arg Leu Arg Gln Lys Lys Val
    290                 295                 300

Leu Leu Ile Val Asp Asp Val Asp Lys His Glu Gln Leu Gln Ala Ile
305                 310                 315                 320

Val Gly Glu Pro Asn Trp Phe Gly Pro Gly Ser Arg Val Ile Ile Thr
                325                 330                 335

Thr Arg Asp Lys Gln Leu Leu Ala Cys His Gln Val Lys Thr Asn Tyr
            340                 345                 350

Glu Val Glu Lys Leu Asn Lys Ser Asp Ala Leu Gln Leu Leu Ser Trp
        355                 360                 365

Lys Ala Phe Lys Thr Asp Lys Val Asp Thr Ser Tyr Val Asn Val Met
    370                 375                 380

Asn Arg Val Val Thr Tyr Ala Ser Gly Leu Pro Leu Ala Leu Glu Val
385                 390                 395                 400

Ile Gly Ser Asn Leu Phe Gly Lys Thr Val Gly Glu Trp Glu Ser Ala
                405                 410                 415

Ile Asn Gln Tyr Glu Lys Ile Pro Asn Asn Gln Ile Phe Lys Ile Leu
            420                 425                 430

Lys Lys Ser Phe Asp Ala Leu Glu Glu Gln Glu Lys Ser Val Phe Leu
        435                 440                 445

Asp Ile Ala Cys Cys Phe Lys Gly Phe Arg Leu Lys Glu Val Glu Asp
    450                 455                 460
```

-continued

```
Ile Leu Cys Ala His Tyr Gly Asp Cys Met Lys Tyr His Ile Arg Val
465                 470                 475                 480

Leu Val Glu Lys Ser Leu Ile Lys Gln Asn Trp Tyr Gly Ala Val Thr
                485                 490                 495

Leu His Asp Leu Ile Glu Asp Met Gly Lys Glu Ile Val Arg Gln Lys
            500                 505                 510

Ser Pro Lys Glu Pro Gly Lys Arg Ser Arg Leu Trp Ser Pro Asp Asp
        515                 520                 525

Ile Ile Gln Val Leu Glu Asp Asp Ser Gly Thr Gly Lys Ile Glu Ile
    530                 535                 540

Ile Cys Leu Asp Phe Ser Leu Leu Asp Lys Glu Glu Ile Val Glu Trp
545                 550                 555                 560

Asn Arg Lys Ala Phe Lys Lys Met Lys Asn Leu Lys Thr Leu Ile Ile
                565                 570                 575

Lys Asn Gly His Phe Ser Lys Gly Pro Lys His Leu Pro Asn Ser Leu
            580                 585                 590

Arg Val Leu Glu Trp Leu Lys Tyr Pro Ser Lys Gly Leu Pro Thr Asp
        595                 600                 605

Phe Cys Ser Lys Lys Leu Ser Ile Cys Lys Leu Pro Lys Ser Cys Phe
    610                 615                 620

Gly Ser Leu Glu Leu Ala Asp Leu Ser Lys Lys Phe Thr Asn Met Thr
625                 630                 635                 640

Val Leu Asn Phe Glu Glu Cys Gln Gly Leu Thr Gln Ile Pro Asp Val
                645                 650                 655

Ser Gly Leu Pro Asn Leu Glu Asn Ile Ser Phe Arg Asn Ser Asp Asn
            660                 665                 670

Leu Ala Thr Ile His Asp Ser Ile Gly Phe Leu Gly Lys Leu Lys Ile
        675                 680                 685

Leu Asn Ala Phe Gly Cys Lys Lys Leu Arg Ser Phe Pro Pro Leu Lys
    690                 695                 700

Leu Glu Ser Leu Glu Lys Leu Glu Leu Ser Tyr Cys Ser Ser Leu Glu
705                 710                 715                 720

Ser Phe Pro Glu Ile Leu Gly Lys Met Glu Asn Ile Thr Glu Leu Val
                725                 730                 735

Leu Glu Ala Ser Ala Ile Lys Asn Phe Pro Val Ser Phe Gln Asn Leu
            740                 745                 750

Thr Gly Leu Gln Glu Leu Leu Leu Arg His Cys Gly Val Leu Thr Leu
        755                 760                 765

Pro Ser Ser Ile Val Met Met Pro Lys Leu Val Gln Ile Ile Ala Trp
    770                 775                 780

Glu Trp Lys Gly Trp Leu Phe Pro Lys Gln Val Glu Gly Glu Glu Lys
785                 790                 795                 800

Val Arg Ser Met Met Ser Ser Asn Val Asn Cys Leu Arg Leu Ser Gly
                805                 810                 815

Cys Asn Leu Ser Asp Asp Phe Phe Ser Ile Gly Leu Ser Trp Phe Ala
            820                 825                 830

Asn Val Lys Glu Leu Asp Leu Ser Arg Asn Asn Phe Lys Val Leu Pro
        835                 840                 845

Glu Cys Ile Ser Asp Cys Gln Phe Leu Leu Glu Leu Asn Leu Asp Tyr
    850                 855                 860

Cys Tyr Cys Leu Gln Glu Ile Arg Gly Ile Pro Pro Ser Ile Glu Leu
865                 870                 875                 880
```

-continued

```
Phe Ser Ala Arg Glu Cys Lys Ser Leu Thr Ser Ser Gly Arg Ser Thr
            885                 890                 895

Leu Val Asn Gln Lys Leu His Glu Val Gly Asn Thr Leu Phe Arg Phe
            900                 905                 910

Ser Gly Ala Arg Phe Pro Glu Trp Phe Asp His Gln Ser Arg Gly Ser
        915                 920                 925

Ser Asn Ser Phe Trp Phe Arg His Lys Phe Pro Ala Ile Cys Leu Cys
    930                 935                 940

Ile Ala Ile Gly Pro Thr His Tyr Glu Tyr Phe Lys Ile Val Gly Pro
945                 950                 955                 960

Thr Leu Thr Ile Asn Gly Ile Glu Cys Leu Pro Asp Asp Glu Asp Phe
            965                 970                 975

Asp Tyr Phe Trp Met Glu Pro Asp His Thr His Leu Phe Asp Leu Gln
            980                 985                 990

Lys Met His Leu Arg Asp Asn Leu  Asp Lys Tyr Val Val  Glu Asn Glu
        995                 1000                1005

Trp Asn  His Val Glu Ile Thr  Tyr His Pro Thr Ile  Gly Glu Arg
    1010                 1015                 1020

Gln Lys  Val Val Glu Ile Pro  Val Phe Thr Glu Thr  Gly Ile Tyr
    1025                 1030                 1035

Val Tyr  Lys Gln Arg Ser Ser  Met Val Asp Ile Gln  Phe Thr Asp
    1040                 1045                 1050

Pro Tyr  Lys Arg Arg Arg Leu  Asp Asp Asp Ser Gly  Ser
    1055                 1060                 1065


<210> SEQ ID NO 19
<211> LENGTH: 3177
<212> TYPE: DNA
<213> ORGANISM: Abrus precatorius

<400> SEQUENCE: 19

atggctgtta gatcatgttc ttcttccttc acctatgcat tcacctatga tgttttcctt     60

agctttagag gctcagatac acgtcatggt tttgttggca atctatttaa agctcttcaa    120

gacaagggaa ttcacacctt cattgatgat gaggggcttc aaagaggaga ggaaatatca    180

ccagcacttg tcaaggcaat tgaagagtca agaattgcca tcgctgtgct ctctaataat    240

tatgcatatt cttcattttg cttagatgaa cttgcccaca tccttgagtg tgttaagaga    300

aaagatacat tggttttgcc cctttttat gatgttgatc cctctcatgt gagataccaa     360

agaggtagtt atggagaagc attggcaagt catggagaaa ggttcaagca taacatggag    420

aagttgcaga aatggaagat ggctttgcat catgtagcta acttgtctgg ctaccatttc    480

aaacacggag atggttatga atacgagttt attgggagga ttgttgagtt ggtttccaac    540

aagattaatc gtgctccttt acatgttgcg gattatcctg ttggactaga gtcacaagtg    600

ctggaagtaa ggaaactttt ggatgttgga tctgatgatg gtgttctaat gatagggatt    660

catggaattg gtgggatagg aaaaacaaca cttgctctgg cagtttacaa tttgattgct    720

gaccattttg atggtttgtg ttttctagaa aatgtgagag aaaattcaga caaacatggg    780

ttacaacatc tccaaagcat cctactttca gaaatacttg gagagacgaa aattaagtta    840

gcgagtgtca aacaaggaat ttcaatacta caacacaggc tccagcgaca gaaggttctc    900

ttgattctag atgatgtcga caagcacgag caattaaatg ccattgttgg aaaacctgat    960

tggtttggtc ctggcagtag agtcatcatc acgacccggg acaaacatct actagcatgt   1020

catgaagtta aaagtacaca tgaggtgaag aaattgaata agaacgatgc tcttcaatta   1080
```

```
cttagttgga aagcatttaa atcagaaaaa gttgatccaa gttatgtgga tgtcatgaat   1140

tgtgcagtag cttatgcttc tggtcatcca ttggctttgg aagtaatcgg ttccaacttg   1200

tttggtaaaa gtatagaaca atggaaatct gctatcaatc aatataaaag aattccaaat   1260

tgtcatatcc taaagatact taaagtaagc tttgatgctt tagaggaaga agagaagagt   1320

gtttttcttg acattgcctg ttgctttaaa ggatataact tagaagaagt tgaagatata   1380

cttcatgctc attatggtga ctccatgaaa tatcatattg ggttgctggt tgaaaaatct   1440

ctcataaagc ttacttgggc tggtggggtg acattgcatg acttgataga ggacatgggt   1500

aaagagattg tccgacagaa atcaccgaaa gatcctggga agcgcagtag attatggtta   1560

ccggaagata taattcatgt tttcgaacac gactcgggaa ctggtgaaat tgaaatcata   1620

cgtctggctt cctccttact tgacaaagaa gaaataatta aatggaatag aaaggccttc   1680

aagaagatga aaaacctcaa aacacttata attaaaaatg gtcatttttc caaaggtccc   1740

aaacatcttc cgaatagttt aagagtactg gaatgggcga aatatccttc acaagggttt   1800

ccagctaatt tttgttcaaa gaaactgagc atatgcaagt tacctaaaag ttgtttctca   1860

ctagagttgg ctgacttatc agagaagttc atgaacatga gtgttttgaa ttttgacgag   1920

tgtgaaggtt taacacaaat accagatgta tcggggctcc aaaatttaga aaaattttca   1980

ttcaaaaatt gtgagaattt aattacaatt catgattcca ttggattcct acataagctt   2040

aaattcttga atgctatagg ttgcagaaag ctcaggagtt ttccacccct caaactgacc   2100

tctcttgaga aacttgaact ttcatattgt tccaatcttg agtgttttcc agaaatatta   2160

gggaaaatgg aaaatataac agaacttgtg ttggaggcct ctgccataaa agaattgcca   2220

ttttcatttc aaaatctcac tgggcttcaa atattacagt tgcgtctagg aggaatgatt   2280

aggttaccta gcagcattgt catgatgcca aaattgactg agattattgc ttgggattgg   2340

aaagggttgc tatggccaag acaggttgag ggtgaagaaa aagtaagctc aatggtgtct   2400

tcaaatgtag attgtctttg tctctcaggc tgcaacctgt ctgatcaatt tttaccagta   2460

gctctctcat ggtttgttaa tgtaaaagat ttagacctat caaggaacaa gttcacagtt   2520

cttcctgaat gcatcagtga atgccatttt ttatggaagc ttattttgga ttattgcaat   2580

tgtcttcgag aaattagagg gatgccacca aacatagaac atttctctgc aagaaactgt   2640

aaatccttga cttcttgtag aagcacatta ctgaatcaga aactgcatga agctggaaac   2700

accatgtttt ggttgtcagg aacatggttt ccagagtggt tcgagcacca cagcaaggga   2760

ctgtctaatt ctttctggtt tcgtgataag tttcctgcca tagctctttg tactgctatt   2820

ggaccaacgc gtgaacagat tacaattgtt ggacctattg tgatcatcaa tggcattgaa   2880

tgttcggttg atgatgagga tgattcctat ttatggatgg agactgatca tacatatctt   2940

tttgatctgc aaaagataaa tttcgcagat aatttggaca aagaacttgt agaaaatgaa   3000

tggaaccatg tggagattac atactcagtc atatccaatg aaaaggaaaa acatgtggag   3060

attccagtct ttatagaaag tggaatctat atattcaaac agaggagtag aatggaggat   3120

attcgattca ctgatcctta taaaaggaga aaattagatg atggtttgga atcataa      3177
```

<210> SEQ ID NO 20
<211> LENGTH: 1057
<212> TYPE: PRT
<213> ORGANISM: Abrus precatorius

<400> SEQUENCE: 20

-continued

```
Met Ala Val Arg Ser Cys Ser Ser Ser Phe Thr Tyr Ala Phe Thr Tyr
1               5                   10                  15

Asp Val Phe Leu Ser Phe Arg Gly Ser Asp Thr Arg His Gly Phe Val
            20                  25                  30

Gly Asn Leu Phe Lys Ala Leu Gln Asp Lys Gly Ile His Thr Phe Ile
        35                  40                  45

Asp Asp Glu Gly Leu Gln Arg Gly Glu Glu Ile Ser Pro Ala Leu Val
    50                  55                  60

Lys Ala Ile Glu Glu Ser Arg Ile Ala Ile Ala Val Leu Ser Asn Asn
65                  70                  75                  80

Tyr Ala Tyr Ser Ser Phe Cys Leu Asp Glu Leu Ala His Ile Leu Glu
                85                  90                  95

Cys Val Lys Arg Lys Asp Thr Leu Val Leu Pro Leu Phe Tyr Asp Val
            100                 105                 110

Asp Pro Ser His Val Arg Tyr Gln Arg Gly Ser Tyr Gly Glu Ala Leu
        115                 120                 125

Ala Ser His Gly Glu Arg Phe Lys His Asn Met Glu Lys Leu Gln Lys
    130                 135                 140

Trp Lys Met Ala Leu His His Val Ala Asn Leu Ser Gly Tyr His Phe
145                 150                 155                 160

Lys His Gly Asp Gly Tyr Glu Tyr Glu Phe Ile Gly Arg Ile Val Glu
                165                 170                 175

Leu Val Ser Asn Lys Ile Asn Arg Ala Pro Leu His Val Ala Asp Tyr
            180                 185                 190

Pro Val Gly Leu Glu Ser Gln Val Leu Glu Val Arg Lys Leu Leu Asp
        195                 200                 205

Val Gly Ser Asp Asp Gly Val Leu Met Ile Gly Ile His Gly Ile Gly
    210                 215                 220

Gly Ile Gly Lys Thr Thr Leu Ala Leu Ala Val Tyr Asn Leu Ile Ala
225                 230                 235                 240

Asp His Phe Asp Gly Leu Cys Phe Leu Glu Asn Val Arg Glu Asn Ser
                245                 250                 255

Asp Lys His Gly Leu Gln His Leu Gln Ser Ile Leu Leu Ser Glu Ile
            260                 265                 270

Leu Gly Glu Thr Lys Ile Lys Leu Ala Ser Val Lys Gln Gly Ile Ser
        275                 280                 285

Ile Leu Gln His Arg Leu Gln Arg Gln Lys Val Leu Leu Ile Leu Asp
    290                 295                 300

Asp Val Asp Lys His Glu Gln Leu Asn Ala Ile Val Gly Lys Pro Asp
305                 310                 315                 320

Trp Phe Gly Pro Gly Ser Arg Val Ile Ile Thr Thr Arg Asp Lys His
                325                 330                 335

Leu Leu Ala Cys His Glu Val Lys Ser Thr His Glu Val Lys Lys Leu
            340                 345                 350

Asn Lys Asn Asp Ala Gln Leu Leu Ser Trp Lys Ala Phe Lys Ser Glu
        355                 360                 365

Lys Val Asp Pro Ser Tyr Val Asp Val Met Asn Cys Ala Val Ala Tyr
    370                 375                 380

Ala Ser Gly His Pro Leu Ala Leu Glu Val Ile Gly Ser Asn Leu Phe
385                 390                 395                 400

Gly Lys Ser Ile Glu Gln Trp Lys Ser Ala Ile Asn Gln Tyr Lys Arg
                405                 410                 415

Ile Pro Asn Cys His Ile Leu Lys Ile Leu Lys Val Ser Phe Asp Ala
```

-continued

```
            420                 425                 430

Leu Glu Glu Glu Glu Lys Ser Val Phe Leu Asp Ile Ala Cys Cys Phe
        435                 440                 445

Lys Gly Tyr Asn Leu Glu Glu Val Glu Asp Ile Leu His Ala His Tyr
    450                 455                 460

Gly Asp Ser Met Lys Tyr His Ile Gly Leu Leu Val Glu Lys Ser Leu
465                 470                 475                 480

Ile Lys Leu Thr Trp Ala Gly Gly Val Thr Leu His Asp Leu Ile Glu
                485                 490                 495

Asp Met Gly Lys Glu Ile Val Arg Gln Lys Ser Pro Lys Asp Pro Gly
            500                 505                 510

Lys Arg Ser Arg Leu Trp Leu Pro Glu Asp Ile Ile His Val Phe Glu
        515                 520                 525

His Asp Ser Gly Thr Gly Glu Ile Glu Ile Ile Arg Leu Ala Ser Ser
    530                 535                 540

Leu Leu Asp Lys Glu Glu Ile Ile Lys Trp Asn Arg Lys Ala Phe Lys
545                 550                 555                 560

Lys Met Lys Asn Leu Lys Thr Leu Ile Ile Lys Asn Gly His Phe Ser
                565                 570                 575

Lys Gly Pro Lys His Leu Pro Asn Ser Leu Arg Val Leu Glu Trp Ala
            580                 585                 590

Lys Tyr Pro Ser Gln Gly Phe Pro Ala Asn Phe Cys Ser Lys Lys Leu
        595                 600                 605

Ser Ile Cys Lys Leu Pro Lys Ser Cys Phe Ser Leu Glu Leu Ala Asp
    610                 615                 620

Leu Ser Glu Lys Phe Met Asn Met Ser Val Leu Asn Phe Asp Glu Cys
625                 630                 635                 640

Glu Gly Leu Thr Gln Ile Pro Asp Val Ser Gly Leu Gln Asn Leu Glu
                645                 650                 655

Lys Phe Ser Phe Lys Asn Cys Glu Asn Leu Ile Thr Ile His Asp Ser
            660                 665                 670

Ile Gly Phe Leu His Lys Leu Lys Phe Leu Asn Ala Ile Gly Cys Arg
        675                 680                 685

Lys Leu Arg Ser Phe Pro Pro Leu Lys Leu Thr Ser Leu Glu Lys Leu
    690                 695                 700

Glu Leu Ser Tyr Cys Ser Asn Leu Glu Cys Phe Pro Glu Ile Leu Gly
705                 710                 715                 720

Lys Met Glu Asn Ile Thr Glu Leu Val Leu Glu Ala Ser Ala Ile Lys
                725                 730                 735

Glu Leu Pro Phe Ser Phe Gln Asn Leu Thr Gly Leu Gln Ile Leu Gln
            740                 745                 750

Leu Arg Leu Gly Gly Met Ile Arg Leu Pro Ser Ser Ile Val Met Met
        755                 760                 765

Pro Lys Leu Thr Glu Ile Ile Ala Trp Asp Trp Lys Gly Leu Leu Trp
    770                 775                 780

Pro Arg Gln Val Glu Gly Glu Glu Lys Val Ser Ser Met Val Ser Ser
785                 790                 795                 800

Asn Val Asp Cys Leu Cys Leu Ser Gly Cys Asn Leu Ser Asp Gln Phe
                805                 810                 815

Leu Pro Val Ala Leu Ser Trp Phe Val Asn Val Lys Asp Leu Asp Leu
            820                 825                 830

Ser Arg Asn Lys Phe Thr Val Leu Pro Glu Cys Ile Ser Glu Cys His
        835                 840                 845
```

```
Phe Leu Trp Lys Leu Ile Leu Asp Tyr Cys Asn Cys Leu Arg Glu Ile
    850                 855                 860

Arg Gly Met Pro Pro Asn Ile Glu His Phe Ser Ala Arg Asn Cys Lys
865                 870                 875                 880

Ser Leu Thr Ser Cys Arg Ser Thr Leu Leu Asn Gln Lys Leu His Glu
                885                 890                 895

Ala Gly Asn Thr Met Phe Trp Leu Ser Gly Thr Trp Phe Pro Glu Trp
            900                 905                 910

Phe Glu His His Ser Lys Gly Leu Ser Asn Ser Phe Trp Phe Arg Asp
        915                 920                 925

Lys Phe Pro Ala Ile Ala Leu Cys Thr Ala Ile Gly Pro Thr Arg Glu
    930                 935                 940

Gln Ile Thr Ile Val Gly Pro Ile Val Ile Ile Asn Gly Ile Glu Cys
945                 950                 955                 960

Ser Val Asp Asp Glu Asp Asp Ser Tyr Leu Trp Met Glu Thr Asp His
                965                 970                 975

Thr Tyr Leu Phe Asp Leu Gln Lys Ile Asn Phe Ala Asp Asn Leu Asp
            980                 985                 990

Lys Glu Leu Val Glu Asn Glu Trp  Asn His Val Glu Ile  Thr Tyr Ser
        995                 1000                1005

Val Ile  Ser Asn Glu Lys Glu  Lys His Val Glu Ile  Pro Val Phe
    1010                 1015                 1020

Ile Glu  Ser Gly Ile Tyr Ile  Phe Lys Gln Arg Ser  Arg Met Glu
    1025                 1030                 1035

Asp Ile  Arg Phe Thr Asp Pro  Tyr Lys Arg Arg Lys  Leu Asp Asp
    1040                 1045                 1050

Gly Leu  Glu Ser
    1055
```

<210> SEQ ID NO 21
<211> LENGTH: 3198
<212> TYPE: DNA
<213> ORGANISM: Vigna unguiculata

<400> SEQUENCE: 21

```
atggctgtgc catcattctc cttttccttc acctatgacg ttttcctgag cttcagagga     60
gaagacactc gttacggttt caccggaaat ctttacagag cccttcgtga cagaggaatt    120
cacaccttca tcgacgacga ggagcttcgc aaaggagacg aaatcacctc tgcacttgag    180
aaggcaatcg aaggttctag aattttcatc atcgttttct ctctcaacta cgcctcttcc    240
tctttttgct tgaacgagct cgcctacatc cttccccacg ctaagagaaa tgctttgctg    300
gttttgccac tcttctacga cgtcgttcct tcccacgtgc gacaccacac gggtagcttt    360
ggagaagcat tggatgctca tgaaaagagg ttcagaggta tgagtcaggg ttttgagctt    420
aacattgaga agctcaacaa atggaagatg gctctgcgtc gagcagctaa cttgtctggc    480
tatcatttca aacatgggga ggaatatgaa taccagttta tcgagaagat agttaaattg    540
gtctctaaca agattaaccg tgttccttta cacgttgcgg attatcaggt aggactagaa    600
aagcgagtgc tggaagtaaa gatgcttgta gatgtaggat ctgatgattg tgtccacatg    660
gtaggaatct atggactcgg tggagttggt aaaaccacac ttgctcttgc actttacaat    720
tccatcgctg accattttga aggtttgtgt ttccttgaaa atgtgagaga gaattcaaac    780
aaacaaggct tacatcatct tcagagaatc cttctttctg aaatggttgg agaaaataat    840
```

-continued

```
atcaacatag gtagtgtgag acaaggaatt tcaatgatgc agcataggct acggcagaag    900
aagattcttt tgattctaga tgatgttgac aagcacgaac agttacaggc aattgttgga    960
agccctgatt ggtttggtcc cggcagtaga gtcatcatca caactaggga caaacaattg   1020
ttgtcatgtc acttggttga aaaattatat gaagtgaaga agttggaaaa gaacgatgct   1080
cttcgattgc tcagttggaa aggttttaga accgaagaag ttgatacaag ttactccaat   1140
gtcatggata gtgtactagc ttatgcttct ggccatccat tggctttgga agtaatcggt   1200
tcgaagttgt tcagaaaaag tgtagaagaa tgggaatctg ccatcaaaca gtatgagaaa   1260
attcctatca gtcaaatcct ggaggtgctt aaaataagtt ttgatgcttt agaggaagta   1320
gagaagagtg tttttcttga cattgcttgt tgcttcaaag gatatgcatt gtcagatata   1380
gaagatattc ttcgtgccca atatggtcat agcatgaaat atcatattgg ggtgttggtt   1440
gaaaaatctc tcataaaata caaatggaaa tttggagtta caatgcatga cttgatagaa   1500
gacatgggta aagaaattgt ccgacagcaa tcaccaaaaa ggccagggaa gcgcagtaga   1560
ttatggtcac cagaagatat aattcaagtt ttggaagaca actcgggaag tggagaaatt   1620
gaaatcatat gtttgaattc ttcattacct gacaaagaag aaataataga atggaacaga   1680
aaggccttca agaagatgaa aaacctcaaa acacttatca ttaaaaaagg taatttttcg   1740
gaaggtccta aatatcttcc aaatagttta agagtactgg aatggttgaa atatccttca   1800
caagggctac cgccagattt tcgttcaaag gaacttgcca tatgcaaatt acctacaagt   1860
tgttttgggt cactcgaatt ggctgagtta tcaaagaaat tcatgaatat gactcttttg   1920
gattttgaag aatgtcaagg tttgacacag atacctgatg tatctgggat gccaaattta   1980
gaaaaaattt cattcaagaa ttgtaagagt ttaaatacaa tccatgactc cattgggttc   2040
ctaggtaagc tgaactcctt gaatgctgtt ggctgcagca agcttaggag ttttcccccc   2100
ctcaaattga cttctctgaa aaatcttgaa ctttcatatt gttacggtct cgagagcttc   2160
ccagaagtat taggaaaaat gggaaagata acaaaacttg tcttggagga ctgtaacata   2220
aaagaattgc cattttcatt tcaaaatctc actgagcttc agacattaca gttgcgtttc   2280
tgtccaatgt tacggttacc aagtagtata gtcatgatgc caaaactggc cgaaattatt   2340
gtttgggaat ctaaaggatg gctatttcca aaacaagttg aggttgaaga gaaagtaagt   2400
tcaatggtgt cttcaaatgt agattgtctt cttctcccac ggtgcaaact ctccgatgat   2460
tttctcccaa tagctcttgc atggtttgct aatgtaaaag agttagacct gtcatggaac   2520
aatttcacgg ttcttccgga atgtattagc aattgtcatt ttttatctaa gcttacttta   2580
gatggctgtc atagtcttcg agagatcaga gggattccac caaacattca acttttacta   2640
gcagtagatt gtaaatcctt cacttcttct tgcagaagca ctttactgaa tcagaaactg   2700
catgaggctg gaaacaccat gtttcggttg tcaggagcaa gctttccaga atggttcgat   2760
caccacaatc agggaccatc gtgttctttc tgggttggca acaaattccc ttcaattgct   2820
ctttgtattg ctattggacc agctcatttg gaacatgtta caattgatag acctatcata   2880
aacatcaatg gcgtcaaatg ttcgcttcat ggggaggaaa aaccttattt aaatatgctc   2940
cctcatcaca catatctttt tgatttgcaa catatagttt tttcagatta tctagacaga   3000
tttgttacag aaaatgaatg gaaccacgtg gagattacat actcagtcaa gcagagattc   3060
aatgaaaaag acaaacatgc ggtgacccca gtctctgtag aaaatggaat ctatgtgttg   3120
aaacagagga gcagcatgga ggatattcaa ttcactgatc cccacaaaaa gagaagatta   3180
gatgttgatc cagagtag                                                 3198
```

<210> SEQ ID NO 22
<211> LENGTH: 1065
<212> TYPE: PRT
<213> ORGANISM: Vigna unguiculata

<400> SEQUENCE: 22

Met Ala Val Pro Ser Phe Ser Phe Ser Phe Thr Tyr Asp Val Phe Leu
1 5 10 15

Ser Phe Arg Gly Glu Asp Thr Arg Tyr Gly Phe Thr Gly Asn Leu Tyr
20 25 30

Arg Ala Leu Arg Asp Arg Gly Ile His Thr Phe Ile Asp Asp Glu Glu
35 40 45

Leu Arg Lys Gly Asp Glu Ile Thr Ser Ala Leu Glu Lys Ala Ile Glu
50 55 60

Gly Ser Arg Ile Phe Ile Ile Val Phe Ser Leu Asn Tyr Ala Ser Ser
65 70 75 80

Ser Phe Cys Leu Asn Glu Leu Ala Tyr Ile Leu Pro His Ala Lys Arg
85 90 95

Asn Ala Leu Leu Val Leu Pro Leu Phe Tyr Asp Val Val Pro Ser His
100 105 110

Val Arg His His Thr Gly Ser Phe Gly Glu Ala Leu Asp Ala His Glu
115 120 125

Lys Arg Phe Arg Gly Met Ser Gln Gly Phe Glu Leu Asn Ile Glu Lys
130 135 140

Leu Asn Lys Trp Lys Met Ala Leu Arg Arg Ala Ala Asn Leu Ser Gly
145 150 155 160

Tyr His Phe Lys His Gly Glu Glu Tyr Glu Tyr Gln Phe Ile Glu Lys
165 170 175

Ile Val Lys Leu Val Ser Asn Lys Ile Asn Arg Val Pro Leu His Val
180 185 190

Ala Asp Tyr Gln Val Gly Leu Glu Lys Arg Val Leu Glu Val Lys Met
195 200 205

Leu Val Asp Val Gly Ser Asp Asp Cys Val His Met Val Gly Ile Tyr
210 215 220

Gly Leu Gly Gly Val Gly Lys Thr Thr Leu Ala Leu Ala Leu Tyr Asn
225 230 235 240

Ser Ile Ala Asp His Phe Glu Gly Leu Cys Phe Leu Glu Asn Val Arg
245 250 255

Glu Asn Ser Asn Lys Gln Gly Leu His His Leu Gln Arg Ile Leu Leu
260 265 270

Ser Glu Met Val Gly Glu Asn Asn Ile Asn Ile Gly Ser Val Arg Gln
275 280 285

Gly Ile Ser Met Met Gln His Arg Leu Arg Gln Lys Lys Ile Leu Leu
290 295 300

Ile Leu Asp Asp Val Asp Lys His Glu Gln Leu Gln Ala Ile Val Gly
305 310 315 320

Ser Pro Asp Trp Phe Gly Pro Gly Ser Arg Val Ile Ile Thr Thr Arg
325 330 335

Asp Lys Gln Leu Leu Ser Cys His Leu Val Glu Lys Leu Tyr Glu Val
340 345 350

Lys Lys Leu Glu Lys Asn Asp Ala Leu Arg Leu Leu Ser Trp Lys Gly
355 360 365

Phe Arg Thr Glu Glu Val Asp Thr Ser Tyr Ser Asn Val Met Asp Ser

```
    370                 375                 380

Val Leu Ala Tyr Ala Ser Gly His Pro Leu Ala Leu Glu Val Ile Gly
385                 390                 395                 400

Ser Lys Leu Phe Arg Lys Ser Val Glu Glu Trp Glu Ser Ala Ile Lys
                405                 410                 415

Gln Tyr Glu Lys Ile Pro Ile Ser Gln Ile Leu Glu Val Leu Lys Ile
            420                 425                 430

Ser Phe Asp Ala Leu Glu Glu Val Glu Lys Ser Val Phe Leu Asp Ile
        435                 440                 445

Ala Cys Cys Phe Lys Gly Tyr Ala Leu Ser Asp Ile Glu Asp Ile Leu
    450                 455                 460

Arg Ala Gln Tyr Gly His Ser Met Lys Tyr His Ile Gly Val Leu Val
465                 470                 475                 480

Glu Lys Ser Leu Ile Lys Tyr Lys Trp Lys Phe Gly Val Thr Met His
                485                 490                 495

Asp Leu Ile Glu Asp Met Gly Lys Glu Ile Val Arg Gln Gln Ser Pro
            500                 505                 510

Lys Arg Pro Gly Lys Arg Ser Arg Leu Trp Ser Pro Glu Asp Ile Ile
        515                 520                 525

Gln Val Leu Glu Asp Asn Ser Gly Ser Gly Glu Ile Glu Ile Ile Cys
    530                 535                 540

Leu Asn Ser Ser Leu Pro Asp Lys Glu Glu Ile Ile Glu Trp Asn Arg
545                 550                 555                 560

Lys Ala Phe Lys Lys Met Lys Asn Leu Lys Thr Leu Ile Ile Lys Lys
                565                 570                 575

Gly Asn Phe Ser Glu Gly Pro Lys Tyr Leu Pro Asn Ser Leu Arg Val
            580                 585                 590

Leu Glu Trp Leu Lys Tyr Pro Ser Gln Gly Leu Pro Pro Asp Phe Arg
        595                 600                 605

Ser Lys Glu Leu Ala Ile Cys Lys Leu Pro Thr Ser Cys Phe Gly Ser
    610                 615                 620

Leu Glu Leu Ala Glu Leu Ser Lys Lys Phe Met Asn Met Thr Leu Leu
625                 630                 635                 640

Asp Phe Glu Glu Cys Gln Gly Leu Thr Gln Ile Pro Asp Val Ser Gly
                645                 650                 655

Met Pro Asn Leu Glu Lys Ile Ser Phe Lys Asn Cys Lys Ser Leu Asn
            660                 665                 670

Thr Ile His Asp Ser Ile Gly Phe Leu Gly Lys Leu Asn Ser Leu Asn
        675                 680                 685

Ala Val Gly Cys Ser Lys Leu Arg Ser Phe Pro Pro Leu Lys Leu Thr
    690                 695                 700

Ser Leu Lys Asn Leu Glu Leu Ser Tyr Cys Tyr Gly Leu Glu Ser Phe
705                 710                 715                 720

Pro Glu Val Leu Gly Lys Met Gly Lys Ile Thr Lys Leu Val Leu Glu
                725                 730                 735

Asp Cys Asn Ile Lys Glu Leu Pro Phe Ser Phe Gln Asn Leu Thr Glu
            740                 745                 750

Leu Gln Thr Leu Gln Leu Arg Phe Cys Pro Met Leu Arg Leu Pro Ser
        755                 760                 765

Ser Ile Val Met Met Pro Lys Leu Ala Glu Ile Ile Val Trp Glu Ser
    770                 775                 780

Lys Gly Trp Leu Phe Pro Lys Gln Val Glu Val Glu Glu Lys Val Ser
785                 790                 795                 800
```

```
Ser Met Val Ser Ser Asn Val Asp Cys Leu Leu Leu Pro Arg Cys Lys
                805                 810                 815

Leu Ser Asp Asp Phe Leu Pro Ile Ala Leu Ala Trp Phe Ala Asn Val
            820                 825                 830

Lys Glu Leu Asp Leu Ser Trp Asn Asn Phe Thr Val Leu Pro Glu Cys
        835                 840                 845

Ile Ser Asn Cys His Phe Leu Ser Lys Leu Thr Leu Asp Gly Cys His
    850                 855                 860

Ser Leu Arg Glu Ile Arg Gly Ile Pro Pro Asn Ile Gln Leu Leu Leu
865                 870                 875                 880

Ala Val Asp Cys Lys Ser Phe Thr Ser Ser Cys Arg Ser Thr Leu Leu
                885                 890                 895

Asn Gln Lys Leu His Glu Ala Gly Asn Thr Met Phe Arg Leu Ser Gly
            900                 905                 910

Ala Ser Phe Pro Glu Trp Phe Asp His His Asn Gln Gly Pro Ser Cys
        915                 920                 925

Ser Phe Trp Val Gly Asn Lys Phe Pro Ser Ile Ala Leu Cys Ile Ala
    930                 935                 940

Ile Gly Pro Ala His Leu Glu His Val Thr Ile Asp Arg Pro Ile Ile
945                 950                 955                 960

Asn Ile Asn Gly Val Lys Cys Ser Leu His Gly Glu Glu Lys Pro Tyr
                965                 970                 975

Leu Asn Met Leu Pro His His Thr Tyr Leu Phe Asp Leu Gln His Ile
            980                 985                 990

Val Phe Ser Asp Tyr Leu Asp Arg  Phe Val Thr Glu Asn  Glu Trp Asn
        995                 1000                1005

His Val  Glu Ile Thr Tyr Ser  Val Lys Gln Arg Phe  Asn Glu Lys
    1010                1015                1020

Asp Lys  His Ala Val Thr Pro  Val Ser Val Glu Asn  Gly Ile Tyr
    1025                1030                1035

Val Leu  Lys Gln Arg Ser Ser  Met Glu Asp Ile Gln  Phe Thr Asp
    1040                1045                1050

Pro His  Lys Lys Arg Arg Leu  Asp Val Asp Pro Glu
    1055                1060                1065


<210> SEQ ID NO 23
<211> LENGTH: 663
<212> TYPE: DNA
<213> ORGANISM: Phakopsora pachyrhizi

<400> SEQUENCE: 23

atgcgatcaa cggtgttggt tggttggata accagtggct ttgtagcact ggtcttacac      60

gccaccagtg caacccaaca gaagaaagga ccagtgattg tttcaaaggt atactttgat     120

attcaacaag gttcaaagag tttgggtagg atcgagatag gtcttttcaa aggtacacca     180

aagactagtg agaacttcag atcactctca gttggtgaga agagatcaaa ggatggaatc     240

gatctatctt acaaaggttc aaagtttcat agagttataa aaaactttat gattcagggt     300

ggtgacttta caaacggtga tggtacaggt gggatttcaa tctacggatc aaaatttcca     360

gatgagaact ttaaacacaa acatactgga gctggaatag tttctatggc taattctggt     420

cctaatacaa atggatctca attctttatc tgcactgctg ttacgtcttg gttagatgga     480

agacacgttg tttttggaaa agttataaaa ggcttagacg ttgttaccaa aattgaacaa     540

tcacctacta atggtaaaga taatcctctc gaagatatca tcatttcaga ttcgggtgag     600
```

atcaagatag aagaagattt ggattcagat ggaaagaaga ttccactgag agtagaatta 660
tga 663

<210> SEQ ID NO 24
<211> LENGTH: 220
<212> TYPE: PRT
<213> ORGANISM: Phakopsora pachyrhizi

<400> SEQUENCE: 24

Met Arg Ser Thr Val Leu Val Gly Trp Ile Thr Ser Gly Phe Val Ala
1 5 10 15

Leu Val Leu His Ala Thr Ser Ala Thr Gln Gln Lys Lys Gly Pro Val
20 25 30

Ile Val Ser Lys Val Tyr Phe Asp Ile Gln Gln Gly Ser Lys Ser Leu
35 40 45

Gly Arg Ile Glu Ile Gly Leu Phe Lys Gly Thr Pro Lys Thr Ser Glu
50 55 60

Asn Phe Arg Ser Leu Ser Val Gly Glu Lys Arg Ser Lys Asp Gly Ile
65 70 75 80

Asp Leu Ser Tyr Lys Gly Ser Lys Phe His Arg Val Ile Lys Asn Phe
85 90 95

Met Ile Gln Gly Gly Asp Phe Thr Asn Gly Asp Gly Thr Gly Gly Ile
100 105 110

Ser Ile Tyr Gly Ser Lys Phe Pro Asp Glu Asn Phe Lys His Lys His
115 120 125

Thr Gly Ala Gly Ile Val Ser Met Ala Asn Ser Gly Pro Asn Thr Asn
130 135 140

Gly Ser Gln Phe Phe Ile Cys Thr Ala Val Thr Ser Trp Leu Asp Gly
145 150 155 160

Arg His Val Val Phe Gly Lys Val Ile Lys Gly Leu Asp Val Val Thr
165 170 175

Lys Ile Glu Gln Ser Pro Thr Asn Gly Lys Asp Asn Pro Leu Glu Asp
180 185 190

Ile Ile Ile Ser Asp Ser Gly Glu Ile Lys Ile Glu Glu Asp Leu Asp
195 200 205

Ser Asp Gly Lys Lys Ile Pro Leu Arg Val Glu Leu
210 215 220

<210> SEQ ID NO 25
<211> LENGTH: 663
<212> TYPE: DNA
<213> ORGANISM: Phakopsora pachyrhizi

<400> SEQUENCE: 25
atgcactcga aagtgttgat atcgtgggtc atgagtgcct ttgtggcaat cgtcctacat 60
gcagctaatt cgatccagga caatgaggag ccaccaatcg ttgcaaaggt gtattttgat 120
atgaaacaag gctcaaagaa tcttggtagg attgagatcg gtttattcaa aaatacgccc 180
aagactagtg aaaacttcag agcacttgca gttggtgata aaaaatcaaa agatgggatt 240
cctctggcct acaagggctc taagtttcac agagtcatta accaatttat gattcaaggt 300
ggagatttta ctaaaggcga tggaactggc ggactatcta tctacggacc aaagtttcaa 360
gacgaaaact ttataaacaa acatactgga cctggaactg tttctatggc aaactctggt 420
cctgatacga acggctctca gtttttttatc tgcactgctc ttacttcttg gttagatggt 480

-continued agacacgtag tttttggaaa agttcttaga ggaatggatg ttgtttttcg aattgaaact 540
ttacctactg acaatggaga caggcccaag gaagatatcg ttatagccga ctctggtgaa 600
ctcaagatcg atgatgaact tgatgcagac ggaaacaagg tggctcctcg tgtagaatta 660
taa 663

<210> SEQ ID NO 26
<211> LENGTH: 220
<212> TYPE: PRT
<213> ORGANISM: Phakopsora pachyrhizi

<400> SEQUENCE: 26

Met His Ser Lys Val Leu Ile Ser Trp Val Met Ser Ala Phe Val Ala
1 5 10 15

Ile Val Leu His Ala Ala Asn Ser Ile Gln Asp Asn Glu Glu Pro Pro
20 25 30

Ile Val Ala Lys Val Tyr Phe Asp Met Lys Gln Gly Ser Lys Asn Leu
35 40 45

Gly Arg Ile Glu Ile Gly Leu Phe Lys Asn Thr Pro Lys Thr Ser Glu
50 55 60

Asn Phe Arg Ala Leu Ala Val Gly Asp Lys Lys Ser Lys Asp Gly Ile
65 70 75 80

Pro Leu Ala Tyr Lys Gly Ser Lys Phe His Arg Val Ile Asn Gln Phe
85 90 95

Met Ile Gln Gly Gly Asp Phe Thr Lys Gly Asp Gly Thr Gly Gly Leu
100 105 110

Ser Ile Tyr Gly Pro Lys Phe Gln Asp Glu Asn Phe Ile Asn Lys His
115 120 125

Thr Gly Pro Gly Thr Val Ser Met Ala Asn Ser Gly Pro Asp Thr Asn
130 135 140

Gly Ser Gln Phe Phe Ile Cys Thr Ala Leu Thr Ser Trp Leu Asp Gly
145 150 155 160

Arg His Val Val Phe Gly Lys Val Leu Arg Gly Met Asp Val Val Phe
165 170 175

Arg Ile Glu Thr Leu Pro Thr Asp Asn Gly Asp Arg Pro Lys Glu Asp
180 185 190

Ile Val Ile Ala Asp Ser Gly Glu Leu Lys Ile Asp Asp Glu Leu Asp
195 200 205

Ala Asp Gly Asn Lys Val Ala Pro Arg Val Glu Leu
210 215 220

<210> SEQ ID NO 27
<211> LENGTH: 8574
<212> TYPE: DNA
<213> ORGANISM: Artificial Sequence
<220> FEATURE:
<223> OTHER INFORMATION: Transient expression vector with Vigna unguiculata FIT1

<400> SEQUENCE: 27
atctcctgtg gttggcatgc acatacaaat ggacgaacgg ataaaccttt tcacgccctt 60
ttaaatatcc gattattcta ataaacgctc ttttctctta ggtttacccg ccaatatatc 120
ctgtcaaaca ctgatagttt aaactgaagg cgggaaacga caatctgcta gtggatctcc 180
cagtcacgac gttgtaaaac gggcgccccg cggaaagctt gctagccaat tggggcccaa 240
cgttctcgag ggatcttct gcaagcatct ctatttcctg aaggtctaac ctcgaagatt 300
taagatttaa ttacgtttat aattacaaaa ttgattctag tatctttaat ttaatgctta 360
tacattatta attaatttag tactttcaat ttgttttcag aaattatttt actatttttt 420
ataaaataaa agggagaaaa tggctattta aatactagcc tattttattt caattttagc 480
ttaaaatcag ccccaattag ccccaatttc aaattcaaat ggtccagccc aattcctaaa 540
taacccaccc ctaacccgcc cggtttcccc ttttgatcca tgcagtcaac gcccagaatt 600
tccctatata attttttaat tcccaaacac ccctaactct atcccatttc tcaccaaccg 660
ccacatagat ctatcctctt atctctcaaa ctctctcgaa ccttccccta accctagcag 720
cctctcatca tcctcacctc aaaacccacc ggatctagaa ggccttggat ccacccggga 780
gaattcgtcg actttgcggc cgcatcgata ctgcaggagc tcggtaccga gcatggctgt 840
gccatcattc tccttttcct tcacctatga cgttttcctg agcttcagag gagaagacac 900
tcgttacggt ttcaccggaa atctttacag agcccttcgt gacagaggaa ttcacacctt 960
catcgacgac gaggagcttc gcaaaggaga cgaaatcacc tctgcacttg agaaggcaat 1020
cgaaggttct agaattttca tcatcgtttt ctctctcaac tacgcctctt cctctttttg 1080
cttgaacgag ctcgcctaca tccttcccca cgctaagaga aatgctttgc tggttttgcc 1140
actcttctac gacgtcgttc cttcccacgt gcgacaccac acgggtagct ttggagaagc 1200
attggatgct catgaaaaga ggttcagagg tatgagtcag ggttttgagc ttaacattga 1260
gaagctcaac aaatggaaga tggctctgcg tcgagcagct aacttgtctg gctatcattt 1320
caaacatggg gaggaatatg aataccagtt tatcgagagg atagttgaat tggtatctaa 1380
gaagattaac cgtgctcctt tacacgttgg ggattatcca gttggactag aggcgcgggt 1440
gctagaagta aagttgcttc tagaagtagg atctgatgat gttgtccact tggtagggat 1500
ccatggactc ggtggaatcg gtaaaaccac acttgctctt gcactctaca attccatcgc 1560
tgaccatttt gaaggtttgt gtttcctcga aaatgtgaga gagaattcaa acaaacacgg 1620
cctacatcat cttcaaagaa tccttctttc tcaagtgctt ggagaaaata atatcaacat 1680
aactagtgtg agacaaggaa tttcaatgat gcagcatagg ctacggcaga agaagattct 1740
cttgattcta gatgatgttg acaagcacga acagttacag gcaattgttg gaagacctga 1800
ttggtttggt cccggcagta gagtcatcat cacaaccagg gacaaacagt tgttgtcgtg 1860
tcacttggtt gaaaaattat ataaagtgaa gaagttggaa aagaacaatg ctcttcgact 1920
gcttagttgg aaaggtttta gaacagaaga agttgataca agttatttga acgtcatgga 1980
tcgtgtacta gcttatgctt ctggacatcc attggctttg gaagtaatag gttcgaagtt 2040
gtttagtaaa agtgtaaaag aatgggaatc tgccatcaaa cagtacgaga aaattcctag 2100
caatcaaatc cttgaggtac ttaaagtaag ttttgatgct ttagaggaag tagagaagag 2160
tgtttttctt gacattgctt gttgtttcaa aggatatgca ttgtcagaga tagaagatat 2220
tcttcgtgct cattatggtg attgcatgaa atatcatatt ggagtgttag ttgaaaaatc 2280
tctcatgaaa tatggctata attctgtagt tacgttgcat gacttgatag aagacatggg 2340
gaaagaaatt gtccgagaga aatcaccaaa aaatccaggg aagcgcagta gattatggtc 2400
accagaagat ataattcaag ttttggaaga caattcggga agtggagaaa ttgaaatcat 2460
atgtttgaat tcctccttac ctgacaaaga agaaatagta ggatggaaca gaaaggcctt 2520
caaaaagatg aaaaacctca aaacacttat cattaaaaaa ggtaaatttt cggaaggtcc 2580
taaatatctt ccaaatagtt taagagtact tgaatggttg aaatatcctt cacaagggct 2640
accaccagat tttcgttcaa agaaacttgc catatgcaaa ttaccttcaa gtagttttgg 2700

-continued

```
gtcactcgaa ttggctgagt tttcaaagaa gttcatgaat atgactcttc tgaattttga   2760
tgaatgtgaa ggtttaacac atatacctga tgtgtctggg ctgccaaatt tagaaaaagt   2820
ttcattcaag aattgtaaga gtttagttac aatccatgac tccttcgggt tcctaggtaa   2880
gcttaactcc ttgagtgctg ttggttgcag caagcttagg agttttcctc ccctcaaatt   2940
gacttctctg gaaaatcttg aactttcata ttgtcacagt ctcgagagct tcccagaaat   3000
attagaaaaa atgggaaaga taacagaact tgtcttggag gattgtcaca taaaagaatt   3060
accattttca tttcataatc tcaccgagct tcaaacatta cagttgcgtt ggtgtccaat   3120
attaaggtta ccaagtagta ttgtcatgat gccaaaactg gcccagatta ttgcttggga   3180
atctaaagga tggctatttc caaaacaggt tgatggggaa gaaaaaggaa gctcaatggt   3240
gtcttcaaat gtagattgtc ttgttctctc agggtgcaaa ctctcagatg actttttccc   3300
agtaattcct gaatggtttt ctaatgtaaa agatttagac ctgtcaagga ataatttcac   3360
ggttcttcct gaatgcatca gcaattgtca ttctttatgc aagcttactt tagatagctg   3420
tcatagtctt caagagattc gagggattcc acctaacata cgacatttat cagcaagaaa   3480
ttgtaaatcc ttcacttcct cttgcagaag cactttactg aatcagaaac tgcatgaggc   3540
tgggaacacc atgttttggt tgtcaggagc aaagtttcca gaatggttcg atcaccacgg   3600
tcggggacca tcttgttctt tctgggttgg caacaaattc ccttcaattg ctctttgtat   3660
tgctattgga caaactcata tcgaacaagt tgaaatcgtt ggacctatca tgatcatcaa   3720
cggcattgaa tgttcatttg atgaggagga ggatccttat ttatatatgc tccctcatca   3780
cacacatatt ttcgatttgc aacatatagt tttttcagat tatctagaca gatatgtttc   3840
agaaaatgaa tggaaccatg tggagatcac atactcagtg gagcagagat tcaataaaaa   3900
agacaaacat gcggtgaccc caatctctat agaaaatgga atctatgtgt tgaaacagag   3960
gagcagcatg gaggatattc aattcactga tccccacaaa aagagaagat tagatgttgt   4020
ctaaccaacg atcgttcaaa catttggcaa taaagtttct taagattgaa tcctgttgcc   4080
ggtcttgcga tgattatcat ataatttctg ttgaattacg ttaagcatgt aataattaac   4140
atgtaatgca tgacgttatt tatgagatgg gtttttatga ttagagtccc gcaattatac   4200
atttaatacg cgatagaaaa caaaatatag cgcgcaaact aggataaatt atcgcgcgcg   4260
gtgtcatcta tgttactaga tccctaggga agttcctatt ccgaagttcc tattctctga   4320
aaagtatagg aacttctttg cgtattgggc gctcttggcc tttttggcca ccggtcgtac   4380
ggttaaaacc accccagtac attaaaaacg tccgcaatgt gttattaagt tgtctaagcg   4440
tcaatttgtt tacaccacaa tatatcctgc caccagccag ccaacagctc cccgaccggc   4500
agctcggcac aaaatcacca ctcgatacag gcagcccatc agtccactag acgctcaccg   4560
ggctggttgc cctcgccgct gggctggcgg ccgtctatgg ccctgcaaac gcgccagaaa   4620
cgccgtcgaa gccgtgtgcg agacaccgca gccgccggcg ttgtggatac ctcgcggaaa   4680
acttggccct cactgacaga tgaggggcgg acgttgacac ttgaggggcc gactcacccg   4740
gcgcggcgtt gacagatgag gggcaggctc gatttcggcc ggcgacgtgg agctggccag   4800
cctcgcaaat cggcgaaaac gcctgatttt acgcgagttt cccacagatg atgtggacaa   4860
gcctggggat aagtgccctg cggtattgac acttgagggg cgcgactact gacagatgag   4920
gggcgcgatc cttgacactt gaggggcaga gtgctgacag atgaggggcg cacctattga   4980
catttgaggg gctgtccaca ggcagaaaat ccagcatttg caagggtttc cgcccgtttt   5040
```

-continued

```
tcggccaccg ctaacctgtc ttttaacctg cttttaaacc aatatttata aaccttgttt   5100
ttaaccaggg ctgcgccctg tgcgcgtgac cgcgcacgcc gaagggggt  gccccccctt   5160
ctcgaaccct cccggcccgc tctcgcgttg gcagcatcac ccataattgt ggtttcaaaa   5220
tcggctccgt cgatactatg ttatacgcca actttgaaaa caactttgaa aaagctgttt   5280
tctggtattt aaggttttag aatgcaagga acagtgaatt ggagttcgtc ttgttataat   5340
tagcttcttg gggtatcttt aaatactgta gaaaagagga aggaaataat aaatggctaa   5400
aatgagaata tcaccggaat tgaaaaaact gatcgaaaaa taccgctgcg taaaagatac   5460
ggaaggaatg tctcctgcta aggtatataa gctggtggga gaaaatgaaa acctatattt   5520
aaaaatgacg gacagccggt ataaagggac cacctatgat gtggaacggg aaaaggacat   5580
gatgctatgg ctggaaggaa agctgcctgt tccaaaggtc ctgcactttg aacggcatga   5640
tggctggagc aatctgctca tgagtgaggc cgatggcgtc ctttgctcgg aagagtatga   5700
agatgaacaa agccctgaaa agattatcga gctgtatgcg gagtgcatca ggctctttca   5760
ctccatcgac atatcggatt gtccctatac gaatagctta gacagccgct tagccgaatt   5820
ggattactta ctgaataacg atctggccga tgtggattgc gaaaactggg aagaagacac   5880
tccatttaaa gatccgcgcg agctgtatga tttttaaag  acggaaaagc ccgaagagga   5940
acttgtcttt tcccacggcg acctgggaga cagcaacatc tttgtgaaag atggcaaagt   6000
aagtggcttt attgatcttg ggagaagcgg cagggcggac aagtggtatg acattgcctt   6060
ctgcgtccgg tcgatcaggg aggatattgg ggaagaacag tatgtcgagc tattttttga   6120
cttactgggg atcaagcctg attgggagaa aataaaatat tatattttac tggatgaatt   6180
gttttagtac ctagatgtgg cgcaacgatg ccggcgacaa gcaggagcgc accgacttct   6240
tccgcatcaa gtgttttggc tctcaggccg aggcccacgg caagtatttg ggcaaggggt   6300
cgctggtatt cgtgcagggc aagattcgga ataccaagta cgagaaggac ggccagacgg   6360
tctacgggac cgacttcatt gccgataagg tggattatct ggacaccaag gcaccaggcg   6420
ggtcaaatca ggaataaggg cacattgccc cggcgtgagt cggggcaatc ccgcaaggag   6480
ggtgaatgaa tcggacgttt gaccggaagg catacaggca agaactgatc gacgcggggt   6540
tttccgccga ggatgccgaa accatcgcaa gccgcaccgt catgcgtgcg ccccgcgaaa   6600
ccttccagtc cgtcggctcg atggtccagc aagctacggc caagatcgag cgcgacagcg   6660
tgcaactggc tccccctgcc ctgcccgcgc catcggccgc cgtggagcgt tcgcgtcgtc   6720
tcgaacagga ggcggcaggt ttggcgaagt cgatgaccat cgacacgcga ggaactatga   6780
cgaccaagaa gcgaaaaacc gccggcgagg acctggcaaa acaggtcagc gaggccaagc   6840
aagccgcgtt gctgaaacac acgaagcagc agatcaagga aatgcagctt tccttgttcg   6900
atattgcgcc gtggccggac acgatgcgag cgatgccaaa cgacacggcc cgctctgccc   6960
tgttcaccac gcgcaacaag aaaatcccgc gcgaggcgct gcaaaacaag gtcattttcc   7020
acgtcaacaa ggacgtgaag atcacctaca ccggcgtcga gctgcgggcc gacgatgacg   7080
aactggtgtg gcagcaggtg ttggagtacg cgaagcgcac ccctatcggc gagccgatca   7140
ccttcacgtt ctacgagctt tgccaggacc tgggctggtc gatcaatggc cggtattaca   7200
cgaaggccga ggaatgcctg tcgcgcctac aggcgacggc gatgggcttc acgtccgacc   7260
gcgttgggca cctggaatcg gtgtcgctgc tgcaccgctt ccgcgtcctg gaccgtggca   7320
agaaaacgtc ccgttgccag gtcctgatcg acgaggaaat cgtcgtgctg tttgctggcg   7380
accactacac gaaattcata tgggagaagt accgcaagct gtcgccgacg gcccgacgga   7440
```

tgttcgacta tttcagctcg caccgggagc cgtacccgct caagctggaa accttccgcc 7500
tcatgtgcgg atcggattcc acccgcgtga agaagtggcg cgagcaggtc ggcgaagcct 7560
gcgaagagtt gcgaggcagc ggcctggtgg aacacgcctg ggtcaatgat gacctggtgc 7620
attgcaaacg ctagggcctt gtggggtcag ttccggctgg gggttcagca gccagcgctt 7680
tactgagatc ctcttccgct tcctcgctca ctgactcgct gcgctcggtc gttcggctgc 7740
ggcgagcggt atcagctcac tcaaaggcgg taatacggtt atccacagaa tcaggggata 7800
acgcaggaaa gaacatgtga gcaaaaggcc agcaaaaggc caggaaccgt aaaaaggccg 7860
cgttgctggc gtttttccat aggctccgcc cccctgacga gcatcacaaa aatcgacgct 7920
caagtcagag gtggcgaaac ccgacaggac tataaagata ccaggcgttt ccccctggaa 7980
gctccctcgt gcgctctcct gttccgaccc tgccgcttac cggatacctg tccgcctttc 8040
tcccttcggg aagcgtggcg ctttctcata gctcacgctg taggtatctc agttcggtgt 8100
aggtcgttcg ctccaagctg ggctgtgtgc acgaaccccc cgttcagccc gaccgctgcg 8160
ccttatccgg taactatcgt cttgagtcca acccggtaag acacgactta tcgccactgg 8220
cagcagccac tggtaacagg attagcagag cgaggtatgt aggcggtgct acagagttct 8280
tgaagtggtg gcctaactac ggctacacta gaagaacagt atttggtatc tgcgctctgc 8340
tgaagccagt taccttcgga aaaagagttg gtagctcttg atccggcaaa caaaccaccg 8400
ctggtagcgg tggttttttt gtttgcaagc agcagattac gcgcagaaaa aaaggatctc 8460
aagaagatcc tttgatcttt tctacggggt ctgacgctca gtggaacgaa aactcacgtt 8520
aagggatttt ggtcatgaga ttatcaaaaa ggatcttcac ctagatcctt ttgg 8574

<210> SEQ ID NO 28
<211> LENGTH: 8577
<212> TYPE: DNA
<213> ORGANISM: Artificial Sequence
<220> FEATURE:
<223> OTHER INFORMATION: Transient expression vector with Phaseolus lunatus FIT1

<400> SEQUENCE: 28
atctcctgtg gttggcatgc acatacaaat ggacgaacgg ataaaccttt tcacgccctt 60
ttaaatatcc gattattcta ataaacgctc ttttctctta ggtttacccg ccaatatatc 120
ctgtcaaaca ctgatagttt aaactgaagg cgggaaacga caatctgcta gtggatctcc 180
cagtcacgac gttgtaaaac gggcgccccg cggaaagctt gctagccaat tggggcccaa 240
cgttctcgag gggatcttct gcaagcatct ctatttcctg aaggtctaac ctcgaagatt 300
taagatttaa ttacgtttat aattacaaaa ttgattctag tatctttaat ttaatgctta 360
tacattatta attaatttag tactttcaat ttgttttcag aaattatttt actatttttt 420
ataaaataaa agggagaaaa tggctattta aatactagcc tattttattt caattttagc 480
ttaaaatcag ccccaattag ccccaatttc aaattcaaat ggtccagccc aattcctaaa 540
taacccaccc ctaacccgcc cggtttcccc ttttgatcca tgcagtcaac gcccagaatt 600
tccctatata attttttaat tcccaaacac ccctaactct atcccatttc tcaccaaccg 660
ccacatagat ctatcctctt atctctcaaa ctctctcgaa ccttccccta accctagcag 720
cctctcatca tcctcacctc aaaacccacc ggatctagaa ggccttggat ccacccggga 780
gaattcgtcg actttgcggc cgcatcgata ctgcaggagc tcggtaccga gcatgtctgt 840
gtcatcattc tcctcttcct tcacctatga cgtcttcctc agcttcagag gagaagacac 900

```
tcgttacggt ttcaccggaa atctctattc agcccttcgt gacggcggaa tttgcacctt    960
catcgatgac gaggagctcc ccaaaggaga cgaaatcacc actgcacttg agaaggctat   1020
cgaaggttcc agaattttca tcatcgtttt ctctcacaac tacgcatctt cttccttttg   1080
cttgaatgag ctcgcctaca ttcttcccta cgctaagaga aatggtttgc tggttttgcc   1140
actcttctac gacgtcgttc cttcccacgt gcgaaaccac acgggtacct ttggagaagc   1200
gttagatact catgaaaaca ggttcaaagc tacgagtgag ggttttgagc ttaacatgga   1260
gaagctcaac agatggaaga tggctctgcg tggagctgct aacttatctg gctatcattt   1320
caaacatggg gaggaatatg aataccagtt tatcaagagg atagtggaat tggtatctaa   1380
caagattaac cgtgctcctt tacatgttgc ggattatcca gttggactag agacacgagt   1440
gctagaagta aaattgcttc tagatgtagg atctgatgat ggtgtccaca tggtagggat   1500
ccatggattc ggtggagttg gtaaaaccac acttgctctt gcagtttaca attccatagc   1560
tgacaatttt gaaggcttgt gtttccttga aaatgtcaga gagaattcaa acaaacacgg   1620
cctacaacat cttcagagtc tccttctttc tcaaatggtt ggagaaaata atatcaacat   1680
aactagtgtg aaacaaggaa tttcaatgat gcagcataga ctacggcaga agaagattct   1740
tttgattctt gatgatgttg acaagcatga acagttacaa gcaattgttg gaagagctga   1800
ttggtttggt cccggcagta gagtgatcat cacaactagg gacaaacatt tgttgtcatg   1860
tcagttggtt gaaaaaatat atgaagtgaa gaagttgaaa aagaaagatg ctcttcgact   1920
gcttagttgg aaaggtttta aaacagaaga agttcatcca agttatgtga atgtcatgga   1980
tcgtgtactg gcttatgctt ctggccatcc attggctttg gaagtaatag gttcgaagtt   2040
gtttagaaaa agtgtaaaag aatgggaatc tgccatccac cagtatgaga aaattcctaa   2100
caatcaaatt ctggagatgc ttaaaataag ttttgattct ttagaggaag tagagaagag   2160
tgtttttctt gacattgctt gttgtttcaa aggatatgcg ttgtcagagg tggaaaatat   2220
acttcgtgct cattatggtg attgcatgaa atatcatatt ggggtgttgg ttgaaaaatc   2280
tctcataaaa tatggatgga attctgtagt tacattgcat gacttgatag aagacatggg   2340
taaagaaatt gtccgacaga aatcaccaaa taagccaggg aagcgcagta gattatggtc   2400
accagaagat ataattcaag ttttggaaga caactcggga agtggagaaa ttgaaatcat   2460
atgtttgaat tactctttac ctgacaaagc agaaatagta gaatggaaca gaaaggcctt   2520
caagaagatg aaaaacctca aaacacttat cattaaaagt ggtaaatttt cggaaggtcc   2580
taagtatctt ccaaacagtt taagagtaat ggaatggtta aaatatcctt cacaagggct   2640
accgccagat tttcgttcaa aggaacttgc catatgcaaa ttacctgcaa gttgttttgg   2700
gtcactcgaa ttggccgagt tatcaaagaa gttcaagaat atgacccttt tgaattttga   2760
cgaatgtgaa ggtttaacac agatacctga tgtatctggg ctgccaaatt tagtagaaat   2820
ttcattcaag aattgtaaga gtttaattac aatccatgac tccattgggt tcctaggtaa   2880
gcttatctcc ttgaatgctg ttggttgcag caagcttagg agtttccccc ccctcaaatt   2940
gacttctctg gaaaatcttg aactttcata ttgttacagt cttgagagct tcccagaaat   3000
attgggaaaa atgggaaaga taacagaact tttgttggag tgctgtgaca taaaagaatt   3060
gccattttca tttcaaaatc tcactgagct tcaaacatta cagttgcgtt actgtccaat   3120
gttgaggttg ccaagtagta ttgtcatgat gccaaaactg accgagatta ttgcttggga   3180
atctaaagga tggctatttc caaaacaggt tgagggtgaa gagaaagtaa gctcaatggt   3240
```

-continued gtcttcaaat gtagattgtc ttcttctccc agggtgcaaa ctctcggatg attttttccc 3300
aataacatgg tttgctaatg taaaagagtt agacctgtca aggaatactt tcacggttct 3360
tcctgaatgc atcagcaatt gtcatttttt atgtaagctt attttagata actgtcagag 3420
tcttcgagag attagaggga ttccgccaaa cgtacgacat ttatcagcaa gatattgtaa 3480
atccttcact tcttcttgca gaagcacttt actgaatcag aaactgcatg aggcgggaaa 3540
caccatgttt tggttttcag gagcaagttt tccagaatgg ttcgagcacc acagtcgggg 3600
accatcttgt tctttctggg ttgacaagaa attccctgcc attgctcttt gtattgttat 3660
tggaccaact catttggaac atactgagat tgttggacct atcataatca tcaatggcgt 3720
tgattgttca cttgttgatg agttggataa tccttattta cggatactcc ctcatcacac 3780
atatcttttc gatttgcaac atatagtttc ttcagattat ctagacagat ttgtttcaga 3840
aaaggaatgg aatcacgtgg agattagata ctcagtcgag cagagattca gtgaagaaga 3900
caaacatgtg gtgataccag tctccgtaga aaatggaatc tatgtgttca aacagaggag 3960
cagcatggag gatattcaat tcactgatcc ccacaaaaag agaagattag atgttgatcc 4020
agagtagcca acgatcgttc aaacatttgg caataaagtt tcttaagatt gaatcctgtt 4080
gccggtcttg cgatgattat catataattt ctgttgaatt acgttaagca tgtaataatt 4140
aacatgtaat gcatgacgtt atttatgaga tgggttttta tgattagagt cccgcaatta 4200
tacatttaat acgcgataga aaacaaaata tagcgcgcaa actaggataa attatcgcgc 4260
gcggtgtcat ctatgttact agatccctag ggaagttcct attccgaagt tcctattctc 4320
tgaaaagtat aggaacttct ttgcgtattg ggcgctcttg gcctttttgg ccaccggtcg 4380
tacggttaaa accaccccag tacattaaaa acgtccgcaa tgtgttatta agttgtctaa 4440
gcgtcaattt gtttacacca caatatatcc tgccaccagc cagccaacag ctccccgacc 4500
ggcagctcgg cacaaaatca ccactcgata caggcagccc atcagtccac tagacgctca 4560
ccgggctggt tgccctcgcc gctgggctgg cggccgtcta tggccctgca aacgcgccag 4620
aaacgccgtc gaagccgtgt gcgagacacc gcagccgccg gcgttgtgga tacctcgcgg 4680
aaaacttggc cctcactgac agatgagggg cggacgttga cacttgaggg gccgactcac 4740
ccggcgcggc gttgacagat gaggggcagg ctcgatttcg gccggcgacg tggagctggc 4800
cagcctcgca aatcggcgaa aacgcctgat tttacgcgag tttcccacag atgatgtgga 4860
caagcctggg gataagtgcc ctgcggtatt gacacttgag ggcgcgact actgacagat 4920
gaggggcgcg atccttgaca cttgaggggc agagtgctga cagatgaggg gcgcacctat 4980
tgacatttga ggggctgtcc acaggcagaa aatccagcat ttgcaagggt ttccgcccgt 5040
ttttcggcca ccgctaacct gtcttttaac ctgcttttaa accaatattt ataaaccttg 5100
tttttaacca gggctgcgcc ctgtgcgcgt gaccgcgcac gccgaagggg ggtgcccccc 5160
cttctcgaac cctcccggcc cgctctcgcg ttggcagcat cacccataat tgtggtttca 5220
aaatcggctc cgtcgatact atgttatacg ccaactttga aaacaacttt gaaaaagctg 5280
ttttctggta tttaaggttt tagaatgcaa ggaacagtga attggagttc gtcttgttat 5340
aattagcttc ttggggtatc tttaaatact gtagaaaaga ggaaggaaat aataaatggc 5400
taaaatgaga atatcaccgg aattgaaaaa actgatcgaa aaataccgct gcgtaaaaga 5460
tacggaagga atgtctcctg ctaaggtata taagctggtg ggagaaaatg aaaacctata 5520
tttaaaaatg acggacagcc ggtataaagg gaccacctat gatgtggaac gggaaaagga 5580
catgatgcta tggctggaag gaaagctgcc tgttccaaag gtcctgcact ttgaacggca 5640

-continued

```
tgatggctgg agcaatctgc tcatgagtga ggccgatggc gtcctttgct cggaagagta   5700
tgaagatgaa caaagccctg aaaagattat cgagctgtat gcggagtgca tcaggctctt   5760
tcactccatc gacatatcgg attgtcccta tacgaatagc ttagacagcc gcttagccga   5820
attggattac ttactgaata acgatctggc cgatgtggat tgcgaaaact gggaagaaga   5880
cactccattt aaagatccgc gcgagctgta tgattttta aagacggaaa agcccgaaga   5940
ggaacttgtc ttttcccacg gcgacctggg agacagcaac atctttgtga aagatggcaa   6000
agtaagtggc tttattgatc ttgggagaag cggcagggcg gacaagtggt atgacattgc   6060
cttctgcgtc cggtcgatca gggaggatat tggggaagaa cagtatgtcg agctattttt   6120
tgacttactg gggatcaagc ctgattggga gaaaataaaa tattatattt tactggatga   6180
attgttttag tacctagatg tggcgcaacg atgccggcga caagcaggag cgcaccgact   6240
tcttccgcat caagtgtttt ggctctcagg ccgaggccca cggcaagtat ttgggcaagg   6300
ggtcgctggt attcgtgcag ggcaagattc ggaataccaa gtacgagaag gacggccaga   6360
cggtctacgg gaccgacttc attgccgata aggtggatta tctggacacc aaggcaccag   6420
gcgggtcaaa tcaggaataa gggcacattg ccccggcgtg agtcggggca atcccgcaag   6480
gagggtgaat gaatcggacg tttgaccgga aggcatacag gcaagaactg atcgacgcgg   6540
ggttttccgc cgaggatgcc gaaaccatcg caagccgcac cgtcatgcgt gcgccccgcg   6600
aaaccttcca gtccgtcggc tcgatggtcc agcaagctac ggccaagatc gagcgcgaca   6660
gcgtgcaact ggctcccct gccctgcccg cgccatcggc cgccgtggag cgttcgcgtc   6720
gtctcgaaca ggaggcggca ggtttggcga agtcgatgac catcgacacg cgaggaacta   6780
tgacgaccaa gaagcgaaaa accgccggcg aggacctggc aaaacaggtc agcgaggcca   6840
agcaagccgc gttgctgaaa cacacgaagc agcagatcaa ggaaatgcag ctttccttgt   6900
tcgatattgc gccgtggccg gacacgatgc gagcgatgcc aaacgacacg gcccgctctg   6960
ccctgttcac cacgcgcaac aagaaaatcc cgcgcgaggc gctgcaaaac aaggtcattt   7020
tccacgtcaa caaggacgtg aagatcacct acaccggcgt cgagctgcgg gccgacgatg   7080
acgaactggt gtggcagcag gtgttggagt acgcgaagcg cacccctatc ggcgagccga   7140
tcaccttcac gttctacgag ctttgccagg acctgggctg gtcgatcaat ggccggtatt   7200
acacgaaggc cgaggaatgc ctgtcgcgcc tacaggcgac ggcgatgggc ttcacgtccg   7260
accgcgttgg gcacctggaa tcggtgtcgc tgctgcaccg cttccgcgtc ctggaccgtg   7320
gcaagaaaac gtcccgttgc caggtcctga tcgacgagga aatcgtcgtg ctgtttgctg   7380
gcgaccacta cacgaaattc atatgggaga agtaccgcaa gctgtcgccg acggcccgac   7440
ggatgttcga ctatttcagc tcgcaccggg agccgtaccc gctcaagctg gaaaccttcc   7500
gcctcatgtg cggatcggat tccacccgcg tgaagaagtg gcgcgagcag gtcggcgaag   7560
cctgcgaaga gttgcgaggc agcggcctgg tggaacacgc ctgggtcaat gatgacctgg   7620
tgcattgcaa acgctagggc cttgtggggt cagttccggc tgggggttca gcagccagcg   7680
ctttactgag atcctcttcc gcttcctcgc tcactgactc gctgcgctcg gtcgttcggc   7740
tgcggcgagc ggtatcagct cactcaaagg cggtaatacg gttatccaca gaatcagggg   7800
ataacgcagg aaagaacatg tgagcaaaag gccagcaaaa ggccaggaac cgtaaaaagg   7860
ccgcgttgct ggcgtttttc cataggctcc gcccccctga cgagcatcac aaaaatcgac   7920
gctcaagtca gaggtggcga aacccgacag gactataaag ataccaggcg tttccccctg   7980
```

-continued gaagctccct cgtgcgctct cctgttccga ccctgccgct taccggatac ctgtccgcct 8040
ttctcccttc gggaagcgtg gcgctttctc atagctcacg ctgtaggtat ctcagttcgg 8100
tgtaggtcgt tcgctccaag ctgggctgtg tgcacgaacc ccccgttcag cccgaccgct 8160
gcgccttatc cggtaactat cgtcttgagt ccaacccggt aagacacgac ttatcgccac 8220
tggcagcagc cactggtaac aggattagca gagcgaggta tgtaggcggt gctacagagt 8280
tcttgaagtg gtggcctaac tacggctaca ctagaagaac agtatttggt atctgcgctc 8340
tgctgaagcc agttaccttc ggaaaaagag ttggtagctc ttgatccggc aaacaaacca 8400
ccgctggtag cggtggtttt tttgtttgca agcagcagat tacgcgcaga aaaaaaggat 8460
ctcaagaaga tcctttgatc ttttctacgg ggtctgacgc tcagtggaac gaaaactcac 8520
gttaagggat tttggtcatg agattatcaa aaaggatctt cacctagatc cttttgg 8577

<210> SEQ ID NO 29
<211> LENGTH: 8583
<212> TYPE: DNA
<213> ORGANISM: Artificial Sequence
<220> FEATURE:
<223> OTHER INFORMATION: Transient expression vector with Vigna radiata FIT1

<400> SEQUENCE: 29
atctcctgtg gttggcatgc acatacaaat ggacgaacgg ataaaccttt tcacgccctt 60
ttaaatatcc gattattcta ataaacgctc ttttctctta ggtttacccg ccaatatatc 120
ctgtcaaaca ctgatagttt aaactgaagg cgggaaacga caatctgcta gtggatctcc 180
cagtcacgac gttgtaaaac gggcgccccg cggaaagctt gctagccaat tggggcccaa 240
cgttctcgag gggatcttct gcaagcatct ctatttcctg aaggtctaac ctcgaagatt 300
taagatttaa ttacgtttat aattacaaaa ttgattctag tatctttaat ttaatgctta 360
tacattatta attaatttag tactttcaat ttgttttcag aaattatttt actatttttt 420
ataaaataaa agggagaaaa tggctattta aatactagcc tattttattt caattttagc 480
ttaaaatcag ccccaattag ccccaatttc aaattcaaat ggtccagccc aattcctaaa 540
taacccaccc ctaacccgcc cggtttcccc ttttgatcca tgcagtcaac gcccagaatt 600
tccctatata atttttaat tcccaaacac ccctaactct atcccatttc tcaccaaccg 660
ccacatagat ctatcctctt atctctcaaa ctctctcgaa ccttccccta accctagcag 720
cctctcatca tcctcacctc aaaacccacc ggatctagaa ggccttggat ccacccggga 780
gaattcgtcg actttgcggc cgcatcgata ctgcaggagc tcggtaccga gcatggctgt 840
ggcatcattc tcttcttcct tcacctatga cgtgttcctc agcttcagag gagaagatac 900
tcgttacagt ttcaccggca atctctacag agcccttcgt gacagaggaa ttcacacctt 960
catcgacgac gagaagcttc ccaaaggaga cgaaatcacc tctgcacttg agaaggcaat 1020
agaaggttcc agaattttca tcatcgtttt ctctcgcaac tacgcctctt cctccttttg 1080
cttgaacgag ctcgcctaca ttcttcccta cgctaataga aatggtttgc tggttttgcc 1140
actcttctac gacgtcgttc cttcccacgt gcgccaccac atgggtagct atggagaagc 1200
tttggatact catgaaaaca ggttcaaagc tacgagtcag ggttttgagc ttaacatgga 1260
gaagctcaac aaatggaaga tggctctgcg tggaacagct aacttatctg gctatcattt 1320
caaacatggg gaggaatatg aatacgagtt tatcaagagg atagttgact tggtttccaa 1380
caagattaac cgtgctcctt tacacgttgc ggattatcca gttggactag agactcgagt 1440

-continued

```
gctagaagta aagttgcttc tggatatagg atctgatgat ggtgtccaca tggtagggat   1500
ccatggactc ggtggagttg gtaaaaccac acttgctctt gcagtttaca attccatcgc   1560
tgaccatttt gaaggcttgt gtttcctcga aaatgtgaga gagaattcaa acaaacacgg   1620
cctacagcat cttcaaagaa tccttctttc tcaaatggtt ggagaaaata atgtcaacat   1680
aactagtgtg agacaaggaa tttcaatgat gcagcatagg ctacgacaga agaagattct   1740
cttgatttta gatgacgttg acaaacatga acagttacaa gctattgttg gaagacctga   1800
ttggtttggt cccggcagta gagtcatcat cacaactagg gacaaacatt tgttgtcatg   1860
tcacttgatc gaaaaattat ataaagtgaa gaagttgaaa aagaacaatg ctcatcgact   1920
gcttagttgg aaagctttta gaacagaaga agttgataca agttatttga atgtaatgga   1980
tcgtgtacta gcttatgctt ctggccatcc attggctttg gaagtaatcg gttcgaagtt   2040
gtttagaaaa agtgtaaagg aatgggaatc tgccatcaaa cagtatgaga aaattcctaa   2100
caatcaaatc ctggaggtgc ttaaaataag ttttgatgct ttagaggaag tagagaagag   2160
tgtttttctt gacatttctt gttgctttaa aggatatgca ttgtcagagg tggaagatat   2220
acttcgtgct cattatggtg attgcatgaa atatcatatt ggggtgttgg ttgaaaagtc   2280
tctcataaaa tatggttgga gttgtgtggt tacaatgcat gacttgatag aagacatggg   2340
taaagaaatt gtccggcaga aatctccaaa taggccaggg aagcgcagta gattatggtc   2400
accagaagag ataattaaag ttttggaaga caacttgggg agtggagaaa ttgaaatcat   2460
atgtttaaat tcctccttac ctgacaaaga agaaatagta gaatggaaca gaaaggcctt   2520
caagaagatg aaaaacctca aaacacttat cattaaaaat ggtaattttt cggaaggtcc   2580
tgaatatctt ccaaatagtt taagagtact ggaatggttg aaatatcctt cacatgggct   2640
accgccagat tttcgttcaa agaaactttc cttatgcaaa ttaccttcaa gttgttttgg   2700
gtcactcgaa ttggctgagt tttcaaagaa gttcatgaat atgactcttc tgaattttga   2760
cgaatgtgaa ggtttaacac agatacctga tctatctggg atgccaaatt tagaaagatt   2820
ttcattcaag aattgtaaga gtttaattac aattcatgac tccattggct tcctaggtaa   2880
gcttaactcc ttgaatgctg ttggttgcag caagcttagg agttttcccc ccctcaaatt   2940
gacttctctg gaaaatcttg aactttcata ttgttacagt cttgagagct tcccagaaat   3000
attaggaaaa atgggacaga taacagaact tgtcttggag gactgtcaca taaaagaatt   3060
gccaatttca tttcaaaatc tcaccgagct tcgaacatta cagttgcgtt cgtgtccaac   3120
gttaaggtta cctagtagta ttgtcatgat gccaaaactg gccaacatta ttgcttggga   3180
atctaaaggg tggctatttc caaaacaggt cgagagggaa gagaaaatag gctcaatggt   3240
gtcttcaaac gtagattgtc ttgttctctc agggtgcaaa ctctcggatg actttttccc   3300
aataattctt gaatggtttg ctaatgtaaa agatttaaac ctatcaagga ataacttcac   3360
ggttcttcct gagtgcatcg ccaattgtca cttgttatgc aagcttactt tagatgcctg   3420
tcatagtctt cgagagatta gagggattcc accaaacata cgacagttac tagcaagaaa   3480
ttgtaaatcc ttcacttctt cttgcagaag aactttactg aatcagaaac tgcatgaggc   3540
tggaaacacc atgttttcgt tttcaggagc aaggtttcca gaatggttcg atcaccacag   3600
tcggggagca tcttgttctt tctgggttgg caaaaaattc ccttccattg ctctttgtat   3660
tgctattgga ccaactcatt tggaacacct tgaaattgtt ggacctatca tgatcatcaa   3720
ctgcattgaa tgttcatttg attgggagga gaatccttat ttatatatgc tccctcatca   3780
cacatatatt ttcgatttgc aaaatatagt ttttccagat tatctagaca gatttgtttc   3840
```

agaaaatgaa tggaaccacg tggagattac atactcagtc aagcagagat tcaagggaaa 3900
agacaaacat gaggtgaccc caatctctat agaaaatgga atctatgtgt tcaaacagaa 3960
gagcagcatg gaggatattc aattcactga tccccacaaa aagagaagat tagatgttga 4020
tccagagttg taaccaacga tcgttcaaac atttggcaat aaagtttctt aagattgaat 4080
cctgttgccg gtcttgcgat gattatcata taatttctgt tgaattacgt taagcatgta 4140
ataattaaca tgtaatgcat gacgttattt atgagatggg tttttatgat tagagtcccg 4200
caattataca tttaatacgc gatagaaaac aaaatatagc gcgcaaacta ggataaatta 4260
tcgcgcgcgg tgtcatctat gttactagat ccctagggaa gttcctattc cgaagttcct 4320
attctctgaa aagtatagga acttctttgc gtattgggcg ctcttggcct ttttggccac 4380
cggtcgtacg gttaaaacca ccccagtaca ttaaaaacgt ccgcaatgtg ttattaagtt 4440
gtctaagcgt caatttgttt acaccacaat atatcctgcc accagccagc caacagctcc 4500
ccgaccggca gctcggcaca aaatcaccac tcgatacagg cagcccatca gtccactaga 4560
cgctcaccgg gctggttgcc ctcgccgctg ggctggcggc cgtctatggc cctgcaaacg 4620
cgccagaaac gccgtcgaag ccgtgtgcga gacaccgcag ccgccggcgt tgtggatacc 4680
tcgcggaaaa cttggccctc actgacagat gaggggcgga cgttgacact tgaggggccg 4740
actcacccgg cgcggcgttg acagatgagg ggcaggctcg atttcggccg gcgacgtgga 4800
gctggccagc ctcgcaaatc ggcgaaaacg cctgatttta cgcgagtttc ccacagatga 4860
tgtggacaag cctggggata agtgccctgc ggtattgaca cttgaggggc gcgactactg 4920
acagatgagg ggcgcgatcc ttgacacttg aggggcagag tgctgacaga tgaggggcgc 4980
acctattgac atttgagggg ctgtccacag gcagaaaatc cagcatttgc aagggtttcc 5040
gcccgttttt cggccaccgc taacctgtct tttaacctgc ttttaaacca atatttataa 5100
accttgtttt taaccagggc tgcgccctgt gcgcgtgacc gcgcacgccg aaggggggtg 5160
cccccccttc tcgaaccctc ccggcccgct ctcgcgttgg cagcatcacc cataattgtg 5220
gtttcaaaat cggctccgtc gatactatgt tatacgccaa ctttgaaaac aactttgaaa 5280
aagctgtttt ctggtattta aggttttaga atgcaaggaa cagtgaattg gagttcgtct 5340
tgttataatt agcttcttgg ggtatcttta aatactgtag aaaagaggaa ggaaataata 5400
aatggctaaa atgagaatat caccggaatt gaaaaaactg atcgaaaaat accgctgcgt 5460
aaaagatacg gaaggaatgt ctcctgctaa ggtatataag ctggtgggag aaaatgaaaa 5520
cctatattta aaaatgacgg acagccggta taaagggacc acctatgatg tggaacggga 5580
aaaggacatg atgctatggc tggaaggaaa gctgcctgtt ccaaaggtcc tgcactttga 5640
acggcatgat ggctggagca atctgctcat gagtgaggcc gatggcgtcc tttgctcgga 5700
agagtatgaa gatgaacaaa gccctgaaaa gattatcgag ctgtatgcgg agtgcatcag 5760
gctctttcac tccatcgaca tatcggattg tccctatacg aatagcttag acagccgctt 5820
agccgaattg gattacttac tgaataacga tctggccgat gtggattgcg aaaactggga 5880
agaagacact ccatttaaag atccgcgcga gctgtatgat tttttaaaga cggaaaagcc 5940
cgaagaggaa cttgtctttt cccacggcga cctgggagac agcaacatct ttgtgaaaga 6000
tggcaaagta agtggcttta ttgatcttgg gagaagcggc agggcggaca agtggtatga 6060
cattgccttc tgcgtccggt cgatcaggga ggatattggg gaagaacagt atgtcgagct 6120
attttttgac ttactgggga tcaagcctga ttgggagaaa ataaaatatt atattttact 6180

-continued

```
ggatgaattg ttttagtacc tagatgtggc gcaacgatgc cggcgacaag caggagcgca   6240
ccgacttctt ccgcatcaag tgttttggct ctcaggccga ggcccacggc aagtatttgg   6300
gcaaggggtc gctggtattc gtgcagggca agattcggaa taccaagtac gagaaggacg   6360
gccagacggt ctacgggacc gacttcattg ccgataaggt ggattatctg gacaccaagg   6420
caccaggcgg gtcaaatcag gaataagggc acattgcccc ggcgtgagtc ggggcaatcc   6480
cgcaaggagg gtgaatgaat cggacgtttg accggaaggc atacaggcaa gaactgatcg   6540
acgcggggtt ttccgccgag gatgccgaaa ccatcgcaag ccgcaccgtc atgcgtgcgc   6600
cccgcgaaac cttccagtcc gtcggctcga tggtccagca agctacggcc aagatcgagc   6660
gcgacagcgt gcaactggct ccccctgccc tgcccgcgcc atcggccgcc gtggagcgtt   6720
cgcgtcgtct cgaacaggag gcggcaggtt tggcgaagtc gatgaccatc gacacgcgag   6780
gaactatgac gaccaagaag cgaaaaaccg ccggcgagga cctggcaaaa caggtcagcg   6840
aggccaagca agccgcgttg ctgaaacaca cgaagcagca gatcaaggaa atgcagcttt   6900
ccttgttcga tattgcgccg tggccggaca cgatgcgagc gatgccaaac gacacggccc   6960
gctctgccct gttcaccacg cgcaacaaga aaatcccgcg cgaggcgctg caaaacaagg   7020
tcattttcca cgtcaacaag gacgtgaaga tcacctacac cggcgtcgag ctgcgggccg   7080
acgatgacga actggtgtgg cagcaggtgt tggagtacgc gaagcgcacc cctatcggcg   7140
agccgatcac cttcacgttc tacgagcttt gccaggacct gggctggtcg atcaatggcc   7200
ggtattacac gaaggccgag gaatgcctgt cgcgcctaca ggcgacggcg atgggcttca   7260
cgtccgaccg cgttgggcac ctggaatcgg tgtcgctgct gcaccgcttc cgcgtcctgg   7320
accgtggcaa gaaaacgtcc cgttgccagg tcctgatcga cgaggaaatc gtcgtgctgt   7380
ttgctggcga ccactacacg aaattcatat gggagaagta ccgcaagctg tcgccgacgg   7440
cccgacggat gttcgactat ttcagctcgc accgggagcc gtacccgctc aagctggaaa   7500
ccttccgcct catgtgcgga tcggattcca cccgcgtgaa gaagtggcgc gagcaggtcg   7560
gcgaagcctg cgaagagttg cgaggcagcg gcctggtgga acacgcctgg gtcaatgatg   7620
acctggtgca ttgcaaacgc tagggccttg tggggtcagt tccggctggg ggttcagcag   7680
ccagcgcttt actgagatcc tcttccgctt cctcgctcac tgactcgctg cgctcggtcg   7740
ttcggctgcg gcgagcggta tcagctcact caaaggcggt aatacggtta tccacagaat   7800
caggggataa cgcaggaaag aacatgtgag caaaaggcca gcaaaaggcc aggaaccgta   7860
aaaaggccgc gttgctggcg tttttccata ggctccgccc ccctgacgag catcacaaaa   7920
atcgacgctc aagtcagagg tggcgaaacc cgacaggact ataaagatac caggcgtttc   7980
cccctggaag ctccctcgtg cgctctcctg ttccgaccct gccgcttacc ggatacctgt   8040
ccgcctttct cccttcggga agcgtggcgc tttctcatag ctcacgctgt aggtatctca   8100
gttcggtgta ggtcgttcgc tccaagctgg gctgtgtgca cgaacccccc gttcagcccg   8160
accgctgcgc cttatccggt aactatcgtc ttgagtccaa cccggtaaga cacgacttat   8220
cgccactggc agcagccact ggtaacagga ttagcagagc gaggtatgta ggcggtgcta   8280
cagagttctt gaagtggtgg cctaactacg gctacactag aagaacagta tttggtatct   8340
gcgctctgct gaagccagtt accttcggaa aaagagttgg tagctcttga tccggcaaac   8400
aaaccaccgc tggtagcggt ggtttttttg tttgcaagca gcagattacg cgcagaaaaa   8460
aaggatctca agaagatcct ttgatctttt ctacggggtc tgacgctcag tggaacgaaa   8520
actcacgtta agggattttg gtcatgagat tatcaaaaag gatcttcacc tagatccttt   8580
```

tgg 8583

<210> SEQ ID NO 30
<211> LENGTH: 8580
<212> TYPE: DNA
<213> ORGANISM: Artificial Sequence
<220> FEATURE:
<223> OTHER INFORMATION: Transient expression vector with Vigna unguiculata FIT1b

<400> SEQUENCE: 30
atctcctgtg gttggcatgc acatacaaat ggacgaacgg ataaaccttt tcacgccctt 60
ttaaatatcc gattattcta ataaacgctc ttttctctta ggtttacccg ccaatatatc 120
ctgtcaaaca ctgatagttt aaactgaagg cgggaaacga caatctgcta gtggatctcc 180
cagtcacgac gttgtaaaac gggcgccccg cggaaagctt gctagccaat tggggcccaa 240
cgttctcgag ggatcttct gcaagcatct ctatttcctg aaggtctaac ctcgaagatt 300
taagatttaa ttacgtttat aattacaaaa ttgattctag tatctttaat ttaatgctta 360
tacattatta attaatttag tactttcaat ttgttttcag aaattatttt actatttttt 420
ataaaataaa agggagaaaa tggctattta aatactagcc tattttattt caattttagc 480
ttaaaatcag ccccaattag ccccaatttc aaattcaaat ggtccagccc aattcctaaa 540
taacccaccc ctaacccgcc cggtttcccc ttttgatcca tgcagtcaac gcccagaatt 600
tccctatata attttttaat tcccaaacac ccctaactct atcccatttc tcaccaaccg 660
ccacatagat ctatcctctt atctctcaaa ctctctcgaa ccttccccta accctagcag 720
cctctcatca tcctcacctc aaaacccacc ggatctagaa ggccttggat ccacccggga 780
gaattcgtcg actttgcggc cgcatcgata ctgcaggagc tcggtaccga gcatggcagt 840
gccaagcttt tccttcagtt ttacttatga tgtcttttta agctttagag gagaggacac 900
tcgttacggt tttacgggaa acctttaccg agccctccgt gacagaggta tacatacctt 960
catcgatgac gaggaattaa gaaaaggaga cgaaataacc agtgcattag agaaagccat 1020
cgagggatca cgtattttca tcatagtatt tagtcttaat tacgccagta gctctttctg 1080
tttgaatgag cttgcatata ttcttccgca cgctaaaagg aacgctcttc tggtgctccc 1140 cctttttac gatgtggttc caagtcacgt tcgtcaccac accggatcat tcggtgaggc 1200
tttagatgcc catgagaaac gttttcgagg catgagtcag ggttttgaat taaacatcga 1260
gaaactcaat aaatggaaaa tggccttacg aagggcagca aaccttagcg gatatcattt 1320
caagcatggc gaagagtatg aataccaatt tatagaaaaa attgttaaac tcgtttccaa 1380
taagataaac agagttccgc tgcacgttgc tgactatcaa gtaggactcg aaaagagagt 1440
cttagaagtg aagatgttag ttgatgtggg atcagatgac tgcgtgcaca tggtgggtat 1500
ctatggttta ggaggagtgg ggaaaactac actcgcactg gctctgtata atagtattgc 1560
agaccacttt gaggggctct gctttttgga gaacgtcaga gagaattcaa acaaacaggg 1620
cctccatcat ctgcagcgta ttctcctgtc agaaatggtg ggagagaaca acataaatat 1680
agggagtgtg cgtcagggta tttcaatgat gcaacatcgt ttaagacaga aaaaaattct 1740
tttaattttg gatgatgtag ataaacacga gcagcttcaa gctatagttg ggagtcctga 1800
ttggttcggg ccaggttccc gagttatcat tactactcgt gataagcagc ttttgtcttg 1860
ccacttagtg gaaaagcttt acgaggtcaa aaaacttgaa aaaaacgacg ctcttcgact 1920
cctgtcttgg aaaggattta ggactgagga agttgacaca tcttattcta acgtcatgga 1980

```
ctccgtttta gcatacgctt ccgggcaccc cttagctttg gaagttatag ggagcaaact   2040
gttccgaaaa agtgtagagg agtgggaatc cgctatcaaa caatacgaga aaataccgat   2100
ctcccagatc cttgaagtat tgaaaatttc ctttgacgcc ttggaagagg tggagaaaag   2160
cgtgtttctc gacatagcct gttgtttcaa gggttatgcc ttgtctgata ttgaggatat   2220
attacgtgca cagtacggac acagtatgaa atatcacatt ggtgttttag tagagaagag   2280
tctgattaag tacaaatgga aattcggtgt taccatgcac gacttgatag aggatatggg   2340
aaaggagatc gtccgacaac agagcccaaa aaggcccgga aaacgaagta ggctctggtc   2400
ccccgaagat ataattcagg tattggagga taacagcggt tctggagaaa tcgagattat   2460
ttgtctgaat agtagcctgc ctgataaaga ggaaattata gagtggaaca gaaaagcttt   2520
caagaaaatg aaaaatttaa aaacattgat aataaaaaaa gggaatttca gcgaggggcc   2580
aaaatacttg cctaatagtc tgagggtttt ggaatggtta aagtacccca gccaaggatt   2640
gccacccgac tttcgttcca aagaattggc tatttgtaaa ctgcctacct catgcttcgg   2700
cagtcttgaa ctggccgaac ttagtaagaa attcatgaac atgactcttc tggattttga   2760
agagtgccaa gggcttacgc agataccgga tgtgtctggc atgccgaatt tagaaaagat   2820
cagttttaaa aattgcaaaa gtttgaacac tatacatgat agtataggct tcttggggaa   2880
attaaatagt ctgaacgcag tagggtgctc caaactgcgt agcttccccc cgctgaagtt   2940
aacaagtctg aaaaatcttg agcttagcta ttgttatggt ttagaatctt tccctgaggt   3000
actgggcaaa atgggaaaaa tcacaaaact tgtcctggag gattgcaaca tcaaagaatt   3060
accgttctct tttcaaaact taacagagct ccaaacgctt cagttacgtt tctgccccat   3120
gctcaggtta ccgagtagta ttgtaatgat gcccaaatta gctgagatta tcgtgtggga   3180
gtcaaaggga tggctgttcc cgaagcaggt agaagtcgaa gagaaagtct catcaatggt   3240
atcatccaat gtagattgtt tacttttacc cagatgtaag ctctctgacg actttctgcc   3300
gatcgccctt gcctggtttg ccaacgtgaa ggagttggat ctcagttgga acaacttcac   3360
cgttctcccg gaatgcatat caaattgcca tttcctgtca aagttgacat tagatggttg   3420
ccacagcctc agggagatac gaggaattcc accgaatatc caactcctgc ttgccgttga   3480
ctgcaagtcc ttcacaagca gctgtcgttc tacattgtta aaccagaagc tgcatgaagc   3540
cgggaacaca atgttccgtt tgagcggagc atcatttcct gaatggtttg atcaccacaa   3600
ccagggcccg tcttgtagtt tctgggtcgg aaacaaattc ccaagcatag ccctttgtat   3660
agcaattggg cctgcccacc tggaacacgt cactattgac cgtccgatta taaatatcaa   3720
cggcgtcaag tgtagtctcc acggggaaga aaagccttat cttaatatgc tcccgcatca   3780
tacctacctg tttgatctgc agcacatcgt ctttagtgac tatcttgacc gattcgtcac   3840
ggagaatgag tggaatcacg tcgagattac atactctgtt aagcaaagat tcaatgaaaa   3900
agacaaacat gcagtgacgc ccgttagcgt cgagaacggt atttatgtgc tcaaacagag   3960
atcatcaatg gaagacattc agtttactga ccctcacaaa aagagacgac tcgatgtaga   4020
tccagagtaa ccaacgatcg ttcaaacatt tggcaataaa gtttcttaag attgaatcct   4080
gttgccggtc ttgcgatgat tatcatataa tttctgttga attacgttaa gcatgtaata   4140
attaacatgt aatgcatgac gttatttatg agatgggttt ttatgattag agtcccgcaa   4200
ttatacattt aatacgcgat agaaaacaaa atatagcgcg caaactagga taaattatcg   4260
cgcgcggtgt catctatgtt actagatccc tagggaagtt cctattccga agttcctatt   4320
```

-continued

```
ctctgaaaag tataggaact tctttgcgta ttgggcgctc ttggcctttt tggccaccgg   4380
tcgtacggtt aaaaccaccc cagtacatta aaaacgtccg caatgtgtta ttaagttgtc   4440
taagcgtcaa tttgtttaca ccacaatata tcctgccacc agccagccaa cagctccccg   4500
accggcagct cggcacaaaa tcaccactcg atacaggcag cccatcagtc cactagacgc   4560
tcaccgggct ggttgccctc gccgctgggc tggcggccgt ctatggccct gcaaacgcgc   4620
cagaaacgcc gtcgaagccg tgtgcgagac accgcagccg ccggcgttgt ggatacctcg   4680
cggaaaactt ggccctcact gacagatgag gggcggacgt tgacacttga ggggccgact   4740
cacccggcgc ggcgttgaca gatgaggggc aggctcgatt tcggccggcg acgtggagct   4800
ggccagcctc gcaaatcggc gaaaacgcct gattttacgc gagtttccca cagatgatgt   4860
ggacaagcct ggggataagt gccctgcggt attgacactt gaggggcgcg actactgaca   4920
gatgaggggc gcgatccttg acacttgagg ggcagagtgc tgacagatga ggggcgcacc   4980
tattgacatt tgaggggctg tccacaggca gaaaatccag catttgcaag ggtttccgcc   5040
cgtttttcgg ccaccgctaa cctgtctttt aacctgcttt taaaccaata tttataaacc   5100
ttgtttttaa ccagggctgc gccctgtgcg cgtgaccgcg cacgccgaag gggggtgccc   5160
ccccttctcg aaccctcccg gcccgctctc gcgttggcag catcacccat aattgtggtt   5220
tcaaaatcgg ctccgtcgat actatgttat acgccaactt tgaaaacaac tttgaaaaag   5280
ctgttttctg gtatttaagg ttttagaatg caaggaacag tgaattggag ttcgtcttgt   5340
tataattagc ttcttggggt atctttaaat actgtagaaa agaggaagga aataataaat   5400
ggctaaaatg agaatatcac cggaattgaa aaaactgatc gaaaaatacc gctgcgtaaa   5460
agatacggaa ggaatgtctc ctgctaaggt atataagctg gtgggagaaa atgaaaacct   5520
atatttaaaa atgacggaca gccggtataa agggaccacc tatgatgtgg aacgggaaaa   5580
ggacatgatg ctatggctgg aaggaaagct gcctgttcca aaggtcctgc actttgaacg   5640
gcatgatggc tggagcaatc tgctcatgag tgaggccgat ggcgtccttt gctcggaaga   5700
gtatgaagat gaacaaagcc ctgaaaagat tatcgagctg tatgcggagt gcatcaggct   5760
ctttcactcc atcgacatat cggattgtcc ctatacgaat agcttagaca gccgcttagc   5820
cgaattggat tacttactga ataacgatct ggccgatgtg gattgcgaaa actgggaaga   5880
agacactcca tttaaagatc cgcgcgagct gtatgatttt ttaaagacgg aaaagcccga   5940
agaggaactt gtcttttccc acggcgacct gggagacagc aacatctttg tgaaagatgg   6000
caaagtaagt ggctttattg atcttgggag aagcggcagg gcggacaagt ggtatgacat   6060
tgccttctgc gtccggtcga tcagggagga tattggggaa gaacagtatg tcgagctatt   6120
ttttgactta ctggggatca agcctgattg ggagaaaata aaatattata ttttactgga   6180
tgaattgttt tagtacctag atgtggcgca acgatgccgg cgacaagcag gagcgcaccg   6240
acttcttccg catcaagtgt tttggctctc aggccgaggc ccacggcaag tatttgggca   6300
aggggtcgct ggtattcgtg cagggcaaga ttcggaatac caagtacgag aaggacggcc   6360
agacggtcta cgggaccgac ttcattgccg ataaggtgga ttatctggac accaaggcac   6420
caggcgggtc aaatcaggaa taagggcaca ttgccccggc gtgagtcggg gcaatcccgc   6480
aaggagggtg aatgaatcgg acgtttgacc ggaaggcata caggcaagaa ctgatcgacg   6540
cggggttttc cgccgaggat gccgaaacca tcgcaagccg caccgtcatg cgtgcgcccc   6600
gcgaaacctt ccagtccgtc ggctcgatgg tccagcaagc tacggccaag atcgagcgcg   6660
acagcgtgca actggctccc cctgccctgc ccgcgccatc ggccgccgtg gagcgttcgc   6720
```

-continued gtcgtctcga acaggaggcg gcaggtttgg cgaagtcgat gaccatcgac acgcgaggaa 6780
ctatgacgac caagaagcga aaaaccgccg gcgaggacct ggcaaaacag gtcagcgagg 6840
ccaagcaagc cgcgttgctg aaacacacga agcagcagat caaggaaatg cagctttcct 6900
tgttcgatat tgcgccgtgg ccggacacga tgcgagcgat gccaaacgac acggcccgct 6960
ctgccctgtt caccacgcgc aacaagaaaa tcccgcgcga ggcgctgcaa aacaaggtca 7020
ttttccacgt caacaaggac gtgaagatca cctacaccgg cgtcgagctg cgggccgacg 7080
atgacgaact ggtgtggcag caggtgttgg agtacgcgaa gcgcacccct atcggcgagc 7140
cgatcacctt cacgttctac gagctttgcc aggacctggg ctggtcgatc aatggccggt 7200
attacacgaa ggccgaggaa tgcctgtcgc gcctacaggc gacggcgatg ggcttcacgt 7260
ccgaccgcgt tgggcacctg gaatcggtgt cgctgctgca ccgcttccgc gtcctggacc 7320
gtggcaagaa aacgtcccgt tgccaggtcc tgatcgacga ggaaatcgtc gtgctgtttg 7380
ctggcgacca ctacacgaaa ttcatatggg agaagtaccg caagctgtcg ccgacggccc 7440
gacggatgtt cgactatttc agctcgcacc gggagccgta cccgctcaag ctggaaacct 7500
tccgcctcat gtgcggatcg gattccaccc gcgtgaagaa gtggcgcgag caggtcggcg 7560
aagcctgcga agagttgcga ggcagcggcc tggtggaaca cgcctgggtc aatgatgacc 7620
tggtgcattg caaacgctag ggccttgtgg ggtcagttcc ggctgggggt tcagcagcca 7680
gcgctttact gagatcctct tccgcttcct cgctcactga ctcgctgcgc tcggtcgttc 7740
ggctgcggcg agcggtatca gctcactcaa aggcggtaat acggttatcc acagaatcag 7800
gggataacgc aggaaagaac atgtgagcaa aaggccagca aaaggccagg aaccgtaaaa 7860
aggccgcgtt gctggcgttt ttccataggc tccgcccccc tgacgagcat cacaaaaatc 7920
gacgctcaag tcagaggtgg cgaaacccga caggactata aagataccag gcgtttcccc 7980
ctggaagctc cctcgtgcgc tctcctgttc cgaccctgcc gcttaccgga tacctgtccg 8040
cctttctccc ttcgggaagc gtggcgcttt ctcatagctc acgctgtagg tatctcagtt 8100
cggtgtaggt cgttcgctcc aagctgggct gtgtgcacga accccccgtt cagcccgacc 8160
gctgcgcctt atccggtaac tatcgtcttg agtccaaccc ggtaagacac gacttatcgc 8220
cactggcagc agccactggt aacaggatta gcagagcgag gtatgtaggc ggtgctacag 8280
agttcttgaa gtggtggcct aactacggct acactagaag aacagtattt ggtatctgcg 8340
ctctgctgaa gccagttacc ttcggaaaaa gagttggtag ctcttgatcc ggcaaacaaa 8400
ccaccgctgg tagcggtggt ttttttgttt gcaagcagca gattacgcgc agaaaaaaag 8460
gatctcaaga agatcctttg atcttttcta cggggtctga cgctcagtgg aacgaaaact 8520
cacgttaagg gattttggtc atgagattat caaaaaggat cttcacctag atccttttgg 8580

<210> SEQ ID NO 31
<211> LENGTH: 8583
<212> TYPE: DNA
<213> ORGANISM: Artificial Sequence
<220> FEATURE:
<223> OTHER INFORMATION: Transient expression vector with Vigna angularis FIT1

<400> SEQUENCE: 31
atctcctgtg gttggcatgc acatacaaat ggacgaacgg ataaaccttt tcacgccctt 60
ttaaatatcc gattattcta ataaacgctc ttttctctta ggtttacccg ccaatatatc 120
ctgtcaaaca ctgatagttt aaactgaagg cgggaaacga caatctgcta gtggatctcc 180

```
cagtcacgac gttgtaaaac gggcgccccg cggaaagctt gctagccaat tggggcccaa    240
cgttctcgag gggatcttct gcaagcatct ctatttcctg aaggtctaac ctcgaagatt    300
taagatttaa ttacgtttat aattacaaaa ttgattctag tatctttaat ttaatgctta    360
tacattatta attaatttag tactttcaat ttgttttcag aaattatttt actatttttt    420
ataaaataaa agggagaaaa tggctattta aatactagcc tattttattt caattttagc    480
ttaaaatcag ccccaattag ccccaatttc aaattcaaat ggtccagccc aattcctaaa    540
taacccaccc ctaacccgcc cggtttcccc ttttgatcca tgcagtcaac gcccagaatt    600
tccctatata atttttaat tcccaaacac ccctaactct atcccatttc tcaccaaccg    660
ccacatagat ctatcctctt atctctcaaa ctctctcgaa ccttccccta accctagcag    720
cctctcatca tcctcacctc aaaacccacc ggatctagaa ggccttggat ccacccggga    780
gaattcgtcg actttgcggc cgcatcgata ctgcaggagc tcggtaccga gcatggcagt    840
tccaagtttt tcatctagct tcacatatga cgtcttcttg tccttccgtg ggaggacac    900
aaggtattca ttcaccggca acttgtacag agcactgagg gatcgaggaa tccatacttt    960
tatcgacgat gaaaagctgc cgaagggcga cgagatcaca tctgcccttg aaaaggcaat   1020
cgagggcagt agaatttca ttattgtatt ttctcgaaac tacgcctcca gctcattctg   1080
cctgaacgag ttggcataca tcttacctta cgctaatagg aacggtcttt tggtacttcc   1140
actgttttat gatgtggtac cgagccatgt tagacaccat acgggctcat tcggagaggc   1200
tttagacact cacgaaaaca ggttcaaggc cacatctcaa ggattcgaat taaatatgga   1260
gaagttaaat aagtggaaga tggcacttcg aggtactgct aacctgtcag gatatcattt   1320
caagcacggc gaagagtatg agtatgagtt tataaaaagg atagttgact tggtttctaa   1380
caaaataaac agggccccac tccatgtggc agattatcct gtaggacttg agacgagggt   1440
actcgaggtc aaattgttat tagatatagg gtctgatgat ggcgttcata tggttgggat   1500
ccatggactg ggaggtgtgg gcaaaacaac tcttgcactc gcagtttaca atagcattgc   1560
tgaccatttt gaaggcctgt gtttctgga aaacgtaaga gagaattcaa acaagcacgg   1620
gctgcagcac ctgcagcgta tcctcttatc acaaatgata ggcgagaaca atgtgaacat   1680
tacatctgcc aggcaaggta tcagcatgat ggagcataga ttaagacaga agaaaatcct   1740
gttgatcctg gacgacgtag ataagcatga gcaattacaa gcaatcgtag gacgtcccga   1800
ctggttcggg ccgggatcca gagtgattat aacaacacga gacaaacacc ttcttagttg   1860
tcacctgatc gaaaagttgt acaaggttaa gaaactggag aaaaacaacg cacttaggtt   1920
gctctcctgg aaagctttcc gtacagagga ggtagatact tcatacctta acgtgatgga   1980
tcgagtcttg gcctatgcat ccggacatcc tttggctctc gaagtcattg ggagcaagct   2040
cttccgtaaa agtgtcaagg agtgggagtc cgccattaaa caatatgaga agattcccaa   2100
caatcaaatt ctcgaagtct taaaaatatc ctttgacgct ctggaagaag ttgagaagag   2160
cgtctttctc gatatttctt gttgtttcaa agcctacgca ctcagtgaag tggaggatat   2220
actcagagcc cattatgggg actgcatgaa gtaccacata ggcgtactcg tcgagaaatc   2280
tttgattaaa tacgggtaca attccgtggt aacgatgcat gaccttatcg aggacatggg   2340
taaggagatc gtccgtcaaa aaagcccgaa caaaccagga aagcgttcca gactctggtc   2400
acccgaagag attattaaag ttttggagga taatcttggc tcaggcgaga tcgaaattat   2460
atgtctcaac agtagcttac ccgataaaga agagatagtg gagtggaata gaaaggtctt   2520
```

-continued

```
caaaaagatg aaaaacctga aaactctcat aattaaaaat ggaaatttct cagaaggacc   2580
cgaatatttg ccaaactcac tccgtgtctt agagtggctc aagtacccca gtcaagggct   2640
tccccccgat tttagatcca agcaactgtc cctctgcaag ctgccctcct cttgcttcgg   2700
atctttggga cttacagagt tttctaagaa gtttatgaat atgactttac tcaattttga   2760
cgagtgcgag ggctgaccc aaatacccga tttaagtgga ttaccgaatt tggaacgatt   2820
tagttttaaa aattgtaaat ccctgataac tattcacgac tctatcggct tcttaggtaa   2880
actcaattca cttaacgccg tcgggtgtag caagcttcgt tcttttcccc cgttgaaatt   2940
gacttcactt gagaatttag agttgagcta ttgctactca ttggaatctt tccccgaaat   3000
cctgggggaaa atggggcaga tcaccgagct ggtcttggag gactgtcata tcaaagaatt   3060
gcctatttcc ttccaaaatc tgacagagtt gcagacactg caattgagat cctgtcccag   3120
attgagactc ccttcctcaa ttgtgatgat gcccaagtta gctaatatca ttgcctggga   3180
aagcaagggt tggttgtttc caaaacaggt ggagggtgaa gagaagatag gctccatggt   3240
tagttccaac gtggactgtc tgtacctgtc cggttgtaaa ttgtctgatc atttcttccc   3300
aataatcctc gaatggtttg ccaacgtaaa ggatttgaat cttagcagga acaactttac   3360
ggtgctcccc gagtgtatcg ctaactgcca tctgctttgt aaattaacgc ttgatgcctg   3420
tcactcactg cgtgagatcc gtgggatccc gcccaatatt cgacaactta gcgcaagaaa   3480
ctgtaagagc ttcacatctt catgcggccg aacattgctg aatcaaaagc tgcatgaagc   3540
aggtaataca atgttttcct tctctggcgc aagatttcct gagtggtttg atcaccatag   3600
ttgggggcct tcatgctcat tttgggtggg taagaaattt ccaagcatag ccctgtgtat   3660
agctattggt ccaacgcacc ttgagcatgt agagatagta gggccaatta tgattatcaa   3720
ttcaatagag tgttcattgg atgaggagga aaacccctac ttgtatatgc tcccgcatca   3780
cactcatata ttcgaccttc agcatattgt attttccgat tatttagata ggttcgtatc   3840
cgagaatgaa tggaatcacg tggagattac ttattccgtc gagcaacgat ttgaagagaa   3900
ggataaacac gctgtaactc aaatctccat cgagaatggg atatacgtct ttaagcaaaa   3960
ctcctctatg gaggatatac aattcacgga ccctcataaa aaaaggagac tcgacgtcga   4020
tccggaactg taaccaacga tcgttcaaac atttggcaat aaagtttctt aagattgaat   4080
cctgttgccg gtcttgcgat gattatcata taatttctgt tgaattacgt taagcatgta   4140
ataattaaca tgtaatgcat gacgttattt atgagatggg tttttatgat tagagtcccg   4200
caattataca tttaatacgc gatagaaaac aaaatatagc gcgcaaacta ggataaatta   4260
tcgcgcgcgg tgtcatctat gttactagat ccctagggaa gttcctattc cgaagttcct   4320
attctctgaa aagtatagga acttctttgc gtattgggcg ctcttggcct ttttggccac   4380
cggtcgtacg gttaaaacca ccccagtaca ttaaaaacgt ccgcaatgtg ttattaagtt   4440
gtctaagcgt caatttgttt acaccacaat atatcctgcc accagccagc caacagctcc   4500
ccgaccggca gctcggcaca aaatcaccac tcgatacagg cagcccatca gtccactaga   4560
cgctcaccgg gctggttgcc ctcgccgctg ggctggcggc cgtctatggc cctgcaaacg   4620
cgccagaaac gccgtcgaag ccgtgtgcga gacaccgcag ccgccggcgt tgtggatacc   4680
tcgcggaaaa cttggccctc actgacagat gaggggcgga cgttgacact tgaggggccg   4740
actcacccgg cgcggcgttg acagatgagg ggcaggctcg atttcggccg gcgacgtgga   4800
gctggccagc ctcgcaaatc ggcgaaaacg cctgatttta cgcgagtttc ccacagatga   4860
tgtggacaag cctggggata agtgccctgc ggtattgaca cttgaggggc gcgactactg   4920
```

acagatgagg ggcgcgatcc ttgacacttg aggggcagag tgctgacaga tgaggggcgc 4980
acctattgac atttgagggg ctgtccacag gcagaaaatc cagcatttgc aagggtttcc 5040
gcccgttttt cggccaccgc taacctgtct tttaacctgc ttttaaacca atatttataa 5100
accttgtttt taaccagggc tgcgccctgt gcgcgtgacc gcgcacgccg aaggggggtg 5160
cccccccttc tcgaaccctc ccggcccgct ctcgcgttgg cagcatcacc cataattgtg 5220
gtttcaaaat cggctccgtc gatactatgt tatacgccaa ctttgaaaac aactttgaaa 5280
aagctgtttt ctggtattta aggttttaga atgcaaggaa cagtgaattg gagttcgtct 5340
tgttataatt agcttcttgg ggtatcttta aatactgtag aaaagaggaa ggaaataata 5400
aatggctaaa atgagaatat caccggaatt gaaaaaactg atcgaaaaat accgctgcgt 5460
aaaagatacg gaaggaatgt ctcctgctaa ggtatataag ctggtgggag aaaatgaaaa 5520
cctatattta aaaatgacgg acagccggta taaagggacc acctatgatg tggaacggga 5580
aaaggacatg atgctatggc tggaaggaaa gctgcctgtt ccaaaggtcc tgcactttga 5640
acggcatgat ggctggagca atctgctcat gagtgaggcc gatggcgtcc tttgctcgga 5700
agagtatgaa gatgaacaaa gccctgaaaa gattatcgag ctgtatgcgg agtgcatcag 5760
gctctttcac tccatcgaca tatcggattg tccctatacg aatagcttag acagccgctt 5820
agccgaattg gattacttac tgaataacga tctggccgat gtggattgcg aaaactggga 5880
agaagacact ccatttaaag atccgcgcga gctgtatgat tttttaaaga cggaaaagcc 5940
cgaagaggaa cttgtctttt cccacggcga cctgggagac agcaacatct ttgtgaaaga 6000
tggcaaagta agtggcttta ttgatcttgg gagaagcggc agggcggaca agtggtatga 6060
cattgccttc tgcgtccggt cgatcaggga ggatattggg gaagaacagt atgtcgagct 6120 atttttttgac ttactgggga tcaagcctga ttgggagaaa ataaaatatt atattttact 6180
ggatgaattg ttttagtacc tagatgtggc gcaacgatgc cggcgacaag caggagcgca 6240
ccgacttctt ccgcatcaag tgttttggct ctcaggccga ggcccacggc aagtatttgg 6300
gcaaggggtc gctggtattc gtgcagggca agattcggaa taccaagtac gagaaggacg 6360
gccagacggt ctacgggacc gacttcattg ccgataaggt ggattatctg gacaccaagg 6420
caccaggcgg gtcaaatcag gaataagggc acattgcccc ggcgtgagtc ggggcaatcc 6480
cgcaaggagg gtgaatgaat cggacgtttg accggaaggc atacaggcaa gaactgatcg 6540
acgcggggtt ttccgccgag gatgccgaaa ccatcgcaag ccgcaccgtc atgcgtgcgc 6600
cccgcgaaac cttccagtcc gtcggctcga tggtccagca agctacggcc aagatcgagc 6660
gcgacagcgt gcaactggct ccccctgccc tgcccgcgcc atcggccgcc gtggagcgtt 6720
cgcgtcgtct cgaacaggag gcggcaggtt tggcgaagtc gatgaccatc gacacgcgag 6780
gaactatgac gaccaagaag cgaaaaaccg ccggcgagga cctggcaaaa caggtcagcg 6840
aggccaagca agccgcgttg ctgaaacaca cgaagcagca gatcaaggaa atgcagcttt 6900
ccttgttcga tattgcgccg tggccggaca cgatgcgagc gatgccaaac gacacggccc 6960
gctctgccct gttcaccacg cgcaacaaga aaatcccgcg cgaggcgctg caaaacaagg 7020
tcattttcca cgtcaacaag gacgtgaaga tcacctacac cggcgtcgag ctgcgggccg 7080
acgatgacga actggtgtgg cagcaggtgt tggagtacgc gaagcgcacc cctatcggcg 7140
agccgatcac cttcacgttc tacgagcttt gccaggacct gggctggtcg atcaatggcc 7200
ggtattacac gaaggccgag gaatgcctgt cgcgcctaca ggcgacggcg atgggcttca 7260
cgtccgaccg cgttgggcac ctggaatcgg tgtcgctgct gcaccgcttc cgcgtcctgg 7320
accgtggcaa gaaaacgtcc cgttgccagg tcctgatcga cgaggaaatc gtcgtgctgt 7380
ttgctggcga ccactacacg aaattcatat gggagaagta ccgcaagctg tcgccgacgg 7440
cccgacggat gttcgactat ttcagctcgc accgggagcc gtacccgctc aagctggaaa 7500
ccttccgcct catgtgcgga tcggattcca cccgcgtgaa gaagtggcgc gagcaggtcg 7560
gcgaagcctg cgaagagttg cgaggcagcg gcctggtgga acacgcctgg gtcaatgatg 7620
acctggtgca ttgcaaacgc tagggccttg tggggtcagt tccggctggg ggttcagcag 7680
ccagcgcttt actgagatcc tcttccgctt cctcgctcac tgactcgctg cgctcggtcg 7740
ttcggctgcg gcgagcggta tcagctcact caaaggcggt aatacggtta tccacagaat 7800
caggggataa cgcaggaaag aacatgtgag caaaaggcca gcaaaaggcc aggaaccgta 7860
aaaaggccgc gttgctggcg tttttccata ggctccgccc ccctgacgag catcacaaaa 7920
atcgacgctc aagtcagagg tggcgaaacc cgacaggact ataaagatac caggcgtttc 7980
cccctggaag ctccctcgtg cgctctcctg ttccgaccct gccgcttacc ggatacctgt 8040
ccgcctttct cccttcggga agcgtggcgc tttctcatag ctcacgctgt aggtatctca 8100
gttcggtgta ggtcgttcgc tccaagctgg gctgtgtgca cgaacccccc gttcagcccg 8160
accgctgcgc cttatccggt aactatcgtc ttgagtccaa cccggtaaga cacgacttat 8220
cgccactggc agcagccact ggtaacagga ttagcagagc gaggtatgta ggcggtgcta 8280
cagagttctt gaagtggtgg cctaactacg gctacactag aagaacagta tttggtatct 8340
gcgctctgct gaagccagtt accttcggaa aaagagttgg tagctcttga tccggcaaac 8400
aaaccaccgc tggtagcggt ggtttttttg tttgcaagca gcagattacg cgcagaaaaa 8460
aaggatctca agaagatcct ttgatctttt ctacggggtc tgacgctcag tggaacgaaa 8520
actcacgtta agggattttg gtcatgagat tatcaaaaag gatcttcacc tagatccttt 8580
tgg 8583

<210> SEQ ID NO 32
<211> LENGTH: 8577
<212> TYPE: DNA
<213> ORGANISM: Artificial Sequence
<220> FEATURE:
<223> OTHER INFORMATION: Transient expression vector with Phaseolus vulgaris FIT1

<400> SEQUENCE: 32
atctcctgtg gttggcatgc acatacaaat ggacgaacgg ataaaccttt tcacgccctt 60
ttaaatatcc gattattcta ataaacgctc ttttctctta ggtttacccg ccaatatatc 120
ctgtcaaaca ctgatagttt aaactgaagg cgggaaacga caatctgcta gtggatctcc 180
cagtcacgac gttgtaaaac gggcgccccg cggaaagctt gctagccaat tggggcccaa 240
cgttctcgag ggatcttcct gcaagcatct ctatttcctg aaggtctaac ctcgaagatt 300
taagatttaa ttacgtttat aattacaaaa ttgattctag tatctttaat ttaatgctta 360
tacattatta attaatttag tactttcaat ttgttttcag aaattatttt actatttttt 420
ataaaataaa agggagaaaa tggctattta aatactagcc tattttattt caattttagc 480
ttaaaatcag ccccaattag ccccaatttc aaattcaaat ggtccagccc aattcctaaa 540
taacccaccc ctaacccgcc cggtttcccc ttttgatcca tgcagtcaac gcccagaatt 600
tccctatata attttttaat tcccaaacac ccctaactct atcccatttc tcaccaaccg 660

-continued

```
ccacatagat ctatcctctt atctctcaaa ctctctcgaa ccttccccta accctagcag    720
cctctcatca tcctcacctc aaaacccacc ggatctagaa ggccttggat ccacccggga    780
gaattcgtcg actttgcggc cgcatcgata ctgcaggagc tcggtaccga gcatggctgt    840
gccgagcttc tcatccagct tcacgtatga tgttttcctt agtttcagag gggaggacac    900
gcgttatgga ttcaccggga atttatatac ggctttgcac gattccggca tctgcacttt    960
tatagacgac gaggagttgc caaagggcga cgagataaca acttccctcc agaaggcaat   1020
agaggcaagt aggattttca taatagtatt tagtcacaat tatgccagca gttcattctg   1080
tttaaacgag ctcgcttata tactccccta tgccaagagg aatggcttat tggtgctgcc   1140
tttattctat gatgttgtac cctcacatgt aagacatcat actggaactt tcggggaagc   1200
actggatact cacgagaata agttcaaagg aacctctgaa ggcttcgaat taaacatgga   1260
aaaactcaat cgttggaaaa tggctcttcg tggggcagct aatttgagtg gataccactt   1320
taaacacggc gaggaatatg agtaccaatt tatcaaaagg attgtcaagc tcgtgagcaa   1380
caagattaac agagcaacac ttcatgttgc agactaccct gtgggcttgg aaacccgtat   1440
gctcgaagta aaacttcttc tggacgtagg ttccgacgac ggcgtacaca tggtgggaat   1500
acatgggttc gggggcgtcg ggaagaccac acttgctctg gctgtgtaca attctattgc   1560
tgataatttt gaaggcctgt gctttttaga aaacgtcagg gagaactcca acaaacatgg   1620
attgcagcat ttacagtccc tgctgttgtc tcaaatggtg ggtgaaaaca acatcaatat   1680
aaccagtgtc aaacagggca tatcaatgat gcaacatcga ctccgacaga aaaaaattct   1740
gctgattctg gatgacgtag ataagcatga gcaacttcag gcaatagtag gacgagccga   1800
ttggttcgga cccggatctc gagtaattat aactacgagg gacaaacatt tattgagctg   1860
ccaactcgta gagaaaattt acgaagtaaa gaagcttaaa aaaaaagatg ccttgaggct   1920
cctttcatgg aaggggttta aaactgagga agtgcatccg tcttatgtga acgtaatggg   1980
gagggtcctg gcctacgcca gcggccaccc actcgctctt gaagtcattg gatcaaaatt   2040
atttcgtaag tccgtcaagg aatgggagtc cgcaatacaa caatatgaaa aaattccgaa   2100
caatcaaatc ttagaaattc ttaaaatttc tttcgattct ttagaggagg tggaaaagag   2160
tgtatttctt gacattgcct gctgctttaa gggatatgca ctgagtgaag ttgagaatat   2220
cttgagggca cactacgggg actgcatgaa gtatcatata ggagtactgg ttgagaagag   2280
tttgatcaaa taccgttgga actctgttgt gaccttgcac gaccttatcg aggacatggg   2340
taaggaaata gtcaggcaaa aatctcctaa taagcccggc aaaagatccc gtttatggtc   2400
acctgaagac atcatccagg tcctggaaga taatagtgga tcaggtgaaa tagaaatcat   2460
ctgcctgaat tactcacttc ccgggaaaga agaaattgtc gagtggaaca ggaaggcttt   2520
caagaaaatg aaaaatctca agacactcat aattaaatct ggaaattttt cagaaggtcc   2580
caaatacctt ccgaattcac tccgtgtgat ggagtggctg aaatatccat ctcaaggcct   2640
ccccccagat ttcaggagta aggaattaac gatctgtaag ttacccgcat cctgcttcgg   2700
cagcctcgag ttagctgagt tatctaagaa atttatgaat atgacgttat taaatttcga   2760
cgaatgtgag ggcctcacac aaatccctga cgtctctgga ctgccgaact tagtagagat   2820
ctctttcaag aactgcaaga gcctgatcac tattcacgat tctatcggat tcttagggaa   2880
actcaatagc ttgaatgctg taggctgctc taagctcagg agcttcccac ctttgaaatt   2940
gacatctctt gaaaaccttg agttgagtta ttgttatagc ctggagagct tcccggaaat   3000
cttaggaaag atgggtaaga ttaccgagct gtttttagag tgctgcgaca taaaagagct   3060
```

-continued

```
tcccttctct tttcagaatc tcacagaatt acagactctg cagctccgat actgcccgat   3120
gctgcgatta ccctctagta tcgtgatgat gccgaaattg acagagatta ttgcttggga   3180
aagtgaggga tggttgtttc ccaaacaggt cgaaggagaa gaaaaggtgt ctagtatggt   3240
gagttcaaac gtagactgcc tcttactgcc cggctgcaag ctcagcgacg atttttttcc   3300
gattacctgg ttcgctaacg taaaggaact tgatctctct agaaacactt ttaccgtcct   3360
gccagaatgt atttctaact gttatttttt gtgtaaattg attttggaca actgtcactc   3420
tctccgtgaa atacgtggga tcccgcctaa catacgacac ttgtccgcca ggtattgcaa   3480
atcattcact agctcctgta ggagcacgct cttgaaccag aagttgcacg agacaggcaa   3540
tactatgttt tggttttcag gcgctagttt tcccgagtgg tttgagcata ggagtcaagg   3600
tcccagttgt agtttctggg tgggaaataa atttcctgcc atcgcactct gtatagtgat   3660
cgggccaaca catcttgacc atatcgagat tgtgggacca atcatgatca ttaacggcat   3720
cgattgtagc ctcgatgatg ggctggtcaa tccctacctt tggattccac ctcaccatac   3780
gtacctgttc gacttacagc acatcgtttc tagtgactat cttgatcgat ttgtctctga   3840
gaaagaatgg aaccatgtcg aaatcagata ttcagtgaaa cagcgttttt cagagaagga   3900
taaacatgta gtcatccctg tgagcattga aaacggaatc tacgttttta agcaaaggag   3960
ctccatggaa gacatacagt ttacggatcc acacaagaaa cgaagattag acgtagatcc   4020
agaataacca acgatcgttc aaacatttgg caataaagtt tcttaagatt gaatcctgtt   4080
gccggtcttg cgatgattat catataattt ctgttgaatt acgttaagca tgtaataatt   4140
aacatgtaat gcatgacgtt atttatgaga tgggttttta tgattagagt cccgcaatta   4200
tacatttaat acgcgataga aaacaaaata tagcgcgcaa actaggataa attatcgcgc   4260
gcggtgtcat ctatgttact agatccctag ggaagttcct attccgaagt tcctattctc   4320
tgaaaagtat aggaacttct ttgcgtattg ggcgctcttg gcctttttgg ccaccggtcg   4380
tacggttaaa accaccccag tacattaaaa acgtccgcaa tgtgttatta agttgtctaa   4440
gcgtcaattt gtttacacca caatatatcc tgccaccagc cagccaacag ctccccgacc   4500
ggcagctcgg cacaaaatca ccactcgata caggcagccc atcagtccac tagacgctca   4560
ccgggctggt tgccctcgcc gctgggctgg cggccgtcta tggccctgca aacgcgccag   4620
aaacgccgtc gaagccgtgt gcgagacacc gcagccgccg gcgttgtgga tacctcgcgg   4680
aaaacttggc cctcactgac agatgagggg cggacgttga cacttgaggg gccgactcac   4740
ccggcgcggc gttgacagat gaggggcagg ctcgatttcg gccggcgacg tggagctggc   4800
cagcctcgca aatcggcgaa aacgcctgat tttacgcgag tttcccacag atgatgtgga   4860
caagcctggg gataagtgcc ctgcggtatt gacacttgag ggcgcgact actgacagat    4920
gaggggcgcg atccttgaca cttgaggggc agagtgctga cagatgaggg gcgcacctat   4980
tgacatttga ggggctgtcc acaggcagaa aatccagcat ttgcaagggt ttccgcccgt   5040
ttttcggcca ccgctaacct gtcttttaac ctgcttttaa accaatattt ataaaccttg   5100
tttttaacca gggctgcgcc ctgtgcgcgt gaccgcgcac gccgaagggg ggtgcccccc   5160
cttctcgaac cctcccggcc cgctctcgcg ttggcagcat cacccataat tgtggtttca   5220
aaatcggctc cgtcgatact atgttatacg ccaactttga aaacaacttt gaaaaagctg   5280
ttttctggta tttaaggttt tagaatgcaa ggaacagtga attggagttc gtcttgttat   5340
aattagcttc ttggggtatc tttaaatact gtagaaaaga ggaaggaaat aataaatggc   5400
```

taaaatgaga atatcaccgg aattgaaaaa actgatcgaa aaataccgct gcgtaaaaga 5460
tacggaagga atgtctcctg ctaaggtata taagctggtg ggagaaaatg aaaacctata 5520
tttaaaaatg acggacagcc ggtataaagg gaccacctat gatgtggaac gggaaaagga 5580
catgatgcta tggctggaag gaaagctgcc tgttccaaag gtcctgcact ttgaacggca 5640
tgatggctgg agcaatctgc tcatgagtga ggccgatggc gtcctttgct cggaagagta 5700
tgaagatgaa caaagccctg aaaagattat cgagctgtat gcggagtgca tcaggctctt 5760
tcactccatc gacatatcgg attgtcccta tacgaatagc ttagacagcc gcttagccga 5820
attggattac ttactgaata acgatctggc cgatgtggat tgcgaaaact gggaagaaga 5880
cactccattt aaagatccgc gcgagctgta tgatttttta aagacggaaa agcccgaaga 5940
ggaacttgtc ttttcccacg gcgacctggg agacagcaac atctttgtga aagatggcaa 6000
agtaagtggc tttattgatc ttgggagaag cggcagggcg gacaagtggt atgacattgc 6060
cttctgcgtc cggtcgatca gggaggatat tggggaagaa cagtatgtcg agctattttt 6120
tgacttactg gggatcaagc ctgattggga gaaaataaaa tattatattt tactggatga 6180
attgttttag tacctagatg tggcgcaacg atgccggcga caagcaggag cgcaccgact 6240
tcttccgcat caagtgtttt ggctctcagg ccgaggccca cggcaagtat ttgggcaagg 6300
ggtcgctggt attcgtgcag ggcaagattc ggaataccaa gtacgagaag gacggccaga 6360
cggtctacgg gaccgacttc attgccgata aggtggatta tctggacacc aaggcaccag 6420
gcgggtcaaa tcaggaataa gggcacattg ccccggcgtg agtcggggca atcccgcaag 6480
gagggtgaat gaatcggacg tttgaccgga aggcatacag gcaagaactg atcgacgcgg 6540
ggttttccgc cgaggatgcc gaaaccatcg caagccgcac cgtcatgcgt gcgccccgcg 6600
aaaccttcca gtccgtcggc tcgatggtcc agcaagctac ggccaagatc gagcgcgaca 6660
gcgtgcaact ggctcccct gccctgcccg cgccatcggc cgccgtggag cgttcgcgtc 6720
gtctcgaaca ggaggcggca ggtttggcga agtcgatgac catcgacacg cgaggaacta 6780
tgacgaccaa gaagcgaaaa accgccggcg aggacctggc aaaacaggtc agcgaggcca 6840
agcaagccgc gttgctgaaa cacacgaagc agcagatcaa ggaaatgcag ctttccttgt 6900
tcgatattgc gccgtggccg gacacgatgc gagcgatgcc aaacgacacg gcccgctctg 6960
ccctgttcac cacgcgcaac aagaaaatcc cgcgcgaggc gctgcaaaac aaggtcattt 7020
tccacgtcaa caaggacgtg aagatcacct acaccggcgt cgagctgcgg gccgacgatg 7080
acgaactggt gtggcagcag gtgttggagt acgcgaagcg cacccctatc ggcgagccga 7140
tcaccttcac gttctacgag ctttgccagg acctgggctg gtcgatcaat ggccggtatt 7200
acacgaaggc cgaggaatgc ctgtcgcgcc tacaggcgac ggcgatgggc ttcacgtccg 7260
accgcgttgg gcacctggaa tcggtgtcgc tgctgcaccg cttccgcgtc ctggaccgtg 7320
gcaagaaaac gtcccgttgc caggtcctga tcgacgagga aatcgtcgtg ctgtttgctg 7380
gcgaccacta cacgaaattc atatgggaga agtaccgcaa gctgtcgccg acggcccgac 7440
ggatgttcga ctatttcagc tcgcaccggg agccgtaccc gctcaagctg gaaaccttcc 7500
gcctcatgtg cggatcggat tccacccgcg tgaagaagtg gcgcgagcag gtcggcgaag 7560
cctgcgaaga gttgcgaggc agcggcctgg tggaacacgc ctgggtcaat gatgacctgg 7620
tgcattgcaa acgctagggc cttgtggggt cagttccggc tgggggttca gcagccagcg 7680
ctttactgag atcctcttcc gcttcctcgc tcactgactc gctgcgctcg gtcgttcggc 7740
tgcggcgagc ggtatcagct cactcaaagg cggtaatacg gttatccaca gaatcagggg 7800
ataacgcagg aaagaacatg tgagcaaaag gccagcaaaa ggccaggaac cgtaaaaagg 7860
ccgcgttgct ggcgtttttc cataggctcc gcccccctga cgagcatcac aaaaatcgac 7920
gctcaagtca gaggtggcga aacccgacag gactataaag ataccaggcg tttccccctg 7980
gaagctccct cgtgcgctct cctgttccga ccctgccgct taccggatac ctgtccgcct 8040
ttctcccttc gggaagcgtg gcgctttctc atagctcacg ctgtaggtat ctcagttcgg 8100
tgtaggtcgt tcgctccaag ctgggctgtg tgcacgaacc ccccgttcag cccgaccgct 8160
gcgccttatc cggtaactat cgtcttgagt ccaacccggt aagacacgac ttatcgccac 8220
tggcagcagc cactggtaac aggattagca gagcgaggta tgtaggcggt gctacagagt 8280
tcttgaagtg gtggcctaac tacggctaca ctagaagaac agtatttggt atctgcgctc 8340
tgctgaagcc agttaccttc ggaaaaagag ttggtagctc ttgatccggc aaacaaacca 8400
ccgctggtag cggtggtttt tttgtttgca agcagcagat tacgcgcaga aaaaaaggat 8460
ctcaagaaga tcctttgatc ttttctacgg ggtctgacgc tcagtggaac gaaaactcac 8520
gttaagggat tttggtcatg agattatcaa aaaggatctt cacctagatc cttttgg 8577

<210> SEQ ID NO 33
<211> LENGTH: 8580
<212> TYPE: DNA
<213> ORGANISM: Artificial Sequence
<220> FEATURE:
<223> OTHER INFORMATION: Transient expression vector with Lablab purpureus FIT1

<400> SEQUENCE: 33
atctcctgtg gttggcatgc acatacaaat ggacgaacgg ataaaccttt tcacgccctt 60
ttaaatatcc gattattcta ataaacgctc ttttctctta ggtttacccg ccaatatatc 120
ctgtcaaaca ctgatagttt aaactgaagg cgggaaacga caatctgcta gtggatctcc 180
cagtcacgac gttgtaaaac gggcgccccg cggaaagctt gctagccaat tggggcccaa 240
cgttctcgag ggatcttcct gcaagcatct ctatttcctg aaggtctaac ctcgaagatt 300
taagatttaa ttacgtttat aattacaaaa ttgattctag tatctttaat ttaatgctta 360
tacattatta attaatttag tactttcaat ttgttttcag aaattatttt actatttttt 420
ataaaataaa agggagaaaa tggctattta aatactagcc tattttattt caattttagc 480
ttaaaatcag ccccaattag ccccaatttc aaattcaaat ggtccagccc aattcctaaa 540
taacccaccc ctaacccgcc cggtttcccc ttttgatcca tgcagtcaac gcccagaatt 600
tccctatata atttttaat tcccaaacac ccctaactct atcccatttc tcaccaaccg 660
ccacatagat ctatcctctt atctctcaaa ctctctcgaa ccttccccta accctagcag 720
cctctcatca tcctcacctc aaaacccacc ggatctagaa ggccttggat ccacccggga 780
gaattcgtcg actttgcggc cgcatcgata ctgcaggagc tcggtaccga gcatggcaga 840
gccctctttc agttcatctt tcacgtatga cgtgtttctc tcctttaggg gcgaggacac 900
gcgatactct tttacaggca acctctacag agctttacga gattctggga tatgcacctt 960
tatcgacgat gaagagttga ggaagggcga cgagataacc agtgccctcg aaaaagctat 1020
agaaggttca cgaatattca tcatcgtcct cagtcataac tacgcaagct cctccttttg 1080
tcttaatgaa ctggcatata ttttgccata tgccaagagg aaagggctcc tcgtgctccc 1140
tctcttttac gacgttgtcc cgagccatgt acgacatcat actggcagct tcggagaagc 1200
actggatact catgagaagc gatttaaagg gacatcagag ggttttgaac tcaatatgga 1260

```
gaagttgaat gaatggaaga tggctcttag acacgttgcc aatttttcag gttaccattt   1320
caaacacggt gaagagtacg aatatgagtt cattaaaaaa atagtggagt tggtgtccaa   1380
caaaatcaac cgtgctcctt tacacgtagc tgactaccct gtagggttgg aatcccgagt   1440
actggaaatc aagctgctct tagatgtcgg cagcgatgat ggagtgcata tggtgggaat   1500
ctatggcctc ggcggggtgg ggaaaacgac gttggccgta gcagtctata atagtatagc   1560
tgaccatttt gaaggtttat gcttcctcga gaatgtaagg gaaaactcaa acaaacacgg   1620
ccttcaccat ctccaatcac tcttactctc tcaaatggtc ggggagaaaa atatcaatat   1680
tagttctgtt aagcagggca tctccataat gcaacatcga cttaggcaaa agaagattct   1740
gctcatcctt gatgatgttg ataagttgga acaattgcag tcaattgtag gacgacctga   1800
ctggtttggc ccaggctctc gtgtgataat aacaacgagg gataaacagc ttctcagctg   1860
tcatcttgtg gaaaagactt atgaagtaaa gaaattgaag aagaaggacg ccttccgatt   1920
gttaagctgg aaaggtttta gaactgagga agtagacact tcctacgtaa acgtgatgga   1980
ccgtgttttg gcttacgcca gtgggcatcc gttggctctg gaagttattg gatccaagct   2040
ttttagaaaa tccatcaagg aatgggagtc agctatcaac caatacgaaa aaatccccaa   2100
taaccaaata cttgaaatac tcaaaatatc atttgatagc ctggaagaag tggagaaatc   2160
cgtctttctt gatatatcct gttgcttcaa aggctatgcc cttagtgaag tggaggacat   2220
attacgtgcc cattacgggg attgcatgaa gtaccacatc ggggtcttag tagagaagtc   2280
attgattaaa taccgatggg gttgcatcgt gactctccac gatttgatag aagacatggg   2340
gaaggagata gtgcgacaga aatctcccca gaagccagga aagaggtcac gtctgtggag   2400
tccggaggat atcattcaag ttcttgagga caattctggc agtggtgaga tcgagattat   2460
ttgccttaat tcctctttat tagataaaga agaaacaatt gagtggaaca gaaaggcttt   2520
caagaagatg aaaaacttga aaacgttaat aataaagaac ggaaacttct cagagggacc   2580
gaaatacttg cccaatagcc tgcgagtgtt ggaatggctc aagtacccaa gtcaaggtct   2640
gcccccgac ttcagatcta aaaaacttgt gatttgtaaa ttgccttcct cttgtttcgg   2700
cactctggaa cttgcagagt tatctaaaaa gtttatgaac atgactgttc tcaattttga   2760
tgaatgtgag ggtcttacgc agatcccaga cgtgagtggc ttacccaact tggagaatat   2820
cagtttcaaa aactgtaagt cccttattac gattcacgac tctatcgggt ttcttgataa   2880
gcttaattcc ctcaacgccg tgggttgctc acgactgaga agcttccccc cactgaagct   2940
gacatcattg gagaacctcg agttatctta ctgctatagc ctggaatgtt tccctgagat   3000
tctgggcaag atggaaaaga tgacggaact ggtcttggag gattgtgaca taaaggagat   3060
tccgttctct tttaaaaacc tgactgaatt gcagactctg gaccttcgtt tttgtaggat   3120
gcttcgattg cctacttcta ttgtcatgat gccaaaattg tccgaaatta tcgcctggga   3180
ggctgaggga tgcttgttcc ccaagcaagt cgagggcgag gaaaaggtta gttctatggt   3240
cagttcaaat gtagactctc tcagactcag cggatgtaag ctctcagatg atttttttccc   3300
aaccactctc gcttggttct ccaatgtgaa ggacttgaac ctctctagaa ataactttac   3360
tgtattgcca gaatgtatca gtaattgcca cttcttgtat aaactgacac tcgactactg   3420
tcattccctc cgtgaaataa ggggcctccc tcctaacatt cagcacttgt ccgcaattaa   3480
ttgtacctct ttcacctcat catgccgttc cacattgctg aatcagaagc tccacgaggc   3540
tggtaacaca atgttcagct ttagtggtgc aatgtttccg gaatggttcg aaaatcactc   3600
```

-continued

```
tcgaggcccg tcttactcct tctgggtagg aaacaaattc ccggcaatcg cattatgcat   3660
agctataggg cctactcatg tggagtatgt gcagatcgta ggcccaatca tgattataaa   3720
cgggattgag tgctctttac caggtgtaga tccttatctt aagatgctgc ccgaccacac   3780
atatttgttc gacctgcaac aaattgtgtt cccagattac cttgacagat ttgtttctga   3840
gaacgaatgg aatcatgtcg aaataacata tgccgtggaa aaacgtttct caaagaaaga   3900
caaacatgtc gttatacctg tctctattga aaacggcata tatgtcagca aacaaaggtc   3960
ttccatggag aacgtaagat tcacggatcc tcgtaagaag agaagactcg acgtggacag   4020
cgaattgtaa ccaacgatcg ttcaaacatt tggcaataaa gtttcttaag attgaatcct   4080
gttgccggtc ttgcgatgat tatcatataa tttctgttga attacgttaa gcatgtaata   4140
attaacatgt aatgcatgac gttatttatg agatgggttt ttatgattag agtcccgcaa   4200
ttatacattt aatacgcgat agaaaacaaa atatagcgcg caaactagga taaattatcg   4260
cgcgcggtgt catctatgtt actagatccc tagggaagtt cctattccga agttcctatt   4320
ctctgaaaag tataggaact tctttgcgta ttgggcgctc ttggcctttt tggccaccgg   4380
tcgtacggtt aaaaccaccc cagtacatta aaaacgtccg caatgtgtta ttaagttgtc   4440
taagcgtcaa tttgtttaca ccacaatata tcctgccacc agccagccaa cagctccccg   4500
accggcagct cggcacaaaa tcaccactcg atacaggcag cccatcagtc cactagacgc   4560
tcaccgggct ggttgccctc gccgctgggc tggcggccgt ctatggccct gcaaacgcgc   4620
cagaaacgcc gtcgaagccg tgtgcgagac accgcagccg ccggcgttgt ggatacctcg   4680
cggaaaactt ggccctcact gacagatgag gggcggacgt tgacacttga ggggccgact   4740
cacccggcgc ggcgttgaca gatgaggggc aggctcgatt tcggccggcg acgtggagct   4800
ggccagcctc gcaaatcggc gaaaacgcct gattttacgc gagtttccca cagatgatgt   4860
ggacaagcct ggggataagt gccctgcggt attgacactt gaggggcgcg actactgaca   4920
gatgaggggc gcgatccttg acacttgagg ggcagagtgc tgacagatga ggggcgcacc   4980
tattgacatt tgaggggctg tccacaggca gaaaatccag catttgcaag ggtttccgcc   5040
cgtttttcgg ccaccgctaa cctgtctttt aacctgcttt taaaccaata tttataaacc   5100
ttgtttttaa ccagggctgc gccctgtgcg cgtgaccgcg cacgccgaag gggggtgccc   5160
ccccttctcg aaccctcccg gcccgctctc gcgttggcag catcacccat aattgtggtt   5220
tcaaaatcgg ctccgtcgat actatgttat acgccaactt tgaaaacaac tttgaaaaag   5280
ctgttttctg gtatttaagg ttttagaatg caaggaacag tgaattggag ttcgtcttgt   5340
tataattagc ttcttggggt atctttaaat actgtagaaa agaggaagga aataataaat   5400
ggctaaaatg agaatatcac cggaattgaa aaaactgatc gaaaaatacc gctgcgtaaa   5460
agatacggaa ggaatgtctc ctgctaaggt atataagctg gtgggagaaa atgaaaacct   5520
atatttaaaa atgacggaca gccggtataa agggaccacc tatgatgtgg aacgggaaaa   5580
ggacatgatg ctatggctgg aaggaaagct gcctgttcca aaggtcctgc actttgaacg   5640
gcatgatggc tggagcaatc tgctcatgag tgaggccgat ggcgtccttt gctcggaaga   5700
gtatgaagat gaacaaagcc ctgaaaagat tatcgagctg tatgcggagt gcatcaggct   5760
ctttcactcc atcgacatat cggattgtcc ctatacgaat agcttagaca gccgcttagc   5820
cgaattggat tacttactga ataacgatct ggccgatgtg gattgcgaaa actgggaaga   5880
agacactcca tttaaagatc cgcgcgagct gtatgatttt ttaaagacgg aaaagcccga   5940
agaggaactt gtcttttccc acggcgacct gggagacagc aacatctttg tgaaagatgg   6000
```

caaagtaagt ggctttattg atcttgggag aagcggcagg gcggacaagt ggtatgacat 6060
tgccttctgc gtccggtcga tcagggagga tattggggaa gaacagtatg tcgagctatt 6120
ttttgactta ctggggatca agcctgattg ggagaaaata aaatattata ttttactgga 6180
tgaattgttt tagtacctag atgtggcgca acgatgccgg cgacaagcag gagcgcaccg 6240
acttcttccg catcaagtgt tttggctctc aggccgaggc ccacggcaag tatttgggca 6300
aggggtcgct ggtattcgtg cagggcaaga ttcggaatac caagtacgag aaggacggcc 6360
agacggtcta cgggaccgac ttcattgccg ataaggtgga ttatctggac accaaggcac 6420
caggcgggtc aaatcaggaa taagggcaca ttgccccggc gtgagtcggg gcaatcccgc 6480
aaggagggtg aatgaatcgg acgtttgacc ggaaggcata caggcaagaa ctgatcgacg 6540
cggggttttc cgccgaggat gccgaaacca tcgcaagccg caccgtcatg cgtgcgcccc 6600
gcgaaacctt ccagtccgtc ggctcgatgg tccagcaagc tacggccaag atcgagcgcg 6660
acagcgtgca actggctccc cctgccctgc ccgcgccatc ggccgccgtg gagcgttcgc 6720
gtcgtctcga acaggaggcg gcaggtttgg cgaagtcgat gaccatcgac acgcgaggaa 6780
ctatgacgac caagaagcga aaaaccgccg gcgaggacct ggcaaaacag gtcagcgagg 6840
ccaagcaagc cgcgttgctg aaacacacga agcagcagat caaggaaatg cagctttcct 6900
tgttcgatat tgcgccgtgg ccggacacga tgcgagcgat gccaaacgac acggcccgct 6960
ctgccctgtt caccacgcgc aacaagaaaa tcccgcgcga ggcgctgcaa aacaaggtca 7020
ttttccacgt caacaaggac gtgaagatca cctacaccgg cgtcgagctg cgggccgacg 7080
atgacgaact ggtgtggcag caggtgttgg agtacgcgaa gcgcacccct atcggcgagc 7140
cgatcacctt cacgttctac gagctttgcc aggacctggg ctggtcgatc aatggccggt 7200
attacacgaa ggccgaggaa tgcctgtcgc gcctacaggc gacggcgatg ggcttcacgt 7260
ccgaccgcgt tgggcacctg gaatcggtgt cgctgctgca ccgcttccgc gtcctggacc 7320
gtggcaagaa aacgtcccgt tgccaggtcc tgatcgacga ggaaatcgtc gtgctgtttg 7380
ctggcgacca ctacacgaaa ttcatatggg agaagtaccg caagctgtcg ccgacggccc 7440
gacggatgtt cgactatttc agctcgcacc gggagccgta cccgctcaag ctggaaacct 7500
tccgcctcat gtgcggatcg gattccaccc gcgtgaagaa gtggcgcgag caggtcggcg 7560
aagcctgcga agagttgcga ggcagcggcc tggtggaaca cgcctgggtc aatgatgacc 7620
tggtgcattg caaacgctag ggccttgtgg ggtcagttcc ggctgggggt tcagcagcca 7680
gcgctttact gagatcctct tccgcttcct cgctcactga ctcgctgcgc tcggtcgttc 7740
ggctgcggcg agcggtatca gctcactcaa aggcggtaat acggttatcc acagaatcag 7800
gggataacgc aggaaagaac atgtgagcaa aaggccagca aaaggccagg aaccgtaaaa 7860
aggccgcgtt gctggcgttt ttccataggc tccgcccccc tgacgagcat cacaaaaatc 7920
gacgctcaag tcagaggtgg cgaaacccga caggactata aagataccag gcgtttcccc 7980
ctggaagctc cctcgtgcgc tctcctgttc cgaccctgcc gcttaccgga tacctgtccg 8040
cctttctccc ttcgggaagc gtggcgcttt ctcatagctc acgctgtagg tatctcagtt 8100
cggtgtaggt cgttcgctcc aagctgggct gtgtgcacga accccccgtt cagcccgacc 8160
gctgcgcctt atccggtaac tatcgtcttg agtccaaccc ggtaagacac gacttatcgc 8220
cactggcagc agccactggt aacaggatta gcagagcgag gtatgtaggc ggtgctacag 8280
agttcttgaa gtggtggcct aactacggct acactagaag aacagtattt ggtatctgcg 8340
ctctgctgaa gccagttacc ttcggaaaaa gagttggtag ctcttgatcc ggcaaacaaa 8400
ccaccgctgg tagcggtggt ttttttgttt gcaagcagca gattacgcgc agaaaaaaag 8460
gatctcaaga agatcctttg atcttttcta cggggtctga cgctcagtgg aacgaaaact 8520
cacgttaagg gattttggtc atgagattat caaaaaggat cttcacctag atccttttgg 8580

<210> SEQ ID NO 34
<211> LENGTH: 8559
<212> TYPE: DNA
<213> ORGANISM: Artificial Sequence
<220> FEATURE:
<223> OTHER INFORMATION: Transient expression vector with Abrus precatorius FIT1

<400> SEQUENCE: 34
atctcctgtg gttggcatgc acatacaaat ggacgaacgg ataaaccttt tcacgccctt 60
ttaaatatcc gattattcta ataaacgctc ttttctctta ggtttacccg ccaatatatc 120
ctgtcaaaca ctgatagttt aaactgaagg cgggaaacga caatctgcta gtggatctcc 180
cagtcacgac gttgtaaaac gggcgccccg cggaaagctt gctagccaat tggggcccaa 240
cgttctcgag gggatcttct gcaagcatct ctatttcctg aaggtctaac ctcgaagatt 300
taagatttaa ttacgtttat aattacaaaa ttgattctag tatctttaat ttaatgctta 360
tacattatta attaatttag tactttcaat ttgttttcag aaattatttt actatttttt 420
ataaaataaa agggagaaaa tggctattta aatactagcc tattttattt caattttagc 480
ttaaaatcag ccccaattag ccccaatttc aaattcaaat ggtccagccc aattcctaaa 540
taacccaccc ctaacccgcc cggtttcccc ttttgatcca tgcagtcaac gcccagaatt 600
tccctatata atttttaat tcccaaacac ccctaactct atcccatttc tcaccaaccg 660
ccacatagat ctatcctctt atctctcaaa ctctctcgaa ccttccccta accctagcag 720
cctctcatca tcctcacctc aaaacccacc ggatctagaa ggccttggat ccacccggga 780
gaattcgtcg actttgcggc cgcatcgata ctgcaggagc tcggtaccga gcatggcagt 840
gcgtagttgc tcttcttctt tcacatacgc ctttacttac gatgtttttc tgagctttag 900
gggatccgat acacgtcacg gattcgtcgg gaatctgttt aaagccttgc aggataaggg 960
aatccatacg ttcattgatg atgagggact ccaacgaggt gaagagataa gtcctgcatt 1020
ggtaaaggcc atagaggaaa gccgaatcgc catcgcagtc cttagcaata actatgctta 1080
tagtagtttc tgcttagatg agcttgccca catattagag tgtgtcaagc gtaaagatac 1140
gttggtctta cctcttttct atgatgttga cccgagccat gtgcgatatc aacgaggctc 1200
ttacggcgaa gcacttgctt cccacggcga acgttttaag cataacatgg aaaaactgca 1260
gaagtggaaa atggccctgc atcatgttgc taatctctca gggtatcact ttaaacatgg 1320
ggatggctac gagtatgagt tcataggacg aattgtcgag cttgtatcta acaagatcaa 1380
tcgtgctcca ttgcatgtag ccgattatcc agtgggttta gagtcacagg tacttgaggt 1440
taggaaactt ttggacgtcg gctcagatga cggggtgttg atgattggta ttcatggaat 1500
cggtggtatc ggtaagacta ctcttgcctt ggctgtctac aatctgattg ctgatcattt 1560
cgatggatta tgtttccttg agaacgtcag agaaaactcc gacaaacatg ggcttcagca 1620
cttacagagt atactccttt ccgagattct tggtgaaacg aaaatcaaac tcgcaagtgt 1680
gaagcaggga atctccatac tgcagcaccg tttgcaaagg cagaaggtgc tgctcatctt 1740
agacgacgtg gacaagcatg agcaattaaa tgcaatcgtg ggaaaaccgg attggttcgg 1800

-continued

```
gcctgggtca agggtaatta tcacaacaag agacaaacac cttctcgctt gtcacgaagt   1860
gaagagcact catgaagtca aaaaactgaa taagaacgac gccttgcagc tcctttcctg   1920
gaaagctttc aaatcagaga aagtggaccc aagctatgtc gacgtcatga actgcgctgt   1980
tgcatacgca tcagggcacc ctctggcctt ggaggtaatt ggaagtaatt tattcggtaa   2040
gagcattgaa cagtggaaat ctgctattaa tcagtacaaa aggatcccta actgtcacat   2100
cttaaaaatc ttaaaagtat catttgatgc actggaagag gaggaaaaga gtgtattctt   2160
ggacattgca tgctgtttca agggctacaa tttggaagaa gtcgaggaca tcctgcacgc   2220
acattacggg gactcaatga agtaccatat tggcctgtta gtggagaagt cactgataaa   2280
gctgacctgg gccggtggcg ttacgcttca cgacttaata gaagacatgg gtaaagaaat   2340
agtgagacag aagtccccaa aagaccctgg aaagcgtagc cgattatggc tgcctgagga   2400
catcattcac gtcttcgaac atgacagtgg cactggcgag attgagataa tacgtcttgc   2460
ctctagtctg ttagataagg aggagattat aaagtggaat cgaaaggctt ttaagaaaat   2520
gaagaacctt aaaacactga taatcaagaa cgggcatttt tccaaaggtc caaagcattt   2580
gccaaatagc ttaagggttt tggagtgggc aaaatacccc agtcagggat ttccagctaa   2640
tttttgttcc aagaagctga gcatctgtaa gctcccgaaa agttgttttt ccttagaact   2700
tgcagatctc agtgagaaat tcatgaatat gtccgtactt aatttcgatg agtgcgaggg   2760
attgacgcaa atcccggacg tgtcaggatt acagaacctt gaaaaatttt catttaaaaa   2820
ttgtgaaaat cttatcacca tccatgacag catcggtttc ctgcacaaac tcaagttcct   2880
gaatgcaatc ggctgccgta aacttaggag cttcccacct ttgaagctga cctcacttga   2940
aaagcttgag ttgtcttatt gctcaaatct tgaatgtttt cccgagatac tgggcaaaat   3000
ggagaacata accgaacttg ttctcgaggc tagcgcaatt aaggagttgc ccttttcctt   3060
tcagaacctg acaggcctcc agatcctcca actgagactg ggtggaatga ttagattgcc   3120
gtcatcaatc gttatgatgc ctaagctgac agaaataata gcatgggatt ggaagggttt   3180
gctttggccg cgtcaagtcg agggggaaga gaaggtgtcc tccatggtgt ctagcaatgt   3240
cgactgctta tgtctgtctg gatgtaatct ttctgaccag ttcctccccg tggcccttag   3300
ttggtttgtt aatgtgaaag atttggacct ctctcgaaat aaattcacag ttctcccgga   3360
gtgtatttcc gagtgccatt tcctctggaa gcttatcctc gactattgta actgtcttag   3420
agagattcgt ggaatgccac caaatattga acatttcagc gctagaaatt gcaagtcact   3480
tactagttgt aggagtaccc ttctgaacca aaagctccac gaggctggaa acacaatgtt   3540
ctggttgagt ggaacgtggt ttcccgaatg gttcgagcat cacagcaagg gcttgagcaa   3600
ttctttctgg ttccgagaca agtttccggc catagctttg tgcacagcca tagggcccac   3660
tagggaacag ataaccatag tcggcccgat agtcattatt aatggaattg aatgcagtgt   3720
tgatgatgag gacgatagtt atttgtggat ggaaaccgac cacacttacc tttttgattt   3780
gcaaaagatc aattttgcag acaatttaga taaggaatta gtcgagaatg agtggaacca   3840
tgtggaaata acgtatagcg taatttctaa cgagaaggag aagcacgttg agatcccagt   3900
cttcattgag tcaggcattt atatatttaa acaaagatcc cgaatggagg atatccgatt   3960
taccgaccct tacaagagaa ggaagctcga cgatggttta gagagttaac caacgatcgt   4020
tcaaacattt ggcaataaag tttcttaaga ttgaatcctg ttgccggtct tgcgatgatt   4080
atcatataat ttctgttgaa ttacgttaag catgtaataa ttaacatgta atgcatgacg   4140
ttatttatga gatgggtttt tatgattaga gtcccgcaat tatacattta atacgcgata   4200
```

gaaaacaaaa tatagcgcgc aaactaggat aaattatcgc gcgcggtgtc atctatgtta 4260
ctagatccct agggaagttc ctattccgaa gttcctattc tctgaaaagt ataggaactt 4320
ctttgcgtat tgggcgctct tggccttttt ggccaccggt cgtacggtta aaaccacccc 4380
agtacattaa aaacgtccgc aatgtgttat taagttgtct aagcgtcaat ttgtttacac 4440
cacaatatat cctgccacca gccagccaac agctccccga ccggcagctc ggcacaaaat 4500
caccactcga tacaggcagc ccatcagtcc actagacgct caccgggctg gttgccctcg 4560
ccgctgggct ggcggccgtc tatggccctg caaacgcgcc agaaacgccg tcgaagccgt 4620
gtgcgagaca ccgcagccgc cggcgttgtg gatacctcgc ggaaaacttg gccctcactg 4680
acagatgagg ggcggacgtt gacacttgag gggccgactc acccggcgcg gcgttgacag 4740
atgaggggca ggctcgattt cggccggcga cgtggagctg gccagcctcg caaatcggcg 4800
aaaacgcctg attttacgcg agtttcccac agatgatgtg gacaagcctg gggataagtg 4860
ccctgcggta ttgacacttg aggggcgcga ctactgacag atgaggggcg cgatccttga 4920
cacttgaggg gcagagtgct gacagatgag gggcgcacct attgacattt gaggggctgt 4980
ccacaggcag aaaatccagc atttgcaagg gtttccgccc gtttttcggc caccgctaac 5040
ctgtctttta acctgctttt aaaccaatat ttataaacct tgtttttaac cagggctgcg 5100
ccctgtgcgc gtgaccgcgc acgccgaagg ggggtgcccc cccttctcga accctcccgg 5160
cccgctctcg cgttggcagc atcacccata attgtggttt caaaatcggc tccgtcgata 5220
ctatgttata cgccaacttt gaaaacaact ttgaaaaagc tgttttctgg tatttaaggt 5280
tttagaatgc aaggaacagt gaattggagt tcgtcttgtt ataattagct tcttggggta 5340
tctttaaata ctgtagaaaa gaggaaggaa ataataaatg gctaaaatga gaatatcacc 5400
ggaattgaaa aaactgatcg aaaaataccg ctgcgtaaaa gatacggaag gaatgtctcc 5460
tgctaaggta tataagctgg tgggagaaaa tgaaaaccta tatttaaaaa tgacggacag 5520
ccggtataaa gggaccacct atgatgtgga acgggaaaag gacatgatgc tatggctgga 5580
aggaaagctg cctgttccaa aggtcctgca ctttgaacgg catgatggct ggagcaatct 5640
gctcatgagt gaggccgatg gcgtcctttg ctcggaagag tatgaagatg aacaaagccc 5700
tgaaaagatt atcgagctgt atgcggagtg catcaggctc tttcactcca tcgacatatc 5760
ggattgtccc tatacgaata gcttagacag ccgcttagcc gaattggatt acttactgaa 5820
taacgatctg gccgatgtgg attgcgaaaa ctgggaagaa gacactccat ttaaagatcc 5880
gcgcgagctg tatgattttt taaagacgga aaagcccgaa gaggaacttg tcttttccca 5940
cggcgacctg ggagacagca acatctttgt gaaagatggc aaagtaagtg gctttattga 6000
tcttgggaga agcggcaggg cggacaagtg gtatgacatt gccttctgcg tccggtcgat 6060
cagggaggat attggggaag aacagtatgt cgagctattt tttgacttac tggggatcaa 6120
gcctgattgg gagaaaataa aatattatat tttactggat gaattgtttt agtacctaga 6180
tgtggcgcaa cgatgccggc gacaagcagg agcgcaccga cttcttccgc atcaagtgtt 6240
ttggctctca ggccgaggcc cacggcaagt atttgggcaa ggggtcgctg gtattcgtgc 6300
agggcaagat tcggaatacc aagtacgaga aggacggcca gacggtctac gggaccgact 6360
tcattgccga taaggtggat tatctggaca ccaaggcacc aggcgggtca aatcaggaat 6420
aagggcacat tgccccggcg tgagtcgggg caatcccgca aggagggtga atgaatcgga 6480
cgtttgaccg gaaggcatac aggcaagaac tgatcgacgc ggggttttcc gccgaggatg 6540

-continued

| | | | | | | |
|---|---|---|---|---|---|---|
| ccgaaaccat | cgcaagccgc | accgtcatgc | gtgcgccccg | cgaaaccttc | cagtccgtcg | 6600 |
| gctcgatggt | ccagcaagct | acggccaaga | tcgagcgcga | cagcgtgcaa | ctggctcccc | 6660 |
| ctgccctgcc | cgcgccatcg | gccgccgtgg | agcgttcgcg | tcgtctcgaa | caggaggcgg | 6720 |
| caggtttggc | gaagtcgatg | accatcgaca | cgcgaggaac | tatgacgacc | aagaagcgaa | 6780 |
| aaaccgccgg | cgaggacctg | gcaaaacagg | tcagcgaggc | caagcaagcc | gcgttgctga | 6840 |
| aacacacgaa | gcagcagatc | aaggaaatgc | agctttcctt | gttcgatatt | gcgccgtggc | 6900 |
| cggacacgat | gcgagcgatg | ccaaacgaca | cggcccgctc | tgccctgttc | accacgcgca | 6960 |
| acaagaaaat | cccgcgcgag | gcgctgcaaa | acaaggtcat | tttccacgtc | aacaaggacg | 7020 |
| tgaagatcac | ctacaccggc | gtcgagctgc | gggccgacga | tgacgaactg | gtgtggcagc | 7080 |
| aggtgttgga | gtacgcgaag | cgcaccccta | tcggcgagcc | gatcaccttc | acgttctacg | 7140 |
| agctttgcca | ggacctgggc | tggtcgatca | atggccggta | ttacacgaag | gccgaggaat | 7200 |
| gcctgtcgcg | cctacaggcg | acggcgatgg | gcttcacgtc | cgaccgcgtt | gggcacctgg | 7260 |
| aatcggtgtc | gctgctgcac | cgcttccgcg | tcctggaccg | tggcaagaaa | acgtcccgtt | 7320 |
| gccaggtcct | gatcgacgag | gaaatcgtcg | tgctgtttgc | tggcgaccac | tacacgaaat | 7380 |
| tcatatggga | gaagtaccgc | aagctgtcgc | cgacggcccg | acggatgttc | gactatttca | 7440 |
| gctcgcaccg | ggagccgtac | ccgctcaagc | tggaaacctt | ccgcctcatg | tgcggatcgg | 7500 |
| attccacccg | cgtgaagaag | tggcgcgagc | aggtcggcga | agcctgcgaa | gagttgcgag | 7560 |
| gcagcggcct | ggtggaacac | gcctgggtca | atgatgacct | ggtgcattgc | aaacgctagg | 7620 |
| gccttgtggg | gtcagttccg | gctgggggtt | cagcagccag | cgctttactg | agatcctctt | 7680 |
| ccgcttcctc | gctcactgac | tcgctgcgct | cggtcgttcg | gctgcggcga | gcggtatcag | 7740 |
| ctcactcaaa | ggcggtaata | cggttatcca | cagaatcagg | ggataacgca | ggaaagaaca | 7800 |
| tgtgagcaaa | aggccagcaa | aaggccagga | accgtaaaaa | ggccgcgttg | ctggcgtttt | 7860 |
| tccataggct | ccgcccccct | gacgagcatc | acaaaaatcg | acgctcaagt | cagaggtggc | 7920 |
| gaaacccgac | aggactataa | agataccagg | cgtttccccc | tggaagctcc | ctcgtgcgct | 7980 |
| ctcctgttcc | gaccctgccg | cttaccggat | acctgtccgc | ctttctccct | tcgggaagcg | 8040 |
| tggcgctttc | tcatagctca | cgctgtaggt | atctcagttc | ggtgtaggtc | gttcgctcca | 8100 |
| agctgggctg | tgtgcacgaa | ccccccgttc | agcccgaccg | ctgcgcctta | tccggtaact | 8160 |
| atcgtcttga | gtccaacccg | gtaagacacg | acttatcgcc | actggcagca | gccactggta | 8220 |
| acaggattag | cagagcgagg | tatgtaggcg | gtgctacaga | gttcttgaag | tggtggccta | 8280 |
| actacggcta | cactagaaga | acagtatttg | gtatctgcgc | tctgctgaag | ccagttacct | 8340 |
| tcggaaaaag | agttggtagc | tcttgatccg | gcaaacaaac | caccgctggt | agcggtggtt | 8400 |
| tttttgtttg | caagcagcag | attacgcgca | gaaaaaaagg | atctcaagaa | gatcctttga | 8460 |
| tcttttctac | ggggtctgac | gctcagtgga | acgaaaactc | acgttaaggg | attttggtca | 8520 |
| tgagattatc | aaaaaggatc | ttcacctaga | tccttttgg | | | 8559 |

PATHOGEN RESISTANCE IN PLANTS

CROSS-REFERENCE TO RELATED APPLICATIONS

This application claims the benefit of U.S. Provisional Application No. 63/108,023 filed on Oct. 30, 2020, which is hereby incorporated by reference in its entirety for all purposes.

STATEMENT REGARDING FEDERALLY SPONSORED RESEARCH OR DEVELOPMENT

This invention was made with Government support under 1844088 by the National Science Foundation. The Government has certain rights to this invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: FOTI_001_01US_SeqList_ST25.txt, date recorded: Oct. 18, 2021, file size 238 kilobytes).

TECHNICAL FIELD

The disclosure relates to the identification and use of nucleic acid sequences for pathogen resistance in plants.

BACKGROUND

Pathogen effector proteins often convergently evolve to target the same or similar plant host proteins to promote virulence. Such proteins may be present in a diverse range of plant pathogens including but not limited to fungi, oomycetes, bacteria, nematodes or viruses.

An example of one such pathogen that causes harm to plants by secreting an effector protein is the obligate biotrophic fungus *Phakopsora pachyrhizi* (and to a lesser extent, the closely related fungus *Phakopsora meibomiae*), which causes Asian soybean rust (ASR). While soybeans make up the primary commercial crop affected by ASR, *Phakopsora* infects leaf tissue from a broad range of leguminous plants, including at least 17 genera (Slaminko et al., 2008). In general, rust fungi (order Pucciniales) constitute one of the most economically important groups of plant pathogens because of their larger range of host and genetic diversity. There are more than 6000 species of rust fungi that cause harm to many plant species, such as wheat (*Puccinia* spp.), common bean (*Uromyces appendiculatus*), soybean (*Phakopsora pachyrhizi*), and coffee (*Hemileia vastatrix*) (Aime et al., 2006).

Infection in commercial crops requires application of various fungicides, which are costly and not always effective. In Brazil alone, control of ASR costs $2 billion annually. Thus, there is a need for plant varieties that are resistant to fungal pathogens.

The foregoing examples of the related art and limitations related therewith are intended to be illustrative and not exclusive. Other limitations of the related art will become apparent to those of skill in the art upon a reading of the specification.

SUMMARY

The present disclosure provides for an isolated, recombinant, or synthetic polynucleotide comprising a nucleic acid sequence encoding a functional FIT1 protein homologous to SEQ ID NO: 2. In some embodiments, the polynucleotide encodes a protein having at least 70% identity to SEQ ID NO: 2. In some aspects, the protein is selected from the group consisting of: SEQ ID NOs: 2, 4, 6, 8, 10, 12, 14, 16, 18, 20 and functional homologs thereof. In some aspects, the isolated, recombinant, or synthetic polynucleotide comprises a nucleic acid sequence selected from the group consisting of SEQ ID NOs: 1, 3, 5, 7, 9, 11, 13, 15, 17, 19 complements thereof, fragments thereof, and sequences at least 70% identical thereto. The disclosure further relates to genetic constructs comprising one or more of these sequences, and transgenic plants, plant parts, or plant cells comprising one or more of these sequences, wherein the plant, plant part, or plant cell is resistant or tolerant to a pathogen.

In another embodiment, the disclosure teaches a method of producing a plant, plant part, or plant cell having resistance or tolerance to a pathogen, wherein the method comprises transforming a plant, plant part, or plant cell with a polynucleotide encoding a functional FIT1 protein. In some aspects, the nucleotide sequence encoding the FIT1 protein has been codon optimized. In some aspects, the FIT1 protein comprises a selected from the group consisting of: SEQ ID NOs: 2, 4, 6, 8, 10, 12, 14, 16, 18, 20 and functional homologs thereof, or is encoded by an isolated, recombinant, or synthetic polynucleotide selected from the group consisting of SEQ ID NOs: 1, 3, 5, 7, 9, 11, 13, 15, 17, 19, complements thereof, fragments thereof, and sequences at least 70% identical thereto.

In another embodiment, the disclosure teaches a method of genetically engineering a pathogen resistance or tolerance trait in a plant, plant part, or plant cell, comprising providing a plant species that is susceptible to a pathogen, identifying within the genome of the plant species a homolog of FIT1, wherein said homolog does not mediate AvrFIT1 recognition; and genetically modifying a plant, plant part, or plant cell from the susceptible plant species with targeted gene editing, wherein said targeted gene editing is directed at the FIT1 homolog, and wherein said targeted gene editing enables the FIT1 homolog to recognize AvrFIT1 and confers resistance or tolerance to a pathogen.

The disclosure further relates to genetically modified plants, plant parts, or plant cells produced by the methods disclosed herein, wherein the plant, plant part, or plant cell exhibits resistance or tolerance to a pathogen. In some aspects, the pathogen is a fungus from the order Cantharellales or Pucciniales. In some aspects, the fungal pathogen is *Rhizoctonia solani, Melampsora* spp., *Phakopsora pachyrhizi, Phakopsora meibomiae, Phakopsora euvitis, Phakopsora* spp., *Puccinia* spp., *Uromyces* spp., *Austropuccinia* spp., *Cronartium* spp. or *Hemileia vastatrix*. In some aspects, the plant, plant part, or plant cell is in the subfamily Papilionoideae. In some aspects, the plant, plant part, or plant cell is *Alysicarpus* spp., *Astragalus* spp., *Baptisia* spp., *Cajanus* spp., *Calopogonium* spp., *Caragana* spp., *Centrosema* spp., *Cologania* spp., *Crotalaria* spp., *Desmodium* spp., *Genista* spp., *Glycine* spp., *Glycyrrhiza* spp., *Indigofera* spp., *Kummerowia* spp., *Lablab* spp., *Lathyrus* spp., *Lespedeza* spp., *Lotus* spp., *Lupinus* spp., *Macroptilium* spp., *Macrotyloma* spp., *Medicago* spp., *Neonotonia* spp., *Pachyrhizus* spp., *Pisum* spp., *Phaseolus* spp., *Pseudovigna* spp., *Psoralea* spp., *Robinia* spp., *Senna* spp., *Sesbania* spp., *Strophostyles* spp., *Tephrosia* spp., *Teramnus* spp., *Trifolium* spp., *Vicia* spp., *Vigna* spp., or *Voandzeia* spp.

The disclosure further relates to methods for identifying a functional FIT1 gene and/or allele thereof comprising isolating a FIT1 homolog or allele thereof; expressing said FIT1 homolog or allele thereof in combination with an effector protein produced by *Phakopsora pachyrhizi* in a plant, plant part, or plant cell; and assaying said plant, plant part, or plant cell for an immune response. In some aspects, the effector protein comprises SEQ ID NO: 24, SEQ ID: 26, or sequences at least 90% identical thereto.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying figures, which are incorporated herein and form a part of the specification, illustrate some, but not the only or exclusive, example embodiments and/or features. It is intended that the embodiments and figures disclosed herein are to be considered illustrative rather than limiting.

FIG. 1 shows a phylogenetic tree of AvrFIT1 homologs identified by performing a BLAST® search of the NCBI protein database. Additional AvrFIT1 sequences were obtained from published *Phakopsora pachyrhizi* transcriptomes and proteomes. The obtained sequences were aligned using Clustal Omega and manually filtered to remove redundant and incomplete sequences. A maximum likelihood phylogenetic tree was constructed from the aligned protein sequences.

FIG. 2 shows photographs of plants inoculated with *Phakopsora* spores at two to four weeks of age. The images were taken at 14 to 21 days post inoculation. Presence of FIT1 in the plant genome correlates with resistance to ASR.

FIG. 3A shows a phylogenetic tree of homologs of *Vigna unguiculata* Vu01g041300.1 (VuFIT1) (SEQ ID NO: 2) identified by performing a BLAST® search and conducting a protein alignment. This figure shows putative FIT1 orthologs in *Vigna radiata* XP_014501487.1 (SEQ ID NO: 4), *Vigna angularis* XP_017423114.1 (SEQ ID NO: 12), *Phaseolus acutifolius* 0056036500.1 (SEQ ID NO: 10), *Phaseolus lunatus* P105g0000042900.1 (SEQ ID NO: 6), *Phaseolus vulgaris* PvUI111.05g037200.1 (SEQ ID NO: 8), *Lablab purpureus* c22535_g1_i3 (SEQ ID NO: 14), *Mucuna pruriens* RDX66260.1 (SEQ ID NO: 16), *Cajanus cajan* XP_020211972.1 (SEQ ID NO: 18), and *Abrus precatorius*) CP_027357710.1 (SEQ ID NO: 20). Also shown is a paralog of FIT1 from *Vigna unguiculata* Vu01g041400.1 (SEQ ID NO: 22) believed to be the result of a recent duplication which accumulated mutations and is thus non-functional. The phylogenetic tree was rooted using paralogs of FIT1 that do not function in AvrFIT1 perception. Activity of each FIT1 homolog to function for recognition of AvrFIT1a and AvrFIT1b, based on transient assays, is indicated. nt=not tested.

FIG. 5A shows the *Vigna unguiculata* allele of FIT1 (VuFIT1), the *Phaseolus lunatus* allele of FIT1 (P1FIT1), the *Vigna radiata* allele of FIT1 (VrFIT1), the *Vigna unguiculata* close paralog of FIT1 (VuFIT1b), and AvrFIT1a. FIG. 5B shows *Vigna angularis* allele of FIT1 (VaFIT1), the *Phaseolus vulgaris* allele of FIT1 (PvFIT1), the *Lablab purpureus* allele of FIT1 (LpFIT1), the *Abrus precatorius* allele of FIT1 (ApFIT1), and AvrFIT1a. FIG. 5C shows *Vigna unguiculata* allele of FIT1 (VuFIT1), the *Phaseolus lunatus* allele of FIT1 (P1FIT1), the *Vigna radiata* allele of FIT1 (VrFIT1), the *Vigna unguiculata* allele of FIT1 (VuFIT1b), and AvrFIT1b. FIG. 5D shows *Vigna angularis* allele of FIT1 (VaFIT1), the *Phaseolus vulgaris* allele of FIT1 (PvFIT1), the *Lablab purpureus* allele of FIT1 (LpFIT1), the *Abrus precatorius* allele of FIT1 (ApFIT1), and AvrFIT1b.

DETAILED DESCRIPTION

Definitions

Figure 3B:
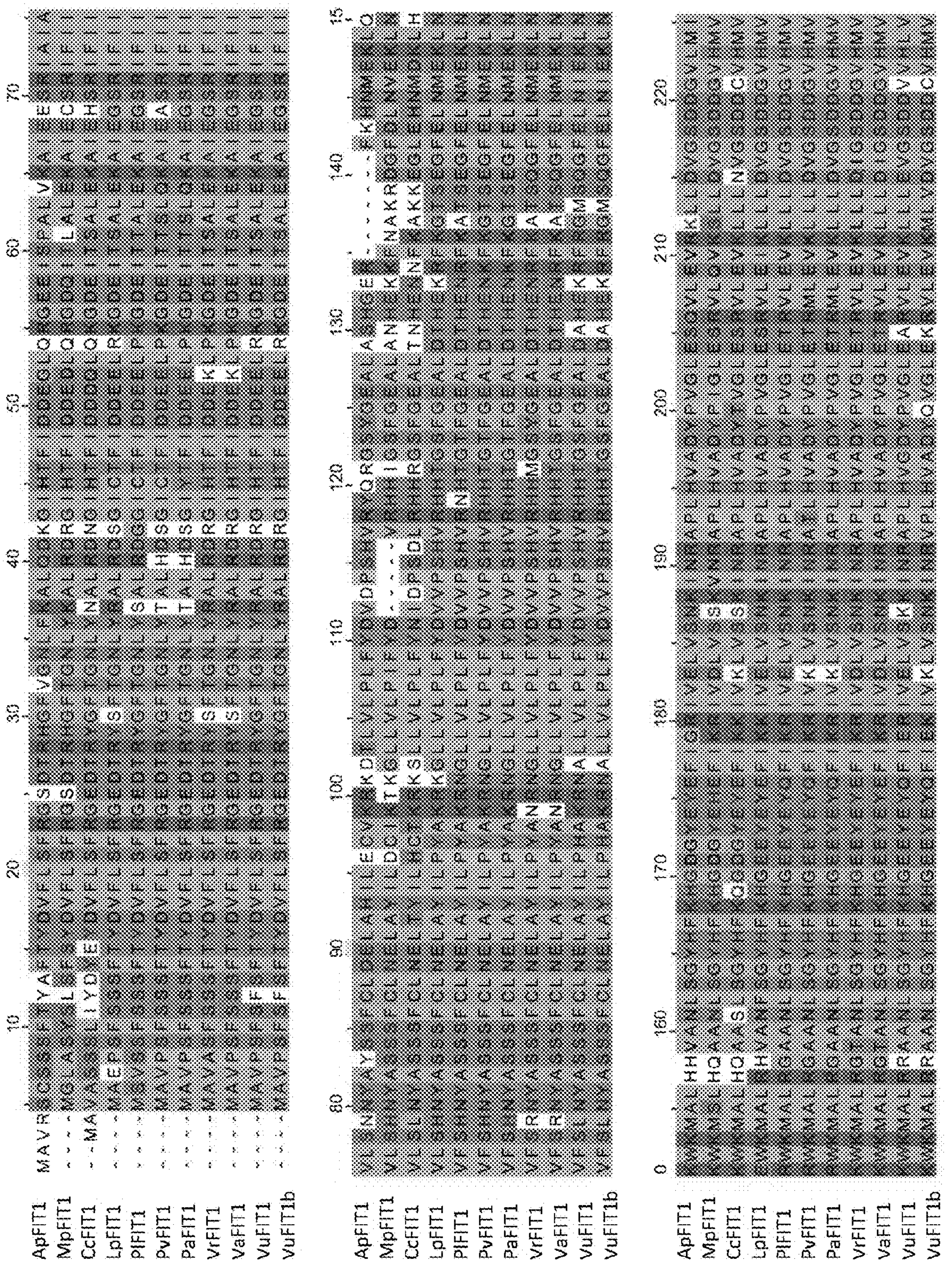
FIG. 3B shows a protein alignment of the amino acid sequences listed in FIG. 3A, specifically of the *Vigna unguiculata* allele of FIT1 (VuFIT1) (SEQ ID NO: 2), the *Vigna unguiculata* close paralog of FIT1 (VuFIT1b) (SEQ ID NO: 22), *Vigna angularis* allele of FIT1 (VaFIT1) (SEQ ID NO: 12), the *Vigna radiata* allele of FIT1 (VrFIT1) (SEQ ID NO: 4), the *Phaseolus acutifolius* allele of FIT1 (PaFIT1) (SEQ ID NO: 10), the *Phaseolus vulgaris* allele of FIT1 (PvFIT1) (SEQ ID NO: 8), the *Phaseolus lunatus* allele of FIT1 (P1FIT1) (SEQ ID NO: 6), the *Lablab purpureus* allele of FIT1 (LpFIT1) (SEQ ID NO: 14), the *Cajanus cajun* allele of FIT1 (CcFIT1) 1 (SEQ ID NO: 18), the *Mucuna pruriens* allele of FIT1 (MpFIT1) (SEQ ID NO: 16), and the *Abrus precatorius* allele of FIT1 (ApFIT1) (SEQ ID NO: 20).
Figure 3B:
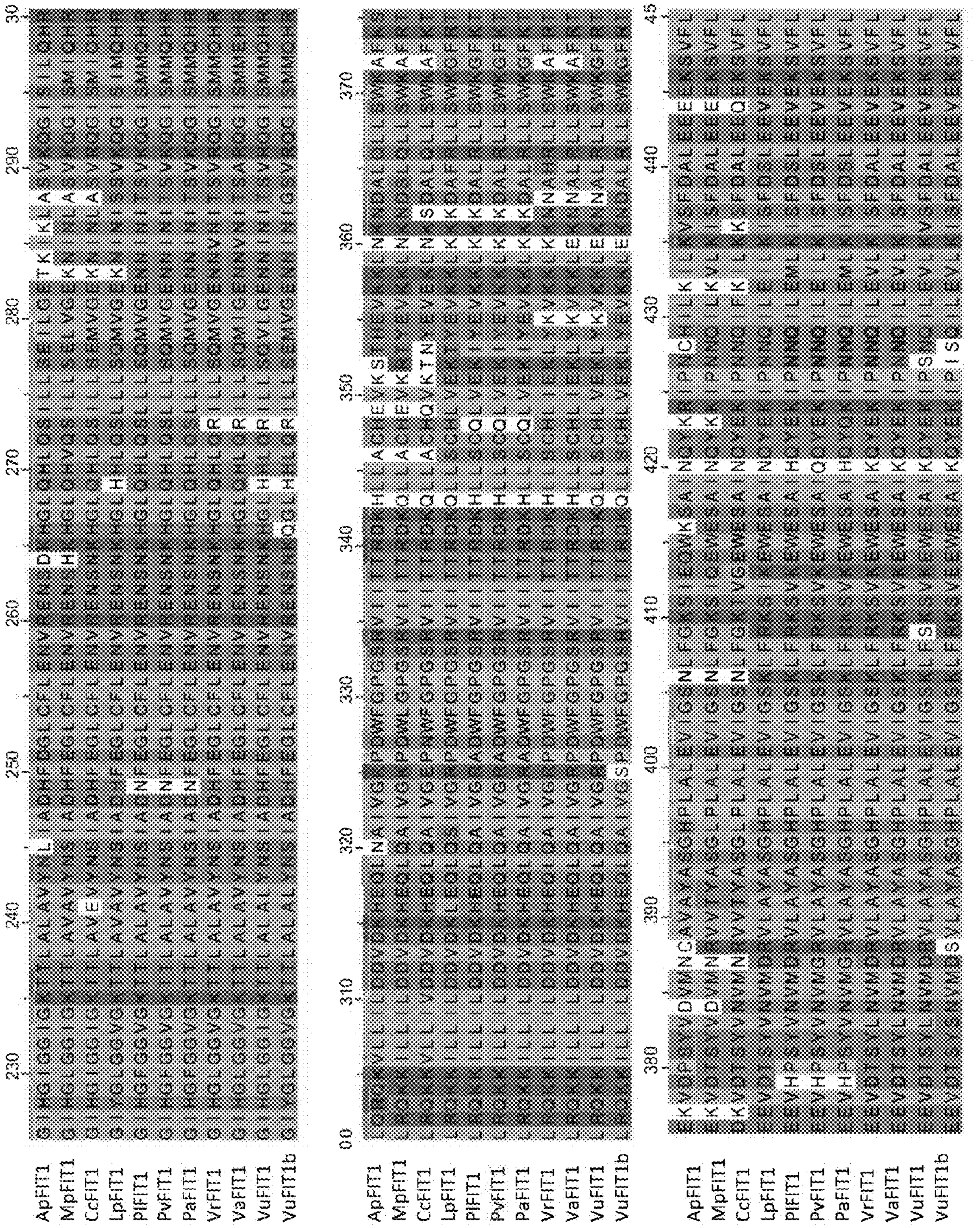
Figure 3B:
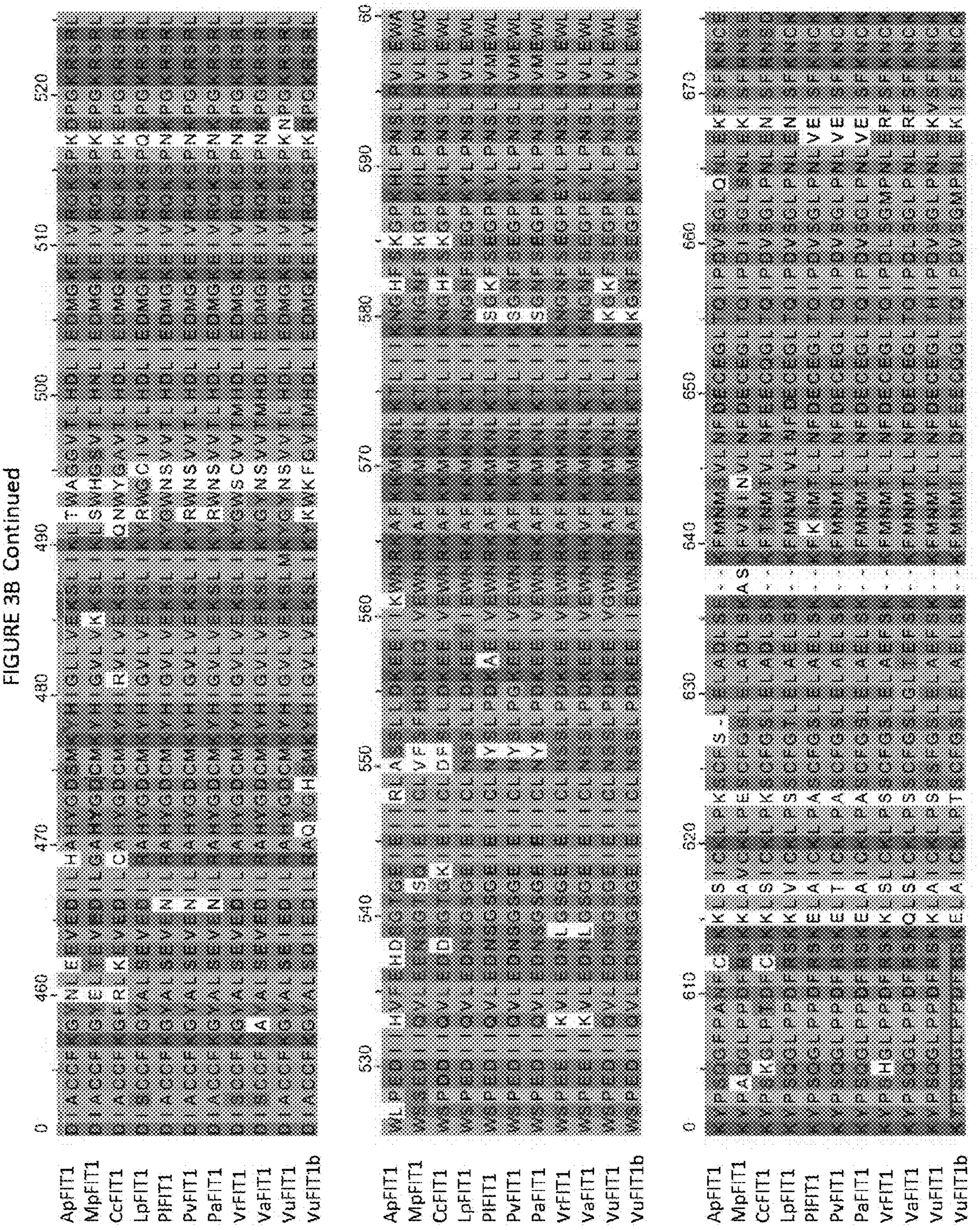
Figure 3B:
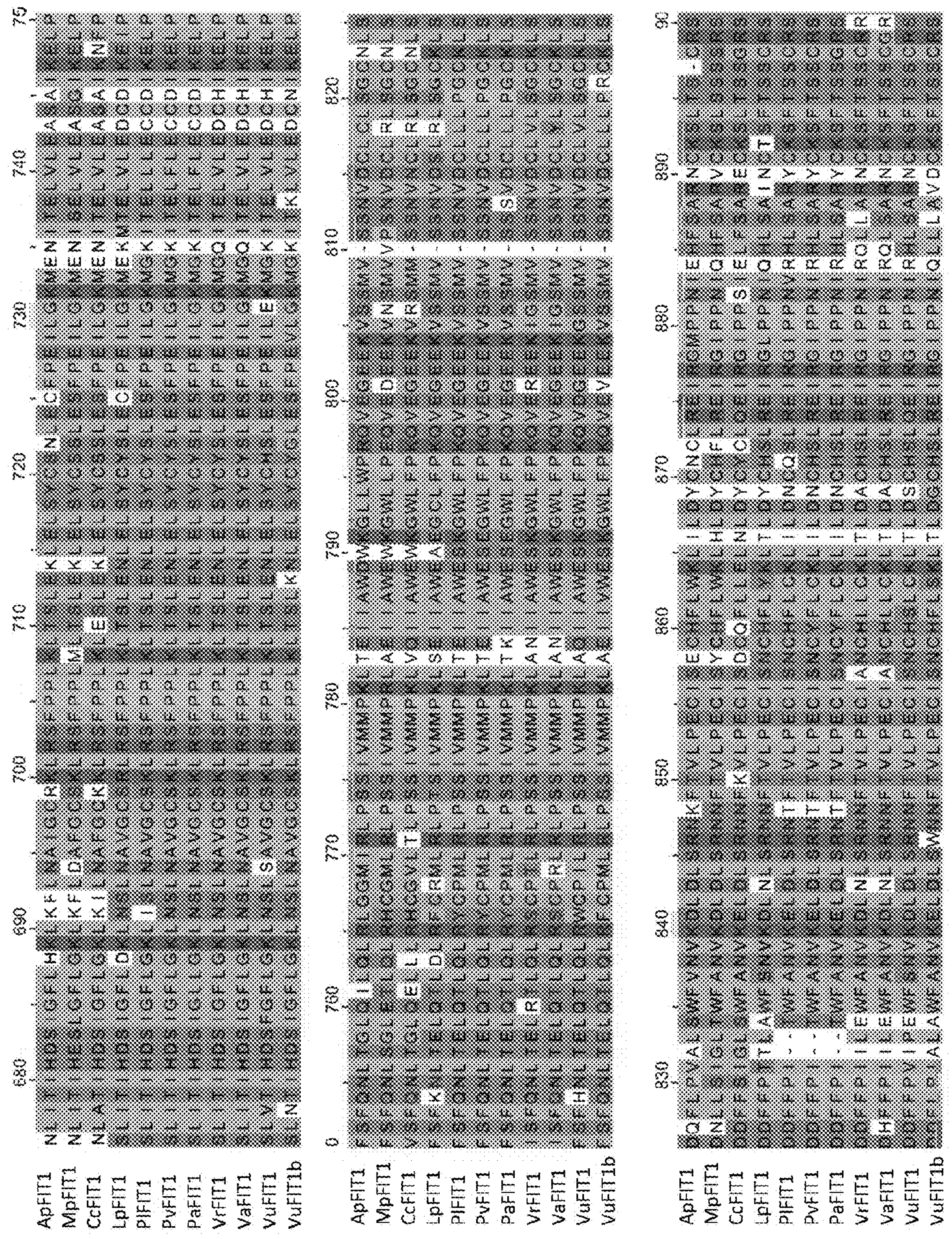
Figure 3B:
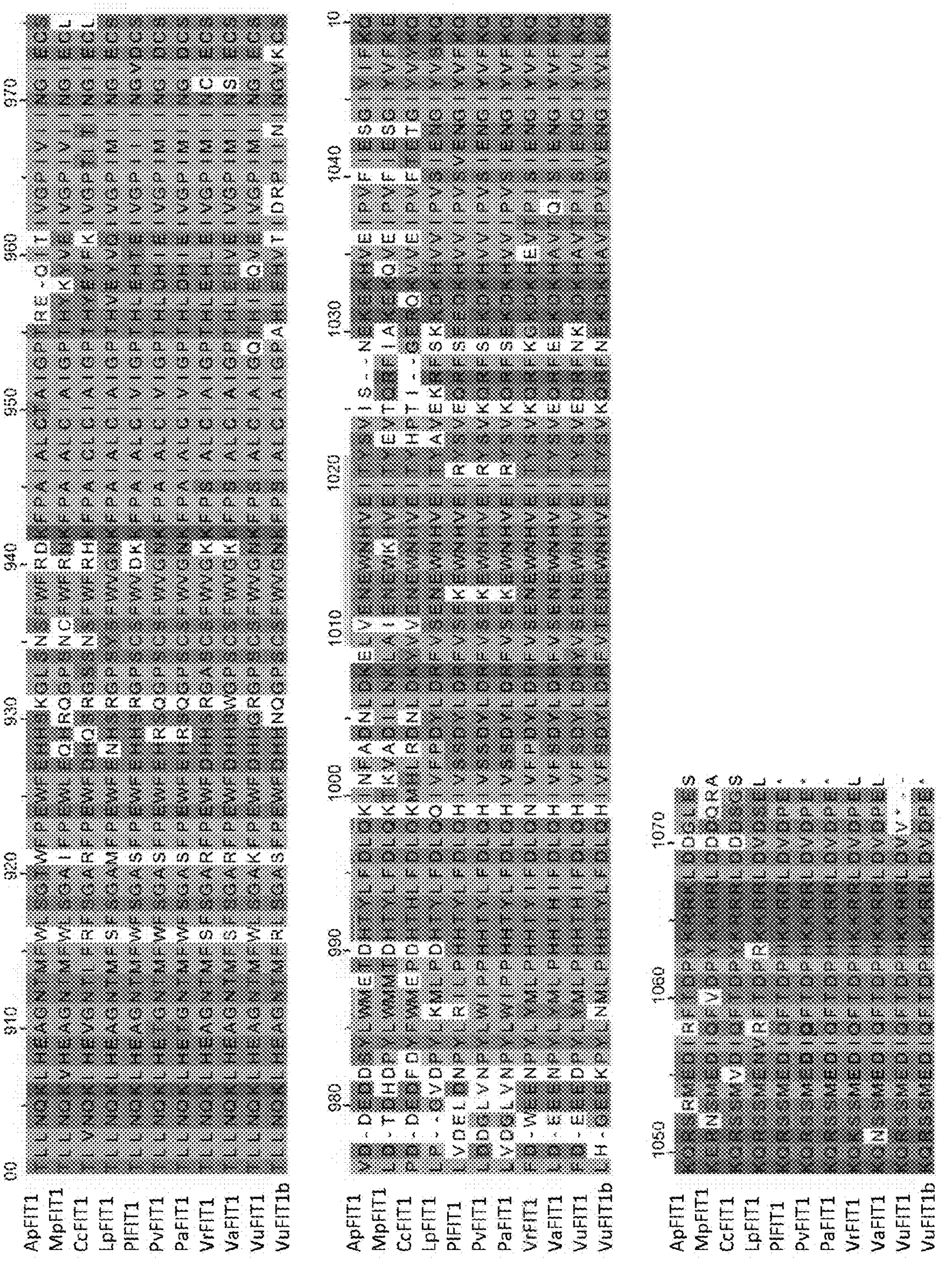

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques and/or substitutions of equivalent techniques that would be apparent to one of skill in the art.

Following long-standing patent law convention, the terms "a," "an," and "the" refer to "one or more" when used in this application, including the claims. For example, the phrase "a cell" refers to one or more cells, and in some embodiments can refer to a tissue and/or an organ. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to all whole number values between 1 and 100 as well as whole numbers greater than 100.

Unless otherwise indicated, all numbers expressing quantities of ingredients, reaction conditions, and so forth used in the specification and claims are to be understood as being modified in all instances by the term "about." The term "about," as used herein when referring to a measurable value such as an amount of mass, weight, time, volume, concentration or percentage is meant to encompass variations of ±10% from the specified amount, as such variations are appropriate to perform the disclosed methods and/or employ the disclosed compositions, nucleic acids, polypeptides, etc. Accordingly, unless indicated to the contrary, the numerical parameters set forth in this specification and attached claims are approximations that can vary depending upon the desired properties sought to be obtained by the presently disclosed subject matter.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D (e.g., AB, AC, AD, BC, BD, CD, ABC, ABD, and BCD). In some embodiments, one or more of the elements to which the "and/or" refers can also individually be present in single or multiple occurrences in the combinations(s) and/or subcombination(s).

As used herein, the term "plant" can refer to any living organism belonging to the kingdom Plantae (i.e., any genus/species in the Plant Kingdom), to a whole plant, any part thereof, or a cell or tissue culture derived from a plant. Thus, the term "plant" can refer to any of whole plants, plant components or organs (e.g., leaves, stems, roots, etc.), plant tissues, seeds and/or plant cells.

A plant cell is a cell of a plant, taken from a plant, or derived through culture from a cell taken from a plant. Thus, the term "plant cell" includes without limitation cells within seeds, suspension cultures, embryos, meristematic regions, callus tissue, leaves, shoots, gametophytes, sporophytes, pollen, and microspores.

The phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like.

As used herein, the term "resistant", or "resistance", describes a plant, line or variety that shows fewer or reduced symptoms to a biotic pest or pathogen than a susceptible (or more susceptible) plant, line or variety to that biotic pest or pathogen. This term is also applied to plants that show no symptoms, and may also be referred to as "high/standard resistance".

As used herein, the term "tolerant" or "tolerance" describes a plant, line, or variety that that shows some symptoms to a biotic pest or pathogen, but that are still able to produce marketable product with an acceptable yield. These lines may also be referred to as having "moderate/intermediate resistance". Tolerant and moderate/intermediate resistant plant types restrict the growth and development of the specified pest or pathogen, but exhibit a greater range of symptoms or damage compared to plant types with high resistance. Plant types with intermediate resistance will show less severe symptoms than susceptible plant varieties, when grown under similar field conditions and pathogen pressure. A "tolerant" plant may also indicate a phenotype of a plant wherein disease-symptoms remain absent upon exposure of said plant to an infective dosage of pathogen, whereby the presence of a systemic or local pathogen infection, pathogen multiplication, at least the presence of pathogen genomic sequences in cells of said plant and/or genomic integration thereof can be established. Tolerant plants are therefore resistant for symptom expression but symptomless carriers of the pathogen. Sometimes, pathogen sequences may be present or even multiply in plants without causing disease symptoms. This phenomenon is also known as "latent infection". In latent infections, the pathogen may exist in a truly latent non-infectious occult form, possibly as an integrated genome or an episomal agent (so that pathogen protein cannot be found in the cytoplasm, while PCR protocols may indicate the present of pathogen nucleic acid sequences) or as an infectious and continuously replicating agent. A reactivated pathogen may spread and initiate an epidemic among susceptible contacts. The presence of a "latent infection" is indistinguishable from the presence of a "tolerant" phenotype in a plant.

Methods of evaluating resistance are well known to one skilled in the art. Such evaluation may be performed by visual observation of a plant or a plant part (e.g., leaves, roots, flowers, fruits et. al) in determining the severity of symptoms. For example, when each plant is given a resistance score on a scale of 1 to 5 based on the severity of the reaction or symptoms, with 1 being the resistance score applied to the most resistant plants (e.g., no symptoms, or with the least symptoms), and 5 the score applied to the plants with the most severe symptoms, then a line is rated as being resistant when at least 75% of the plants have a resistance score at a 1, 2, or 3 level, while susceptible lines are those having more than 25% of the plants scoring at a 4 or 5 level. If a more detailed visual evaluation is possible, then one can use a scale from 1 to 10 so as to broaden out the range of scores and thereby hopefully provide a greater scoring spread among the plants being evaluated. Additional methods for evaluating resistance are well known in the art (see for example, jircas.go.jp/sites/default/files/publication/manual_guideline/manual_guideline-_-_73.pdf available on the world wide web).

In addition to such visual evaluations, disease evaluations can be performed by determining the pathogen bio-density in a plant or plant part using electron and/or light microscopy and/or through molecular biological methods, such as protein quantification (e.g., ELISA, measuring pathogen protein density) and/or nucleic acid quantification (e.g., RT-PCR, measuring pathogen RNA density). Another method relies on quantifying the spores produced by the pathogen, which can be quantified using a hemacytometer and evaluated per uredinium, per leaf area, or per leaf.

As used herein, the term "susceptible" is used herein to refer to a plant that is unable to prevent entry of the pathogen into the plant and/or slow multiplication and systemic spread of the pathogen, resulting in disease symptoms. The term "susceptible" is therefore equivalent to "non-resistant".

As used herein, the term "homologous" or "homolog" is used as it is known in the art and refers to related sequences that share a common ancestor. The term "homolog" is sometimes used to apply to the relationship between genes separated by the event of speciation ("ortholog") or to the relationship between genes separated by the event of genetic duplication within the same species ("paralog"). Homology can be determined using software programs readily available in the art, such as those discussed in *Current Protocols in Molecular Biology* (F. M. Ausubel et al., eds., 1987) Supplement 30, section 7.718, Table 7.71.

As used herein, the term "allele" is used both as it is known in the art as one of two or more versions of a gene or peptide, and also to refer to synthetic variants of a gene or peptide containing one or more changes from the native sequence.

As used herein, the term "functional" used in the context of a homolog means that the homolog has the same or very similar function. For example, a functional homolog of FIT1 would recognize an AvrFIT1 effector protein. A "nonfunctional FIT1 homolog" would not recognize AvrFIT1, though it may still be functional in that it is able recognize other effector proteins.

As used herein, the term "sequence identity" refers to the presence of identical nucleotides or amino acids at corresponding positions of two sequences. Readily available sequence comparison and multiple sequence alignment algorithms are, respectively, the Basic Local Alignment Search Tool (BLAST®) and ClustalW/ClustalW2/Clustal Omega programs available on the Internet (e.g., the website of the EMBL-EBI). Some alignment programs are MacVector (Oxford Molecular Ltd, Oxford, U.K.) and ALIGN Plus (Scientific and Educational Software, Pennsylvania). Other non-limiting alignment programs include Sequencher (Gene Codes, Ann Arbor, Mich.), AlignX, and Vector NTI (Invitrogen, Carlsbad, Calif.). Other suitable programs include, but are not limited to, GAP, BestFit, Plot Similarity, and FASTA, which are part of the Accelrys GCG Package available from Accelrys, Inc. of San Diego, Calif., United States of America. See also Smith & Waterman, 1981; Needleman & Wunsch, 1970; Pearson & Lipman, 1988; Ausubel et al., 1988; and Sambrook & Russell, 2001. Unless otherwise noted, alignments disclosed herein utilized Clustal Omega.

As used herein, the phrases "DNA construct", "expression cassette", "chimeric construct", "construct", and "recombinant DNA construct" are used interchangeably herein. A recombinant DNA construct comprises an artificial combination of nucleic acid fragments, e.g., regulatory and coding sequences that are not found together in nature. For example, a construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997*, Proc. Natl. Acad. Sci. U.S.A.* 94:12744-12746).

As used herein "cisgene" refers to a gene from the same species, or a species closely related enough to be conventionally bred. "Transgene" refers to a gene from a different species, and may also be referred to as "heterologous" (an amino acid or a nucleic acid sequence which is not naturally found in the particular organism). Both transgenes and heterologous sequences would be considered "exogenous" as referring to a substance coming from some source other than its native source.

The term "operably linked" refers to the juxtaposition of two or more components (such as sequence elements) having a functional relationship. For example, the sequential arrangement of the promoter polynucleotide with a further oligo- or polynucleotide, resulting in transcription of the further polynucleotide.

As used herein, "promoter" refers to a DNA sequence capable of controlling the expression of a coding sequence or functional RNA. In some embodiments, the promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue specificity of a promoter.

As used herein, "selectable marker" is a nucleic acid segment that allows one to select for a molecule (e.g., a plasmid) or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

The following description includes information that may be useful in understanding the present disclosure. It is not an admission that any of the information provided herein is prior art or relevant to the presently claimed disclosures, or that any publication specifically or implicitly referenced is prior art.

Overview

The present disclosure provides an isolated, recombinant, or synthetic polynucleotide comprising a FIT1 protein, and homologs, fragments, and variations thereof. The disclosure further relates to plants, plant parts, and plant cells that have been transformed with these polynucleotides, and exhibit resistance or tolerance to a plant pathogen, such as *Phakopsora pachyrhizi*. The disclosure further relates to methods of identifying pathogen resistant genes, and methods of genetically engineering a pathogen resistance or tolerance trait in a plant, plant part, or plant cell, comprising targeted gene editing of a homolog (such as FIT1), and plants produced therefrom.

Plant Pathogens

There are more than 6000 species of rust fungi, including for example, *Phakopsora pachyrhizi, Puccinia* spp., *Uromyces appendiculatus*, and *Hemileia vastatrix*, that infect a wide range of important crops and ornamental varieties. Some examples of varieties that may be infected include, but are not limited to, *Avena sativa* (oats), *Vicia faba* (broad beans), *Coffea arabica* (coffee), *Chrysanthemum, Cydonia* (quince), Fuchsia spp. (garlic), *Hordeum vulgare* (barley), *Juniperus virginiana* (red cedar), *Juniperus communis* (juniper), *Allium ampeloprasum* (leek), Malta spp. (apple), *Mentha piperita* (peppermint), *Mespilus* (medlar), Onion, *Pelargonium, Primula* vulgaris (primrose), *Pyrus* (pear), *Rosa* spp. (roses), *Triticum* spp. (wheat), *Secale cereale* (rye), *Vitis vinifera* (grape), *Saccharum* spp. (sugarcane) and *Glycine max* (soybean).

In soybean, rust pathogen infections have been reported in South America, Africa, Australia, and Asia, and were first reported on soybean crops in the southern United States in 2004. Asian soybean rust (ASR), caused by *Phakopsora*

*pachyrhizi*, spreads quickly and can lead to significant yield loss. Initial symptoms of ASR include yellow discoloration on the upper surfaces of foliage, followed by tan or reddish-brown lesions on the undersides of the leaves and sometimes on petioles, stems or pods. Blisters develop within the lesions, which break open and release spores. Soybean plants infected with ASR will exhibit reduced pod production and can result in a yield loss of greater than 50%. Another disease, New World soybean rust, caused by *Phakopsora meibomiae*, is generally not as harmful as ASR. *P. meibomiae* has not yet been reported in the U.S.

Successful infection of rust fungi relies on the secretion of effector proteins with functions that facilitate host colonization. The effector proteins suppress plant immunity and manipulate the host metabolism to benefit the pathogen (Jones and Dangl, 2006). AvrFIT1 is one such effector protein secreted by *Phakopsora pachyrhizi* that causes ASR. AvrFIT1 is present in several sequenced *Phakopsora pachyrhizi* strains isolated from various locations across the world, including Brazil and North America. A phylogenetic tree of close homologs of AvrFIT1 reveals that there are two similar copies of AvrFIT1 in *Phakopsora pachyrhizi* (FIG. 1), (PpAvrFIT1a and PpAvrFIT1b), both of which are recognized by FIT1 in transient assays. AvrFIT1 is also conserved in many other fungal species. Thai1, LA04-1 and MG2006 are three strains of *Phakopsora pachyrhizi* that all contain recognized alleles of AvrFIT1 (Elmore et al., 2020; Link et al., 2014, and information on *Phakopsora pachyrhizi* from the genome portal of the Department of Energy Joint Genome Institute available on the worldwide web.). *Phakopsora pachyrhizi* BR is an unspecified Brazilian population which also contains recognized alleles of AvrFIT1 (de Carvalho et al., 2017). AvrFIT1 is present in species of rust pathogens that cause disease on poplar (Melampsora larici-populina), cereals (*Puccinia* spp.) and other plants. Putative orthologs of AvrFIT1 are also present in more distantly related fungal species including both pathogenic and non-pathogenic fungi. For example, AvrFIT1 is present in *Rhizoctonia solani*, a non-rust pathogen that can be problematic for herbaceous plants, causing diseases such as collar rot, root rot, damping off, and wire stem.

AvrFIT1 is a putative peptidyl prolyl isomerase and is predicted to disrupt or perturb the function of one or more plant host proteins. While not wishing to be bound by any particular theory, it is possible that AvrFIT1 could be modifying an unknown plant protein, possibly a conserved component of the plant immune system, and FIT1 could be "guarding" the unknown protein and be activated if the protein is modified by AvrFIT1. There are many examples of NLR receptors acting this way in the literature. Pathogen effectors often convergently evolve to target the same or similar plant host proteins to promote virulence. There are many examples of two different pathogen effector proteins evolving to target the same plant protein independently. Thus, it is possible that another pathogen might have an effector protein that is unrelated to AvrFIT1 but acts on the same protein as AvrFIT1 and therefore is also capable of being perceived by FIT1. By guarding against proteins with a similar activity or molecular target as AvrFIT1, FIT1 can mediate resistance against pathogens which don't have a close homolog of AvrFIT1 but do have a protein which has evolved to have a similar activity or molecular target as FIT1. Such proteins may be present in a diverse range of plant pathogens including but not limited to fungi, oomycetes, bacteria, nematodes, or viruses.

Plant Resistance

Plants have, in some cases, evolved immunity in which resistance gene products recognize the activity of specific effectors resulting in effector-trigger immunity (ETI) (Jones and Dangl, 2006). ETI leads to robust defenses, such as the hypersensitive response (HR), which is a form of programmed cell death that results in the formation of a localized lesion that inhibits pathogen growth at the initial infection site (Dodds and Rathjen, 2010). If the plant has an immune receptor capable of recognizing the pathogen effector protein, the effector protein activates a strong immune response conferring immunity. The perception of intracellular pathogen effector proteins in plants is frequently mediated by proteins from a large gene family known as the nucleotide binding, leucine-rich repeat (NLR) proteins (Jones et al., 2016).

Plant disease resistance traits are often encoded by NLR genes. NLR genes can be incorporated into a susceptible crop variety to confer resistance through a variety of methods including introgression breeding, transformation or genome editing. A typical plant has hundreds of NLR immune receptor genes (Jones et al., 2016). These genes are typically expressed at relatively low levels with the NLR proteins passively surveilling for the presence of cognate effector proteins from invading pathogens. Prior to activation, the NLR proteins have essentially no impact on plant metabolism or growth. Upon activation by a cognate ligand, typically a pathogen effector protein or a protein substrate of an effector, the NLR protein initiates a signalling cascade that activates endogenous plant defense pathways to inhibit pathogen growth. Using NLRs is a natural, safe, and environmentally sustainable mechanism to develop disease-resistant crop varieties to improve plant yields and reduce the need for chemical controls.

FIT1

FIT1 is a plant Toll-like interleukin-1 receptor (TIR) nucleotide binding leucine rich repeat (NLR) immune receptor protein discovered by Applicants. It was identified from *Vigna unguiculata* (cowpea) and is responsible for AvrFIT1 recognition. As shown in FIG. 2, expression of FIT1 correlates with resistance to ASR. Accessions of *Vigna radiata*, (PI 378026), *Phaseolus lunatus* (PI 180324), and *Vigna unguiculata* (LG104, Baker Creek Heirloom Seeds) which contain functional copies of FIT1 genes show strong resistance to *Phakopsora pachyrhizi*. In contrast, accessions of *Glycine max* (Williams 82), *Pachyrhizus erosus* (AB 105, Baker Creek Heirloom Seeds), and *Glycine peratosa* (PI 583964), which all lack functional FIT1, are highly susceptible to *Phakopsora pachyrhizi* as observed by large disease lesions and spore production. These results indicate a correlation between the presence of FIT1 and resistance to *Phakopsora pachyrhizi* and suggest that expression of FIT1 in plants can confer disease resistance. Additionally, the widespread distribution of AvrFIT1 discussed above suggests that FIT1 can confer disease resistance against a broad range of pathogenic species.

Thus, an embodiment of the present disclosure provides an isolated, recombinant, or synthetic polynucleotide comprising a nucleic acid sequence encoding a FIT1 protein, wherein the protein is selected from the group consisting of: SEQ ID NOs: 2, 4, 6, 8, 10, 12, 14, 16, 18, 20, functional homologs, and/or fragments and variations thereof. In some cases, the functional FIT1 homolog shares at least about 70% identity to SEQ ID NO: 2 and recognizes an effector protein secreted by a plant pathogen. In some cases, the functional FIT1 homolog recognizes at least one of AvrFIT1a and AvrFIT1b. In some cases, the functional FIT1 homolog shares at least about 70%, about 71%, about 72%, about 73%, about 74%, about 75%, about 76%, about 77%, about 78%, about 79%, 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to SEQ ID NO: 2.

In some cases, the functional FIT1 homolog shares at least about 70%, about 71%, about 72%, about 73%, about 74%, about 75%, about 76%, about 77%, about 78%, about 79%, 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to SEQ ID NO: 4.

In some cases, the functional FIT1 homolog shares at least about 70%, about 71%, about 72%, about 73%, about 74%, about 75%, about 76%, about 77%, about 78%, about 79%, 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to SEQ ID NO: 6.

In some cases, the functional FIT1 homolog shares at least about 70%, about 71%, about 72%, about 73%, about 74%, about 75%, about 76%, about 77%, about 78%, about 79%, 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to SEQ ID NO: 8.

In some cases, the functional FIT1 homolog shares at least about 70%, about 71%, about 72%, about 73%, about 74%, about 75%, about 76%, about 77%, about 78%, about 79%, 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to SEQ ID NO: 10.

In some cases, the functional FIT1 homolog shares at least about 70%, about 71%, about 72%, about 73%, about 74%, about 75%, about 76%, about 77%, about 78%, about 79%, 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to SEQ ID NO: 12

In some cases, the functional FIT1 homolog shares at least about 70%, about 71%, about 72%, about 73%, about 74%, about 75%, about 76%, about 77%, about 78%, about 79%, 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to SEQ ID NO: 14.

In some cases, the functional FIT1 homolog shares at least about 70%, about 71%, about 72%, about 73%, about 74%, about 75%, about 76%, about 77%, about 78%, about 79%, 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to SEQ ID NO: 16.

In some cases, the functional FIT1 homolog shares at least about 70%, about 71%, about 72%, about 73%, about 74%, about 75%, about 76%, about 77%, about 78%, about 79%, 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to SEQ ID NO: 18.

In some cases, the functional FIT1 homolog shares at least about 70%, about 71%, about 72%, about 73%, about 74%, about 75%, about 76%, about 77%, about 78%, about 79%, 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to SEQ ID NO: 20.

In some aspects, the isolated, recombinant, or synthetic polynucleotide comprises a nucleic acid sequence encoding SEQ ID NO: 2, or an amino acid sequence at least 90% identical thereto. In some aspects, the isolated, recombinant, or synthetic polynucleotide comprises a nucleic acid sequence encoding SEQ ID NO: 4, or an amino acid sequence at least 90% identical thereto. In some aspects, the isolated, recombinant, or synthetic polynucleotide comprises a nucleic acid sequence encoding SEQ ID NO: 6, or an amino acid sequence at least 90% identical thereto. In some aspects, the isolated, recombinant, or synthetic polynucleotide comprises a nucleic acid sequence encoding SEQ ID NO: 8, or an amino acid sequence at least 90% identical thereto. In some aspects, the isolated, recombinant, or synthetic polynucleotide comprises a nucleic acid sequence encoding SEQ ID NO: 10, or an amino acid sequence at least 90% identical thereto. In some aspects, the isolated, recombinant, or synthetic polynucleotide comprises a nucleic acid sequence encoding SEQ ID NO: 12, or an amino acid sequence at least 90% identical thereto. In some aspects, the isolated, recombinant, or synthetic polynucleotide comprises a nucleic acid sequence encoding SEQ ID NO: 14, or an amino acid sequence at least 90% identical thereto. In some aspects, the isolated, recombinant, or synthetic polynucleotide comprises a nucleic acid sequence encoding SEQ ID NO: 16, or an amino acid sequence at least 90% identical thereto. In some aspects, the isolated, recombinant, or synthetic polynucleotide comprises a nucleic acid sequence encoding SEQ ID NO: 18, or an amino acid sequence at least 90% identical thereto. In some aspects, the isolated, recombinant, or synthetic polynucleotide comprises a nucleic acid sequence encoding SEQ ID NO: 20, or an amino acid sequence at least 90% identical thereto.

In another embodiment, the disclosure relates to a transgenic plant, plant part, or cell having resistance or tolerance to at least one plant pathogen, wherein the resistance or tolerance is conferred by a polynucleotide encoding at least one of the functional FIT1 homologs disclosed herein.

In another embodiment, the present disclosure provides an isolated, recombinant, or synthetic polynucleotide, wherein the polynucleotide comprises a nucleic acid sequence selected from the group consisting of SEQ ID NOs: 1, 3, 5, 7, 9, 11, 13, 15, 17, 19 complements thereof, fragments thereof, and sequences at least 70% identical thereto, wherein said sequences encode a functional FIT1 protein. In some cases, the polynucleotide shares at least about 70%, at least about 71%, about 72%, about 73%, about 74%, about 75%, about 76%, about 77%, about 78%, about 79%, 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to SEQ ID NO: 1. In some embodiments, the disclosure relates to genetic constructs comprising these sequences.

In some cases, the polynucleotide shares at least about 70%, at least about 71%, about 72%, about 73%, about 74%, about 75%, about 76%, about 77%, about 78%, about 79%, 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to SEQ ID NO: 3. In some embodiments, the disclosure relates to genetic constructs comprising these sequences.

In some cases, the polynucleotide shares at least about 70%, at least about 71%, about 72%, about 73%, about 74%, about 75%, about 76%, about 77%, about 78%, about 79%, 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to SEQ ID NO: 5. In some embodiments, the disclosure relates to genetic constructs comprising these sequences.

In some cases, the polynucleotide shares at least about 70%, at least about 71%, about 72%, about 73%, about 74%, about 75%, about 76%, about 77%, about 78%, about 79%, 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to SEQ ID NO: 7. In some embodiments, the disclosure relates to genetic constructs comprising these sequences.

In some cases, the polynucleotide shares at least about 70%, at least about 71%, about 72%, about 73%, about 74%, about 75%, about 76%, about 77%, about 78%, about 79%, 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to SEQ ID NO: 9. In some embodiments, the disclosure relates to genetic constructs comprising these sequences.

In some cases, the polynucleotide shares at least about 70%, at least about 71%, about 72%, about 73%, about 74%, about 75%, about 76%, about 77%, about 78%, about 79%, 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to SEQ ID NO: 11. In some embodiments, the disclosure relates to genetic constructs comprising these sequences.

In some cases, the polynucleotide shares at least about 70%, at least about 71%, about 72%, about 73%, about 74%, about 75%, about 76%, about 77%, about 78%, about 79%, 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to SEQ ID NO: 13. In some embodiments, the disclosure relates to genetic constructs comprising these sequences.

In some cases, the polynucleotide shares at least about 70%, at least about 71%, about 72%, about 73%, about 74%, about 75%, about 76%, about 77%, about 78%, about 79%, 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to SEQ ID NO: 15. In some embodiments, the disclosure relates to genetic constructs comprising these sequences.

In some cases, the polynucleotide shares at least about 70%, at least about 71%, about 72%, about 73%, about 74%, about 75%, about 76%, about 77%, about 78%, about 79%, 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to SEQ ID NO: 17. In some embodiments, the disclosure relates to genetic constructs comprising these sequences.

In some cases, the polynucleotide shares at least about 70%, at least about 71%, about 72%, about 73%, about 74%, about 75%, about 76%, about 77%, about 78%, about 79%, 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to SEQ ID NO: 19. In some embodiments, the disclosure relates to genetic constructs comprising these sequences.

The disclosure also encompasses variants and fragments of proteins of an amino acid sequence encoded by the nucleic acid sequences of FIT1, orthologs of FIT1 and/or paralogs of FIT1. The variants may contain alterations in the amino acid sequences of the constituent proteins. The term "variant" with respect to a polypeptide refers to an amino acid sequence that is altered by one or more amino acids with respect to a reference sequence. The variant can have "conservative" changes, or "nonconservative" changes, e.g., analogous minor variations can also include amino acid deletions or insertions, or both.

Functional fragments and variants of a polypeptide include those fragments and variants that maintain one or more functions or domains of the parent polypeptide. As used herein, a protein domain is a distinct functional and/or structural unit in a protein, and are usually responsible for a particular function or interaction. It is recognized that the gene or cDNA encoding a polypeptide can be considerably mutated without materially altering one or more of the polypeptide's functions and/or domains. First, the genetic code is well-known to be degenerate, and thus different codons encode the same amino acids. Second, even where an amino acid substitution is introduced, the mutation can be conservative and have no material impact on the essential function(s) of a protein. See, e.g., *Stryer Biochemistry* $3^{rd}$ Ed., 1988. Third, part of a polypeptide chain can be deleted without impairing or eliminating all of its functions. Fourth, insertions or additions can be made in the polypeptide chain for example, adding epitope tags, without impairing or eliminating its functions (Ausubel et al. *J. Immunol.* 159(5): 2502-12, 1997). Other modifications that can be made without materially impairing one or more functions of a polypeptide can include, for example, in vivo or in vitro chemical and biochemical modifications or the incorporation of unusual amino acids. Such modifications include, but are not limited to, for example, acetylation, carboxylation, phosphorylation, glycosylation, ubiquination, labelling, e.g., with radionucleotides, and various enzymatic modifications, as will be readily appreciated by those well skilled in the art. A variety of methods for labelling polypeptides, and labels useful for such purposes, are well known in the art, and include radioactive isotopes such as $^{32}P$, ligands which bind to or are bound by labelled specific binding partners (e.g., antibodies), fluorophores, chemiluminescent agents, enzymes, and anti-ligands. Functional fragments and variants can be of varying length. For example, some fragments have at least 10, 25, 50, 75, 100, 200, or even more amino acid residues. These mutations can be natural or purposely changed. In some embodiments, mutations containing alterations that produce silent substitutions, additions, or deletions, but do not alter the properties or activities of the proteins or how the proteins are made are an embodiment of the present disclosure.

Conservative amino acid substitutions are those substitutions that, when made, least interfere with the properties of the original protein, that is, the structure and especially the function of the protein is conserved and not significantly changed by such substitutions. Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain. Further information about conservative substitutions can be found, for instance, in Ben Bassat et al. (*J. Bacteriol.,* 169:751-757, 1987), O'Regan et al. (*Gene,* 77:237-251, 1989), Sahin-Toth et al. (*Protein Sci.,* 3:240-247, 1994), Hochuli et al. (*Bio/Technology,* 6:1321-1325, 1988) and in widely used textbooks of genetics and molecular biology. The Blosum matrices are commonly used for determining the relatedness of polypeptide sequences. The Blosum matrices were created using a large database of trusted alignments (the BLOCKS database), in which pairwise sequence alignments related by less than some threshold percentage identity were counted (Henikoff et al., *Proc. Natl. Acad. Sci. USA,* 89:10915-10919, 1992). A threshold of 90% identity was used for the highly conserved target frequencies of the BLOSUM90 matrix. A threshold of 65% identity was used for the BLOSUM65 matrix. Scores of zero and above in the Blosum matrices are considered "conservative substitutions" at the percentage identity selected. The following table 1 shows exemplary conservative amino acid substitutions.

TABLE 1

| Original Residue | Very Highly - Conserved Substitutions | Highly Conserved Substitutions (from the Blosum90 Matrix) | Conserved Substitutions (from the Blosum65 Matrix) |
|---|---|---|---|
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

Codon Optimization

In some cases, variants may differ from the disclosed sequences by alteration of the coding region to fit the codon usage bias of the particular organism into which the molecule is to be introduced. In other cases, the coding region may be altered by taking advantage of the degeneracy of the genetic code to alter the coding sequence such that, while the nucleotide sequence is substantially altered, it nevertheless encodes a protein having an amino acid sequence substantially similar to the disclosed amino acid sequences of FIT1, orthologs of FIT1 and/or paralogs of FIT1, and/or fragments and variations thereof.

Protein expression is governed by a host of factors including those that affect transcription, mRNA processing, and stability and initiation of translation. Optimization can thus address any of a number of sequence features of any particular gene. Translation may be paused due to the presence of codons in the polynucleotide of interest that are rarely used in the host organism, and this may have a negative effect on protein translation due to their scarcity in the available tRNA pool. Specifically, it can result in reduced protein expression.

Alternate translational initiation also can result in reduced heterologous protein expression. Alternate translational initiation can include a synthetic polynucleotide sequence inadvertently containing motifs capable of functioning as a ribosome binding site (RBS). These sites can result in initiating translation of a truncated protein from a gene-internal site. One method of reducing the possibility of producing a truncated protein includes eliminating putative internal RBS sequences from an optimized polynucleotide sequence.

Repeat-induced polymerase slippage can result in reduced heterologous protein expression. Repeat-induced polymerase slippage involves nucleotide sequence repeats that have been shown to cause slippage or stuttering of DNA polymerase which can result in frameshift mutations. Such repeats can also cause slippage of RNA polymerase. In an organism with a high G+C content bias, there can be a higher degree of repeats composed of G or C nucleotide repeats. Therefore, one method of reducing the possibility of inducing RNA polymerase slippage, includes altering extended repeats of G or C nucleotides.

Interfering secondary structures also can result in reduced heterologous protein expression. Secondary structures can sequester the RBS sequence or initiation codon and have been correlated to a reduction in protein expression. Stem-loop structures can also be involved in transcriptional pausing and attenuation. An optimized polynucleotide sequence can contain minimal secondary structures in the RBS and gene coding regions of the nucleotide sequence to allow for improved transcription and translation.

The optimization process can begin, for example, by identifying the desired amino acid sequence to be expressed by the host. From the amino acid sequence, a candidate polynucleotide or DNA sequence can be designed. During the design of the synthetic DNA sequence, the frequency of codon usage can be compared to the codon usage of the host expression organism and rare host codons can be removed from the synthetic sequence. Additionally, the synthetic candidate DNA sequence can be modified in order to remove undesirable enzyme restriction sites and add or remove any desired signal sequences, linkers or untranslated regions. The synthetic DNA sequence can be analyzed for the presence of secondary structure that may interfere with the translation process, such as G/C repeats and stem-loop structures.

Optimized coding sequences containing codons preferred by a particular host can be prepared, for example, to increase the rate of translation or to produce recombinant RNA transcripts having desirable properties, such as a longer half-life, as compared with transcripts produced from a non-optimized sequence.

Functional Fragments, Chimeric, and Synthetic Polypeptides

In some cases, functional fragments derived from FIT1 orthologs of the present disclosure can still confer resistance to pathogens when expressed in a plant. In some cases, the functional fragments contain one or more conserved regions shared by two or more FIT1 orthologs.

In some cases, functional chimeric or synthetic polypeptides derived from the FIT1 orthologs of the present disclosure are provided. The functional chimeric or synthetic polypeptides can still confer resistance to pathogens when expressed in a plant. In some cases, the functional chimeric or synthetic polypeptides contain one or more conserved regions shared by two or more FIT1 orthologs.

DNA Constructs

In some embodiments, the disclosure relates to a DNA construct comprising at least one FIT1 sequence disclosed herein. In some cases, the FIT1 sequence is a polynucleotide comprising a nucleic acid sequence encoding a FIT1 protein, wherein the protein is selected from the group consisting of: SEQ ID NOs: 2, 4, 6, 8, 10, 12, 14, 16, 18, 20, functional homologs, and/or fragments and variations thereof. In some cases, the FIT1 protein shares at least about 70% identity to SEQ ID NO: 2. In some cases, the FIT1 sequence is selected from SEQ ID NOs: 1, 3, 5, 7, 9, 11, 13, 15, 17, 19 complements thereof, fragments thereof, and sequences at least 70% identical thereto. In some cases, two or more FIT1 sequences are stacked to increase pathogen resistance in a plant. In some cases, at least one FIT1 sequence is stacked with another pathogen resistance gene.

The expression control elements used to regulate the expression of a given protein can either be the expression control element that is normally found associated with the coding sequence (homologous expression element) or can be a heterologous expression control element. A variety of homologous and heterologous expression control elements are known in the art and can readily be used to make DNA constructs for use in the present disclosure. Transcription initiation regions, for example, can include any of the various opine initiation regions, such as octopine, mannopine, nopaline and the like that are found in the Ti plasmids of *Agrobacterium tumefaciens*. Alternatively, plant viral promoters can also be used, such as the cauliflower mosaic virus 19S and 35S promoters (CaMV 19S and CaMV 35S promoters, respectively) to control gene expression in a plant (U.S. Pat. Nos. 5,352,605; 5,530,196 and 5,858,742 for example). Enhancer sequences derived from the CaMV can also be utilized (U.S. Pat. Nos. 5,164,316; 5,196,525; 5,322,938; 5,530,196; 5,352,605; 5,359,142; and 5,858,742 for example). Lastly, plant promoters such as prolifera promoter, fruit specific promoters, Ap3 promoter, heat shock promoters, seed specific promoters, etc. can also be used.

Either a gamete-specific promoter, a constitutive promoter (such as the CaMV or Nos promoter), an organ-specific promoter (such as the E8 promoter from tomato), or an inducible promoter is typically ligated to the protein or antisense encoding region using standard techniques known in the art. The DNA construct may be further optimized by employing supplemental elements such as transcription terminators and/or enhancer elements.

Thus, for expression in plants, the DNA construct will typically contain, in addition to the protein sequence, a plant promoter region, a transcription initiation site and a transcription termination sequence. Unique restriction enzyme sites at the 5' and 3' ends of the expression unit are typically included to allow for easy insertion into a pre-existing vector.

In the construction of heterologous promoter/gene of interest or antisense combinations, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette can also contain a transcription termination region downstream of the gene to provide for efficient termination. The termination region may be obtained from the same gene as the promoter sequence or may be obtained from different genes. If the mRNA encoded by the gene is to be efficiently processed, DNA sequences which direct polyadenylation of the RNA are also commonly added to the vector construct. Polyadenylation sequences include, but are not limited to the *Agrobacterium* octopine synthase signal (Gielen et al., EMBO J 3:835-846 (1984)) or the nopaline synthase signal (Depicker et al., Mol. and Appl. Genet. 1:561-573 (1982)).

The resulting expression unit is ligated into or otherwise constructed to be included in a vector that is appropriate for higher plant transformation. One or more expression units may be included in the same vector.

Selection

A DNA construct will typically contain a selectable marker gene expression unit by which transformed plant cells can be identified in culture. Usually, the marker gene will encode resistance to an antibiotic, such as G418, hygromycin, bleomycin, kanamycin, or gentamicin or to an herbicide, such as glyphosate (Round-Up) or glufosinate (BASTA) or atrazine. Replication sequences, of bacterial or viral origin, are generally also included to allow the vector to be cloned in a bacterial or phage host; preferably a broad host range for prokaryotic origin of replication is included. A selectable marker for bacteria may also be included to allow selection of bacterial cells bearing the desired construct. Suitable prokaryotic selectable markers include resistance to antibiotics such as ampicillin, kanamycin or tetracycline. Other DNA sequences encoding additional functions may also be present in the vector, as is known in the art. For instance, in the case of *Agrobacterium* transformations, T-DNA sequences will also be included for subsequent transfer to plant chromosomes.

For positive selection, for example, a foreign gene is supplied to a plant cell that allows it to utilize a substrate present in the medium that it otherwise could not use, such as mannose or xylose (for example, refer U.S. Pat. Nos. 5,767,378; 5,994,629). More typically, however, negative selection is used because it is more efficient, utilizing selective agents such as herbicides or antibiotics that either kill or inhibit the growth of non-transformed plant cells and reducing the possibility of chimeras. Resistance genes that are effective against negative selective agents are provided on the introduced foreign DNA used for the plant transformation. For example, one of the most popular selective agents used is the antibiotic kanamycin, together with the resistance gene neomycin phosphotransferase (nptII), which confers resistance to kanamycin and related antibiotics (see, for example, Messing & Vierra, *Gene* 19: 259-268 (1982); Bevan et al., *Nature* 304:184-187 (1983)). However, many different antibiotics and antibiotic resistance genes can be used for transformation purposes (refer U.S. Pat. Nos. 5,034,322, 6,174,724 and 6,255,560). In addition, several herbicides and herbicide resistance genes have been used for transformation purposes, including the bar gene, which confers resistance to the herbicide phosphinothricin (White et al., *Nucl Acids Res* 18: 1062 (1990), Spencer et al., *Theor Appl Genet* 79: 625-631(1990), U.S. Pat. Nos. 4,795,855, 5,378,824 and 6,107,549). In addition, the dhfr gene, which confers resistance to the anticancer agent methotrexate, has been used for selection (Bourouis et al., *EMBO J.* 2(7): 1099-1104 (1983).

Transgenic Plants Comprising Sequences Disclosed Herein

In one embodiment, the present disclosure relates to a transgenic plant, plant part, or plant cell, wherein the transgene comprises at least one polynucleotide coding for FIT1, orthologs of FIT1 and/or paralogs of FIT1, and/or fragments and variations thereof, and exhibit resistance or tolerance to a pathogen. In some cases, the polynucleotide encodes a protein selected from the group consisting of: SEQ ID NOs: 2, 4, 6, 8, 10, 12, 14, 16, 18, 20, and proteins at least 90% identical thereto functional homologs thereof. In some cases, the polynucleotide comprises a nucleic acid sequence selected from the group consisting of SEQ ID NOs: 1, 3, 5, 7, 9, 11, 13, 15, 17, 19 complements thereof, fragments thereof, and sequences at least 70% identical thereto. In some cases, the pathogen is a fungus. In some cases, the fungus is from the order Cantharellales or Pucciniales. In some cases, the fungal pathogen is *Rhizoctonia solani*, Melampsora spp., *Phakopsora pachyrhizi, Phakopsora meibomiae, Phakopsora euvitis, Phakopsora* spp., *Puccinia* spp., *Uromyces* spp., *Austropuccinia* spp., *Cronartium* spp. or *Hemileia vastatrix.*

In some cases, the plant, plant part, or plant cell is in the subfamily Papilionoideae. In some cases, the plant, plant part, or plant cell is *Alysicarpus* spp., *Astragalus* spp., *Baptisia* spp., *Cajanus* spp., *Calopogonium* spp., *Caragana* spp., *Centrosema* spp., *Cologania* spp., *Crotalaria* spp., *Desmodium* spp., *Genista* spp., *Glycine* spp., *Glycyrrhiza* spp., *Indigofera* spp., *Kummerowia* spp., *Lablab* spp., *Lathyrus* spp., *Lespedeza* spp., *Lotus* spp., *Lupinus* spp., *Macroptilium* spp., *Macrotyloma* spp., *Medicago* spp., *Neonotonia* spp., *Pachyrhizus* spp., *Pisum* spp., *Phaseolus* spp., *Pseudovigna* spp., *Psoralea* spp., *Robinia* spp., *Senna* spp., *Sesbania* spp., *Strophostyles* spp., *Tephrosia* spp., *Teramnus* spp., Trifolium spp., *Vicia* spp., *Vigna* spp., or *Voandzeia* spp.

In some cases, the plant, plant part, or plant cell is *Glycine max*, and the plant, plant part, or plant cell is resistant to Asian Soybean Rust caused by *Phakopsora pachyrhizi.*

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and *Agrobacterium*-mediated transformation. See, for example, U.S. Pat. Nos. 5,405,765; 5,472,869; 5,538,877; 5,538,880; 5,550,318; 5,641,664; 5,736,369 and 5,736,369; International Patent Application Publication Nos. WO2002/038779 and WO/2009/117555; Lu et al., (Plant Cell Reports, 2008, 27:273-278); Watson et al., Recombinant DNA, Scientific American Books (1992); Hinchee et al., Bio/Tech. 6:915-922 (1988); McCabe et al., Bio/Tech. 6:923-926 (1988); Toriyama et al., Bio/Tech. 6:1072-1074 (1988); Fromm et al., Bio/Tech. 8:833-839 (1990); Mullins et al., Bio/Tech. 8:833-839 (1990); Hiei et al., Plant Molecular Biology 35:205-218 (1997); Ishida et al., Nature Biotechnology 14:745-750 (1996); Zhang et al., Molecular Biotechnology 8:223-231 (1997); Ku et al., Nature Biotechnology 17:76-80 (1999); and, Raineri et al., Bio/Tech. 8:33-38 (1990)), each of which is expressly incorporated herein by reference in their entirety.

Microprojectile bombardment is also known as particle acceleration, biolistic bombardment, and the gene gun (Biolistic® Gene Gun). The gene gun is used to shoot pellets that are coated with genes (e.g., for desired traits) into plant seeds or plant tissues in order to get the plant cells to then express the new genes. The gene gun uses an actual explosive (.22 caliber blank) to propel the material. Compressed air or steam may also be used as the propellant. The Biolistic® Gene Gun was invented in 1983-1984 at Cornell University by John Sanford, Edward Wolf, and Nelson Allen. It and its registered trademark are now owned by E. I. du Pont de Nemours and Company. Most species of plants can be been transformed using this method.

The most common method for the introduction of new genetic material into a plant genome involves the use of living cells of the bacterial pathogen *Agrobacterium tumefaciens. Agrobacterium tumefaciens* is a naturally occurring bacterium that is capable of inserting its DNA (genetic information) into plants, resulting in a type of injury to the plant known as crown gall. Most species of plants can now be transformed using this method. There are numerous patents governing *Agrobacterium* mediated transformation and particular DNA delivery plasmids designed specifically for use with *Agrobacterium*—for example, U.S. Pat. No. 4,536,475, EP0265556, EP0270822, WO8504899, WO8603516, U.S. Pat. No. 5,591,616, EP0604662, EP0672752, WO8603776, WO9209696, WO9419930, WO9967357, U.S. Pat. No. 4,399,216, WO8303259, U.S. Pat. No. 5,731,179, EP068730, WO9516031, U.S. Pat. Nos. 5,693,512, 6,051,757 and EP904362A1. Methods of *Agrobacterium*-mediated plant transformation that involve using vectors with no T-DNA are also well known to those skilled in the art and can be used with the methods of the present disclosure. See, for example, U.S. Pat. No. 7,250,554, which utilizes P-DNA instead of T-DNA in the transformation vector. A transgenic plant formed using *Agrobacterium* transformation methods typically contains a single gene on one chromosome, although multiple copies are possible. Such transgenic plants can be referred to as being hemizygous for the added gene, or may be referred to as an independent segregant, because each transformed plant represents a unique T-DNA integration event (U.S. Pat. No. 6,156,953).

Direct plant transformation methods using DNA have also been reported. The first of these to be reported historically is electroporation, which utilizes an electrical current applied to a solution containing plant cells (M. E. Fromm et al., Nature, 319, 791 (1986); H. Jones et al., Plant Mol. Biol., 13, 501 (1989) and H. Yang et al., Plant Cell Reports, 7, 421 (1988).

Another direct method, called "biolistic bombardment", uses ultrafine particles, usually tungsten or gold, that are coated with DNA and then sprayed onto the surface of a plant tissue with sufficient force to cause the particles to penetrate plant cells, including the thick cell wall, membrane and nuclear envelope (U.S. Pat. Nos. 5,204,253, 5,015,580).

A third direct method uses fibrous forms of metal or ceramic consisting of sharp, porous or hollow needle-like projections that impale the cells, and also the nuclear envelope of cells. Both silicon carbide and aluminium borate whiskers have been used for plant transformation (Mizuno et al., 2004; Petolino et al., 2000; U.S. Pat. No. 5,302,523 US Application 20040197909) and also for bacterial and animal transformation (Kaepler et al., 1992; Raloff, 1990; Wang, 1995).

Examples of viral vectors include, but are not limited to, recombinant plant viruses. Non-limiting examples of plant viruses include, TMV-mediated (transient) transfection into tobacco (Tuipe, T-H et al (1993), J. Virology Meth, 42: 227-239), ssDNA genomes viruses (e.g., family Geminiviridae), reverse transcribing viruses (e.g., families Caulimoviridae, Pseudoviridae, and Metaviridae), dsNRA viruses (e.g., families Reoviridae and Partitiviridae), (−) ssRNA viruses (e.g., families Rhabdoviridae and Bunyaviridae), (+) ssRNA viruses (e.g., families Bromoviridae, Closteroviridae, Comoviridae, Luteoviridae, Potyviridae, Sequiviridae and Tombusviridae) and viroids (e.g., families Pospiviroldae and Avsunviroidae). Detailed classification information of plant viruses can be found in Fauquet et al (2008, "Geminivirus strain demarcation and nomenclature". *Archives of Virology* 153:783-821, incorporated herein by reference in its entirety), and Khan et al. (Plant viruses as molecular pathogens; Publisher Routledge, 2002, ISBN 1560228954, 9781560228950). Examples of non-viral vectors include, but are not limited to, liposomes, polyamine derivatives of DNA, and the like.

Non-limiting examples of binary vectors suitable for soybean species transformation and transformation methods are described by Yi et al. 2006 (Transformation of multiple soybean cultivars by infecting cotyledonary-node with *Agrobacterium tumefaciens, African Journal of Biotechnology* Vol. 5 (20), pp. 1989-1993, 16 Oct. 2006), Paz et al., 2004 (Assessment of conditions affecting *Agrobacterium*-mediated soybean transformation using the cotyledonary node explant, Euphytica 136: 167-179, 2004), U.S. Pat. Nos. 5,376,543, 5,416,011, 5,968,830, and 5,569,834, or by similar experimental procedures well known to those skilled in the art.

Genes can also be introduced in a site directed fashion using homologous recombination. Homologous recombination permits site-specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451, 513; 5,501,967 and 5,527,695.

Genetically Engineering a Pathogen Resistance or Tolerance Trait in a Plant, Plant Part, or Plant Cell An embodiment of the present disclosure teaches a method of genetically engineering a pathogen resistance or tolerance trait in a plant, plant part, or plant cell, comprising: providing a plant species that is susceptible to a pathogen; identifying within the genome of the plant species a homolog of FIT1, wherein said homolog is nonfunctional (does not mediate AvrFIT1 recognition), and genetically modifying a plant, plant part, or plant cell from the susceptible plant species with targeted gene editing, wherein said targeted gene editing is directed towards the nonfunctional FIT1 homolog, and wherein said targeted gene editing restores the function of FIT1 (enables the FIT1 homolog to recognize AvrFIT1) and confers resistance or tolerance to a pathogen. In some embodiments, the pathogen is a fungus.

As used herein, a "nonfunctional" FIT1 homolog is a homolog that does not recognize a pathogen effector protein homolog of AvrFIT1, such as AvrFIT1a and/or AvrFIT1b. FIT1 homologous may identified by any number of means known in the art. Methods of alignment of sequences for comparison are well known in the art. Various programs and alignment algorithms are described in: Smith and Waterman (*Adv. Appl. Math.,* 2:482, 1981); Needleman and Wunsch (*J. Mol. Biol.,* 48:443, 1970); Pearson and Lipman (*Proc. Natl. Acad. Sci.,* 85:2444, 1988); Higgins and Sharp (*Gene,* 73:237-44, 1988); Higgins and Sharp (*CABIOS,* 5:151-53, 1989); Corpet et al. (*Nuc. Acids Res.,* 16:10881-90, 1988); Huang et al. (*Comp. Appls Biosci.,* 8:155-65, 1992); and Pearson et al. (*Meth. Mol. Biol.,* 24:307-31, 1994). Altschul et al. (*Nature Genet.,* 6:119-29, 1994) presents a detailed consideration of sequence alignment methods and homology calculations.

Restoring the function of a FIT1 homolog as used herein relates to modifying the allele such that it restores the recognition of a pathogen effector protein such as AvrFIT1a and/or AvrFIT1b, and confers resistance or tolerance to a pathogen. Restoring the function of a homologous gene by way of genetic engineering has been done and is well known in the art (see for example, Ivies Z, et al., (1997), "Molecular reconstruction of Sleeping Beauty, a Tc1-like transposon from fish, and its transposition in human cells", *Cell.* 91 (4): 501-510, and recently, Suh S, et al., Restoration of visual function in adult mice with an inherited retinal disease via adenine base editing, *Nat Biomed Eng* (2020) and Sedeek K, et al., Plant genome engineering for targeted improvement of crop traits, *Front. Plant Sci.,* 12 Feb. 2019).

In some embodiments, the targeted gene editing uses an engineered or natural nuclease selected from the group consisting of homing endonucleases/meganucleases (EMNs), zinc finger nucleases (ZFNs), and transcription activator-like effector nucleases (TALEN5). In some embodiments, the targeted gene editing uses a clustered regularly interspaced short palindromic repeats (CRISPR)-Cas nuclease. In some embodiments, the nuclease is selected from the group consisting of Cas9, Cas12, Cas13, CasX, and CasY. The disclosure also relates to plants, plant parts, and plant cells exhibiting resistance or tolerance to a pathogen produced by genetic modification of a FIT1 homolog.

Gene Editing Using CRISPR

Targeted gene editing can be done using CRISPR technology (Saunders & Joung, Nature Biotechnology, 32, 347-355, 2014). CRISPR is a type of genome editing system that stands for Clustered Regularly Interspaced Short Palindromic Repeats. This system and CRISPR-associated (Cas) genes enable organisms, such as select bacteria and archaea, to respond to and eliminate invading genetic material. Ishino, Y., et al. *J. Bacteriol.* 169, 5429-5433 (1987). These repeats were known as early as the 1980s in *E. coli*, but Barrangou and colleagues demonstrated that *S. thermophilus* can acquire resistance against a bacteriophage by integrating a fragment of a genome of an infectious virus into its CRISPR locus. Barrangou, R., et al. *Science* 315, 1709-1712 (2007). Many plants have already been modified using the CRISPR system, including soybean (see for example, Han J, et al., Creation of early flowering germplasm of soybean by CRISPR/Cas9 Technology, *Front. Plant Sci.,* 22 Nov. 2019), and many Cas genes have now been characterized and used with the system (see for example, Wang J, et al., The rapidly advancing Class 2 CRISPR-Cas technologies: A customizable toolbox for molecular manipulations. *J Cell Mol Med.* 2020; 24(6):3256-3270).

Gene editing can also be done using crRNA-guided surveillance systems for gene editing. Additional information about crRNA-guided surveillance complex systems for gene editing can be found in the following documents, which are incorporated by reference in their entirety: U.S. Application Publication No. 2010/0076057 (Sontheimer et al., Target DNA Interference with crRNA); U.S. Application Publication No. 2014/0179006 (Feng, CRISPR-CAS Component Systems, Methods, and Compositions for Sequence Manipulation); U.S. Application Publication No. 2014/0294773 (Brouns et al., Modified Cascade Ribonucleoproteins and Uses Thereof); Sorek et al., *Annu. Rev. Biochem.* 82:237-266, 2013; and Wang, S. et al., *Plant Cell Rep* (2015) 34: 1473-1476.

Gene Editing Using TALENs

Transcription activator-like effector nucleases (TALENs) have been successfully used to introduce targeted mutations via repair of double stranded breaks (DSBs) either through non-homologous end joining (NHEJ), or by homology-directed repair (HDR) and homology-independent repair in the presence of a donor template. Thus, TALENs are another mechanism for targeted genome editing in plants. The technique is well known in the art; see for example Malzahn, Aimee et al. "Plant genome editing with TALEN and CRISPR" *Cell & Bioscience* vol. 7 21. 24 Apr. 2017.

Other Methods of Genome Editing

In addition to CRISPR and TALENs, two other types of engineered nucleases can be used for genome editing: engineered homing endonucleases/meganucleases (EMNs), and zinc finger nucleases (ZFNs). These methods are well known in the art. See for example, Petilino, Joseph F. "Genome editing in plants via designed zinc finger nucleases" *In Vitro Cell Dev Biol Plant.* 51(1): pp. 1-8 (2015); and Daboussi, Fayza, et al. "Engineering Meganuclease for Precise Plant Genome Modification" in *Advances in New Technology for Targeted Modification of Plant Genomes.* Springer Science+Business. pp 21-38 (2015).

Breeding Methods

Once a gene has been introduced into a plant, or a gene has been genetically modified, that plant can then be used in conventional plant breeding schemes (e.g., pedigree breeding, single-seed-descent breeding schemes, recurrent selection, backcross breeding) to produce progeny which also contain the gene or modified trait. Thus, another aspect of the present disclosure relates to breeding with, or asexually propagating, plants having been transformed with a FIT1 homolog or an immune receptor gene coding for a protein that recognizes AvrFIT1a and/or AvrFIT1b, or plants wherein a FIT1 nonfunctional homolog was genetically modified to recognize AvrFIT1a and/or AvrFIT1b, wherein the plants exhibit resistance or tolerance to a pathogen. The disclosure further relates to progeny plants produced therefrom.

In some cases, plants or progeny therefrom comprising the gene or modified trait may further comprise one or more additional desired traits. In some cases, the one or more additional desired traits are stacked on the same construct as the gene (for example, the FIT1 genes disclosed herein). In another case, the one or more additional desired traits may be introgressed by conventional breeding.

Backcross Breeding

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent. As used herein, backcross breeding is synonymous with introgression. Plants produced therefrom may be referred to a single locus converted or single gene converted plants.

A non-limiting example of a backcross breeding protocol would be the following: a) the first generation $F_1$ produced by the cross of the recurrent parent A by the donor parent B is backcrossed to parent A, b) selection is practiced for the plants having the desired trait of parent B, c) selected plants are self-pollinated to produce a population of plants where selection is practiced for the plants having the desired trait of parent B and physiological and morphological characteristics of parent A, d) the selected plants are backcrossed one, two, three, four, five, six, seven, eight, nine, or more times to parent A to produce selected backcross progeny plants comprising the desired trait of parent B and the physiological and morphological characteristics of parent A. Step (c) may or may not be repeated and included between the backcrosses of step (d).

Examples of desired traits include, but are not limited to, herbicide resistance (such as bar or pat genes), resistance for bacterial, fungal, or viral disease (such as gene I used for BCMV resistance), insect resistance, enhanced nutritional quality (such as 2s albumin gene), industrial usage, agronomic qualities (such as the "persistent green gene"), yield stability, and yield enhancement.

Pedigree Selection

Pedigree breeding is used commonly for the improvement of self-pollinating crops or inbred lines of cross-pollinating crops. Two parents possessing favorable, complementary traits are crossed to produce an $F_1$. An $F_2$ population is produced by selfing one or several $F_1$s or by intercrossing two $F_1$s (sib mating). The dihaploid breeding method could also be used. Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release of new cultivars. Similarly, the development of new cultivars through the dihaploid system requires the selection of the cultivars followed by two to five years of testing in replicated plots.

Open-Pollination

The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes for flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988). For population improvement methods specific for soybean see, e.g., J. R. Wilcox, editor (1987) SOYBEANS: Improvement, Production, and Uses, Second Edition, American Society of Agronomy, Inc., Crop Science Society of America, Inc., and Soil Science Society of America, Inc., publishers, 888 pages.

Hand-Pollination Method

Hand pollination describes the crossing of plants via the deliberate fertilization of female ovules with pollen from a desired male parent plant. In some cases the donor or recipient female parent and the donor or recipient male parent line are planted in the same field or in the same greenhouse. The inbred male parent can be planted earlier than the female parent to ensure adequate pollen supply at the pollination time. Pollination is started when the female parent flower is ready to be fertilized. Female flower buds that are ready to open in the following days are identified, covered with paper cups or small paper bags that prevent bee or any other insect from visiting the female flowers, and marked with any kind of material that can be easily seen the next morning. The male flowers of the male parent are collected in the early morning before they are open and visited by pollinating insects. The covered female flowers of the female parent, which have opened, are un-covered and pollinated with the collected fresh male flowers of the male parent, starting as soon as the male flower sheds pollen. The pollinated female flowers are again covered after pollination to prevent bees and any other insects visit. The pollinated female flowers are also marked. The marked flowers are harvested. In some cases, the male pollen used for fertilization has been previously collected and stored.

Bee-Pollination Method

Using the bee-pollination method, the parent plants are usually planted within close proximity. More female plants may be planted to allow for a greater production of seed. Insects are placed in the field or greenhouses for transfer of pollen from the male parent to the female flowers of the female parent.

Mass Selection

In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

Synthetics

A synthetic variety is produced by crossing inter se a number of genotypes selected for good combining ability in all possible hybrid combinations, with subsequent maintenance of the variety by open pollination. Parents are selected on general combining ability, sometimes by test crosses or toperosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Hybrids

A hybrid is an individual plant resulting from a cross between parents of differing genotypes. Commercial hybrids are now used extensively in many crops, including corn (maize), sorghum, sugar beet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, Commercial Hybrid Seed Production 8:161-176, In Hybridization of Crop Plants.

Bulk Segregation Analysis (BSA)

BSA, a.k.a. bulked segregation analysis, or bulk segregant analysis, is a method described by Michelmore et al. (Michelmore et al., 1991, Identification of markers linked to disease-resistance genes by bulked segregant analysis: a rapid method to detect markers in specific genomic regions by using segregating populations. *Proceedings of the National Academy of Sciences*, USA, 99:9828-9832) and Quarrie et al. (Quarrie et al., Bulk segregant analysis with molecular markers and its use for improving drought resistance in maize, 1999*, Journal of Experimental Botany,* 50(337): 1299-1306).

For BSA of a trait of interest, parental lines with certain different phenotypes are chosen and crossed to generate $F_2$, doubled haploid or recombinant inbred populations with QTL analysis. The population is then phenotyped to identify individual plants or lines having high or low expression of the trait. Two DNA bulks are prepared, one from the individuals having one phenotype (e.g., resistant to pathogen), and the other from the individuals having reversed phenotype (e.g., susceptible to pathogen), and analyzed for allele frequency with molecular markers. Only a few individuals are required in each bulk (e.g., 10 plants each) if the markers are dominant (e.g., RAPDs). More individuals are needed when markers are co-dominant (e.g., RFLPs). Markers linked to the phenotype can be identified and used for breeding or QTL mapping.

Gene Pyramiding

The method to combine into a single genotype a series of target genes identified in different parents is usually referred as gene pyramiding. The first part of a gene pyramiding breeding is called a pedigree and is aimed at cumulating one copy of all target genes in a single genotype (called root genotype). The second part is called the fixation steps and is aimed at fixing the target genes into a homozygous state, that is, to derive the ideal genotype (ideotype) from the root genotype. Gene pyramiding can be combined with marker assisted selection (MAS, see Hospital et al., 1992, 1997a, and 1997b, and Moreau et al, 1998) or marker based recurrent selection (MBRS, see Hospital et al., 2000).

Examples of Additional Desired Traits that May be Stacked with the Pathogen Resistance or Tolerance Traits Disclosed Herein In some cases, multiple FIT1 alleles may be combined in a single plant to increase pathogen resistance. In some cases, one or more FIT1 alleles are combined with additional desired traits. These traits may be introduced to a plant through conventional breeding methods, stacked on one or more DNA constructs, and/or generated through targeted mutagenesis. Examples of additional desired traits include, but are not limited to, male sterility, herbicide resistance, resistance for bacterial, fungal, or viral disease, insect resistance, male fertility, enhanced nutritional quality, industrial usage, yield stability, and yield enhancement. Several of these traits are described in, for example, U.S. Pat. Nos. 5,959,185, 5,973,234, and 5,977,445.

Examples of Plant Species that May be Transformed or Modified, or Serve as a Source of Functional FIT1

The methods disclosed herein may be applied to a wide range of plants. Non-limiting examples of plants which may be transformed or modified using the methods and sequences disclosed herein include, but are not limited to, corn (*Zea mays*), *Brassica* spp. (e.g., *Brassica napus, Brassica rapa, Brassica juncea*), alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (Carthamus tinctorius), wheat (*Triticum aestivum*), soybean (*Glycine max*), broad beans (*Vicia faba*), tobacco (*Nicotiana tabacum*), potato (*Solanum tuberosum*), peanuts (*Arachis hypogaea*), cotton (*Gossypium barbadense, Gossypium hirsutum*), quince (*Cydonia*), sweet potato (*Ipomoea batatas*), cassava (*Manihot esculenta*), coffee (*Coffea* spp.), coconut (*Cocos nucifera*), pineapple (*Ananas comosus*), citrus trees (Citrus spp.), apple (Malus spp.), medlar (*Mespilus*), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), *papaya* (*Carica papaya*), pear (*Pyrus*), cashew (*Anacardium occidentale*), macadamia (*Macadamia integrifolia*), almond (*Prunus amygdalus*), sugar beets (*Beta vulgaris*), sugarcane (*Saccharum* spp.), oats (for example *Avena sativa*), barley (for example *Hordeum vulgare*), vegetables and herbs (for example onion, leek, garlic peppermint), ornamentals (for example, *Chrysanthemum, Fuchsia* spp., *Pelargonium, Rosa* spp. *Primula vulgaris*), red cedar (*Juniperus virginiana*), and conifers (for example juniper (*Juniperus communis*)).

Examples of plants in the subfamily Papilionoideae include, but are not limited to, *Alysicarpus* spp., *Astragalus* spp., *Baptisia* spp., *Cajanus* spp., *Calopogonium* spp., *Caragana* spp., *Centrosema* spp., *Cologania* spp., *Crotalaria* spp., *Desmodium* spp., *Genista* spp., *Glycine* spp., *Glycyrrhiza* spp., *Indigofera* spp., *Kummerowia* spp., *Lablab* spp., *Lathyrus* spp., *Lespedeza* spp., *Lotus* spp., *Lupinus* spp., *Macroptilium* spp., *Macrotyloma* spp., *Medicago* spp., *Neonotonia* spp., *Pachyrhizus* spp., *Pisum* spp., *Phaseolus* spp., *Pseudovigna* spp., *Psoralea* spp., *Robinia* spp., *Senna* spp., *Sesbania* spp., *Strophostyles* spp., *Tephrosia* spp., *Teramnus* spp., *Trifolium* spp., *Vicia* spp., *Vigna* spp., or *Voandzeia* spp.

Examples of legumes include, but are not limited to, the genus *Phaseolus* (e.g., French bean, dwarf bean, climbing bean (*Phaseolus vulgaris*), lima bean (*Phaseolus lunatus*), Tepary bean (*Phaseolus acutifolius*), runner bean (*Phaseolus coccineus*)); the genus *Glycine* (e.g., *Glycine soja*, soybeans (*Glycine max* (L.)); pea (*Pisum*) (e.g., shelling peas (sometime called smooth or round seeded peas; *Pisum sativum*); marrowfat pea (*Pisum sativum*), sugar pea (*Pisum sativum*), also called snow pea, edible-podded pea or mangetout, (*Pisum granda*)); peanut (*Arachis hypogaea*), clover (*Trifolium* spp.), medick (*Medicago*), kudzu vine (*Pueraria lobata*), common lucerne, alfalfa (*Medicago sativa*), chickpea (*Cicer*), lentils (*Lens culinaris*), lupins (*Lupinus*); vetches (*Vicia*), field bean, broad bean (*Vicia faba*), vetchling (*Lathyrus*) (e.g., chickling pea (*Lathyrus sativus*), heath pea (*Lathyrus tuberosus*)); genus *Vigna* (e.g., moth bean (*Vigna aconitifolia*), adzuki bean (*Vigna angularis*), urd bean (*Vigna mungo*), mung bean (*Vigna radiata*), bambara groundnut (*Vigna subterrane*), rice bean (*Vigna umbellata*), *Vigna vexillata, Vigna unguiculata* (also known as asparagus bean, cowpea)); pigeon pea (*Cajanus cajan*), the genus *Macrotyloma* (e.g., geocarpa groundnut (*Macro tyloma geocarpum*), horse bean (*Macrotyloma uniflorum*; goa bean (*Psophocarpus tetragonolobus*), African yam bean (*Sphenostylis stenocarpa*), Egyptian black bean, lablab bean (*Lablab purpureus*), yam bean (*Pachyrhizus erosus*), guar bean (*Cyamopsis tetragonolobus*); and/or the genus *Canavalia* (e.g., jack bean (*Canavalia ensiformis*)), sword bean (*Canavalia gladiata*).

EXAMPLES

The following examples are provided to illustrate further the various applications and are not intended to limit the disclosure beyond the limitations set forth in the appended claims.

Example 1: FIT1 Homologs

Figure 3C:
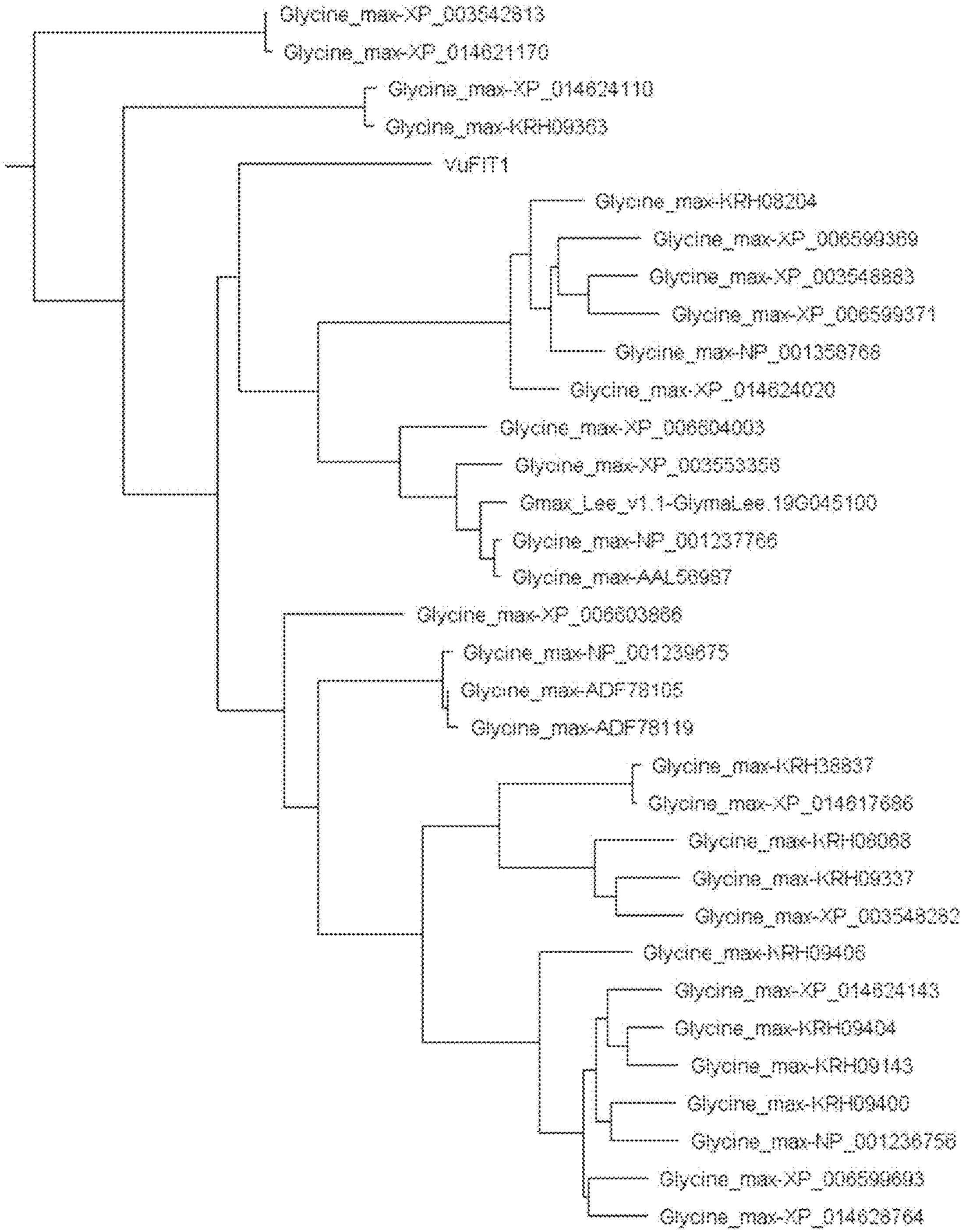
FIG. 3C shows a phylogenetic tree of homologs of *Vigna unguiculata* FIT1 in *Glycine* identified by performing a BLAST® search and constructing a protein alignment and phylogenetic tree of the resulting sequences. The tree was rooted using an outgroup of distantly related TIR-NLR proteins from non-legumes.

As will be understood by one skilled in the art, homologs of FIT1 may be found in any number of species by methods described herein and methods well known in the art. Examples of homologs of FIT1 identified are shown in FIGS. 3A-3C. FIG. 3A shows a phylogenetic tree of homologs of *Vigna unguiculata* FIT1 identified by performing a BLAST® search and constructing a protein alignment and phylogenetic tree of the resulting sequences. This figure shows putative FIT1 orthologs in *Vigna radiata, Vigna angularis, Phaseolus acutifolius, Phaseolus lunatus, Phaseolus vulgaris, Lablab purpureus, Mucuna pruriens, Cajanus cajan*, and *Abrus precatorius*. The phylogenetic tree was rooted using paralogs of FIT1 that do not function in AvrFIT1 perception.

FIG. 3B shows a protein alignment of the amino acid sequences listed in FIG. 3A, specifically of the *Vigna unguiculata* allele of FIT1 (VuFIT1) (SEQ ID NO: 2), the *Vigna unguiculata* close paralog of FIT1 (VuFIT1b) (SEQ ID NO: 22), *Vigna angularis* allele of FIT1 (VaFIT1) (SEQ ID NO: 12), the *Vigna radiata* allele of FIT1 (VrFIT1) (SEQ ID NO: 4), the *Phaseolus acutifolius* allele of FIT1 (PaFIT1) (SEQ ID NO: 10), the *Phaseolus vulgaris* allele of FIT1 (PvFIT1) (SEQ ID NO: 8), the *Phaseolus lunatus* allele of FIT1 (P1FIT1) (SEQ ID NO: 6), the *Lablab purpureus* allele of FIT1 (LpFIT1) (SEQ ID NO: 14), the *Cajanus cajun* allele of FIT1 (CcFIT1) 1 (SEQ ID NO: 18), the *Mucuna pruriens* allele of FIT1 (MpFIT1) (SEQ ID NO: 16), and the *Abrus precatorius* allele of FIT1 (ApFIT1) (SEQ ID NO: 20).

FIG. 3C shows a phylogenetic tree of FIT1 homologs in *Glycine max. G. max* (soybean) lacks an ortholog of VuFIT1 but contains many homologs of VuFIT1 paralogs, which can be identified by BLAST® search. Protein homologs of VuFIT1 from soybean were obtained from NCBI and Phytozome, curated for completeness and to remove duplicates, and used to generate the phylogenetic tree shown in FIG. 3C. The tree was rooted using an outgroup of distantly related TIR-NLR proteins from non-legumes.

Sequence alignments of FIT1 homologs with functional FIT1 genes (such as VuFIT1) can show what genetic changes could be induced to restore recognition of AvrFIT, and confer resistance or tolerance to a pathogen. Such targeted genetic editing is well known in the art and also described herein.

Example 2: Transient Expression of FIT1 Alleles in Leaf Tissue

Figure 4:
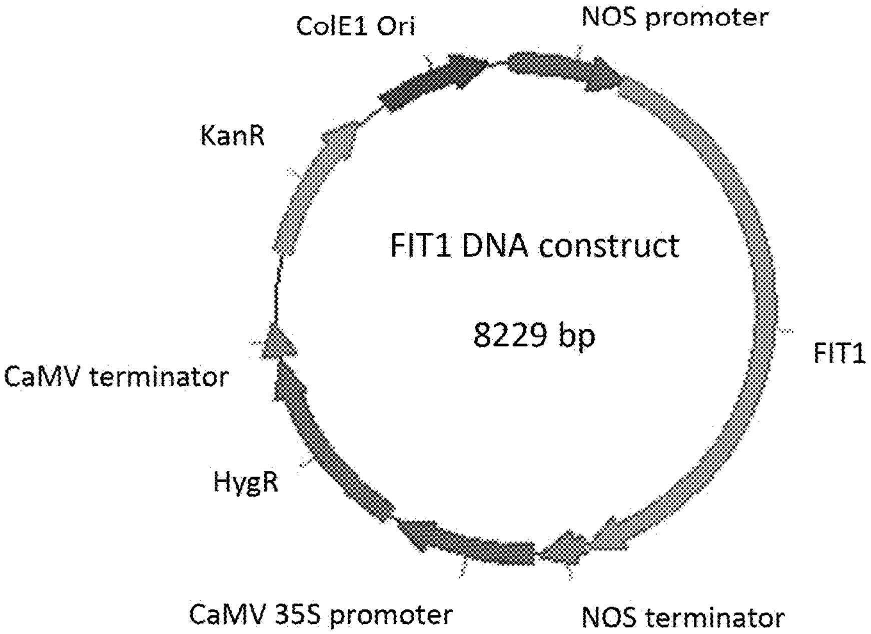
FIG. 4 shows a map of an example DNA construct comprising VuFIT1 (SEQ ID NO: 1) that can be used for transformation of a plant cell, selection of transformed cells, and expression of FIT1.

Leaf tissue from a plant lacking an endogenous FIT1 was transformed with constructs containing various FIT1 sequences, AvrFIT1a, AvrFIT1b, and/or Bs3 using standard transformation technology (an example construct comprising VuFIT1 is shown in FIG. 4). Suspensions containing the desired expression constructs were infiltrated into the leaf tissue ($OD_{600}$=0.4 total) using needleless syringe and imaged four days post infiltration. The site of each infiltration is visible by a small punch through the leaf.

Figure 5:
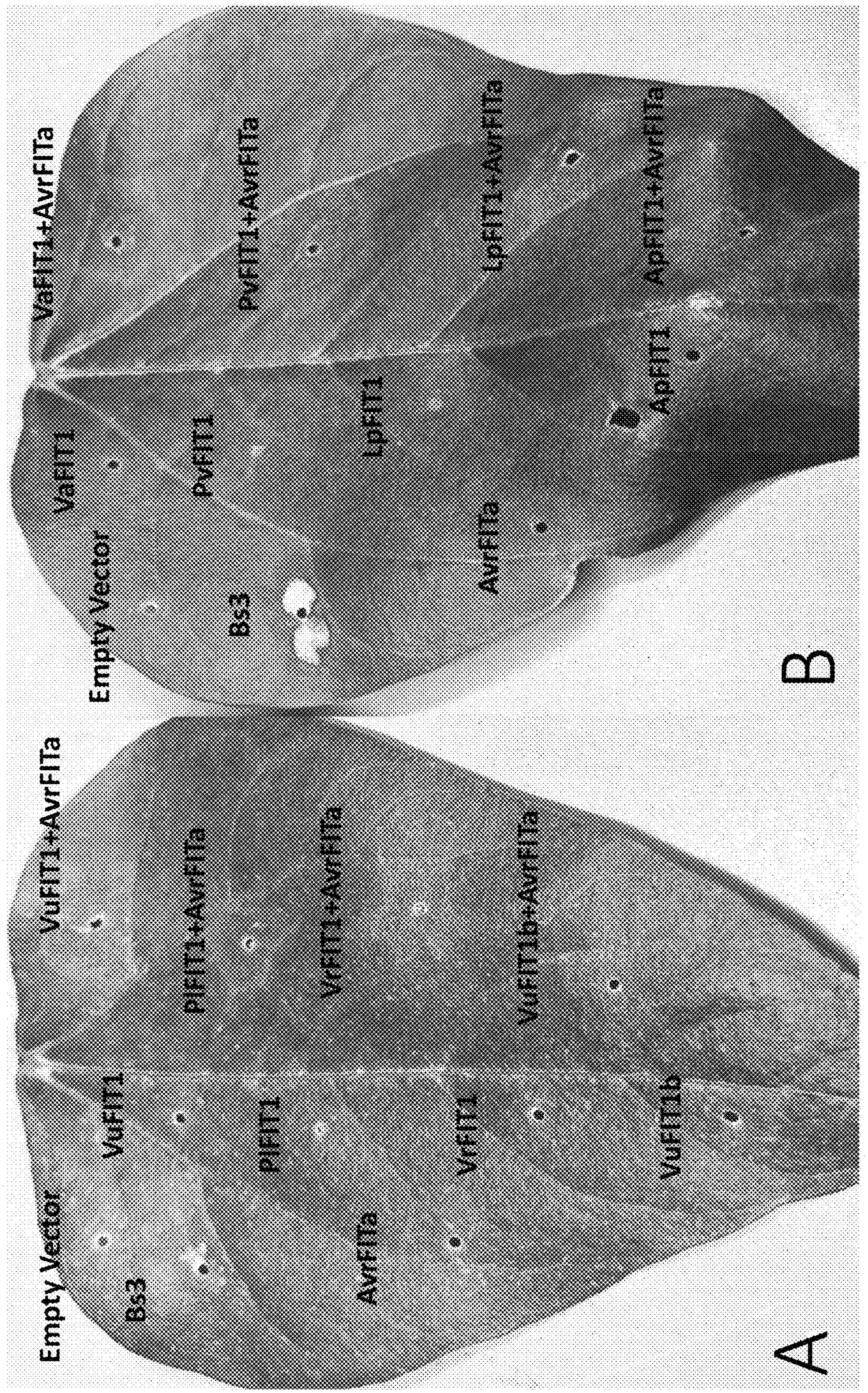
FIGS. 5A-5D depict results showing transient expression of various FIT1 alleles in leaf tissue from a plant lacking an endogenous FIT1.
Figure 5:
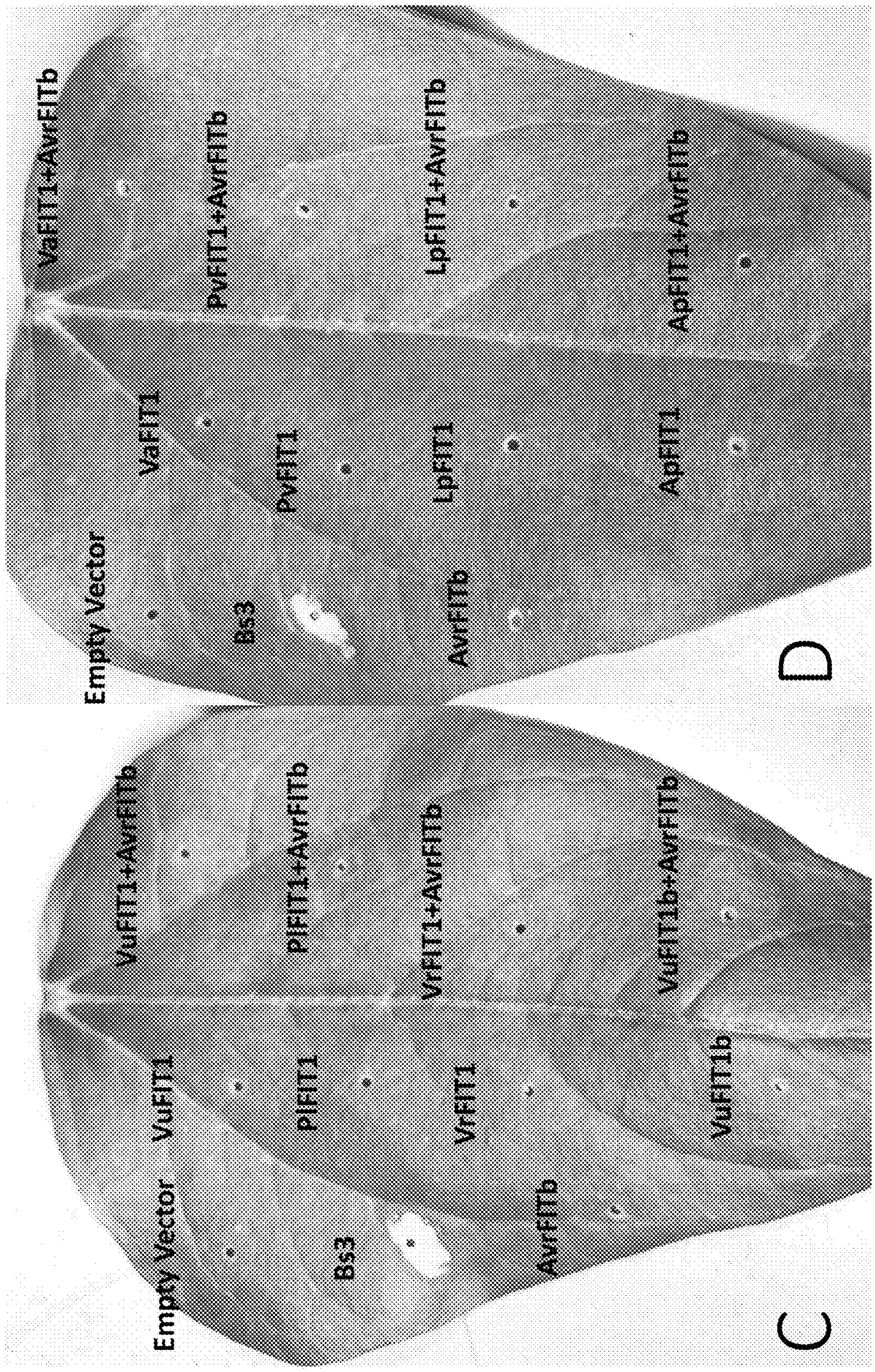
Figure 6:
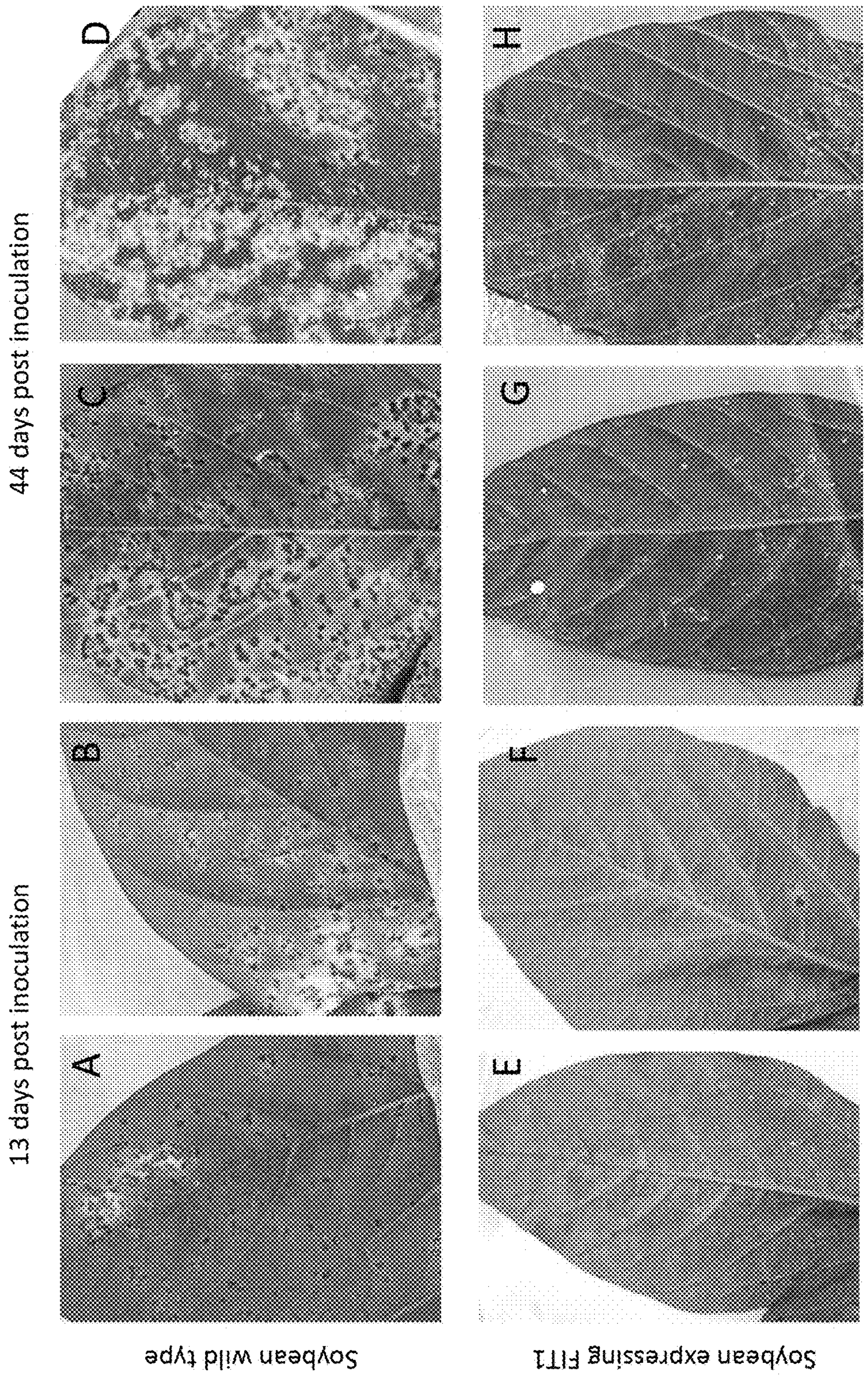
FIGS. 6A-6H depict wild type soybean leaves (lacking FIT1) (FIGS. 6A-6D) and leaves from soybean plants expressing FIT1 (FIG. 6E-6H) inoculated with *Phakopsora pachyrhizi*. The leaves were photographed at 13- and 44-days post inoculation as indicated.

As shown in FIGS. 5A and 5B, co-expression of AvrFIT1a (SEQ ID NO: 23) with either *Vigna unguiculata* (VuFIT1) (SEQ ID NO: 27), *Phaseolus lunatus* (P1FIT1) (SEQ ID NO: 28), *Vigna radiata* (VrFIT1) (SEQ ID NO: 29), *Vigna angularis* (VaFIT1) (SEQ ID NO: 31), *Phaseolus vulgaris* (PvFIT1) (SEQ ID NO: 32), *Lablab purpureus* (LpFIT1) (SEQ ID NO: 33), or *Abrus precatoris* (ApFIT1) (SEQ ID NO: 34) resulted in a strong cell death response, indicative of immune activation, but no response was observed when the proteins were expressed individually. No immune response was observed when the non-functional paralog VuFIT1b (SEQ ID NO: 30) was expressed individually or with AvrFIT1a.

As shown in FIGS. 5C and 5D, co-expression of AvrFIT1b (SEQ ID NO: 25) with either *Phaseolus lunatus* (P1FIT1), *Vigna radiata* (VrFIT1), *Vigna angularis* (VaFIT1), *Phaseolus vulgaris* (PvFIT1), or *Lablab purpureus* (LpFIT1) resulted in a cell death response, indicative of immune activation, but no response was observed when the proteins were expressed individually.

Expression of the executor Bs3, a positive control for cell death response, triggers a similar response. This demonstrates that FIT1 mediates the perception of AvrFIT1, and thus can confer resistance or tolerance to pathogens that secrete the effector protein AvrFIT1.

Example 3: Stable Expression of *Vigna unguiculata* FIT1 in *Glycine* Max

Soybean plants stably expressing VuFIT1 (SEQ ID NO: 1, example construct shown in FIG. 4) were generated and tested for resistance to ASR (*Phakopsora pachyrhizi*). FIGS. 6A-6D depicts wild type soybean leaves lacking functional FIT1 (top row) and FIGS. 6E-6H show leaves from soybean plants expressing VuFIT1 (bottom row). Plants were inoculated with *Phakopsora pachyrhizi* and the leaves were photographed at 13-days (FIGS. 6A-6B and 6E-6F) and 44-days (FIGS. 6C-6D and 6G-61I) post inoculation. The wild type soybean leaves showed susceptibility to *Phakopsora* as seen by the development of large lesions and many fungal spores. However, soybean expressing VuFIT1 showed strong resistance to the pathogen (FIGS. 6E-6H).

Figures 7A, 7B:
FIGS. 7A-7B are photographs of wild type soybean plants (FIG. 7A) and transgenic soybean plants expressing FIT1 (FIG. 7B).
Figure 7C:
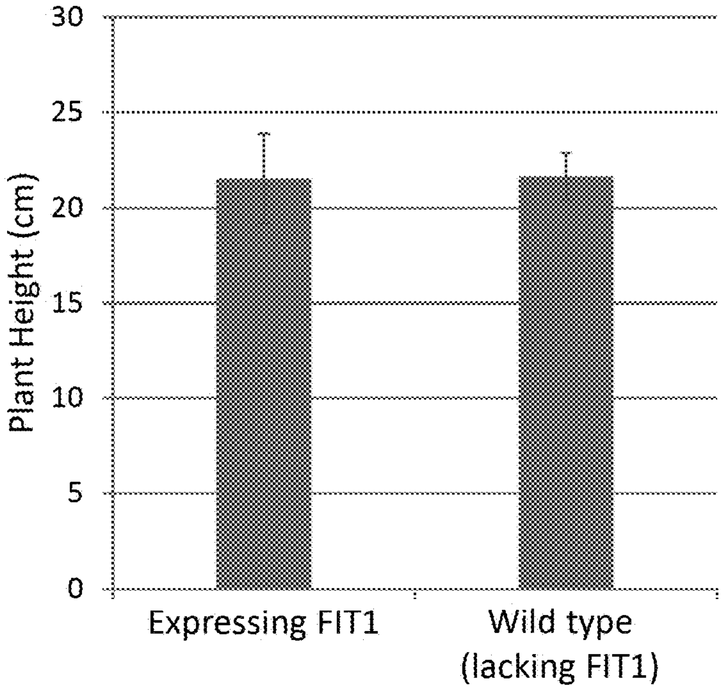
FIG. 7C is a bar graph of the height of the plants shown in FIG. 9A and FIG. 9B 24 days after planting. The error bars indicate the standard deviation of the plant height from the individual plants (n>8).

Transgenic expression of VuFIT1 in soybean did not affect plant growth or morphology. Photographs of wild type soybean plants (FIG. 7A) and transgenic soybean plants expressing VuFIT1 (FIG. 7B) had no obvious growth abnormalities. The height of the plants was measured at 24 days after planting and no significant difference was observed between the wild type plants and the plants containing FIT1 (FIG. 7C). The error bars indicate the standard deviation of the plant height from the individual plants (n>8).

Example 4: Introducing FIT1 Homologs into Other Plant Species

The FIT1 sequences isolated and described herein can be introduced into other plant species to create a plant having resistance or tolerance to a pathogen.

For example, a sequence encoding any one of the proteins of SEQ ID NOs: 2, 4, 6, 8, 10, 12, 14, 16, 18, 20 and functional homologs thereof, or sequences of SEQ ID NOs: 1, 3, 5, 7, 9, 11, 13, 15, 17, 19 complements thereof, fragments thereof, and sequences at least 70% identical thereto can be introduced into a plant to confer resistance or tolerance to a pathogen. For example, as described above, *Glycine max*, which does not possess a functional FIT1 gene and is susceptible to ASR, may be transformed with a transgene comprising SEQ ID NO: 1, or a nucleotide sequence encoding the amino acid sequence of SEQ ID NO: 2, to confer resistance to plant pathogens, such as *Phakopsora pachyrhizi*, that secrete the effector protein AvrFIT1, and cause diseases like ASR. Based on the transient assays described herein (FIG. 5A-5D), resistance could also be achieved with a transgene comprising any one of SEQ ID NOs: 3, 5, 7, 9, 11, 13, 15, 17, and/or 19, or a sequence encoding any one of the proteins of SEQ ID NOs: 2, 4, 6, 8, 10, 12, 14, 16, 18, and/or 20.

Additional plant species susceptible to ASR or pathogens secreting AvrFIT1-like effector proteins, such as *Alysicarpus* spp., *Astragalus* spp., *Baptisia* spp., *Cajanus* spp., *Calopogonium* spp., *Caragana* spp., *Centrosema* spp., *Cologania* spp., *Crotalaria* spp., *Desmodium* spp., *Genista* spp., *Glycine* spp., *Glycyrrhiza* spp., *Indigofera* spp., *Kummerowia* spp., *Lablab* spp., *Lathyrus* spp., *Lespedeza* spp., *Lotus* spp., *Lupinus* spp., *Macroptilium* spp., *Macrotyloma* spp., *Medicago* spp., *Neonotonia* spp., *Pachyrhizus* spp., *Pisum* spp., *Phaseolus* spp., *Pseudovigna* spp., *Psoralea* spp., *Robinia* spp., *Senna* spp., *Sesbania* spp., *Strophostyles* spp., *Tephrosia* spp., *Teramnus* spp., *Trifolium* spp., *Vicia* spp., *Vigna* spp., or *Voandzeia* spp. could also be transformed with any of the FIT1 sequences disclosed herein to confer resistance to a pathogen.

Example 5: Methods of Identifying Pathogen Resistant Genes

FIT1 orthologs are likely present in additional species and genera within the Fabaceae family. FIT1 orthologs may identified by any number of means known in the art. This includes sequencing the genome or transcriptome of a plant species, identifying FIT1 homologs using a BLAST search, identifying putative FIT1 orthologs by constructing a phylogenetic tree of the homologous proteins, and then testing the identified putative FIT1 genes for AvrFIT1 recognition activity using a transient assay such as that shown in FIG. 5A-5D. Alternatively, synthetic alleles of FIT1 may be designed by combining fragments of naturally occurring FIT1 alleles or by introducing amino acid substitutions at positions shown to be variable in an alignment of functional FIT1 proteins and similarly tested for functionality by transient assay. Methods of alignment of sequences for comparison are well known in the art. Various programs and alignment algorithms are described in: Smith and Waterman (*Adv. Appl. Math.*, 2:482, 1981); Needleman and Wunsch (*J. Mol. Biol.*, 48:443, 1970); Pearson and Lipman (*Proc. Natl. Acad. Sci.*, 85:2444, 1988); Higgins and Sharp (Gene, 73:237-44, 1988); Higgins and Sharp (*CABIOS*, 5:151-53, 1989); Corpet et al. (*Nuc. Acids Res.*, 16:10881-90, 1988); Huang et al. (*Comp. Appls Biosci.*, 8:155-65, 1992); and Pearson et al. (*Meth. Mol. Biol.*, 24:307-31, 1994). Altschul et al. (*Nature Genet.*, 6:119-29, 1994) presents a detailed consideration of sequence alignment methods and homology calculations.

Figure 8:
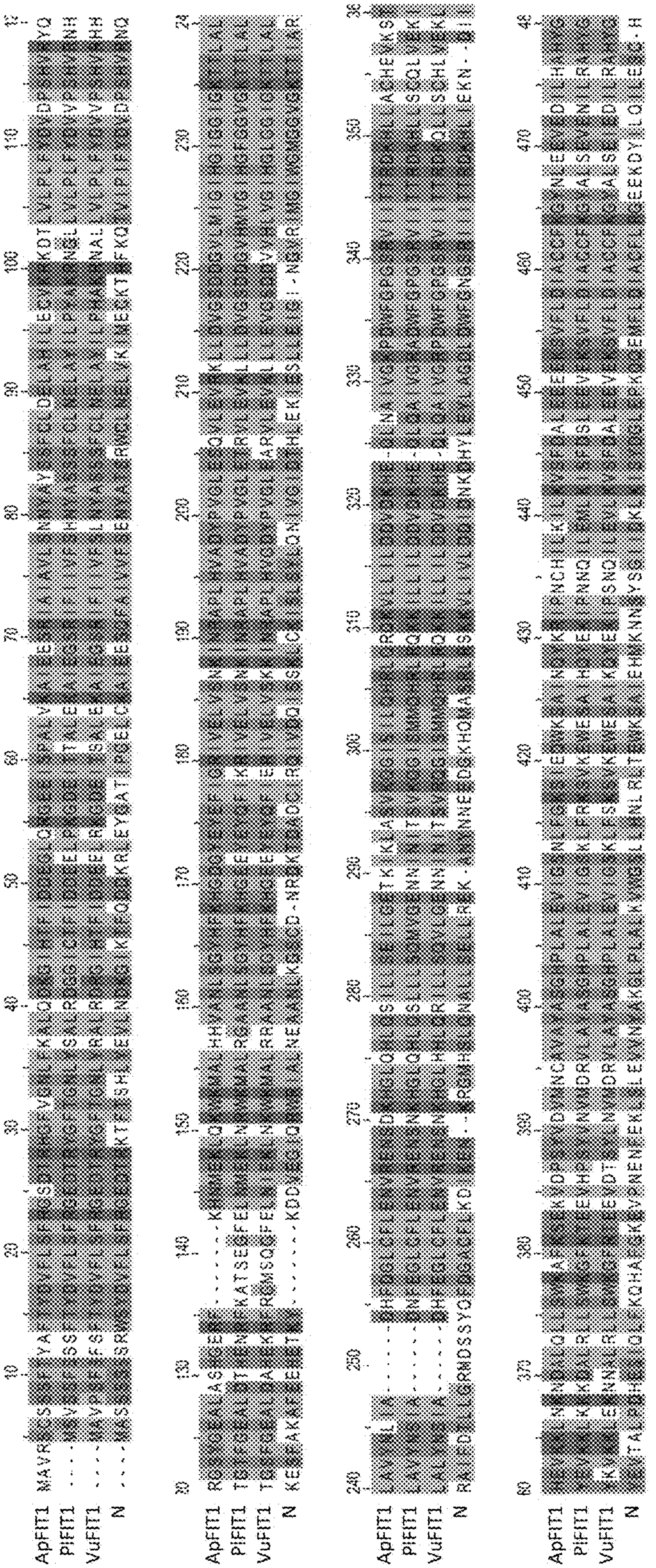
FIG. 8 depicts an alignment between the FIT1 alleles from *Vigna unguiculata* (VuFIT1), *Phaseolus lunatus* (P1FIT1), *Abrus precatorius* (ApFIT1), and the N gene, which gives TMV resistance. The LRR domain is poorly conserved between the FIT1 alleles and the N gene.
Figure 8:
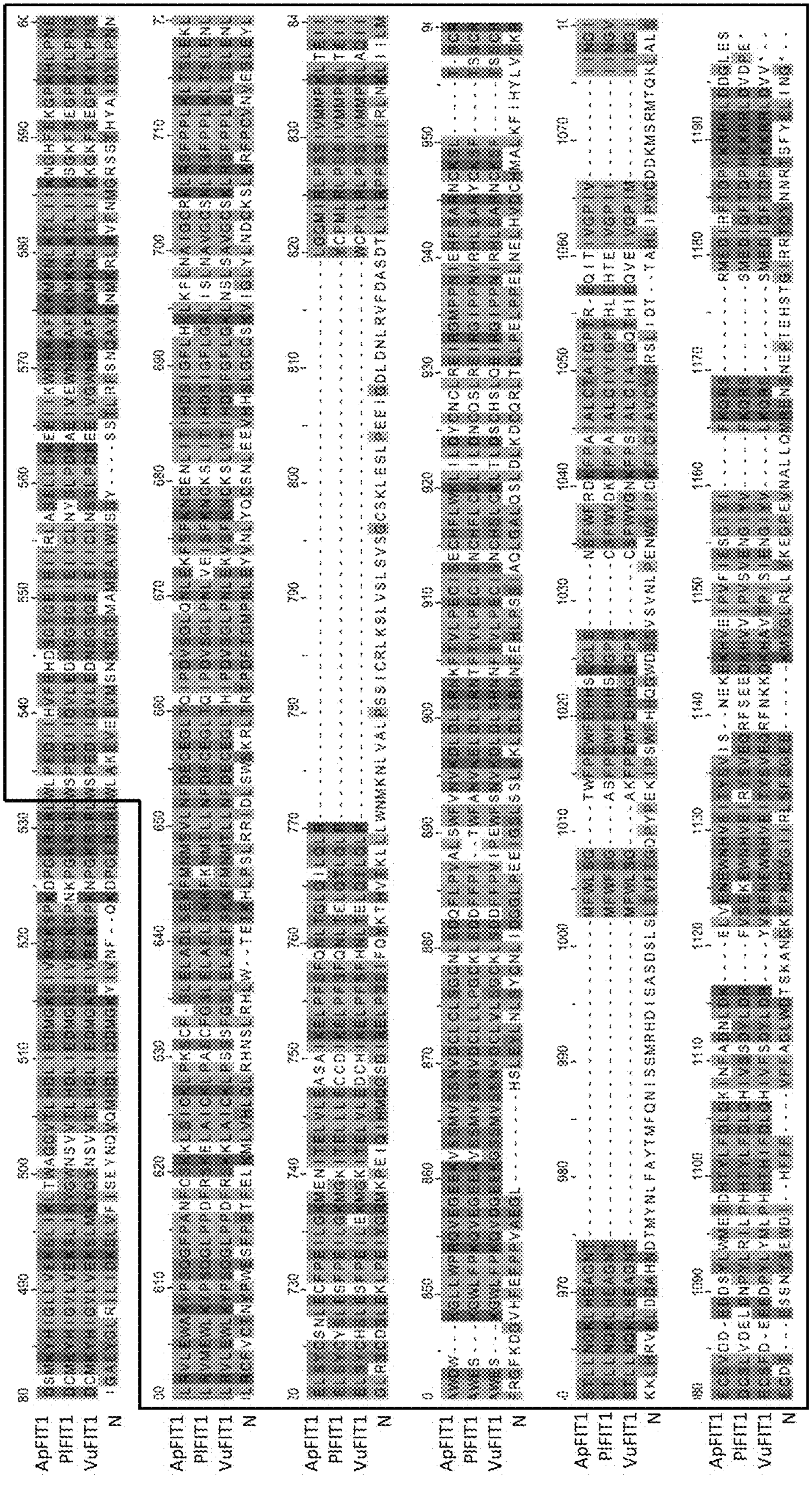

While previous reports have listed some FIT1 homologs as predicted TMV resistance proteins, this is unlikely. FIG. 8 depicts an alignment between the FIT1 alleles from *Vigna unguiculata* (VuFIT1), *Phaseolus lunatus* (P1FIT1), *Abrus precatorius* (ApFIT1), and the N gene, which gives TMV resistance. The LRR domain is poorly conserved between the FIT1 alleles and the N gene. Therefore, FIT1 is not expected to have the same activity as the N gene (which recognizes the P50 protein and confers resistance to Tobacco Mosaic Virus). This prediction can be confirmed by transient expression of the proteins, which demonstrates that the N gene can recognize P50 but not AvrFIT1a or AvrFITb and that FIT1 is not able to recognize P50.

The ability of other potential FIT1 homologs or synthetic genes to function for AvrFIT1 perception can be easily and quickly tested using the transient expression assays shown and described herein or similar methods well known in the art. For example, once a FIT1 ortholog is identified in a plant species that is resistant to ASR, the gene can be cloned and tested for effector protein recognition using transient expression assays and the AvrFIT1a (SEQ ID NO: 23) and AvrFIT1b sequences (SEQ ID NO: 25) described herein (see for example FIGS. 5A-D). Examples of leaf tissue suitable for use in a FIT1-AvrFIT1 assay include, but are not limited to, species or accessions of *Nicotiana, Solanum, Physalis, Capsicum, Lactuca, Alysicarpus, Astragalus, Baptisia, Cajanus, Calopogonium, Caragana, Centrosema, Cologania, Crotalaria, Desmodium, Genista, Glycine, Glycyrrhiza, Indigofera, Kummerowia, Lablab, Lathyrus, Lespedeza, Lotus, Lupinus, Macroptihum, Macrotyloma, Medicago, Neonotonia, Pachyrhizus, Pisum, Phaseolus, Pseudovigna, Psoralea, Robinia, Senna, Sesbania, Strophostyles, Tephrosia, Teramnus, Trifohum, Vicia, Vigna*, and *Voandzeia* that lack a functional native FIT1 gene. Similarly, resistance genes for other pathogens may be identified using this same method, wherein a potential gene is identified, cloned, and tested in transient assays with pathogen effector proteins.

BRIEF DESCRIPTION OF THE SEQUENCE LISTINGS

SEQ ID NO: 1 shows the nucleic acid sequence of *Vigna unguiculata* FIT1.

SEQ ID NO: 2 shows the corresponding amino acid sequence of SEQ ID NO: 1.

SEQ ID NO: 3 shows the nucleic acid sequence of *Vigna radiata* FIT1.

SEQ ID NO: 4 shows the corresponding amino acid sequence of SEQ ID NO: 3.

SEQ ID NO: 5 shows the nucleic acid sequence of *Phaseolus lunatus* FIT1.

SEQ ID NO: 6 shows the corresponding amino acid sequence of SEQ ID NO: 5.

SEQ ID NO: 7 shows the nucleic acid sequence of *Phaseolus vulgaris* FIT1.

SEQ ID NO: 8 shows the corresponding amino acid sequence of SEQ ID NO: 7.

SEQ ID NO: 9 shows the nucleic acid sequence of *Phaseolus acutifolius* FIT1.

SEQ ID NO: 10 shows the corresponding amino acid sequence of SEQ ID NO: 9.

SEQ ID NO: 11 shows the nucleic acid sequence of *Vigna angularis* FIT1.

SEQ ID NO: 12 shows the corresponding amino acid sequence of SEQ ID NO: 11.

SEQ ID NO: 13 shows the nucleic acid sequence of *Lablab purpureus* FIT1

SEQ ID NO: 14 shows the corresponding amino acid sequence of SEQ ID NO: 13.

SEQ ID NO: 15 shows the nucleic acid sequence of *Mucuna pruriens* FIT1.

SEQ ID NO: 16 shows the corresponding amino acid sequence of SEQ ID NO: 15.

SEQ ID NO: 17 shows the nucleic acid sequence of *Cajanus cajun* FIT1.

SEQ ID NO: 18 shows the corresponding amino acid sequence of SEQ ID NO: 17.

SEQ ID NO: 19 shows the nucleic acid sequence of *Abrus precatorius* FIT1.

SEQ ID NO: 20 shows the corresponding amino acid sequence of SEQ ID NO: 19.

SEQ ID NO: 21 shows the nucleic acid sequence of *Vigna unguiculata* FIT1b.

SEQ ID NO: 22 shows the corresponding amino acid sequence of SEQ ID NO: 21.

SEQ ID NO: 23 shows the nucleic acid sequence of *Phakopsora pachyrhizi* ALL40704.1 (AvrFIT1a).

SEQ ID NO: 24 shows the corresponding amino acid sequence of SEQ ID NO: 23.

SEQ ID NO: 25 shows the nucleic acid sequence of *Phakopsora pachyrhizi* ALL41167.1 (AvrFIT1b).

SEQ ID NO: 26 shows the corresponding amino acid sequence of SEQ ID NO: 25.

SEQ ID NO: 27 shows the nucleic acid sequence of the transient expression vector with *Vigna unguiculata* FIT1.

SEQ ID NO: 28 shows the nucleic acid sequence of the transient expression vector with *Phaseolus lunatus* FIT1.

SEQ ID NO: 29 shows the nucleic acid sequence of the transient expression vector with *Vigna radiata* FIT1.

SEQ ID NO: 30 shows the nucleic acid sequence of the transient expression vector with *Vigna unguiculata* FIT1b.

SEQ ID NO: 31 shows the nucleic acid sequence of the transient expression vector with *Vigna angularis* FIT.

SEQ ID NO: 32 shows the nucleic acid sequence of the transient expression vector with *Phaseolus vulgaris* FIT1.

SEQ ID NO: 33 shows the nucleic acid sequence of the transient expression vector with *Lablab purpureus* FIT1.

SEQ ID NO: 34 shows the nucleic acid sequence of the transient expression vector with *Abrus precatorius* FIT1.

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

Numbered Embodiments

1. An isolated, recombinant, or synthetic polynucleotide comprising a nucleic acid sequence encoding a functional FIT1 protein homologous to SEQ ID NO: 2.
2. The isolated, recombinant, or synthetic polynucleotide of embodiment 1, wherein the polynucleotide encodes a protein having at least 70% identity to SEQ ID NO: 2.
3. The isolated, recombinant, or synthetic polynucleotide of embodiment 2, wherein the polynucleotide encodes a FIT1 protein from *Abrus precatorius*.
4. The isolated, recombinant, or synthetic polynucleotide of embodiment 3, wherein the polynucleotide comprises SEQ ID NO: 19, a polynucleotide encoding SEQ ID NO: 20, complements thereof, or fragments thereof.
5. The isolated, recombinant, or synthetic polynucleotide of embodiment 2, wherein the polynucleotide encodes a FIT1 protein from *Cajanus cajan*.
6. The isolated, recombinant, or synthetic polynucleotide of embodiment 5, wherein the polynucleotide comprises SEQ ID NO: 17, or a polynucleotide encoding SEQ ID NO: 18.
7. The isolated, recombinant, or synthetic polynucleotide of embodiment 1, wherein the polynucleotide encodes a protein having at least 75% identity to SEQ ID NO: 2.
8. The isolated, recombinant, or synthetic polynucleotide of embodiment 7, wherein the polynucleotide encodes a FIT1 protein from *Mucuna pruriens*.
9. The isolated, recombinant, or synthetic polynucleotide of embodiment 8, wherein the polynucleotide comprises SEQ ID NO: 15, a polynucleotide encoding SEQ ID NO: 16, complements thereof, or fragments thereof.
10. The isolated, recombinant, or synthetic polynucleotide of embodiment 1, wherein the polynucleotide encodes a protein having at least 80% identity to SEQ ID NO: 2.
11. The isolated, recombinant, or synthetic polynucleotide of embodiment 1, wherein the polynucleotide encodes a protein having at least 85% identity to SEQ ID NO: 2.
12. The isolated, recombinant, or synthetic polynucleotide of embodiment 11, wherein the polynucleotide encodes a FIT1 protein from *Lablab purpureus*.
13. The isolated, recombinant, or synthetic polynucleotide of embodiment 12, wherein the polynucleotide comprises SEQ ID NO: 13, a polynucleotide encoding SEQ ID NO: 14, complements thereof, or fragments thereof.
14. The isolated, recombinant, or synthetic polynucleotide of embodiment 11, wherein the polynucleotide encodes a FIT1 protein from *Phaseolus lunatus*.
15. The isolated, recombinant, or synthetic polynucleotide of embodiment 14, wherein the polynucleotide comprises SEQ ID NO: 5, a polynucleotide encoding SEQ ID NO: 6, complements thereof, or fragments thereof.
16. The isolated, recombinant, or synthetic polynucleotide of embodiment 11, wherein the polynucleotide encodes a FIT1 protein from *Phaseolus vulgaris*.
17. The isolated, recombinant, or synthetic polynucleotide of embodiment 16, wherein the polynucleotide comprises SEQ ID NO: 7, a polynucleotide encoding SEQ ID NO: 8, complements thereof, or fragments thereof.
18. The isolated, recombinant, or synthetic polynucleotide of embodiment 11, wherein the polynucleotide encodes a FIT1 protein from *Phaseolus acutifolius*.
19. The isolated, recombinant, or synthetic polynucleotide of embodiment 18, wherein the polynucleotide comprises SEQ ID NO: 9, a polynucleotide encoding SEQ ID NO: 10, complements thereof, or fragments thereof.
20. The isolated, recombinant, or synthetic polynucleotide of embodiment 11, wherein the polynucleotide encodes a FIT1 protein from *Vigna radiata*.
21. The isolated, recombinant, or synthetic polynucleotide of embodiment 20, wherein the polynucleotide comprises SEQ ID NO: 3, a polynucleotide encoding SEQ ID NO: 4, complements thereof, or fragments thereof.
22. The isolated, recombinant, or synthetic polynucleotide of embodiment 1, wherein the polynucleotide encodes a protein having at least 90% identity to SEQ ID NO: 2.
23. The isolated, recombinant, or synthetic polynucleotide of embodiment 22, wherein the polynucleotide encodes a FIT1 protein from *Vigna angularis*.
24. The isolated, recombinant, or synthetic polynucleotide of embodiment 23, wherein the polynucleotide comprises SEQ ID NO: 11, a polynucleotide encoding SEQ ID NO: 12, complements thereof, or fragments thereof.

25. The isolated, recombinant, or synthetic polynucleotide of embodiment 1, wherein the polynucleotide encodes a protein having at least 95% identity to SEQ ID NO: 2.

26. The isolated, recombinant, or synthetic polynucleotide of embodiment 1, wherein the polynucleotide encodes a protein having at least 96% identity to SEQ ID NO: 2.

27. The isolated, recombinant, or synthetic polynucleotide of embodiment 1, wherein the polynucleotide encodes a protein having at least 97% identity to SEQ ID NO: 2.

28. The isolated, recombinant, or synthetic polynucleotide of embodiment 1, wherein the polynucleotide encodes a protein having at least 98% identity to SEQ ID NO: 2.

29. The isolated, recombinant, or synthetic polynucleotide of embodiment 1, wherein the polynucleotide encodes a protein having at least 99% identity to SEQ ID NO: 2.

30. An isolated, recombinant, or synthetic polynucleotide comprising a nucleic acid sequence encoding a FIT1 protein, wherein the protein is selected from the group consisting of: SEQ ID NOs: 2, 4, 6, 8, 10, 12, 14, 16, 18, 20 and functional homologs thereof.

31. The isolated, recombinant, or synthetic polynucleotide of embodiment 30, wherein the polynucleotide comprises a nucleic acid sequence selected from the group consisting of SEQ ID NOs: 1, 3, 5, 7, 9, 11, 13, 15, 17, 19 complements thereof, fragments thereof, and sequences at least 70% identical thereto.

32. A genetic construct comprising at least one of the nucleic acid sequences of any one of embodiments 1-31.

33. A plant, plant part, or plant cell transformed with at least one of the nucleic acid sequences of any one of embodiments 1-31 or the genetic construct of embodiment 32, wherein said plant, plant part or plant cell is resistant or tolerant to a pathogen.

34. The plant, plant part, or plant cell of embodiment 33, wherein the pathogen is a fungus from the order Cantharellales or Pucciniales.

35. The plant, plant part, or plant cell of embodiment 33 or 34, wherein the fungal pathogen is *Rhizoctonia solani*, Melampsora spp., *Phakopsora pachyrhizi, Phakopsora meibomiae, Phakopsora euvitis, Phakopsora* spp., *Puccinia* spp., *Uromyces* spp., *Austropuccinia* spp., *Cronartium* spp. or *Hemileia vastatrix.*

36. The plant, plant part, or plant cell of any one of embodiments 33-35, wherein the plant, plant part, or plant cell is in the subfamily Papilionoideae.

37. The plant, plant part, or plant cell of any one of embodiments 33-36, wherein the plant, plant part, or plant cell is *Alysicarpus* spp., *Astragalus* spp., *Baptisia* spp., *Cajanus* spp., *Calopogonium* spp., *Caragana* spp., *Centrosema* spp., *Cologania* spp., *Crotalaria* spp., *Desmodium* spp., *Genista* spp., *Glycine* spp., *Glycyrrhiza* spp., *Indigofera* spp., *Kummerowia* spp., *Lablab* spp., *Lathyrus* spp., *Lespedeza* spp., *Lotus* spp., *Lupinus* spp., *Macroptilium* spp., *Macrotyloma* spp., *Medicago* spp., *Neonotonia* spp., *Pachyrhizus* spp., *Pisum* spp., *Phaseolus* spp., *Pseudovigna* spp., *Psoralea* spp.,
*Robinia* spp., *Senna* spp., *Sesbania* spp., *Strophostyles* spp., *Tephrosia* spp., *Teramnus* spp., *Trifolium* spp., *Vicia* spp., *Vigna* spp., or *Voandzeia* spp.

38. The plant, plant part, or plant cell of any one of embodiments 33-37, wherein the plant, plant part, or plant cell is *Glycine max*, and wherein the plant, plant part, or plant cell is resistant to Asian Soybean Rust caused by *Phakopsora pachyrhizi.*

39. The plant, plant part, or plant cell of embodiment 38, wherein the resistance to Asian Soybean Rust is conferred by a transgene comprising SEQ ID NO: 1, or a nucleotide sequence encoding the amino acid sequence of SEQ ID NO: 2.

40. The plant, plant part, or plant cell of embodiment 38, wherein the resistance to Asian Soybean Rust is conferred by a transgene comprising SEQ ID NO: 3, or a nucleotide sequence encoding the amino acid sequence of SEQ ID NO: 4.

41. The plant, plant part, or plant cell of embodiment 38, wherein the resistance to Asian Soybean Rust is conferred by a transgene comprising SEQ ID NO: 5, or a nucleotide sequence encoding the amino acid sequence of SEQ ID NO: 6.

42. The plant, plant part, or plant cell of embodiment 38, wherein the resistance to Asian Soybean Rust is conferred by a transgene comprising SEQ ID NO: 7, or a nucleotide sequence encoding the amino acid sequence of SEQ ID NO: 8.

43. The plant, plant part, or plant cell of embodiment 38, wherein the resistance to Asian Soybean Rust is conferred by a transgene comprising SEQ ID NO: 9, or a nucleotide sequence encoding the amino acid sequence of SEQ ID NO: 10.

44. The plant, plant part, or plant cell of embodiment 38, wherein the resistance to Asian Soybean Rust is conferred by a transgene comprising SEQ ID NO: 11, or a nucleotide sequence encoding the amino acid sequence of SEQ ID NO: 12.

45. The plant, plant part, or plant cell of embodiment 38, wherein the resistance to Asian Soybean Rust is conferred by a transgene comprising SEQ ID NO: 13, or a nucleotide sequence encoding the amino acid sequence of SEQ ID NO: 14.

46. The plant, plant part, or plant cell of embodiment 38, wherein the resistance to Asian Soybean Rust is conferred by a transgene comprising SEQ ID NO: 15, or a nucleotide sequence encoding the amino acid sequence of SEQ ID NO: 16.

47. The plant, plant part, or plant cell of embodiment 38, wherein the resistance to Asian Soybean Rust is conferred by a transgene comprising SEQ ID NO: 17, or a nucleotide sequence encoding the amino acid sequence of SEQ ID NO: 18.

48. The plant, plant part, or plant cell of embodiment 38, wherein the resistance to Asian Soybean Rust is conferred by a transgene comprising SEQ ID NO: 19, or a nucleotide sequence encoding the amino acid sequence of SEQ ID NO: 20.

49. A method of producing a plant, plant part, or plant cell having resistance or tolerance to a pathogen, wherein the method comprises:

transforming a plant, plant part, or plant cell with a nucleotide sequence encoding a Toll-like Interleukin-1 Receptor (TIR) Nucleotide binding, Leucine-rich Repeat (NLR) immune receptor protein, wherein said immune receptor protein mediates the perception of pathogen effector protein AvrFIT1 or homologs thereof; and wherein expression of the immune receptor protein prevents the pathogen from colonizing the plant, or prevents the pathogen from affecting plant growth or yield.

50. The method of embodiment 49, wherein the pathogen effector protein comprises SEQ ID NO: 24, SEQ ID: 26, or sequences at least 90% identical thereto.

51. The method of embodiment 49 or 50, wherein the nucleotide sequence encoding the immune receptor protein has been codon optimized.
52. The method of any one of embodiments 49-51, wherein the immune receptor protein is selected from the group consisting of:
    an isolated, recombinant, or synthetic polynucleotide comprising a nucleic acid sequence encoding a FIT1 protein, wherein the protein is selected from the group consisting of: SEQ ID NOs: 2, 4, 6, 8, 10, 12, 14, 16, 18, 20 and functional homologs thereof, or
    an isolated, recombinant, or synthetic polynucleotide encoding a FIT1 protein, wherein the nucleic acid sequence is selected from the group consisting of SEQ ID NOs: 1, 3, 5, 7, 9, 11, 13, 15, 17, 19 complements thereof, fragments thereof, and sequences at least 70% identical thereto.
53. The method of any one of embodiments 49-52, wherein the plant, plant part, or plant cell is transformed with one or more additional desired traits.
54. The method of embodiment 49, wherein the one or more additional desired traits are stacked together with the immune receptor protein on the same DNA construct.
55. The method of any one of embodiments 49-23, further comprising introgressing one or more additional desired traits.
56. The method of any one of embodiments 49-55, wherein the one or more additional desired traits are resistance traits to a disease, pest, or abiotic stress.
57. A plant, plant part, or plant cell produced by the method of any one of embodiments 49-56, wherein the plant, plant part, or plant cell is resistant to a pathogen.
58. A plant, plant part, or plant cell produced by the method of any one of embodiments 49-56, wherein the plant, plant part, or plant cell is tolerant to a pathogen.
59. The plant, plant part, or plant cell of embodiment 57 or 58, wherein the immune receptor protein is transiently expressed.
60. The plant, plant part, or plant cell of embodiment 57 or 58, wherein the immune receptor protein is stably expressed.
61. The plant, plant part, or plant cell of any one of embodiments 49-60, wherein the plant, plant part, or plant cell is in the subfamily Papilionoideae.
62. The plant, plant part, or plant cell of embodiment 61, wherein the plant, plant part, or plant cell is *Alysicarpus* spp., *Astragalus* spp., *Baptisia* spp., *Cajanus* spp., *Calopogonium* spp., *Caragana* spp., *Centrosema* spp., *Cologania* spp., *Crotalaria* spp., *Desmodium* spp., *Genista* spp., *Glycine* spp., *Glycyrrhiza* spp., *Indigofera* spp., *Kummerowia* spp., *Lablab* spp., *Lathyrus* spp., *Lespedeza* spp., *Lotus* spp., *Lupinus* spp., *Macroptihum* spp., *Macrotyloma* spp., *Medicago* spp., *Neonotonia* spp., *Pachyrhizus* spp., *Pisum* spp., *Phaseolus* spp., *Pseudovigna* spp., *Psoralea* spp., *Robinia* spp., *Senna* spp., *Sesbania* spp., *Strophostyles* spp., *Tephrosia* spp., *Teramnus* spp., Trifohum spp., *Vicia* spp., *Vigna* spp., or *Voandzeia* spp.
63. The plant, plant part, or plant cell of any one of embodiments 57-62, wherein the plant is *Glycine max*, wherein the plant, plant part, or plant cell is resistant to Asian Soybean Rust caused by *Phakopsora pachyrhizi*.
64. A method of genetically engineering a pathogen resistance or tolerance trait in a plant, plant part, or plant cell, comprising:
    providing a plant species that is susceptible to a pathogen;
    identifying within the genome of the plant species a homolog of FIT1, wherein said homolog does not mediate AvrFIT1 recognition; and
    genetically modifying a plant, plant part, or plant cell from the susceptible plant species with targeted gene editing, wherein said targeted gene editing is directed at the FIT1 homolog, and wherein said targeted gene editing enables the FIT1 homolog to recognize AvrFIT1 and confers resistance or tolerance to a pathogen.
65. The method of embodiment 64, wherein the targeted gene editing uses an engineered or natural nuclease selected from the group consisting of homing endonucleases/meganucleases (EMNs), zinc finger nucleases (ZFNs), and transcription activator-like effector nucleases (TALEN5).
66. The method of embodiment 64 or 65, wherein targeted gene editing uses a clustered regularly interspaced short palindromic repeats (CRISPR)-Cas nuclease.
67. The method of embodiment 66, wherein the nuclease is selected from the group consisting of Cas9, Cas12, Cas13, CasX, and CasY.
68. The method of any one of embodiments 64-67, further comprising breeding with, or asexually propagating the plant.
69. A genetically modified plant, plant part, or plant cell produced by the method of any one of embodiments 64-68, wherein said plant, plant part, or plant cell exhibits resistance or tolerance to a pathogen.
70. The genetically modified plant, plant part, or plant cell of embodiment 69, wherein the pathogen is a fungus from the order Cantharellales or Pucciniales.
71. The genetically modified plant, plant part, or plant cell of embodiment 70, wherein the fungal pathogen is *Rhizoctonia solani*, Melampsora spp., *Phakopsora pachyrhizi, Phakopsora meibomiae, Phakopsora euvitis, Phakopsora* spp., *Puccinia* spp., *Uromyces* spp., *Austropuccinia* spp., *Cronartium* spp. or *Hemileia vastatrix.*
72. The genetically modified plant, plant part, or plant cell of any one of embodiments 69-71, wherein the fungal pathogen is *Phakopsora pachyrhizi* and the plant, plant part, or plant cell is *Glycine* max.
73. A method for identifying a functional FIT1 gene and/or allele thereof comprising:
    isolating a FIT1 homolog or allele thereof;
    expressing all or a substantial fragment of said FIT1 homolog or allele thereof in combination with a homolog of AvrFIT1 in a plant, plant part, or plant cell; and
    assaying said plant, plant part, or plant cell for an immune response.
74. The method of embodiment 73, wherein the effector protein comprises SEQ ID NO: 24, SEQ ID: 26, or sequences at least 90% identical thereto.
75. The method of embodiment 73 or 74, wherein the FIT1 allele is a synthetic variant.
76. The method of any one of embodiments 73-75, wherein the plant, plant part, or plant cell is a species of *Nicotiana, Solanum, Physalis, Capsicum, Lactuca, Alysicarpus, Astragalus, Baptisia, Cajanus, Calopogonium, Caragana, Centrosema, Cologania, Crotalaria, Desmodium, Genista, Glycine, Glycyrrhiza, Indigofera, Kummerowia, Lablab, Lathyrus, Lespedeza, Lotus, Lupinus, Macroptilium, Macrotyloma, Medicago, Neonotonia, Pachyrhizus, Pisum, Phaseolus, Pseudovigna, Psoralea, Robinia,*

*Senna, Sesbania, Strophostyles, Tephrosia, Teramnus, Trifolium, Vicia, Vigna*, and *Voandzeia* that lacks a functional native FIT1 gene.

77. A transgenic plant, plant part, or plant cell having resistance to Asian Soybean Rust, wherein the resistance is conferred by a transgene comprising SEQ ID NO: 1, or a sequence at least 70% identical thereto.

78. A transgenic plant, plant part, or plant cell having resistance to Asian Soybean Rust, wherein the resistance is conferred by a transgene comprising SEQ ID NO: 1, or a sequence at least 80% identical thereto.

79. A transgenic plant, plant part, or plant cell having resistance to Asian Soybean Rust, wherein the resistance is conferred by a transgene comprising SEQ ID NO: 1, or a sequence at least 90% identical thereto.

80. A transgenic plant, plant part, or plant cell having resistance to Asian Soybean Rust, wherein the resistance is conferred by a transgene comprising a nucleotide sequence encoding the amino acid sequence of SEQ ID NO: 2, or an amino acid sequence at least 90% identical thereto.

81. A transgenic plant, plant part, or plant cell having resistance to Asian Soybean Rust, wherein the resistance is conferred by a transgene comprising SEQ ID NO: 3, or a sequence at least 70% identical thereto.

82. A transgenic plant, plant part, or plant cell having resistance to Asian Soybean Rust, wherein the resistance is conferred by a transgene comprising SEQ ID NO: 3, or a sequence at least 80% identical thereto.

83. A transgenic plant, plant part, or plant cell having resistance to Asian Soybean Rust, wherein the resistance is conferred by a transgene comprising SEQ ID NO: 3, or a sequence at least 90% identical thereto.

84. A transgenic plant, plant part, or plant cell having resistance to Asian Soybean Rust, wherein the resistance is conferred by a transgene comprising a nucleotide sequence encoding the amino acid sequence of SEQ ID NO: 4, or an amino acid sequence at least 90% identical thereto.

85. A transgenic plant, plant part, or plant cell having resistance to Asian Soybean Rust, wherein the resistance is conferred by a transgene comprising SEQ ID NO: 5, or a sequence at least 70% identical thereto.

86. A transgenic plant, plant part, or plant cell having resistance to Asian Soybean Rust, wherein the resistance is conferred by a transgene comprising SEQ ID NO: 5, or a sequence at least 80% identical thereto.

87. A transgenic plant, plant part, or plant cell having resistance to Asian Soybean Rust, wherein the resistance is conferred by a transgene comprising SEQ ID NO: 5, or a sequence at least 90% identical thereto.

88. A transgenic plant, plant part, or plant cell having resistance to Asian Soybean Rust, wherein the resistance is conferred by a transgene comprising a nucleotide sequence encoding the amino acid sequence of SEQ ID NO: 6, or an amino acid sequence at least 90% identical thereto.

89. A transgenic plant, plant part, or plant cell having resistance to Asian Soybean Rust, wherein the resistance is conferred by a transgene comprising SEQ ID NO: 7, or a sequence at least 70% identical thereto.

90. A transgenic plant, plant part, or plant cell having resistance to Asian Soybean Rust, wherein the resistance is conferred by a transgene comprising SEQ ID NO: 7, or a sequence at least 80% identical thereto.

91. A transgenic plant, plant part, or plant cell having resistance to Asian Soybean Rust, wherein the resistance is conferred by a transgene comprising SEQ ID NO: 7, or a sequence at least 90% identical thereto.

92. A transgenic plant, plant part, or plant cell having resistance to Asian Soybean Rust, wherein the resistance is conferred by a transgene comprising a nucleotide sequence encoding the amino acid sequence of SEQ ID NO: 8, or an amino acid sequence at least 90% identical thereto.

93. A transgenic plant, plant part, or plant cell having resistance to Asian Soybean Rust, wherein the resistance is conferred by a transgene comprising SEQ ID NO: 9, or a sequence at least 70% identical thereto.

94. A transgenic plant, plant part, or plant cell having resistance to Asian Soybean Rust, wherein the resistance is conferred by a transgene comprising SEQ ID NO: 9, or a sequence at least 80% identical thereto.

95. A transgenic plant, plant part, or plant cell having resistance to Asian Soybean Rust, wherein the resistance is conferred by a transgene comprising SEQ ID NO: 9, or a sequence at least 90% identical thereto.

96. A transgenic plant, plant part, or plant cell having resistance to Asian Soybean Rust, wherein the resistance is conferred by a transgene comprising a nucleotide sequence encoding the amino acid sequence of SEQ ID NO: 10, or an amino acid sequence at least 90% identical thereto.

97. A transgenic plant, plant part, or plant cell having resistance to Asian Soybean Rust, wherein the resistance is conferred by a transgene comprising SEQ ID NO: 11, or a sequence at least 70% identical thereto.

98. A transgenic plant, plant part, or plant cell having resistance to Asian Soybean Rust, wherein the resistance is conferred by a transgene comprising SEQ ID NO: 11, or a sequence at least 80% identical thereto.

99. A transgenic plant, plant part, or plant cell having resistance to Asian Soybean Rust, wherein the resistance is conferred by a transgene comprising SEQ ID NO: 11, or a sequence at least 90% identical thereto.

100. A transgenic plant, plant part, or plant cell having resistance to Asian Soybean Rust, wherein the resistance is conferred by a transgene comprising a nucleotide sequence encoding the amino acid sequence of SEQ ID NO: 12, or an amino acid sequence at least 90% identical thereto.

101. A transgenic plant, plant part, or plant cell having resistance to Asian Soybean Rust, wherein the resistance is conferred by a transgene comprising SEQ ID NO: 13, or a sequence at least 70% identical thereto.

102. A transgenic plant, plant part, or plant cell having resistance to Asian Soybean Rust, wherein the resistance is conferred by a transgene comprising SEQ ID NO: 13, or a sequence at least 80% identical thereto.

103. A transgenic plant, plant part, or plant cell having resistance to Asian Soybean Rust, wherein the resistance is conferred by a transgene comprising SEQ ID NO: 13, or a sequence at least 90% identical thereto.

104. A transgenic plant, plant part, or plant cell having resistance to Asian Soybean Rust, wherein the resistance is conferred by a transgene comprising a nucleotide sequence encoding the amino acid sequence of SEQ ID NO: 14, or an amino acid sequence at least 90% identical thereto.

105. A transgenic plant, plant part, or plant cell having resistance to Asian Soybean Rust, wherein the resistance is conferred by a transgene comprising SEQ ID NO: 15, or a sequence at least 70% identical thereto.

106. A transgenic plant, plant part, or plant cell having resistance to Asian Soybean Rust, wherein the resistance is conferred by a transgene comprising SEQ ID NO: 15, or a sequence at least 80% identical thereto.

107. A transgenic plant, plant part, or plant cell having resistance to Asian Soybean Rust, wherein the resistance is conferred by a transgene comprising SEQ ID NO: 15, or a sequence at least 90% identical thereto.

108. A transgenic plant, plant part, or plant cell having resistance to Asian Soybean Rust, wherein the resistance is conferred by a transgene comprising a nucleotide sequence encoding the amino acid sequence of SEQ ID NO: 16, or an amino acid sequence at least 90% identical thereto.

109. A transgenic plant, plant part, or plant cell having resistance to Asian Soybean Rust, wherein the resistance is conferred by a transgene comprising SEQ ID NO: 17, or a sequence at least 70% identical thereto.

110. A transgenic plant, plant part, or plant cell having resistance to Asian Soybean Rust, wherein the resistance is conferred by a transgene comprising SEQ ID NO: 17, or a sequence at least 80% identical thereto.

111. A transgenic plant, plant part, or plant cell having resistance to Asian Soybean Rust, wherein the resistance is conferred by a transgene comprising SEQ ID NO: 17, or a sequence at least 90% identical thereto.

112. A transgenic plant, plant part, or plant cell having resistance to Asian Soybean Rust, wherein the resistance is conferred by a transgene comprising a nucleotide sequence encoding the amino acid sequence of SEQ ID NO: 18, or an amino acid sequence at least 90% identical thereto.

113. A transgenic plant, plant part, or plant cell having resistance to Asian Soybean Rust, wherein the resistance is conferred by a transgene comprising SEQ ID NO: 19, or a sequence at least 70% identical thereto.

114. A transgenic plant, plant part, or plant cell having resistance to Asian Soybean Rust, wherein the resistance is conferred by a transgene comprising SEQ ID NO: 19, or a sequence at least 80% identical thereto.

115. A transgenic plant, plant part, or plant cell having resistance to Asian Soybean Rust, wherein the resistance is conferred by a transgene comprising SEQ ID NO: 19, or a sequence at least 90% identical thereto.

116. A transgenic plant, plant part, or plant cell having resistance to Asian Soybean Rust, wherein the resistance is conferred by a transgene comprising a nucleotide sequence encoding the amino acid sequence of SEQ ID NO: 20, or an amino acid sequence at least 90% identical thereto.

The invention claimed is:

1. A recombinant DNA construct comprising a nucleic acid sequence, wherein the nucleic acid sequence encodes a protein comprising SEQ ID NO: 6, or a protein at least 90% identical thereto, and wherein the construct is capable of conferring resistance to a fungal pathogen when transformed into a plant.

2. A transgenic plant, plant part, or plant cell having resistance or tolerance to a fungal pathogen, wherein the resistance or tolerance is conferred by a transgene comprising a nucleic acid sequence encoding a protein comprising SEQ ID NO: 6, or a protein at least 90% identical thereto.

3. The transgenic plant, plant part, or plant cell of claim 2, wherein the fungal pathogen is from the order Cantharellales or Pucciniales.

4. The transgenic plant, plant part, or plant cell of claim 3, wherein the fungal pathogen is *Rhizoctonia solani, Melampsora* spp., *Phakopsora pachyrhizi, Phakopsora mei-*

*bomiae, Phakopsora euvitis, Phakopsora* spp., *Puccinia* spp., *Uromyces* spp., *Austropuccinia* spp., *Cronartium* spp., *Austropuccinia* spp., *Cronartium* spp. or *Hemileia vastatrix.*

5. The transgenic plant, plant part, or plant cell of claim 2, wherein the plant, plant part, or plant cell is in the subfamily Papilionoideae.

6. The transgenic plant, plant part, or plant cell of claim 2, wherein the plant, plant part, or plant cell is *Alysicarpus* spp., *Astragalus* spp., *Baptisia* spp., *Cajanus* spp., *Calopogonium* spp., *Caragana* spp., *Centrosema* spp., *Cologania* spp., *Crotalaria* spp., *Desmodium* spp., *Genista* spp., *Glycine* spp., *Glycyrrhiza* spp., *Indigofera* spp., *Kummerowia* spp., *Lablab* spp., *Lathyrus* spp., *Lespedeza* spp., *Lotus* spp., *Lupinus* spp., *Macroptilium* spp., *Macrotyloma* spp., *Medicago* spp., *Neonotonia* spp., *Pachyrhizus* spp., *Pisum* spp., *Phaseolus* spp., *Pseudovigna* spp., *Psoralea* spp., *Robinia* spp., *Senna* spp., *Sesbania* spp., *Strophostyles* spp., *Tephrosia* spp., *Teramnus* spp., *Trifolium* spp., *Vicia* spp., *Vigna* spp., or *Voandzeia* spp.

7. The transgenic plant, plant part, or plant cell of claim 6, wherein the plant, plant part, or plant cell is *Glycine max*, and wherein the plant, plant part, or plant cell is resistant to Asian Soybean Rust caused by *Phakopsora pachyrhizi.*

8. The transgenic plant, plant part, or plant cell of claim 7, wherein the resistance to Asian Soybean Rust is conferred by a transgene comprising SEQ ID NO: 5, or by a sequence at least 70% identical thereto.

9. The transgenic plant, plant part, or plant cell of claim 7, wherein the resistance to Asian Soybean Rust is conferred by a transgene comprising a nucleotide sequence encoding the amino acid sequence of SEQ ID NO: 6, SEQ ID NO: 8, or SEQ ID NO: 10.

10. A method of producing a plant, plant part, or plant cell having resistance or tolerance to a fungal pathogen, wherein the method comprises:

transforming a plant, plant part, or plant cell with an isolated, recombinant, or synthetic polynucleotide comprising:

a nucleic acid sequence encoding a functional FIT1 protein, wherein the protein is at least 90% identical to SEQ ID NO: 6 and selecting a plant comprising the polynucleotide and having resistance or tolerance to a fungal pathogen.

11. The method of claim 10, wherein the nucleotide sequence encoding the FIT1 protein has been codon optimized.

12. The method of claim 10, wherein the plant, plant part, or plant cell is transformed with two or more polynucleotides encoding different FIT1 proteins.

13. The method of claim 10, wherein the plant, plant part, or plant cell is transformed or introgressed with one or more additional desired traits.

14. The method of claim 13, wherein the one or more additional desired traits are resistance traits to a disease, pest, or abiotic stress.

15. A plant, plant part, or plant cell produced by the method of claim 10, wherein the plant, plant part, or plant cell is resistant or tolerant to a fungal pathogen.

16. The plant, plant part, or plant cell of claim 15, wherein the FIT1 protein is transiently expressed.

17. The plant, plant part, or plant cell of claim 15, wherein the FIT1 protein is stably expressed.

18. The plant, plant part, or plant cell of claim 15, wherein the plant, plant part, or plant cell is in the subfamily Papilionoideae.

19. The plant, plant part, or plant cell of claim 15, wherein the plant, plant part, or plant cell is *Alysicarpus* spp., *Astragalus* spp., *Baptisia* spp., *Cajanus* spp., *Calopogonium* spp., *Caragana* spp., *Centrosema* spp., *Cologania* spp., *Crotalaria* spp., *Desmodium* spp., *Genista* spp., *Glycine* spp., *Glycyrrhiza* spp., *Indigofera* spp., *Kummerowia* spp., *Lablab* spp., *Lathyrus* spp., *Lespedeza* spp., *Lotus* spp., *Lupinus* spp., *Macroptilium* spp., *Macrotyloma* spp., *Medicago* spp., *Neonotonia* spp., *Pachyrhizus* spp., *Pisum* spp., *Phaseolus* spp., *Pseudovigna* spp., *Psoralea* spp., *Robinia* spp., *Senna* spp., *Sesbania* spp., *Strophostyles* spp., *Tephrosia* spp., *Teramnus* spp., *Trifolium* spp., *Vicia* spp., *Vigna* spp., or *Voandzeia* spp.

20. The plant, plant part, or plant cell of claim 15, wherein the plant is *Glycine max*, wherein the plant, plant part, or plant cell is resistant or tolerant to Asian Soybean Rust caused by *Phakopsora pachyrhizi.*

21. The transgenic plant, plant part, or plant cell of claim 15, wherein the plant, plant part, or plant cell is resistant or tolerant to Asian Soybean Rust, and wherein the resistance or tolerance is conferred by a transgene comprising SEQ ID NO: 5, or by a sequence at least 70% identical thereto.

22. The transgenic plant, plant part, or plant cell of claim 15, wherein the plant, plant part, or plant cell is resistant or tolerant to Asian Soybean Rust, and wherein the resistance or tolerance is conferred by a transgene comprising a nucleotide sequence encoding the amino acid sequence of SEQ ID NO: 6, SEQ ID NO: 8, or SEQ ID NO: 10.

* * * * *

UNITED STATES PATENT AND TRADEMARK OFFICE

CERTIFICATE OF CORRECTION

PATENT NO. : 11,530,419 B2
APPLICATION NO. : 17/512329
DATED : December 20, 2022
INVENTOR(S) : Alexander Christiaan Schultink et al.

It is certified that error appears in the above-identified patent and that said Letters Patent is hereby corrected as shown below:

In the Claims

At Column 198, Line 36 (Claim 21): "The transgenic plant" should be --The plant--.

At Column 198, Line 41 (Claim 22): "The transgenic plant" should be --The plant--.

Signed and Sealed this
Ninth Day of May, 2023

Katherine Kelly Vidal

Katherine Kelly Vidal
*Director of the United States Patent and Trademark Office*